(12) United States Patent
Alanine et al.

(10) Patent No.: US 7,576,088 B2
(45) Date of Patent: Aug. 18, 2009

(54) BENZODIOXOLE DERIVATIVES

(75) Inventors: Alexander Alanine, Schlierbach (FR);
Konrad Bleicher, Freiburg (DE);
Wolfgang Guba, Muellheim (DE);
Wolfgang Haap, Loerrach (DE);
Dagmar Kube, Rochester, MN (US);
Thomas Luebbers, Loerrach (DE);
Jean-Marc Plancher, Knoeringue (FR);
Olivier Roche, Folgensbourg (FR);
Mark Rogers-Evans, Binningen (CH);
Gisbert Schneider, Oberursel (DE);
Jochen Zuegge, Frankfurt (DE)

(73) Assignee: Hoffman-La Roche Inc., Nutley, NJ (US)

( * ) Notice: Subject to any disclaimer, the term of this patent is extended or adjusted under 35 U.S.C. 154(b) by 526 days.

(21) Appl. No.: 11/062,973

(22) Filed: Feb. 22, 2005

(65) Prior Publication Data
US 2005/0143373 A1  Jun. 30, 2005

Related U.S. Application Data

(62) Division of application No. 10/626,681, filed on Jul. 24, 2003, now Pat. No. 6,900,227.

(30) Foreign Application Priority Data
Jul. 29, 2002  (EP) ................... 02016831

(51) Int. Cl.
*A61K 31/496* (2006.01)
*C07D 411/02* (2006.01)
(52) U.S. Cl. .................... 514/254.11; 544/377; 544/62; 514/218; 514/217.03; 514/228.2; 540/575; 540/596
(58) Field of Classification Search .................. 514/321, 514/218, 254.11, 217.03, 228.2; 544/377, 544/62; 540/575, 596
See application file for complete search history.

(56) References Cited

U.S. PATENT DOCUMENTS

| 5,624,941 | A | 4/1997 | Barth et al. |
|---|---|---|---|
| 6,432,984 | B1 | 8/2002 | Barth et al. |
| 2001/0034344 | A1 | 10/2001 | Mittendorf et al. |
| 2002/0019383 | A1 | 2/2002 | Achard et al. |

FOREIGN PATENT DOCUMENTS

| EP | 0216831 | 8/1987 |
|---|---|---|
| EP | 576357 | 6/1995 |
| EP | 656354 | 6/1995 |
| EP | 658546 | 6/1995 |
| EP | 761673 A1 * | 3/1997 |
| FR | 2 789 078 | 8/2000 |
| WO | WO 92 18490 | 10/1992 |
| WO | WO9719063 | 5/1997 |
| WO | WO0015609 | 3/2000 |
| WO | WO0046209 | 8/2000 |
| WO | WO 01 28557 | 4/2001 |
| WO | WO 01 29007 | 4/2001 |
| WO | WO0132663 | 5/2001 |
| WO | WO0158869 | 8/2001 |
| WO | WO0164632 | 9/2001 |
| WO | WO0164633 | 9/2001 |
| WO | WO0164634 | 9/2001 |
| WO | WO0224630 | 3/2002 |
| WO | WO0228346 | 4/2002 |
| WO | WO 02 36590 | 5/2002 |
| WO | WO 02 42248 | 5/2002 |

OTHER PUBLICATIONS

Pozharskii et. al. Heterocycles in Life and Society Wiley, 1997, pp. 1-6.*
P. H. Reggio "Endocannabinoid structure-activity relationships for interaction at the cannabinoid receptors" Prostaglandins, Leukotrienes and Essential Fatty Acids 2002, 66, 143-160.*
Martin, Yvonne C. et. al. "Do Structurally Similar Molecules Have Similar Biological Activity?" Journal of Medicinal Chemistry 2002, 45, 4350-4358.*
Lea W. Padgett "Recent developments in cannabinoid ligands" Life Sciences 2005, 77, 1767-1798.*
D. Shire, et. al, J. Biol. Chem. 270 (8) (1995) 3726-31.
S. Munro, et. al. Nature 365 (1993) 61-61.
Y. Gaoni, et. al. J. Am. Chem. Soc, 86 (1964) 16.
R. Mechoulam (Ed.) in "Cannabinoids as therapeutic Agents", (1986), pp. 1-20, CRC Pr.
E.M. Williamson, F. J. Evans, Drugs 60 (6) (2000) 1303-1314.
R. G. Pertwee, Curr. Med. Chem., 6 (8) (1999) 635-664.

(Continued)

*Primary Examiner*—Rita J Desai
*Assistant Examiner*—David K O'Dell
(74) *Attorney, Agent, or Firm*—George W. Johnston; Dennis P. Tramaloni; Brian C. Remy

(57) ABSTRACT

The present invention relates to compounds of the general formula

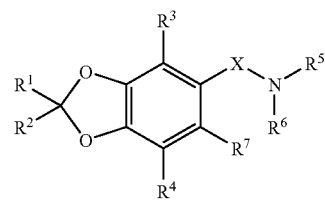

and pharmaceutically acceptable salts thereof. The compounds are useful for the treatment and/or prophylaxis of diseases such as obesity by selective modulation of CB1 receptors.

16 Claims, No Drawings

OTHER PUBLICATIONS

W.A. Devane, et. al. Science 258 (1992) 1946-9.

V. Di Marzo, et. al., Trends in Neuroscience 21 (12) (1998) 521-8.

A.C. Porter, C.C. Felder, Pharmacol. Ther., 90 (1) (2001) 45-60.

C.M. Williams, T.C. Kirkham, Psychopharmacology 143 (3) (1999) 315-317.

C.C. Felder, et. al., Proc. Natl. Acad. Sci. USA 90 (16) (1993) 7656-7660.

G. Colombo, et. al., Life Sci. 63 (8) (1998) L113-PL117.

V. Di Marzo, et. al., Nature 410 (6830) 822-825.

F. Barth, et. al. "Cannabinoid antagonists: From research tools to potential new drugs", Abstracts of Papers, 222$^{nd}$ ACS National Meeting, Chicago, IL, United States, Aug. 26-30, 2001.

AAI; M. Pacheco, et. al. Exp. Ther. 257 (1) (1991) 170-183.

F.M. Casiano, et. al. NIDA Res. Monogr. 105 (1991) 295-6.

AM630, K. Hosohata, et. al. Life. Sci 61 (1997) 115-118.

R. Pertwee, et. al., Life Sci. 56 (23-24) (1995) 1949-55.

LY320135, C.C. Felder, et. al., J. Pharmacol. Exp. Ther. 284, (1) (1998) 291-297 disclosed in WO9602248.

M. Kanyonyo, et. al., Bioorg. Med. Chem. Lett. 9 (15) (1999) 2233-2236.

F. Ooms, et. al., J. Med. Chem. 45 (9) (2002) 1748-1756.

Patent Abstracts of Japan, vol. 015, No. 001, (1991) & JP 02 0255673 A., Fuji Photo File Co Ltd, (1990).

* cited by examiner

BENZODIOXOLE DERIVATIVES

PRIORITY TO RELATED APPLICATIONS

This application is a Division of Ser. No. 10/626,681, filed Jul. 24, 2003, which is now pending.

BACKGROUND OF THE INVENTION

The present invention relates to the use of antagonists of the $CB_1$ cannabinnoid receptor. Two different subtypes of cannabinoid receptors ($CB_1$ and $CB_2$) have been isolated and both belong to G protein coupled receptor superfamily. An alternative spliced form of $CB_1$, $CB_{1A}$, has also been described, but it did not exhibit different properties in terms of ligand binding and receptor activation than $CB_1$ (D.Shire, C. Carrillon, M. Kaghad, B. Calandra, M. Rinaldi-Carmona, G. Le Fur, D. Caput, P. Ferrara, J. Biol. Chem. 270 (8) (1995) 3726-31). The $CB_1$ receptor is mainly located in the brain, whereas the $CB_2$ receptor is predominately distributed in the periphery primarily localized in spleen and cells of the immune system (S. Munro, K. L. Thomas, M. Abu-Shaar, Nature 365 (1993) 61-61).

Therefore in order to avoid side effects a $CB_1$-selective compound is desirable. $\Delta^9$-tetrahydrocannabinol ($\Delta^9$-THC) is the principal psychoactive compound in the Indian hemp (Y. Gaoni, R. Mechoulam, J. Am. Chem. Soc., 86 (1964) 1646), *canabis savita* (marijuana), which is used in medicine since ages (R. Mechoulam (Ed.) in "*Cannabinoids as therapeutic Agents*", 1986, pp. 1-20, CRC Press). $\Delta^9$-THC is a non-selective $CB_1/_2$ receptor agonist and is available in the USA as dronabinol (marinol®) for the alleviation of cancer chemotherapy-induced emesis (CIE) and the reversal of body weight loss experienced by AIDS patients through appetite stimulation. In the UK Nabolinone (LY-109514, Cesamet®), a synthetic analogue of $\Delta^9$-THC, is used for CIE (R. G. Pertwee, Pharmaceut. Sci. 3 (11) (1997) 539-545, E. M. Williamson, F. J. Evans, Drugs 60 (6) (2000) 1303-1314).

Anandamide (arachidonylethanolamide) was identified as the endogenous ligand (agonist) for $CB_1$ (R. G. Pertwee, Curr. Med. Chem., 6 (8) (1999) 635-664;W. A. Devane, L. Hanus, A. Breuer, R. G. Pertwee, L. A. Stevenson, G. Griffin, D. Gibson, A. Mandelbaum, A. Etinger, R. Mechoulam, Science 258 (1992) 1946-9). Anandamide and 2-arachidonoylglycerol (2-AG) modulate at the presynaptic nerve teminal negatively adenylate cyclase and voltage-sensitive $Ca^{2+}$ channels and activates the inwardly rectifying $K^+$ channel (V. Di Marzo, D. Melck, T. Bisogno, L. De Petrocellis, Trends in Neuroscience 21 (12) (1998) 521-8), thereby affecting neurotransmitter release and/or action, which decreases the release of neurotransmitter (A. C. Porter, C. C. Felder, Pharmacol. Ther., 90 (1) (2001) 45-60).

Anandamide as $\Delta^9$-THC also increases feeding through $CB_1$ receptor-mediated mechanism. $CB_1$ selective antagonists block the increase in feeding associated with administration of anandamide (C. M. Williams, T. C. Kirkham, Psychopharmacology 143 (3) (1999) 315-317; C. C. Felder, E. M. Briley, J. Axelrod, J. T. Simpson, K. Mackie, W. A. Devane, Proc. Natl. Acad. Sci. U. S. A. 90 (16) (1993) 7656-60) and caused appetite suppression and weight loss (G. Colombo, R. Agabio, G. Diaz, C. Lobina, R. Reali, G. L. Gessa, Life Sci. 63 (8) (1998) L113-PL117).

Leptin is the primary signal through which the hypothalamus senses nutritional state and modulates food intake and energy balance. Following temporary food restriction, CB1 receptor knockout mice eat less than their wild-type littermates, and the CB1 antagonist SR141716A reduces food intake in wild-type but not knockout mice. Furthermore, defective leptin signaling is associated with elevated hypothalamic, but not cerebellar, levels of endocannabinoids in obese db/db and ob/ob mice and Zucker rats. Acute leptin treatment of normal rats and ob/ob mice reduces anandamide and 2-arachidonoyl glycerol in the hypothalamus. These findings indicate that endocannabinoids in the hypothalamus may tonically activate CB1 receptors to maintain food intake and form part of the neural circuitry regulated by leptin (V. Di Marzo, S. K. Goparaju, L. Wang, J. Liu, S. Bitkai, Z. Jarai, F. Fezza, G. I. Miura, R. D. Palmiter, T. Sugiura, G. Kunos, Nature 410 (6830) 822-825).

SR-141716A, a CB1 selective antagonist/inverse agonist is currently undergoing phase III clinical trials for the treatment of obesity. In a double blind placebo-controlled study, at the doses of 5, 10 and 20 mg daily, SR 141716 significantly reduced body weight when compared to placebo (F. Barth, M. Rinaldi-Carmona, M. Arnone, H. Heshmati, G. Le Fur, "*Cannabinoid antagonists: From research tools to potential new drugs.*" Abstracts of Papers, 222nd ACS National Meeting, Chicago, Ill., United States, Aug. 26-30, 2001).

Other compounds which have been proposed as CB1 receptor antagonists are aminoalkylindols (AAI; M. Pacheco, S. R. Childers, R. Arnold, F. Casiano, S. J. Ward, J. Pharmacol. Exp. Ther. 257 (1) (1991) 170-183), like 6-bromo-(WIN54661; F. M. Casiano, R. Arnold, D. Haycock, J. Kuster, S. J. Ward, NIDA Res. Monogr. 105 (1991) 295-6) or 6-iodopravadoline (AM630, K. Hosohata, R. M. Quock, R. M; Hosohata, T. H. Burkey, A. Makriyannis, P. Consroe, W. R. Roeske, H. I. Yamamura, Life Sci. 61 (1997) 115-118; R. Pertwee, G. Griffin, S. Fernando, X. Li, A. Hill, A. Makriyannis, Life Sci. 56 (23-24) (1995) 1949-55). Arylbenzo[b]thiophene and benzo[b]ffuran (LY320135, C. C. Felder, K. E. Joyce, E. M. Briley, M. Glass, K. P. Mackie, K. J. Fahey, G. J. Cullinan, D. C. Hunden, D. W. Johnson, M. O. Chaney, G. A. Koppel, M. Brownstein, J. Pharmacol. Exp. Ther. 284 (1) (1998) 291-7) disclosed in WO9602248, U.S. Pat. No. 5,596,106, 3-alkyl-(5,5-diphenyl)imidazolidinediones (M. Kanyonyo, S. J. Govaerts, E. Hermans, J. H. Poupaert, D. M. Lambert, Bioorg. Med. Chem. Lett. 9 (15) (1999) 2233-2236.) as well as 3-alkyl-5-arylimidazolidinediones (F. Ooms, J. Wouters, O. Oscaro. T. Happaerts, G. Bouchard, P.-A. Carrupt, B. Testa, D. M. Lambert, J. Med. Chem. 45 (9) (2002) 1748-1756) are known to antagonize the $CB_1$ receptor respectively act as an inverse agonist on the $hCB_1$ receptor. WO0015609 (FR2783246-A1), WO0164634 (FR2805817-A1), WO0228346, WO0164632 (FR2805818-A1), WO0164633 (FR2805810-A1) disclosed substituted 1-bis (aryl)methyl-azetidines derivatives as antagonists of $CB_1$. In WO0170700 4,5-dihydro-1H-pyrazole derivatives are described as $CB_1$ antagonists. In several patents bridged and non-bridged 1,5-diphenyl-3-pyrazolecarboxamide derivatives are disclosed as $CB_1$ antagonists/inverse agonists (WO0132663, WO0046209, WO9719063, EP658546, EP656354, U.S. Pat. No. 5,624,941, EP576357, U.S. Pat. No. 3,940,418). More recently other diverse structural classes have been disclosed as CB receptor modulators (WO0158869, WO0224630).

SUMMARY OF THE INVENTION

The present invention is concerned with novel benzodioxole derivatives of the formula:

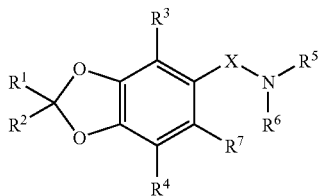

their manufacture, pharmaceutical compositions containing them and their use as medicaments. The active compounds of the present invention are selective $CB_1$ receptor antagonists and are useful in treating obesity and other disorders.

DETAILED DESCRIPTION OF THE INVENTION

The present invention relates to compounds of formula (I):

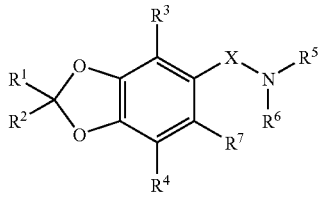

wherein $R^1$ and $R^2$ are independently unsubstituted phenyl, or phenyl which is mono-, di- or tri-substituted, independently, by hydroxy, lower alkyl, lower alkoxy, perfluoro-lower alkyl, perfluoro-lower alkoxy, alkanoyl, cyano, nitro or halogen; or $R^1$ and $R^2$ together with the carbon atom to which they are attached form a 10',11'-dihydro-2,5'-[5H]dibenzo-[a,d]cycloheptene residue;

$R^3$ and $R^4$ are independently hydrogen, halogen, hydroxy, lower alkyl, lower alkoxy, perfluoro-lower alkyl, alkanoyl or cyano;

$R^5$ is hydrogen, lower alkyl, lower alkylsulfonyl, cycloalkyl lower alkyl or hydroxy-lower alkyl;

$R^6$ is Y—$R^8$, lower alkyl, lower alkoxy, hydroxy-lower alkyl, lower alkoxy-lower alkyl, lower alkylaminocarbonyl-lower alkyl, heterocyclyl, cycloalkyl, phenyl or phenyl lower alkyl, wherein the phenyl moiety may optionally be mono-, di- or tri-substituted, independently, by lower alkyl, lower alkoxy, halogen, perfluoro-lower alkyl, hydroxy, alkanoyl or cyano; or $R^6$ is hydrogen when X is —C(O)— or —$SO_2$—; or $R^5$ and $R^6$ together with the nitrogen atom to which they are attached form a 4-, 5-, 6- or 7-membered monocyclic or a 8-, 9-, 10-, or 12-membered bicyclic, saturated or unsaturated heterocyclic ring which may optionally contain one or two further heteroatoms independently selected from O, N and S, said heterocyclic ring being optionally mono-, di- or tri-substituted, independently, by lower alkyl, lower alkoxycarbonyl, hydroxy lower alkyl, lower alkoxy-lower alkyl, di-lower alkylcarbamoyl, carbamoyl, lower alkylcarbonyl amino, oxo, dioxo, alkanoyl, amino lower alkyl, hydroxy, lower alkoxy, halogen, perfluoro-lower alkyl, cyano, heteroaryl, or by phenyl or phenyl lower alkyl, wherein the phenyl moiety may optionally be mono-, di- or tri-substituted, independently, by lower alkyl, lower alkoxy, halogen, perfluoro-lower alkyl, hydroxy, alkanoyl or cyano;

$R^7$ is hydrogen, halogen, lower alkyl or cyano;

$R^8$ is phenyl, cycloalkyl, heterocyclyl or heteroaryl;

X is a single bond, —$CH_2$—, —C(O)—, —$SO_2$— or —$SO_2NH$—;

Y is —$CH_2$—, —C(O)—, —NH— or —$SO_2$—;

and pharmaceutically acceptable salts thereof.

Unless otherwise indicated, the following definitions are set forth to define the meaning and scope of the various terms used to describe the invention herein.

In this specification the term "lower" is used to mean a group consisting of one to six, preferably of one to four carbon atom(s).

The term "halogen" refers to fluorine, chlorine, bromine and iodine, preferably to chlorine, fluorine and bromine, most preferably to chlorine and fluorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethyl-butyl and the like.

The term "cycloalkyl" refers to a monovalent carbocyclic radical of three to six, preferably three to five carbon atoms. This term is further exemplified by radicals such as cyclopropyl, cyclobutyl, cyclopentyl, cyclohexyl and cycloheptyl.

The term "lower alkylsulfonyl" refers to the group R'—$SO_2$—, wherein R' is lower alkyl.

The term "lower alkylcarbonyl" refers to the group R'—CO—, wherein R' is lower alkyl.

The term "alkoxy" refers to the group R'—O—, wherein R' is alkyl. The term "lower-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy, with methoxy being especially preferred.

The term "lower alkoxycarbonyl" refers to the group R'—O—C(O)—, wherein R' is lower alkyl.

The term "perfluoro-lower alkyl" refers to a lower alkyl group wherein all of the hydrogens of the lower alkyl group are substituted or replaced by fluoro. Among the preferred perfluoro-lower alkyl groups are trifluoromethyl, pentafluoroethyl and heptafluoropropyl, with trifluoromethyl being especially preferred.

The term "alkanoyl" refers to a group C(O)—R wherein R is hydrogen or lower alkyl.

Examples of alkanoyl groups are formyl, acetyl, propionyl and the like.

The term "phenyl-lower alkyl" refers to a phenyl group which is attached to the remainder of the molecule via a lower alkylene group, such as methylene, ethylene propylene or butylene, preferably methylene and ethylene. Preferable phenyl-lower alkyl residues are benzyl and 1-phenylethyl.

The term "amino lower alkyl" refers to a lower alkyl radical substituted with an amino group.

The term "heterocyclyl" refers to a 5- or 6-membered saturated heterocyclic residue containing one or two heteroatoms selected from nitrogen, oxygen and sulfur. Examples of heterocyclyl residues are morpholino, tetrahydrofuranyl, pyrrolidinyl, piperidinyl and azepanyl.

The term "heteroaryl" refers to an aromatic monovalent mono- or poly-carbocyclic radical having at least one heteroatom selected from N, O and S. Examples of heteroaryl groups are pyridinyl, pyrazinyl and pyrimidinyl. Such heteroaryl residues may optionally be mono-, di-, or tri-substituted, independently, by lower alkoxy, lower alkyl, perfluoro-lower alkyl, cyano and alkanoyl, preferably by halogen and perfluoro-lower alkyl.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In one embodiment, the present invention relates to compounds of formula (I):

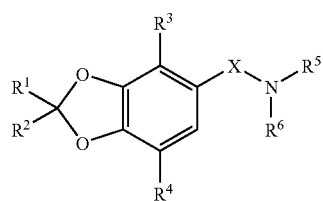

(I)

wherein $R^1$ and $R^2$ are independently unsubstituted phenyl, or phenyl which is mono-, di- or tri-substituted, independently, by hydroxy, lower alkyl, lower alkoxy, perfluoro-lower alkyl, alkanoyl, cyano or halogen;

$R^3$ and $R^4$ are independently hydrogen, halogen, hydroxy, lower alkyl, lower alkoxy, perfluoro-lower alkyl, alkanoyl or cyano;

$R^5$ is hydrogen or lower alkyl;

$R^6$ is phenyl or phenyl lower alkyl, wherein the phenyl moiety may optionally be mono-, di- or tri-substituted, independently, by lower alkyl, lower alkoxy, halogen, perfluoro-lower alkyl, hydroxy, alkanoyl or cyano; or $R^5$ and $R^6$ together with the nitrogen atom to which they are attached form a 5-, 6- or 7-membered monocyclic or a 9- or 10-membered bicyclic, saturated or unsaturated heterocyclic ring which may optionally contain one or two further heteroatoms independently selected from O, N and S, said heterocyclic ring being optionally mono-, di- or tri-substituted, independently, by lower alkyl, lower alkoxycarbonyl, hydroxy lower alkyl, alkanoyl, amino lower alkyl, hydroxy, lower alkoxy, halogen, perfluoro-lower alkyl, cyano, heteroaryl, or by phenyl or phenyl lower alkyl, wherein the phenyl moiety may optionally be mono-, di- or tri-substituted, independently, by lower alkyl, lower alkoxy, halogen, perfluoro-lower alkyl, hydroxy, alkanoyl or cyano;

X is —$CH_2$—, —C(O)— or —$SO_2$—;

and pharmaceutically acceptable salts thereof.

In one ebodiment, $R^1$ and $R^2$ are unsubstituted phenyl. In another embodiment $R^1$ and $R^2$ are independently phenyl which is mono-, di- or tri-substituted, preferably mono- or di-substituted, independently, by hydroxy, lower alkyl such as methyl, lower alkoxy such as methoxy, perfluoro-lower alkyl such as trifluoromethyl, perfluoro-lower alkoxy such as trifluoromethoxy, alkanoyl, cyano, nitro or halogen such as chlorine, fluorine and bromine.

In another embodiment $R^1$ and $R^2$ are independently unsubstituted phenyl or phenyl which is mono-, di- or tri-substituted, preferably mono- or di-substituted, independently, by lower alkyl such as methyl, lower alkoxy such as methoxy, perfluoro-lower alkyl such as trifluoromethyl, perfluoro-lower alkoxy such as trifluoromethoxy, cyano, nitro or halogen such as chlorine, fluorine and bromine.

In another embodiment, the present invention relates to a compound of formula (I) as defined above, wherein $R^1$ and $R^2$ are independently phenyl, which is mono-, di- or tri-substituted, independently, by hydroxy, lower alkyl, lower alkoxy, perfluoro-lower alkyl, alkanoyl, cyano or halogen; preferable substituents of phenyl residues $R^1$ and $R^2$ are lower alkyl, such as methyl, lower alkoxy, such as methoxy, and halogen, such as fluoro and chloro. Preferably $R^1$ and $R^2$ are independently phenyl which is mono- or di-substituted, independently, by halogen, preferably fluoro, chloro or bromo, more preferably fluoro or chloro, or by lower alkoxy, preferably methoxy.

Substituted phenyl residues $R^1$ and $R^2$ are preferably substitued as described above in ortho- and/or para-position, more preferably in para-position.

In another embodiment, $R^1$ and $R^2$ together with the carbon atom to which they are attached form a 10',11'-dihydro-2,5'-[5H]dibenzo[a,d]cycloheptene residue.

In one embodiment, the present invention relates to a compound of formula (I) as defined above, wherein $R^3$ and $R^4$ are independently hydrogen, halogen, hydroxy, lower alkyl, lower alkoxy, perfluoro-lower alkyl, alkanoyl or cyano. Preferred halogen residues $R^3$ and $R^4$ are fluoro, chloro and bromo, with fluoro being especially preferred. Preferred lower alkyl residue in $R^3$ and $R^4$ is methyl. Preferred lower alkoxy residue in $R^3$ and $R^4$ is methoxy. Preferred perfluoro-lower alkyl residue in $R^3$ and $R^4$ is trifluoromethyl.

In another preferred embodiment, the present invention relates to a compound of formula (I) as defined above, wherein $R^3$ and $R^4$ are independently hydrogen, hydroxy or halogen, such as fluoro, chloro or bromo. Preferred substituents $R^3$ and $R^4$ are hydrogen, and fluoro, with hydrogen being especially preferred.

In one embodiment, the present invention related to compounds of formula (I) as defined above, wherein $R^5$ and $R^6$ together with the nitrogen atom to which they are attached form a 4-, 5-, 6- or 7-membered monocyclic or a 8-, 9-, 10- or 12-membered bicyclic, saturated or unsaturated heterocyclic ring which may optionally contain one or two further heteroatoms independently selected from O, N and S, said heterocyclic ring being optionally mono-, di- or tri-substituted, preferably mono- or di-substituted, independently, by lower alkyl, lower alkoxycarbonyl, hydroxy lower alkyl, lower alkoxy-lower alkyl, di-lower alkylcarbamoyl, carbamoyl, lower alkylcarbonyl amino, oxo, alkanoyl, amino lower alkyl, hydroxy, lower alkoxy, halogen, perfluoro-lower alkyl, cyano, heteroaryl, or by phenyl or phenyl lower alkyl, wherein the phenyl moiety may optionally be mono-, di- or tri-substituted, preferably mono- or di-substituted, independently, by lower alkyl, lower alkoxy, halogen, perfluoro-lower alkyl, hydroxy, alkanoyl or cyano.

In another embodiment, the present invention relates to a compound of formula (I) as defined above, wherein $R^5$ and $R^6$ together with the nitrogen atom to which they are attached form a 5-, 6- or 7-membered monocyclic or a 9- or 10-membered bicyclic, saturated or unsaturated heterocyclic ring which may optionally contain one or two further heteroatoms independently selected from O and N, said heterocyclic ring being optionally mono- or di-substituted, independently, by lower alkyl, lower alkoxycarbonyl, hydroxy lower alkyl, alkanoyl, hydroxy, or by phenyl or phenyl lower alkyl, wherein the phenyl moiety may optionally be mono- or di-substituted, independently, by lower alkyl, lower alkoxy, halogen or perfluoro-lower alkyl.

In still another preferred embodiment, the present invention relates to a compound of formula (I) as defined above, wherein $R^5$ and $R^6$ together with the nitrogen atom to which they are attached form a 5- or 6-membered monocyclic saturated heterocyclic ring which may optionally contain one further heteroatom selected from O and S, said heterocyclic ring being optionally mono- or di-substituted, independently, by hydroxy or by halogen such as fluoro.

In one embodiment, preferable heterocyclic rings formed by $R^5$ and $R^6$ together with the nitrogen atom to which they are attached are piperazinyl, morpholino, piperidinyl, piperidin-4-one, pyrrolidinyl, thiomorpholino, azepanyl, 1,2,3,4-tetrahydro-isoquinolinyl, 1,2,3,6-tetrahydro-pyridinyl, [1,4]-diazepanyl, 1,4-dioxa-8-aza-spiro[4.5]dec-8-yl, 2,3,5,6-tetrahydro-[1,2']bipyrazinyl-4yl and 3-hydroxy-8-aza-bicyclo[3.2.1.]oct-8-yl, optionally substituted as indicated above, preferably mono-, di- or tri-substituted, preferably mono- or di-substituted, independently, by lower alkyl such as methyl and isopropyl; by lower alkoxycarbonyl such as ethoxycarbonyl; by hydroxy lower alkyl such as hydroxymethyl; by lower alkoxy-lower alkyl such as methoxymethyl; by di-lower alkylcarbamoyl such as dimethylcarbamoyl; by carbamoyl; by lower alkylcarbonyl amino such as acetylamino; by oxo; by dioxo; by alkanoyl such as formyl; by hydroxy; by lower alkoxy such as methoxy and ethoxy; by halogen such as fluoro; by perfluoro-lower alkyl such as trifluoromethyl; by heteroaryl such as unsubstituted pyrazinyl, unsubstituted pyridinyl, pyridinyl disubstituted by chloro and/or trifluoromethyl; or by phenyl or phenyl lower alkyl such as benzyl, wherein the phenyl moiety may optionally be mono-, di- or tri-substituted, preferably mono- or di-substituted, independently, by lower alkyl such as methyl, by lower alkoxy such as methoxy, by halogen such as chloro and fluoro, or by perfluoro-lower alkyl such as trifluoromethyl.

In another embodiment, preferable heterocyclic rings formed by $R^5$ and $R^6$ together with the nitrogen atom to which they are attached are piperazinyl, morpholino, piperidinyl, piperidin-4-one, pyrrolidinyl, 1,2,3,4-tetrahydro-isoquinolinyl, 1,2,3,6-tetrahydro-pyridinyl, [1,4]-diazepanyl and 1,4-dioxa-8-aza-spiro[4.5]dec-8-yl, with piperazinyl, morpholino and piperidinyl being especially preferred. In another preferable embodiment, the heterocyclic ring formed by $R^5$ and $R^6$ together with the nitrogen atom to which they are attached is piperidinyl.

Further preferable heterocyclic rings formed by $R^5$ and $R^6$ together with the nitrogen atom to which they are attached are piperidinyl, morpholino, thiomorpholino and pyrrolidinyl, optionally substituted as indicated above, preferably optionally mono- or di-substituted, independently, by hydroxy or by halogen such as fluoro. Most preferable heterocyclic ring formed by $R^5$ and $R^6$ together with the nitrogen atom to which they are attached is morpholino.

In one embodiment, the heterocyclic rings formed by $R^5$ and $R^6$ together with the nitrogen atom to which they are attached are unsubstituted.

In another embodiment, the heterocyclic rings formed by $R^5$ and $R^6$ together with the nitrogen atom to which they are attached are mono-, di- or tri-substituted, preferably mono- or di-substituted, independently, by lower alkyl such as methyl and isopropyl; by lower alkoxycarbonyl such as ethoxycarbonyl; by hydroxy lower alkyl such as hydroxymethyl; by lower alkoxy-lower alkyl such as methoxymethyl; by di-lower alkylcarbamoyl such as dimethylcarbamoyl; by carbamoyl; by lower alkylcarbonyl amino such as acetylamino; by oxo; by dioxo; by alkanoyl such as formyl; by hydroxy; by lower alkoxy such as methoxy and ethoxy; by halogen such as fluoro; by perfluoro-lower alkyl such as trifluoromethyl; by heteroaryl such as unsubstituted pyrazinyl, unsubstituted pyridinyl, pyridinyl disubstituted by chloro and/or trifluoromethyl; or by phenyl or phenyl lower alkyl such as benzyl, wherein the phenyl moiety may optionally be mono-, di- or tri-substituted, preferably mono- or di-substituted, independently, by lower alkyl such as methyl, by lower alkoxy such as methoxy, by halogen such as chloro and fluoro, or by perfluoro-lower alkyl such as trifluoromethyl.

In another embodiment, the heterocyclic rings formed by $R^5$ and $R^6$ together with the nitrogen atom to which they are attached are preferably mono- or di-substituted, independently, by methyl, propyl, ethoxycarbonyl, hydroxymethyl, formyl, hydroxy, unsubstituted pyrazinyl, unsubstituted pyridinyl, pyridinyl disubstituted by chloro and/or trifluoromethyl; or by phenyl or phenyl methyl, wherein the phenyl moiety may optionally be mono- or di- substituted, independently, by methyl, methoxy, chloro, fluoro and/or trifluoromethyl.

In a preferable embodiment, the heterocyclic rings formed by $R^5$ and $R^6$ together with the nitrogen atom to which they are attached are optionally mono- or di-substituted, independently, by hydroxy or by halogen such as fluoro.

Substituted 6-membered heterocyclic rings formed by $R^5$ and $R^6$ together with the nitrogen atom to which they are attached rings are preferably substituted at position 4 of the ring; substituted 5-membered rings are preferably substituted at position 3 of the ring.

In one embodiment, the present invention related to compounds of formula (I) as defined above, wherein $R^5$ is hydrogen, lower alkyl, lower alkylsulfonyl, cycloalkyl lower alkyl or hydroxy-lower alkyl. Preferable lower alkyl residues $R^5$ are methyl and ethyl, with methyl being especially preferred. Preferable lower alkylsulfonyl residue $R^5$ is n-butylsulfonyl. Preferable cycloalkyl lower alkyl residue $R^5$ is cyclopropylmethyl. Preferable hydroxy-lower alkyl residue $R^5$ is 2-hydroxyethyl.

In one embodiment, the present invention related to compounds of formula (I) as defined above, wherein $R^6$ is $Y-R^8$, lower alkyl, lower alkoxy, hydroxy-lower alkyl, lower alkoxy-lower alkyl, lower alkylcarbamoyl-lower alkyl, heterocyclyl, cycloalkyl, phenyl or phenyl lower alkyl, wherein the phenyl moiety may optionally be mono-, di- or tri-substituted, preferably mono- or di-substituted, independently, by lower alkyl, lower alkoxy, halogen, perfluoro-lower alkyl, hydroxy, alkanoyl or cyano.

In another embodiment, the present invention related to compounds of formula (I) as defined above, wherein $R^6$ is lower alkyl, lower alkoxy, hydroxy-lower alkyl, lower alkoxy-lower alkyl, lower alkylcarbamoyl-lower alkyl, heterocyclyl, cycloalkyl, phenyl or phenyl lower alkyl, wherein the phenyl moiety may optionally be mono-, di- or tri-substituted, preferably mono- or di-substituted, independently, by lower alkyl, lower alkoxy, halogen, perfluoro-lower alkyl, hydroxy, alkanoyl or cyano.

Preferable lower alkyl residues $R^6$ are ethyl, n-propyl and isopropyl. Preferable lower alkoxy residues $R^6$ are tert-butoxy and methoxy. Preferable hydroxy-lower alkyl residue $R^6$ is 2-hydroxy-ethyl. Preferable lower alkoxy-lower alkyl residue $R^6$ is methoxyethyl. Preferable heterocyclyl residues $R^6$ are morpholino, tetrahydrofuranyl and pyrrolidinyl. Heterocyclyl residues $R^6$, preferably pyrrolidinyl residue $R^6$, may optionally be mono-substituted by lower alkoxy-lower alkyl such as methoxymethyl. Preferable cycloalkyl residues $R^6$ are cyclopropyl, cyclobutyl, cyclopentyl and cycloheptyl. Preferable phenyl lower alkyl residues $R^6$ are benzyl and phenylethyl. The phenyl moieties of phenyl lower alkyl residues $R^6$, preferably of phenylethyl residue $R^6$, may optionally be mono-substituted by lower alkoxy such as methoxy. Preferable lower alkylcarbamoyl-lower alkyl residue $R^6$ is 2,2-dimethyl-1-methylcarbamoyl-propyl.

In another embodiment, the present invention relates to compounds of formula (I) as defined above, wherein $R^6$ is $Y—R^8$.

In still another embodiment, the present invention relates to compounds of formula (I) as defined above, wherein $R^6$ is hydrogen when X is —C(O)— or —SO$_2$—.

In one embodiment, the present invention relates to a compound of formula (I) as defined above, wherein $R^7$ is hydrogen, cyano, halogen such as fluoro, or lower alkyl such as methyl. In another embodiment, $R^7$ is cyano, halogen such as fluoro, or lower alkyl such as methyl. In still another embodiment, the present invention relates to a compound of formula (I) as defined above, wherein $R^7$ is hydrogen. Preferably, $R^7$ is halogen, with fluoro being especially preferred.

In another embodiment, the present invention relates to a compound of formula (I) as defined above, wherein $R^8$ is phenyl, cycloalkyl, heterocyclyl or heteroaryl.

Preferable cycloalkyl residue $R^8$ is cyclohexyl. Preferable lower alkyl resdues $R^8$ are n-propyl, for example when Y is —C(O)—, methyl and n-butyl (for example when Y is —SO2-). Preferable heterocyclyl residues $R^8$ are morpholino, piperidinyl and azepanyl. Preferable heteroary residue $R^8$ is pyridinyl.

In a preferrable embodiment, $R^8$ is a heterocyclyl residue such as morpholino, piperidinyl and azepanyl, with piperidinyl being especially preferred.

In one embodiment, the present invention relates to compounds of formula (I) as defined above, wherein X is a single bond, —CH$_2$—, —C(O)—, —SO$_2$— or —SO$_2$NH—.

In another embodiment, the present invention relates to compounds of formula (I) as defined above, wherein X is a single bond, $R^3$, $R^4$ and $R^7$ are hydrogen and $R^1$, $R^2$, $R^5$ and $R^6$ are as defined above.

In a preferred embodiment, the present invention relates to a compound of formula (I) as defined above, wherein X is —C(O)— or —SO$_2$—, with —C(O)— being especially preferred.

In another embodiment, the present invention relates to a compound of formula (I) as defined above, wherein Y is —CH$_2$—, —C(O)—, —NH— or —SO$_2$—. Preferably, Y is —CH$_2$— or —NH—.

In a preferable embodiment, the present invention relates to compounds of formula (I), wherein $R^1$ and $R^2$ are independently phenyl which is mono- or di-substituted, independently, by lower alkoxy such as methoxy or preferably by halogen such as fluoro, chloro and bromo; $R^3$ and $R^4$ are each hydrogen; $R^5$ and $R^6$ together with the nitrogen atom to which they are attached form a 5- or 6-membered monocyclic saturated heterocyclic ring which may optionally contain one further heteroatom selected from O and S, such as piperidinyl, morpholino, thiomorpholino and pyrrolidinyl, said heterocyclic ring being optionally mono- or di-substituted, independently, by hydroxy or by halogen such as fluoro; $R^7$ is halogen such as fluoro; X is —C(O)—; and pharmaceutically acceptable salts thereof Preferred compounds of general formula (I) are those selected from the group consisting of:
1-(2,2-Diphenyl-benzo[1,3]dioxole-5-sulfonyl)-piperidine,
1-(4-Chloro-phenyl)-4-(2,2-diphenyl-benzo[1,3]dioxole-5-sulfonyl)-piperazine,
1-(2,3-Dimethyl-phenyl)-4-(2,2-diphenyl-benzo[1,3]dioxole-5-sulfonyl)-piperazine,
1-(2,4-Dichloro-phenyl)-4-(2,2-diphenyl-benzo[1,3]dioxole-5-sulfonyl)-piperazine,
1-(2,2-Diphenyl-benzo[1,3]dioxole-5-sulfonyl)-4-(4-fluoro-phenyl)-piperazine,
1-(2,2-Diphenyl-benzo[1,3]dioxole-5-sulfonyl)-4-(3-chloro-phenyl)-piperazine,
4-(2,2-Diphenyl-benzo[1,3]dioxole-5-sulfonyl)-morpholine,
1-(2,2-Diphenyl-benzo[1,3]dioxole-5-sulfonyl)-4-phenyl-piperazine,
1-(2,2-Diphenyl-benzo[1,3]dioxole-5-sulfonyl)-pyrrolidine,
1-(2,2-Diphenyl-benzo[1,3]dioxole-5-sulfonyl)-4-(3-methoxy-phenyl)-piperazine,
1-(2,2-Diphenyl-benzo[1,3]dioxole-5-sulfonyl)-4-(4-methoxy-phenyl)-piperazine,
1-(2,2-Diphenyl-benzo[1,3]dioxole-5-sulfonyl)-4-(2-methoxy-phenyl)-piperazine,
1-(2,2-Diphenyl-benzo[1,3]dioxole-5-sulfonyl)-4-(2-chloro-phenyl)-piperazine,
1-(2,2-Diphenyl-benzo[1,3]dioxole-5-sulfonyl)-4-(2-fluoro-phenyl)-piperazine,
2,2-Diphenyl-benzo[1,3]dioxole-5-sulfonic acid phenethyl-amide,
Benzo[1,3]dioxol-5-yl-4-(2,2-diphenyl-benzo[1,3]dioxole-5-sulfonyl)-piperazine,
4-Benzyl-1-(2,2-diphenyl-benzo[1,3]dioxole-5-sulfonyl)-piperidine,
2-(2,2-Diphenyl-benzo[1,3]dioxole-5-sulfonyl)-1,2,3,4-tetrahydro-isoquinoline,
2,2-Diphenyl-benzo[1,3]dioxole-5-sulfonic acid benzyl-methyl-amide,
2,2-Diphenyl-benzo[1,3]dioxole-5-sulfonic acid benzylamide,
1-(2,2-Diphenyl-benzo[1,3]dioxole-5-sulfonyl)-4-methyl-[1,4]diazepane,
1-(3-Chloro-5-trifluoromethyl-pyridin-2-yl)-4-(2,2-diphenyl-benzo[1,3]dioxole-5-sulfonyl)-[1,4]diazepane,
2,2-Diphenyl-benzo[1,3]dioxole-5-sulfonic acid phenylamide,
2,2-Diphenyl-benzo[1,3]dioxole-5-sulfonic acid[2-(4-methoxy-phenyl)-ethyl]-amide,
1-(2,2-Diphenyl-benzo[1,3]dioxole-5-sulfonyl)-4-methyl-piperazine,
1-(2,2-Diphenyl-benzo[1,3]dioxole-5-sulfonyl)-4-(4-fluoro-phenyl)-1,2,3,6-tetrahydro-pyridine,
4-(4-Chloro-phenyl)-1-(2,2-diphenyl-benzo[1,3]dioxole-5-sulfonyl)-1,2,3,6-tetrahydro-pyridine,
1-(2,2-Diphenyl-benzo[1,3]dioxole-5-sulfonyl)-4-phenyl-1,2,3,6-tetrahydro-pyridine,
racemic 1-[2-(2-Chloro-phenyl)-2-(4-methoxy-phenyl)-benzo[1,3]dioxole-5-sulfonyl]-piperidine,
racemic 1-[2-(2-Chloro-phenyl)-2-(4-fluoro-phenyl)-benzo[1,3]dioxole-5-sulfonyl]-piperidine,
racemic 1-[2-(2-Chloro-phenyl)-2-p-tolyl-benzo[1,3]dioxole-5-sulfonyl]-piperidine,
racemic 1-[2-(4-Chloro-phenyl)-2-(4-methoxy-phenyl)-benzo[1,3]dioxole-5-sulfonyl]-piperidine, racemic 1-[2-(4-Chloro-phenyl)-2-p-tolyl-benzo[1,3]dioxole-5-sulfonyl]-piperidine,
1-[2,2-Bis-(4-chloro-phenyl)-benzo[1,3]dioxole-5-sulfonyl]-piperidine,
racemic 1-[2-(4-Fluoro-phenyl)-2-phenyl-benzo[1,3]dioxole-5-sulfonyl]-piperidine,
racemic 1-[2-(4-Methoxy-phenyl)-2-phenyl-benzo[1,3]dioxole-5-sulfonyl]-piperidine,
racemic 1-[2-(4-Chloro-phenyl)-2-p-tolyl-benzo[1,3]dioxole-5-sulfonyl]-4-(4-fluoro-phenyl)-1,2,3,6-tetrahydro-pyridine,
racemic 1-[2-(4-Chloro-phenyl)-2-(4-fluoro-phenyl)-benzo[1,3]dioxole-5-sulfonyl]-piperidine,
racemic 1-[2-(2,4-Dichloro-phenyl)-2-(4-fluoro-phenyl)-benzo[1,3]dioxole-5-sulfonyl]-piperidine,
1-[2,2-Bis-(4-fluoro-phenyl)-benzo[1,3]dioxole-5-sulfonyl]-piperidine,
racemic 1-[2-(3-Chloro-phenyl)-2-(4-fluoro-phenyl)-benzo[1,3]dioxole-5-sulfonyl]-piperidine,
racemic 1-[2-(4-Chloro-phenyl)-2-(2-chloro-phenyl)-benzo[1,3]dioxole-5-sulfonyl]-piperidine,
racemic (2,2-Diphenyl-benzo[1,3]dioxol-5-yl)-(3-hydroxy-pyrrolidin-1-yl)-methanone,
4-(2,2-Diphenyl-benzo[1,3]dioxole-5-carbonyl)-piperazine-1-carbaldehyde,
(2,2-Diphenyl-benzo[1,3]dioxol-5-yl)-(4-hydroxymethyl-piperidin-1-yl)-methanone,
(1,4-Dioxa-8-aza-spiro[4.5]dec-8-yl)-(2,2-diphenyl-benzo[1,3]dioxol-5-yl)-methanone
(2,2-Diphenyl-benzo[1,3]dioxol-5-yl)-morpholin-4-yl-methanone,
(2,2-Diphenyl-benzo[1,3]dioxol-5-yl)-(4-methyl-piperazin-1-yl)-methanone,
(2,2-Diphenyl-benzo[1,3]dioxol-5-yl)-(4-isopropyl-piperazin-1-yl)-methanone,
1-(2,2-Diphenyl-benzo[1,3]dioxole-5-carbonyl)-piperidin-4-one,
(2,2-Diphenyl-benzo[1,3]dioxol-5-yl)-(4-hydroxy-piperidin-1-yl)-methanone,
(2,2-Diphenyl-benzo[1,3]dioxol-5-yl)-pyrrolidin-1-yl-methanone,
racemic 1-(2,2-Diphenyl-benzo[1,3]dioxole-5-carbonyl)-piperidine-3-carboxylic acid ethyl ester,
[4-(5-Chloro-2-methoxy-phenyl)-piperazin-1-yl]-(2,2-diphenyl-benzo[1,3]dioxol-5-yl)-methanone,
(2,2-Diphenyl-benzo[1,3]dioxol-5-yl)-(4-m-tolyl-piperazin-1-yl)-methanone,
(2,2-Diphenyl-benzo[1,3]dioxol-5-yl)-piperidin-1-yl-methanone,
(2,2-Diphenyl-benzo[1,3]dioxol-5-yl)-(4-o-tolyl-piperazin-1-yl)-methanone,
racemic 1-(2,2-Diphenyl-benzo[1,3]dioxole-5-carbonyl)-piperidine-2-carboxylic acid ethyl ester,
[4-(2,3-Dichloro-phenyl)-piperazin-1-yl]-(2,2-diphenyl-benzo[1,3]dioxol-5-yl)-methanone,
[4-(4-Chloro-3-trifluoromethyl-phenyl)-piperazin-1-yl]-(2,2-diphenyl-benzo[1,3]dioxol-5-yl)-methanone,
racemic (2,2-Diphenyl-benzo[1,3]dioxol-5-yl)-(3-hydroxymethyl-piperidin-1-yl)-methanone,
(2,2-Diphenyl-benzo[1,3]dioxol-5-yl)-(2,3,5,6-tetrahydro-[1,2']bipyrazinyl-4-yl)-methanone,
(2,2-Diphenyl-benzo[1,3]dioxol-5-yl)-(4-pyridin-2-yl-piperazin-1-yl)-methanone,
(4-Fluoro-2,2-diphenyl-benzo[1,3]dioxol-5-yl)-(4-methyl-piperazin-1-yl)-methanone,
(4-Fluoro-2,2-diphenyl-benzo[1,3]dioxol-5-yl)-morpholin-4-yl-methanone,
(4-Fluoro-2,2-diphenyl-benzo[1,3]dioxol-5-yl)-piperidin-1-yl-methanone,
(4,7-Dichloro-2,2-diphenyl-benzo[1,3]dioxol-5-yl)-piperidin-1-yl-methanone,
(4,7-Dichloro-2,2-diphenyl-benzo[1,3]dioxol-5-yl)-morpholin-4-yl-methanone,
(4,7-Dichloro-2,2-diphenyl-benzo[1,3]dioxol-5-yl)-(4-methyl-piperazin-1-yl)-methanone,
(7-Bromo-4-chloro-2,2-diphenyl-benzo[1,3]dioxol-5-yl)-(4-methyl-piperazin-1-yl)-methanone,
(7-Bromo-4-chloro-2,2-diphenyl-benzo[1,3]dioxol-5-yl)-piperidin-1-yl-methanone,
(7-Bromo-4-chloro-2,2-diphenyl-benzo[1,3]dioxol-5-yl)-morpholin-4-yl-methanone,
(7-Hydroxy-2,2-diphenyl-benzo[1,3]dioxol-5-yl)-piperidin-1-yl-methanone,
(2,2-Diphenyl-benzo[1,3]dioxol-5-yl)-[4-(4-fluoro-phenyl)-3,6-dihydro-2H-pyridin-1-yl]-methanone,
1-(2,2-Diphenyl-benzo[1,3]dioxol-5-ylmethyl)-4-(4-fluoro-phenyl)-1,2,3,6-tetrahydro-pyridine, and pharmaceutically acceptable salts thereof.

Further preferred compounds of general formula (I) are those selected from the group consisting of:
N-(2,2-Diphenyl-benzo[1,3]dioxol-5-yl)-benzenesulfonamide,
N,N-bis(methylsulfonyl)-2,2-diphenyl-1,3-benzodioxol-5-amine,
N,N-bis(butylsulfonyl)-2,2-diphenyl-1,3-benzodioxol-5-amine,
Cyclohexanecarboxylic acid (2,2-diphenyl-benzo[1,3]dioxol-5-yl)-amide,
Butane-1-sulfonic acid (2,2-diphenyl-benzo[1,3]dioxol-5-yl)-amide,
N-(2,2-Diphenyl-benzo[1,3]dioxol-5-yl)-butyramide,
Morpholine-4-carboxylic acid (2,2-diphenyl-benzo[1,3]dioxol-5-yl)-amide,
Piperidine-1-sulfonic acid (2,2-diphenyl-benzo[1,3]dioxol-5-yl)-amide,
Piperidine-1-carboxylic acid (2,2-diphenyl-benzo[1,3]dioxol-5-yl)-amide,
[2-(4-Chloro-phenyl)-2-(2-fluoro-4-methoxy-phenyl)-benzo[1,3]dioxol-5-yl]-morpholin-4-yl-methanone,
4-[2-(4-Chloro-phenyl)-2-(2-fluoro-4-methoxy-phenyl)-benzo[1,3]dioxole-5-sulfonyl]-morpholine,
[2-(4-Methoxy-phenyl)-2-(3-nitro-phenyl)-benzo[1,3]dioxol-5-yl]-morpholin-4-yl-methanone,
4-[2-(4-Methoxy-phenyl)-2-(3-nitro-phenyl)-benzo[1,3]dioxole-5-sulfonyl]-morpholine,
4-[2-(4-Methoxy-phenyl)-5-(morpholine-4-carbonyl)-benzo[1,3]dioxol-2-yl]-benzonitrile,
4-[2-(4-Methoxy-phenyl)-5-(morpholine-4-sulfonyl)-benzo[1,3]dioxol-2-yl]-benzonitrile,
[2-(2-Fluoro-4-methoxy-phenyl)-2-(4-fluoro-phenyl)-benzo[1,3]dioxol-5-yl]-morpholin-4-yl-methanone,
4-[2-(2-Fluoro-4-methoxy-phenyl)-2-(4-fluoro-phenyl)-benzo[1,3]dioxole-5-sulfonyl]-morpholine,
(6-Fluoro-2,2-diphenyl-benzo[1,3]dioxol-5-yl)-piperidin-1-yl-methanone,
[2-(2,4-Dichloro-phenyl)-6-fluoro-2-(4-fluoro-phenyl)-benzo[1,3]dioxol-5-yl]-piperidin-1-yl-methanone,
[6-Fluoro-2-(4-fluoro-phenyl)-2-phenyl-benzo[1,3]dioxol-5-yl]-piperidin-1-yl-methanone,
[2-(2-Chloro-phenyl)-6-fluoro-2-(4-methoxy-phenyl)-benzo[1,3]dioxol-5-yl]-piperidin-1-yl-methanone,
(6-Fluoro-2,2-diphenyl-benzo[1,3]dioxol-5-yl)-morpholin-4-yl-methanone,

[6-Fluoro-2-(4-fluoro-phenyl)-2-phenyl-benzo[1,3]dioxol-5-yl]-morpholin-4-yl-methanone,
[2-(2-Chloro-phenyl)-6-fluoro-2-(4-methoxy-phenyl)-benzo[1,3]dioxol-5-yl]-morpholin-4-yl-methanone,
(6-Fluoro-2,2-diphenyl-benzo[1,3]dioxol-5-yl)-[4-(4-fluoro-phenyl)-piperazin-1-yl]-methanone,
[6-Fluoro-2-(4-fluoro-phenyl)-2-phenyl-benzo[1,3]dioxol-5-yl]-[4-(4-fluoro-phenyl)-piperazin-1-yl]-methanone,
[2-(2-Chloro-phenyl)-6-fluoro-2-(4-methoxy-phenyl)-benzo[1,3]dioxol-5-yl]-[4-(4-fluoro-phenyl)-piperazin-1-yl]-methanone,
[2-(2,4-Dichloro-phenyl)-6-fluoro-2-(4-methoxy-phenyl)-benzo[1,3]dioxol-5-yl]-piperidin-1-yl-methanone,
[2-(2,4-Dichloro-phenyl)-6-fluoro-2-(4-methoxy-phenyl)-benzo[1,3]dioxol-5-yl]-morpholin-4-yl-methanone,
[2-(2,4-Dichloro-phenyl)-6-fluoro-2-(4-methoxy-phenyl)-benzo[1,3]dioxol-5-yl]-fluoro-phenyl)-piperazin-1-yl]-methanone,
[2-(2,4-Dichloro-phenyl)-6-fluoro-2-(4-fluoro-phenyl)-benzo[1,3]dioxol-5-yl]-morpholin-4-yl-methanone,
(6-Methyl-2,2-diphenyl-benzo[1,3]dioxol-5-yl)-piperidin-1-yl-methanone,
[6-Fluoro-2,2-bis-(4-fluoro-phenyl)-benzo[1,3]dioxol-5-yl]-morpholin-4-yl-methanone,
(6-Bromo-2,2-diphenyl-benzo[1,3]dioxol-5-yl)-piperidin-1-yl-methanone,
(+)-[2-(2,4-Dichloro-phenyl)-6-fluoro-2-(4-fluoro-phenyl)-benzo[1,3]dioxol-5-yl]-morpholin-4-yl-methanone,
(−)-[2-(2,4-Dichloro-phenyl)-6-fluoro-2-(4-fluoro-phenyl)-benzo[1,3]dioxol-5-yl]-morpholin-4-yl-methanone,
[2-(2,4-Dichloro-phenyl)-2-(4-fluoro-phenyl)-benzo[1,3]dioxol-5-yl]-morpholin-4-yl-methanone,
[2-(2,4-Dichloro-phenyl)-2-(4-fluoro-phenyl)-benzo[1,3]dioxol-5-yl]-piperidin-1-yl-methanone,
(6-Chloro-2,2-diphenyl-benzo[1,3]dioxol-5-yl)-piperidin-1-yl-methanone,
(6-Chloro-2,2-diphenyl-benzo[1,3]dioxol-5-yl)-morpholin-4-yl-methanone,
2-(2,4-Dichloro-phenyl)-6-fluoro-2-(4-fluoro-phenyl)-benzo[1,3]dioxole-5-carboxylic acid ethyl-methyl-amide,
2-(2,4-Dichloro-phenyl)-6-fluoro-2-(4-fluoro-phenyl)-benzo[1,3]dioxole-5-carboxylic acid methyl-propyl-amide,
[2-(2,4-Dichloro-phenyl)-6-fluoro-2-(4-fluoro-phenyl)-benzo[1,3]dioxol-5-yl]-(2-methyl-pyrrolidin-1-yl)-methanone,
2-(2,4-Dichloro-phenyl)-6-fluoro-2-(4-fluoro-phenyl)-benzo[1,3]dioxole-5-carboxylic acid azepan-1-ylamide,
Azetidin-1-yl-[2-(2,4-dichloro-phenyl)-6-fluoro-2-(4-fluoro-phenyl)-benzo[1,3]dioxol-5-yl]-methanone,
Azepan-1-yl-[2-(2,4-dichloro-phenyl)-6-fluoro-2-(4-fluoro-phenyl)-benzo[1,3]dioxol-5-dioxol-yl]-methanone,
2-(2,4-Dichloro-phenyl)-6-fluoro-2-(4-fluoro-phenyl)-benzo[1,3]dioxole-5-carboxylic acid (2,2-dimethyl-1-methylcarbamoyl-propyl)-amide,
[2-(2,4-Dichloro-phenyl)-6-fluoro-2-(4-fluoro-phenyl)-benzo[1,3]dioxol-5-yl]-(2S-methoxymethyl-pyrrolidin-1-yl)-methanone,
[2-(2,4-Dichloro-phenyl)-6-fluoro-2-(4-fluoro-phenyl)-benzo[1,3]dioxol-5-yl]-(2R-hydroxymethyl-pyrrolidin-1-yl)-methanone,
1-[2-(2,4-Dichloro-phenyl)-6-fluoro-2-(4-fluoro-phenyl)-benzo[1,3]dioxole-5-carbonyl]-pyrrolidine-2R-carboxylic acid dimethylamide,
2-(2,4-Dichloro-phenyl)-6-fluoro-2-(4-fluoro-phenyl)-benzo[1,3]dioxole-5-carboxylic acid cyclobutylamide,
2-(2,4-Dichloro-phenyl)-6-fluoro-2-(4-fluoro-phenyl)-benzo[1,3]dioxole-5-carboxylic acid morpholin-4-ylamide,
[2-(2,4-Dichloro-phenyl)-6-fluoro-2-(4-fluoro-phenyl)-benzo[1,3]dioxol-5-yl]-(2,3,5,6-tetrahydro-[1,2']bipyrazinyl-4-yl)-methanone,
1-[2-(2,4-Dichloro-phenyl)-6-fluoro-2-(4-fluoro-phenyl)-benzo[1,3]dioxole-5-carbonyl]-pyrrolidine-2S-carboxylic acid amide,
2-(2,4-Dichloro-phenyl)-6-fluoro-2-(4-fluoro-phenyl)-benzo[1,3]dioxole-5-carboxylic acid tert-butoxy-amide,
2-(2,4-Dichloro-phenyl)-6-fluoro-2-(4-fluoro-phenyl)-benzo[1,3]dioxole-5-carboxylic acid cyclopentylamide,
2-(2,4-Dichloro-phenyl)-6-fluoro-2-(4-fluoro-phenyl)-benzo[1,3]dioxole-5-carboxylic acid (tetrahydro-furan-2-ylmethyl)-amide,
[2-(2,4-Dichloro-phenyl)-6-fluoro-2-(4-fluoro-phenyl)-benzo[1,3]dioxol-5-yl]-thiomorpholin-4-yl-methanone,
2-(2,4-Dichloro-phenyl)-6-fluoro-2-(4-fluoro-phenyl)-benzo[1,3]dioxole-5-carboxylic acid isopropylamide,
2-(2,4-Dichloro-phenyl)-6-fluoro-2-(4-fluoro-phenyl)-benzo[1,3]dioxole-5-carboxylic acid pyrrolidin-1-ylamide,
2-(2,4-Dichloro-phenyl)-6-fluoro-2-(4-fluoro-phenyl)-benzo[1,3]dioxole-5-carboxylic acid methoxy-methyl-amide,
[2-(2,4-Dichloro-phenyl)-6-fluoro-2-(4-fluoro-phenyl)-benzo[1,3]dioxol-5-yl]-(3R-hydroxy-pyrrolidin-1-yl)-methanone,
2-(2,4-Dichloro-phenyl)-6-fluoro-2-(4-fluoro-phenyl)-benzo[1,3]dioxole-5-carboxylic acid bis-cyclopropylmethyl-amide,
[2-(2,4-Dichloro-phenyl)-6-fluoro-2-(4-fluoro-phenyl)-benzo[1,3]dioxol-5-yl]-(4-fluoro-piperidin-1-yl)-methanone,
[2-(2,4-Dichloro-phenyl)-6-fluoro-2-(4-fluoro-phenyl)-benzo[1,3]dioxol-5-yl]-(1,4-dioxa-8-aza-spiro[4.5]dec-8-yl)-methanone,
[2-(2,4-Dichloro-phenyl)-6-fluoro-2-(4-fluoro-phenyl)-benzo[1,3]dioxol-5-yl]-(4-hydroxymethyl-piperidin-1-yl)-methanone,
[2-(2,4-Dichloro-phenyl)-6-fluoro-2-(4-fluoro-phenyl)-benzo[1,3]dioxol-5-yl]-(4-hydroxy-4-methyl-piperidin-1-yl)-methanone,
[2-(2,4-Dichloro-phenyl)-6-fluoro-2-(4-fluoro-phenyl)-benzo[1,3]dioxol-5-yl]-pyrrolidin-1-yl-methanone,
N-{1-[2-(2,4-Dichloro-phenyl)-6-fluoro-2-(4-fluoro-phenyl)-benzo[1,3]dioxole-5-carbonyl]-pyrrolidin-3S-yl}-acetamide,
2-(2,4-Dichloro-phenyl)-6-fluoro-2-(4-fluoro-phenyl)-benzo[1,3]dioxole-5-carboxylic acid cycloheptylamide,
2-(2,4-Dichloro-phenyl)-6-fluoro-2-(4-fluoro-phenyl)-benzo[1,3]dioxole-5-carboxylic acid N'-pyridin-2-yl-hydrazide,
2-(2,4-Dichloro-phenyl)-6-fluoro-2-(4-fluoro-phenyl)-benzo[1,3]dioxole-5-carboxylic acid (2S-methoxymethyl-pyrrolidin-1-yl)-amide,
[2-(2,4-Dichloro-phenyl)-6-fluoro-2-(4-fluoro-phenyl)-benzo[1,3]dioxol-5-yl]-(1,1-dioxo-thiomorpholin-4-yl)-methanone,
[2-(2,4-Dichloro-phenyl)-6-fluoro-2-(4-fluoro-phenyl)-benzo[1,3]dioxol-5-yl]-(3-hydroxy-8-aza-bicyclo[3.2.1]oct-8-yl)-methanone,
[2-(2,4-Dichloro-phenyl)-6-fluoro-2-(4-fluoro-phenyl)-benzo[1,3]dioxol-5-yl]-(2R-methoxymethyl-pyrrolidin-1-yl)-methanone,

[2-(2,4-Dichloro-phenyl)-6-fluoro-2-(4-fluoro-phenyl)-benzo[1,3]dioxol-5-yl]-(3S-hydroxy-pyrrolidin-1-yl)-methanone,
N-{1-[2-(2,4-Dichloro-phenyl)-6-fluoro-2-(4-fluoro-phenyl)-benzo[1,3]dioxole-5-carbonyl]-pyrrolidin-3R-yl}-acetamide,
[2-(2,4-Dichloro-phenyl)-6-fluoro-2-(4-fluoro-phenyl)-benzo[1,3]dioxol-5-yl]-(2S-hydroxymethyl-pyrrolidin-1-yl)-methanone,
[2-(2,4-Dichloro-phenyl)-6-fluoro-2-(4-fluoro-phenyl)-benzo 1,3]dioxol-5-yl]-morpholin-4-yl-methanethione,
[2-(4-Chloro-phenyl)-2-(2,4-dichloro-phenyl)-6-fluoro-benzo[1,3]dioxol-5-yl]-morpholin-4-yl-methanone,
6-(Morpholine-4-carbonyl)-2,2-diphenyl-benzo[1,3]dioxole-5-carbonitrile,
[2-(4-Chloro-phenyl)-2-(2,4-dichloro-phenyl)-6-fluoro-benzo[1,3]dioxol-5-yl]-piperidin-1-yl-methanone,
[2-(4-Chloro-phenyl)-2-(2,4-dichloro-phenyl)-6-fluoro-benzo[1,3]dioxol-5-yl]-pyrrolidin-1-yl-methanone,
[2,2-Bis-(2,4-difluoro-phenyl)-benzo[1,3]dioxol-5-yl]-morpholin-4-yl-methanone,
[2,2-Bis-(2,4-difluoro-phenyl)-benzo[1,3]dioxol-5-yl]-piperidin-1-yl-methanone,
[6-Fluoro-2,2-bis-(4-fluoro-phenyl)-benzo[1,3]dioxol-5-yl]-pyrrolidin-1-yl-methanone,
[6-Fluoro-2,2-bis-(4-fluoro-phenyl)-benzo[1,3]dioxol-5-yl]-piperidin-1-yl-methanone,
[2,2-Bis-(4-bromo-phenyl)-6-fluoro-benzo[1,3 ]dioxol-5-yl]-morpholin-4-yl-methanone,
4-[2,2-Bis-(4-cyano-phenyl)-6-fluoro-benzo[1,3]dioxole-5-carbonyl]-morpholine,
4-[2-(4-Bromo-phenyl)-5-fluoro-6-(morpholine-4-carbonyl)-benzo[1,3]dioxol-2-yl]-benzonitrile,
[2,2-Bis-(2,4-difluoro-phenyl)-6-fluoro-benzo[1,3]dioxol-5-yl]-morpholin-4-yl-methanone,
[2,2-Bis-(4-chloro-phenyl)-6-fluoro-benzo[1,3]dioxol-5-yl]-morpholin-4-yl-methanone,
[6-Chloro-2,2-bis-(2,4-difluoro-phenyl)-benzo[1,3]dioxol-5-yl]-morpholin-4-yl-methanone,
[2-(2-Chloro-4-fluoro-phenyl)-2-(4-fluoro-phenyl)-benzo [1,3]dioxol-5-yl]-piperidin-1-yl-methanone,
[6-Fluoro-2,2-bis-(2-fluoro-phenyl)-benzo[1,3]dioxol-5-yl]-morpholin-4-yl-methanone,
[2,2-Bis-(2,4-dichloro-phenyl)-6-fluoro-benzo[1,3]dioxol-5-yl]-morpholin-4-yl-methanone,
4-[2,2-Bis-(2,4-difluoro-phenyl)-6-fluoro-benzo[1,3]dioxole-5-sulfonyl]-morpholine,
4-[2-(2,4-Dichloro-phenyl)-6-fluoro-2-(4-fluoro-phenyl)-benzo[1,3]dioxole-5-sulfonyl]-morpholine,
[2-(2,4-Dichloro-phenyl)-6-fluoro-2-(4-fluoro-phenyl)-benzo[1,3]dioxol-5-yl]-(4,4-difluoro-piperidin-1-yl)-methanone,
[2-(2,4-Dichloro-phenyl)-6-fluoro-2-(4-fluoro-phenyl)-benzo[1,3]dioxol-5-yl]-(4-trifluoromethyl-piperidin-1-yl)-methanone,
[2-(2,4-Dichloro-phenyl)-6-fluoro-2-(4-fluoro-phenyl)-benzo[1,3]dioxol-5-yl]-(3S-ethoxy-pyrrolidin-1-yl)-methanone,
2-(2,4-Dichloro-phenyl)-6-fluoro-2-(4-fluoro-phenyl)-benzo[1,3]dioxole-5-carboxylic acid (1R-phenyl-ethyl)-amide,
[2-(2,4-Dichloro-phenyl)-6-fluoro-2-(4-fluoro-phenyl)-benzo[1,3]dioxol-5-yl]-(1-oxo-thiomorpholin-4-yl)-methanone,
[2,2-Bis-(2-chloro-phenyl)-6-fluoro-benzo[1,3]dioxol-5-yl]-morpholin-4-yl-methanone,
[6-Fluoro-2,2-bis-(4-trifluoromethyl-phenyl)-benzo[1,3]dioxol-5-yl]-morpholin-4-yl-methanone,
[6-Fluoro-2,2-bis-(3-fluoro-phenyl)-benzo[1,3]dioxol-5-yl]-morpholin-4-yl-methanone,
[2-(2-Chloro-4-fluoro-phenyl)-2-(4-fluoro-phenyl)-benzo[1,3]dioxol-5-yl]-morpholin-yl-methanone,
[2,2-Bis-(3,4-difluoro-phenyl)-benzo[1,3]dioxol-5-yl]-piperidin-1-yl-methanone,
[2,2-Bis-(3,4-difluoro-phenyl)-benzo[1,3]dioxol-5-yl]-morpholin-4-yl-methanone,
[2,2-Bis-(2,4-dichloro-phenyl)-6-fluoro-benzo[1,3]dioxol-5-yl]-(3-hydroxy-pyrrolidin-yl)-methanone,
[2,2-Bis-(2,4-dichloro-phenyl)-6-fluoro-benzo[1,3]dioxol-5-yl]-(4-hydroxy-piperidin-1-yl)-methanone,
2,2-Bis-(2,4-dichloro-phenyl)-6-fluoro-benzo[1,3]dioxole-5-carboxylic acid ethyl-methyl-amide,
2,2-Bis-(2,4-dichloro-phenyl)-6-fluoro-benzo[1,3]dioxole-5-carboxylic acid bis-(2-hydroxy-ethyl)-amide,
[2,2-Bis-(4-chloro-phenyl)-6-fluoro-benzo[1,3]dioxol-5-yl]-piperidin-1-yl-methanone,
[2,2-Bis-(4-chloro-phenyl)-6-fluoro-benzo[1,3]dioxol-5-yl]-pyrrolidin-1-yl-methanone,
[2,2-Bis-(2-chloro-4-fluoro-phenyl)-benzo[1,3]dioxol-5-yl]-piperidin-1-yl-methanone,
[2,2-Bis-(3,4-difluoro-phenyl)-6-fluoro-benzo[1,3]dioxol-5-yl]-morpholin-4-yl-methanone,
[2,2-Bis-(2,5-difluoro-phenyl)-6-fluoro-benzo[1,3]dioxol-5-yl]-morpholin-4-yl-methanone,
[2,2-Bis-(2-chloro-4-fluoro-phenyl)-benzo[1,3]dioxol-5-yl]-morpholin-4-yl-methanone,
[2,2-Bis-(2-chloro-4-fluoro-phenyl)-6-fluoro-benzo[1,3]dioxol-5-yl]-morpholin-4-yl-methanone,
[6-Chloro-2,2-bis-(2-chloro-4-fluoro-phenyl)-benzo[1,3]dioxol-5-yl]-morpholin-4-yl-methanone,
2-(2,4-Dichloro-phenyl)-6-fluoro-2-(4-fluoro-phenyl)-benzo[1,3]dioxole-5-carboxylic acid amide,
[2,2-Bis-(4-bromo-2-fluoro-phenyl)-6-fluoro-benzo[1,3]dioxol-5-yl]-morpholin-4-yl-methanone,
[2-(2,4-Dichloro-phenyl)-6-fluoro-2-(4-fluoro-phenyl)-benzo[1,3]dioxol-5-yl]-(3,4-cis-dihydroxy-pyrrolidin-1-yl)-methanone,
[2,2-Bis-(2,3-difluoro-phenyl)-6-fluoro-benzo[1,3]dioxol-5-yl]-morpholin-4-yl-methanone,
[6-Fluoro-2,2-bis-(4-trifluoromethoxy-phenyl)-benzo[1,3]dioxol-5-yl]-morpholin-4-yl-methanone,
[2,2-Bis-(2-chloro-4,5-difluoro-phenyl)-benzo[1,3]dioxol-5-yl]-piperidin-1-yl-methanone,
4-[2,2-Bis-(2-chloro-4-fluoro-phenyl)-6-fluoro-benzo[1,3]dioxole-5-sulfonyl]-morpholine,
[2,2-Bis-(2,4-difluoro-phenyl)-6-fluoro-benzo[1,3]dioxol-5-yl]-piperidin-1-yl-methanone,
[2,2-Bis-(2,4-difluoro-phenyl)-6-fluoro-benzo[1,3]dioxol-5-yl]-(4-fluoro-piperidin-1-yl)-methanone,
[2,2-Bis-(2,4-difluoro-phenyl)-6-fluoro-benzo[1,3]dioxol-5-yl]-(4,4-difluoro-piperidin-1-yl)-methanone,
[2,2-Bis-(2,4-difluoro-phenyl)-6-fluoro-benzo[1,3]dioxol-5-yl]-(4-trifluoromethyl-piperidin-1-yl)-methanone,
[2,2-Bis-(2,4-difluoro-phenyl)-6-fluoro-benzo[1,3]dioxol-5-yl]-(4-hydroxy-piperidin-1-yl)-methanone,
[2,2-Bis-(2,4-difluoro-phenyl)-6-fluoro-benzo[1,3]dioxol-5-yl]-thiomorpholin-4-yl-methanone,
[2,2-Bis-(2,4-difluoro-phenyl)-6-fluoro-benzo[1,3]dioxol-5-yl]-pyrrolidin-1-yl-methanone,
[2,2-Bis-(2,4-difluoro-phenyl)-6-fluoro-benzo[1,3]dioxol-5-yl]-(3S-hydroxy-pyrrolidin-1-yl)-methanone,
[2,2-Bis-(2,4-difluoro-phenyl)-6-fluoro-benzo[1,3]dioxol-5-yl]-(2S-hydroxymethyl-pyrrolidin-1-yl)-methanone,

[2,2-Bis-(2,4-difluoro-phenyl)-6-fluoro-benzo[1,3]dioxol-5-yl]-(2S-methoxymethyl-pyrrolidin-1-yl)-methanone,
(6-Chloro-2,2-di-p-tolyl-benzo[1,3]dioxol-5-yl)-morpholin-4-yl-methanone,
4-[{6-Chloro-10',11'-dihydro-spiro[1,3-benzodioxole-2,5'-[5H]dibenzo[a,d]cyclohepten]-5-yl}carbonyl]-morpholine,
[6-Fluoro-2,2-bis-(4-fluoro-phenyl)-benzo[1,3]dioxol-5-yl]-(4-fluoro-piperidin-1-yl)-methanone,
(4,4-Difluoro-piperidin-1-yl)-[6-fluoro-2,2-bis-(4-fluoro-phenyl)-benzo[1,3]dioxol-5-yl]-methanone,
[6-Fluoro-2,2-bis-(4-fluoro-phenyl)-benzo[1,3]dioxol-5-yl]-(4-trifluoromethyl-piperidin-1-yl)-methanone,
[6-Fluoro-2,2-bis-(4-fluoro-phenyl)-benzo[1,3]dioxol-5-yl]-thiomorpholin-4-yl-methanone,
(3S-Ethoxy-pyrrolidin-1-yl)-[6-fluoro-2,2-bis-(4-fluoro-phenyl)-benzo[1,3]dioxol-5-yl]-methanone,
[6-Fluoro-2,2-bis-(4-fluoro-phenyl)-benzo[1,3]dioxol-5-yl]-[(S)-(2-methoxymethyl-pyrrolidin-1-yl)]-methanone,
[6-Fluoro-2,2-bis-(4-fluoro-phenyl)-benzo[1,3]dioxol-5-yl]-[(S)-2-hydroxymethyl-pyrrolidin-1-yl]-methanone,
[6-Fluoro-2,2-bis-(4-fluoro-phenyl)-benzo[1,3]dioxol-5-yl]-[(S)-3-hydroxy-pyrrolidin-1-yl]-methanone,
[6-Fluoro-2,2-bis-(4-fluoro-phenyl)-benzo[1,3]dioxol-5-yl]-(4-hydroxy-piperidin-1-yl)-methanone,
4-[2,2-Bis-(2-chloro-4,5-difluoro-phenyl)-6-fluoro-benzo[1,3]dioxole-5-sulfonyl]-morpholine,
(2,2-Di-p-tolyl-benzo[1,3]dioxol-5-yl)-piperidin-1-yl-methanone,
(2,2-Di-p-tolyl-benzo[1,3]dioxol-5-yl)-morpholin-4-yl-methanone,
4-[6-Fluoro-2,2-bis-(4-fluoro-phenyl)-benzo[1,3]dioxole-5-sulfonyl]-morpholine,
4-(6-Fluoro-2,2-di-p-tolyl-benzo[1,3]dioxole-5-sulfonyl)-morpholine,
1-{6-Fluoro-10',11'-dihydrospiro[1,3-benzodioxole-2,5'-[5H]dibenzo[a,d]cycloheptene]-5-yl}sulfonyl]-piperidine,
4-{6'-Fluoro-10',11'-dihydrospiro[1,3-benzodioxole-2,5'-[5H]dibenzo[a,d]cycloheptene]-5-yl}sulfonyl]-morpholine,
4-[{10',11'-Dihydro-spiro[1,3-benzodioxole-2,5'-[5H]dibenzo[a,d]cycloheptene]-5-yl}carbonyl]-morpholine,
1-[{10',11'-dihydro-spiro[1,3-benzodioxole-2,5'-[5H]dibenzo[a,d]cycloheptene]-5-yl}carbonyl]-piperidine,
[6-Fluoro-2,2-bis-(4-fluoro-phenyl)-benzo[1,3]dioxol-5-yl]-(3-methoxy-piperidin-1-yl)-methanone,
1-[6-Fluoro-2,2-bis-(4-fluoro-phenyl)-benzo[1,3]dioxole-5-sulfonyl]-pyrrolidine,
1-[6-Fluoro-2,2-bis-(4-fluoro-phenyl)-benzo[1,3]dioxole-5-sulfonyl]-piperidine,
4-[6-Fluoro-2,2-bis-(4-fluoro-phenyl)-benzo[1,3]dioxole-5-sulfonyl]-thiomorpholine,
1-[2,2-Bis-(2,4-difluoro-phenyl)-6-fluoro-benzo[1,3]dioxole-5-sulfonyl]-piperidine,
1-[2,2-Bis-(2-chloro-4-fluoro-phenyl)-6-fluoro-benzo[1,3]dioxole-5-sulfonyl]-piperidine,
1-[2,2-Bis-(2,4-difluoro-phenyl)-6-fluoro-benzo[1,3]dioxole-5-sulfonyl]-pyrrolidine,
1-[2,2-Bis-(2,4-difluoro-phenyl)-6-fluoro-benzo[1,3]dioxole-5-sulfonyl]-4-fluoro-piperidine,
1-[2,2-Bis-(2,4-difluoro-phenyl)-6-fluoro-benzo[1,3]dioxole-5-sulfonyl]-4,4-difluoro-piperidine,
1-[2,2-Bis-(2,4-difluoro-phenyl)-6-fluoro-benzo[1,3]dioxole-5-sulfonyl]-4-trifluoromethyl-piperidine,
4-[2,2-Bis-(2,4-difluoro-phenyl)-6-fluoro-benzo[1,3]dioxole-5-sulfonyl]-thiomorpholine,
1-[2,2-Bis-(2,4-difluoro-phenyl)-6-fluoro-benzo[1,3]dioxole-5-sulfonyl]-2S-methoxymethyl-pyrrolidine,
2,2-Bis-(2,4-difluoro-phenyl)-6-fluoro-benzo[1,3]dioxole-5-sulfonic acid (2S-methoxymethyl-pyrrolidin-1-yl)-amide,
{1-[2,2-Bis-(2,4-difluoro-phenyl)-6-fluoro-benzo[1,3]dioxole-5-sulfonyl]-pyrrolidin-2S-yl}-methanol,
1-[2,2-Bis-(2,4-difluoro-phenyl)-6-fluoro-benzo[1,3]dioxole-5-sulfonyl]-pyrrolidin-3S-ol,
1-[2,2-Bis-(2,4-difluoro-phenyl)-6-fluoro-benzo[1,3]dioxole-5-sulfonyl]-piperidin-4-ol,
1-[2,2-Bis-(2-chloro-4,5-difluoro-phenyl)-6-fluoro-benzo[1,3]dioxole-5-sulfonyl]-piperidine,
4-[{6-Fluoro-10',11'-dihydro-spiro[1,3-benzodioxole-2,5'-[5H]dibenzo[a,d]cyclohepten]-5-yl}-carbonyl]-morpholine,
(6-Fluoro-2,2-di-p-tolyl-benzo[1,3]dioxol-5-yl)-morpholin-4-yl-methanone,
1-(6-Fluoro-2,2-di-p-tolyl-benzo[1,3]dioxole-5-sulfonyl)-piperidine,
[6-Fluoro-2,2-bis-(2-fluoro-phenyl)-benzo[1,3]dioxol-5-yl]-piperidin-1-yl-methanone,
[6-Fluoro-2,2-bis-(2-fluoro-phenyl)-benzo[1,3]dioxol-5-yl]-(4-hydroxy-piperidin-1-yl)-methanone,
4-Fluoro-1-[6-fluoro-2,2-bis-(4-fluoro-phenyl)-benzo[1,3]dioxole-5-sulfonyl]-piperidine,
4,4-Difluoro-1-[6-fluoro-2,2-bis-(4-fluoro-phenyl)-benzo[1,3]dioxole-5-sulfonyl]-piperidine,
1-[6-Fluoro-2,2-bis-(4-fluoro-phenyl)-benzo[1,3]dioxole-5-sulfonyl]-4-trifluoromethyl-piperidine,
1-[6-Fluoro-2,2-bis-(4-fluoro-phenyl)-benzo[1,3]dioxole-5-sulfonyl]-2-methoxymethyl-pyrrolidine,
1-[6-Fluoro-2,2-bis-(4-fluoro-phenyl)-benzo[1,3]dioxole-5-sulfonyl]-pyrrolidin-3S-ol,
1-[6-Fluoro-2,2-bis-(4-fluoro-phenyl)-benzo[1,3]dioxole-5-sulfonyl]-piperidin-4-ol,
[2,2-Bis-(3-chloro-phenyl)-benzo[1,3]dioxol-5-yl]-piperidin-1-yl-methanone,
[2,2-bis-(4-cyano-2-fluoro-phenyl)-6-fluoro-benzo[1,3]dioxol-5-yl]-morpholin-4-yl-methanone,
[2,2-Bis-(3,5-difluoro-phenyl)-benzo[1,3]dioxol-5-yl]-piperidin-1-yl-methanone,
[2,2-Bis-(3,5-difluoro-phenyl)-benzo[1,3]dioxol-5-yl]-morpholin-4-yl-methanone,
6-Fluoro-[2,2-bis-(2-fluoro-phenyl)-benzo[1,3]dioxol-5-yl]-[(S)-3-hydroxy-pyrrolidin-1-yl)]-methanone,
6-Fluoro-2,2-bis-(2-fluoro-phenyl)-benzo[1,3]dioxole-5-carboxylic acid ethyl-methyl-amide,
6-Fluoro-2,2-bis-(2-fluoro-phenyl)-benzo[1,3]dioxole-5-carboxylic acid (2-methoxy-ethyl)-methyl-amide,
[2,2-Bis-(3,5-dichloro-phenyl)-benzo[1,3]dioxol-5-yl]-piperidin-1-yl-methanone,
[2,2-Bis-(3,5-dichloro-phenyl)-benzo[1,3]dioxol-5-yl]-morpholin-4-yl-methanone,
[2,2-Bis-(3-bromo-phenyl)-6-fluoro-benzo[1,3]dioxol-5-yl]-morpholin-4-yl-methanone,
[6-Fluoro-2,2-bis-(3-methoxy-phenyl)-benzo[1,3]dioxol-5-yl]-morpholin-4-yl-methanone,
[2,2-Bis-(3-methoxy-phenyl)-benzo[1,3]dioxol-5-yl]-piperidin-1-yl-methanone,
[2,2-Bis-(3-chloro-phenyl)-6-fluoro-benzo[1,3]dioxol-5-yl]-morpholin-4-yl-methanone, and pharmaceutically acceptable salts thereof.

Especially preferred compounds of general formula (I) are those selected from the group consisting of:

[2-(2,4-Dichloro-phenyl)-6-fluoro-2-(4-fluoro-phenyl)-benzo[1,3]dioxol-5-yl]-piperidin-1-yl-methanone,

[2-(2,4-Dichloro-phenyl)-6-fluoro-2-(4-methoxy-phenyl)-benzo[1,3]dioxol-5-yl]-piperidin-1-yl-methanone,

[2-(2,4-Dichloro-phenyl)-6-fluoro-2-(4-methoxy-phenyl)-benzo[1,3]dioxol-5-yl]-morpholin-4-yl-methanone,

[2-(2,4-Dichloro-phenyl)-6-fluoro-2-(4-fluoro-phenyl)-benzo[1,3]dioxol-5-yl]-morpholin-4-yl-methanone, (+)-[2-(2,4-Dichloro-phenyl)-6-fluoro-2-(4-fluoro-phenyl)-benzo[1,3]dioxol-5-yl]-morpholin-4-yl-methanone, (−)-[2-(2,4-Dichloro-phenyl)-6-fluoro-2-(4-fluoro-phenyl)-benzo[1,3]dioxol-5-yl]-morpholin-4-yl-methanone,

[2-(2,4-Dichloro-phenyl)-6-fluoro-2-(4-fluoro-phenyl)-benzo[1,3]dioxol-5-yl]-thiomorpholin-4-yl-methanone,

[2-(2,4-Dichloro-phenyl)-6-fluoro-2-(4-fluoro-phenyl)-benzo[1,3]dioxol-5-yl]-(4-fluoro-piperidin-1-yl)-methanone,

[2-(4-Chloro-phenyl)-2-(2,4-dichloro-phenyl)-6-fluoro-benzo[1,3]dioxol-5-yl]-morpholin-4-yl-methanone,

[2-(4-Chloro-phenyl)-2-(2,4-dichloro-phenyl)-6-fluoro-benzo[1,3]dioxol-5-yl]-piperidin-1-yl-methanone,

[2-(4-Chloro-phenyl)-2-(2,4-dichloro-phenyl)-6-fluoro-benzo[1,3]dioxol-5-yl]-pyrrolidin-1-yl-methanone,

[2,2-Bis-(2,4-difluoro-phenyl)-6-fluoro-benzo[1,3]dioxol-5-yl]-morpholin-4-yl-methanone,

[2-(2,4-Dichloro-phenyl)-6-fluoro-2-(4-fluoro-phenyl)-benzo[1,3]dioxol-5-yl]-(4,4-difluoro-piperidin-1-yl)-methanone,

[2,2-Bis-(4-chloro-phenyl)-6-fluoro-benzo[1,3]dioxol-5-yl]-piperidin-1-yl-methanone,

[2,2-Bis-(4-chloro-phenyl)-6-fluoro-benzo[1,3]dioxol-5-yl]-pyrrolidin-1-yl-methanone,

[2,2-Bis-(4-bromo-2-fluoro-phenyl)-6-fluoro-benzo[1,3]dioxol-5-yl]-morpholin-4-yl-methanone,

[2,2-Bis-(2,4-difluoro-phenyl)-6-fluoro-benzo[1,3]dioxol-5-yl]-(4,4-difluoro-piperidin-1-yl)-methanone,

[2,2-Bis-(2,4-difluoro-phenyl)-6-fluoro-benzo[1,3]dioxol-5-yl]-(4-hydroxy-piperidin-1-yl)-methanone,

[2,2-Bis-(2,4-difluoro-phenyl)-6-fluoro-benzo[1,3]dioxol-5-yl]-(3S-hydroxy-pyrrolidin-1-yl)-methanone, and pharmaceutically acceptable salts thereof The present invention also relates to a process for the manufacture of compounds of formula (I) as defined above. The compounds of formula (I) can be manufactured by the methods given below, by the methods given in the Examples or by analogous methods. Appropriate reaction conditions for the individual reaction steps are known to the person skilled in the art. Starting materials are either commercially available or can be prepared by methods analogous to the methods given below or in the Examples or by methods known in the art.

The compound of formula (I) wherein $R^1$ to $R^7$ and X are as previously defined may be prepared using the general methods depicted in Scheme 1 as further described below.

Scheme 1:

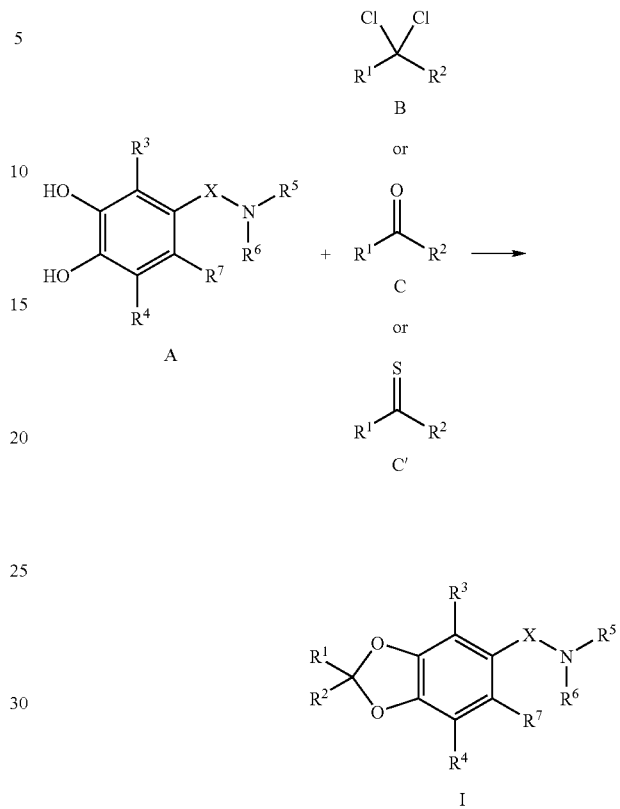

According to Scheme 1, a catechol intermediate of formula A can be ketalized with a bis-substituted dichloromethane derivative of formula B in an inert solvent (e.g. toluene or pyridine) or neat, with or without the presence of a base (e.g. pyridine) at elevated temperature (e.g. >100° C.) to yield product I. Alternatively, a compound of formula (I) may be prepared by reacting the catechol intermediate of formula A with a ketone of formula C at elevated temperature (e.g. >150° C.) neat or in an inert solvent (e.g. toluene) with or without the removal of water by distillation, azeotropic distillation or addition of drying agents (e.g. molecular sieves or 2,2-dimethoxypropane) by methods known in the art (see e.g. T. R. Kelly, A. Szabados, Y.-J. Lee, J. Org. Chem. 62 (2) (1997) 428).

Alternatively, a compound of formula (I) may be prepared by reacting the catechol intermediate of formula A with a thioketone of formula (C') neat or in an inert solvent (e.g. acetonitrile) with or without the presence of a base (e.g. triethylamine) with a metal salt (e.g. $Cu^1$) by methods known in the art (see e.g. I. Shibuya, E. Katoh, Y. Gama, A. Oishi, Y. Taguchi and T. Tsuchiya, Heterocycles, 43 (1996) 851). Compounds of formula (I) wherein X is —$CH_2$— can also be obtained by reduction of a corresponding compound of formula (I) wherein X is —CO— by means known in the art.

Scheme 2:

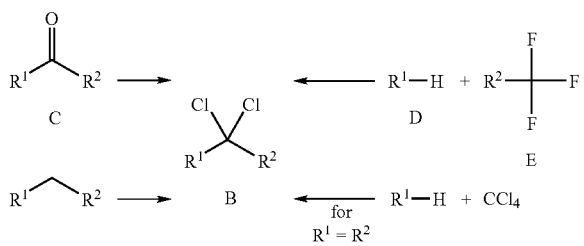

The bis-substituted dichloromethane derivatives of formula B can be easily prepared by methods known in the art from the corresponding ketone by reaction with thionyl chloride in the presence of DMF or another N-formylated agent, by reaction with phosphorus pentachloride at elevated temperature (e.g. >100° C.) with or without the presence of a suitable solvent (e.g. phosphorus oxide chloride), by electrophilic aromatic substitution of the trifluoromethyl derivative E with a benzene derivative of formula D in the presence of a Lewis acid (e.g. aluminium trichloride) in an inert solvent (e.g. 1,2-dichloroethane) (e.g. R. K. Ramchandani, R. D. Wakharkar, A. Sudalai, Tetrahedron Lett. 37 (23) (1996) 4063), by chlorination of a bisarylmethane derivative (e.g. U.S. Pat. No. 5,578,737 or W. Deuschel, Helv. Chim. Acta 34 (1951) 2403) or in case of symmetrically bis-substituted dichloromethane derivatives of formula B by electrophilic aromatic substitution of a benzene derivative with tetrachloromethane in the presence of a Lewis acid (e.g. $AlCl_3$) in an inert solvent (e.g. 1,2-dichloroethane) (see e.g. J. P. Picard, C. Kearns, Can. J. Res. 28 (1950) 56).

Catechols of formula A can be easily prepared from the corresponding diphenylmethylene protected ketals of formula (Ia) by treatment with an acid (e.g. trifluoroacetic acid) in a suitable inert solvent (e.g. methylene chloride) or by treatment with an acid (e.g. trifluoroacetic acid) in the presence of a suitable reducing agent (e.g. triethylsilane), neat or with a suitable inert solvent (e.g. methylene chloride). Alternatively, a catechol of formula A can be easily prepared from a corresponding bis-benzyl protected catechol of formula (A') by reduction (e.g hydrogenation in the presence of a suitable catalyst (e.g. palladium on carbon)) by means known in the art). Alternatively a catechol derivative of formula F can be coupled with an appropriate amine in a suitable inert solvent (e.g. DMF, methylene chloride, pyridine or THF) in the presence of a base (e.g. triethyl amine). Either the corresponding acid chlorides (X=CO, Z=Cl) respectively the corresponding sulfonyl chlorides (X=$SO_2$, Z=Cl) or the corresponding carboxylic acids (X=CO, Z=OH) after activation with an appropriate coupling agent (e.g. carbonyldiimidazole) are used for the preparation of catechols of formula A by methods known in the art. Compounds of formula (A) wherein X is —$CH_2$— can be obtained by reduction of a corresponding compound of formula (A) wherein X is —CO— by means known in the art.

Scheme 3:

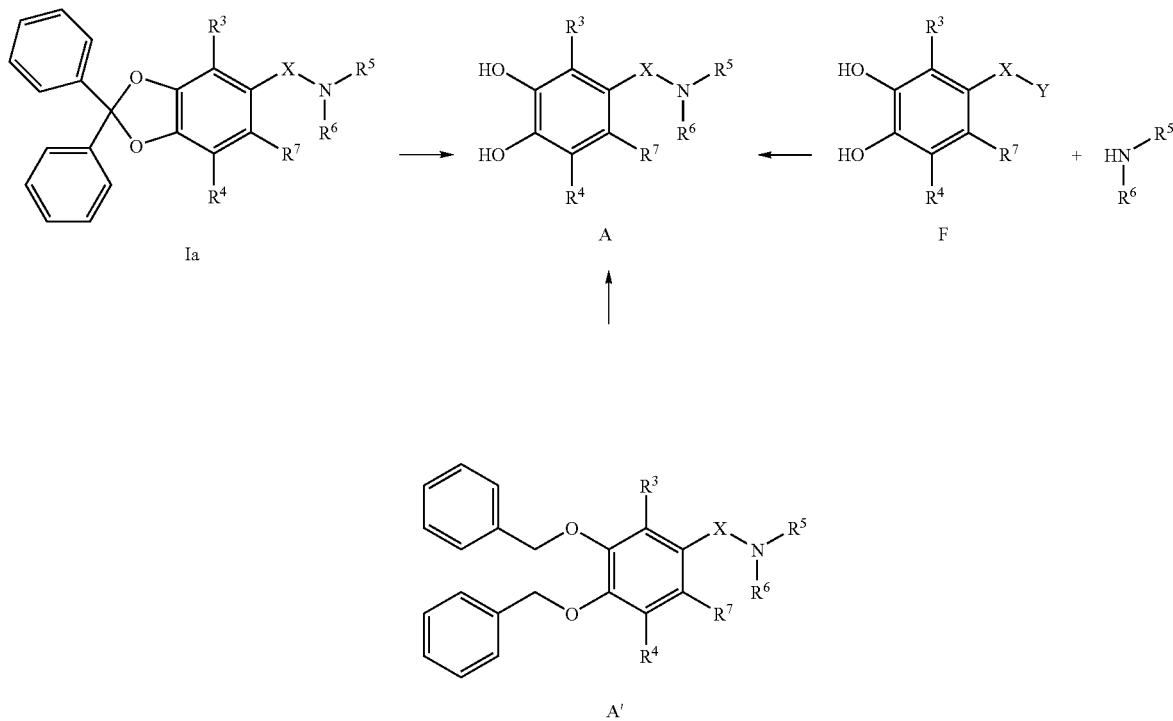

Scheme 4:

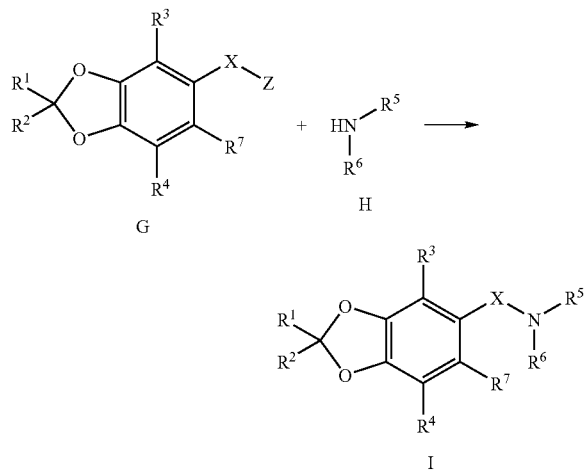

Compounds of formula G can be coupled with an appropriate amine in a suitable inert solvent (e.g. DMF, methylene chloride, pyridine or THF) in the presence of a base (e.g. triethyl amine) to yield benzodioxoles of formula (I). Either the corresponding acid chlorides (X=CO, Z=Cl) respectively the corresponding sulfonyl chlorides (X=SO$_2$, Z=Cl) or the corresponding carboxylic acids (X=CO, Z=OH) after activation with an appropriate coupling agent (e.g. carbonyldiimidazole) are used for the preparation of benzodioxoles of formula (I) by methods known in the art.

Scheme 5:

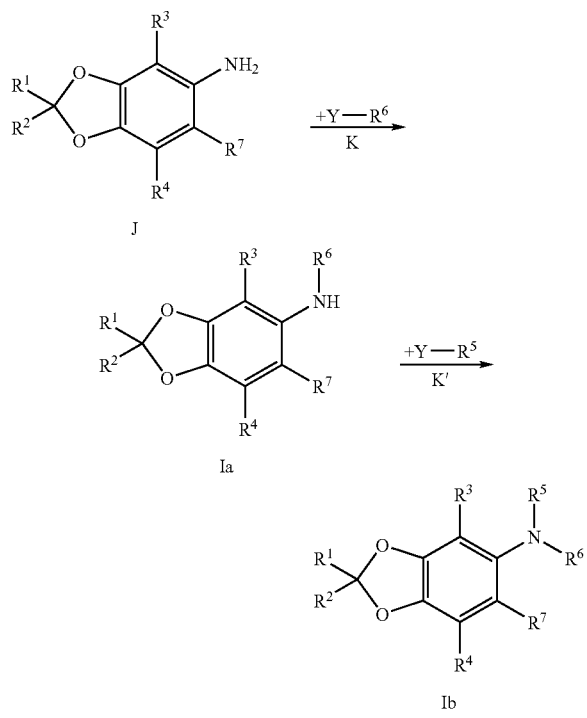

Benzodioxoles of formula (I) in which X is a single bond may also be prepared according to Scheme 5 above by coupling an aniline of formula J with a compound of formula K in a suitable inert solvent (e.g. DMF, methylene chloride, pyridine or THF) in the presence of a base (e.g. triethyl amine) to yield benzodioxoles of formula (Ia). Benzodioxoles of formula (Ia) may then be further coupled with a compound of formula K' in a suitable inert solvent (e.g. DMF, methylene chloride, pyridine or THF) in the presence of a base (e.g. triethyl amine) to yield benzodioxoles of formula (Ib). Compounds of formulae K and K' may be either the corresponding acid chlorides, respectively the corresponding sulfonyl chlorides, respectively the corresponding carbamoyl chlorides, respectively the corresponding sulfamoyl chlorides or the corresponding carboxylic acids of $R^5$ and $R^6$, respectively, after activation with an appropriate coupling agent (e.g. carbonyldiimidazole).

The invention further relates to compounds of formula (I) as defined above, when manufactured according to a process as defined above.

Some compounds of formula (I) may possess asymmetric centres and are therefore capable of existing in more than one stereoisomeric form. The invention thus also relates to compounds in substantially pure isomeric form at one or more asymmetric centres as well as mixtures, including racemic mixtures, thereof. Such isomers may be prepared by asymmetric synthesis, for example using chiral intermediate, or mixtures may be resolved by conventional methods, eg., chromatography (chromatography with a chiral adsorbent or eluant), or use of a resolving agent.

It will be appreciated, that the compounds of general formula (I) in this invention may be derivatised at functional groups to provide derivatives which are capable of conversion back to the parent compound in vivo.

As described above, the compounds of formula (I) or pharmaceutically acceptable salts thereof can be used as medicaments for the treatment and/or prophylaxis of diseases which are associated with the modulation of the CB1 receptors.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with the modulation of CB1 receptors.

In another embodiment, the invention relates to a method for the treatment and/or prophylaxis of diseases which are associated with the modulation of CB1 receptors, which method comprises administering a compound as defined above to a human being or animal.

The invention further relates to the use of compounds as defined above for the treatment and/or prophylaxis of diseases which are associated with the modulation of CB1 receptors.

In addition, the invention relates to the use of compounds as defined above for the preparation of medicaments for the treatment and/or prophylaxis of diseases which are associated with the modulation of CB1 receptors. Such medicaments comprise a compound as defined above.

In this context, the expression 'diseases associated with modulation of CB1 receptors' means diseases which can be treated and/or prevented by modulation of CB1 receptors. Such diseases encompass, but are not limited to, psychic disorders, especially anxiety and anxiety disorders, psychosis, schizophrenia, depression, substance abuse disorders including abuse of psychotropes, for example for the abuse and/or dependence of substances, including alcohol dependency and nicotine dependency, neuropathies, migraine, stress, epilepsy, dyskinesias, Parkinson's disease, amnesia, memory and cognitive disorders, senile dementia, Alzheimer's disease, eating disorders, obesity, diabetes type II or non insulin dependent diabetes (NIDD), gastrointestinal diseases, vomiting, diarrhea, urinary disorders, cardiovascular disorders, infertility disorders, inflammations, infections, cancer, demyelinisation related disorders, neuroinflammation, in particular in atherosclerosis, or the Guillain-Barré syndrome, viral encephalitis, cerebral vascular incidents and cranial trauma.

In a preferable aspect, the expression 'diseases associated with modulation of CB1 receptors' relates to eating disorders, obesity, diabetes type II or non insulin dependent diabetes (NIDD), neuroinflammation, diarrhea, abuse and/or dependence of a substances, including alcohol dependency and nicotine dependency. In a more preferable aspect, the said term related to eating disorders, obesity, diabetes type II or non insulin dependent diabetes (NIDD), abuse and/or dependence of a substances, including alcohol dependency and nicotine dependency, with obesity being especially preferred.

It is a further preferred object to provide a method of treatment or prevention of Type II diabetes (non-insulin dependent diabetes mellitus (NIDDM) in a human which comprises administration of a therapeutically effective amount of a compound according to formula (I) in combination or association with a therapeutically effective amount of a lipase inhibitor, particularly, wherein the lipase inhibitor is orlistat. Also an object of the invention is the method as described above for the simultaneous, separate or sequential administration of a compound according to formula (I) and a lipase inhibitor, particularly tetrahydrolipstatin.

It is a further preferred object to provide a method for the treatment or prevention of obesity and obesity related disorders which comprises administration of a therapeutically effective amount of a compound according to formula (I) in combination or association with a therapeutically effective amount of other drugs for the treatment of obesity or eating disorders so that together they give effective relief. Suitable other drugs include but are not limited to anorectic agents, lipase inhibitors and selective serotonin reuptake inhibitors (SSRI). Combinations or associations of the above agents may be encompassing separate, sequential or simultaneous administration.

Preferable lipase inhibitor is tetrahydrolipstatin.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine, and pharmaceutically acceptable salts thereof.

Most preferable anorectic agents are sibutramine and phentermine.

Suitable selective serotonin reuptake inhibitors of use in combination with a compound of the present invention include: fluoxetine, fluvoxamine, paroxetine and sertraline, and pharmaceutically acceptable salts thereof.

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

In addition, to demonstrate CNS activities of the compounds of the present invention, the following in vivo assays may be used.

Method for Testing Task Learning and Spatial Memory

The Morris Water Maze is routinely used to assess task learning and spatial memory (Jaspers et al., Neurosci. Lett. 117:149-153, 1990; Morris, J. Neurosci. Methods 11:47-60, 1984). In this assay, animals are placed in a water pool which is divided into quadrants. One platform is hidden in one of the quadrants. The animal is placed in the water pool and is expected to locate the hidden platform within a predetermined time. During a number of training trials, the animal learns the location of the platform and escape from the pool. The animal receives multiple trials in this task. Total distance traveled, number of trials to locate platform, latency to find platform, and the swimming path is recorded for each animal. The animal's learning ability is measured by the length of time or number of trials required to find the hidden platform. Memory deficit or improvement is determined by the number of trials or the latency to find the platform at predetermined delay time after acquisition. Leaning and memory may be measured by the number of times that the animal crosses the quadrant where the platform was located during the acquisition phase.

Method for Testing Drug Dependence

Self-administration in animals is a predictor of a compound's abuse potential in humans. Modifications to this procedure may also be used to identify compounds that prevent or block the reinforcing properties of drugs that have abuse potential. A compound that extinguishes the self-administration of a drug may prevent that drug's abuse or its dependence. (Ranaldi et al., Psychopharmacol. 161:442-448, 2002; Campbell et al., Exp. Clin. Psychopharmacol. 8:312-25, 2000). In a self-administration test, animals are placed in the operant chambers containing both an active and inactive lever. Each response on the active lever produces an infusion of either the test compound or a drug known to be selfadministered. Presses on the inactive lever have no effect, but are also recorded. Animals are then trained to self-administer compound/drug over a set period of time by having drug access during each daily session. Illumination of the chamber house light signals the beginning of the session and the availability of the compound/drug. When the session ends, the house light is turned off Initially, a drug infusion occurs with every press of the active lever. Once lever-pressing behavior has been established, the number of presses to produce a drug infusion is increased. After stable compound/drug self-administration is obtained, the effect of a second compound on the drug-reinforced behavior may be evaluated. Administration of this second compound prior to the session can either potentiate, extinguish, or produce no change to the self-administrating behavior.

The following tests were carried out in order to determine the activity of the compounds of formula (I).

The affinity of the compounds of the invention for cannabinoid CB1 receptors was determined using membrane preparations of human embryonic kidney (HEK) cells in which the human cannabis CB1 receptor is transiently transfected using the Semliki Forest Virus system in conjunction with [3H]-CP-55,940 as radioligand. After incubation of a freshly prepared cell membrane preparation with the [3H]-ligand, with or without addition of compounds of the invention, separation of bound and free ligand was performed by filtration over glass-fiber filters. Radioactivity on the filter was measured by liquid scintillation counting.

The affinity of the compounds of the invention for cannabinoid CB2 receptors was determined using membrane preparations of human embryonic kidney (HEK) cells in which the human cannabis CB2 receptor is transiently transfected using the Semliki Forest virus system in conjunction with [3H]-CP-55,940 as radioligand. After incubation of a freshly prepared cell membrane preparation with the [3H]-ligand, with or without addition of compounds of the invention, separation of bound of bound and free ligand was performed by filtration over glassfiber filters. Radioactivity on the filter was measured by liquid scintillation counting.

The cannabinoid CB1 antagonistic activity of compounds of the invention was determined by functional studies using CHO cells in which human cannabinoid CB1 receptors are stably expressed (see M. Rinaldi-Carmona et. al., J. Pharmacol. Exp. Ther. 278 (1996) 871). The stable expression of the human cannabinoid receptor in cell systems was first described in Nature 1990, 346, 561-564 (CB1) and Nature 1993, 365, 61-65 (CB2) respectively. Adenylyl cyclase was stimulated using forskolin and measured by quantifying the amount of accumulated cyclic AMP. Concomitant activation of CB1 receptors by CB1 receptor agonists (e.g. CP-55,940 or (R)-WIN-55212-2) can attenuate the forskolin-induced accumulation of cAMP in a concentration dependent manner. This CB1 receptor mediated response can be antagonised by CB1 receptor antagonists such as the compounds of the invention.

The compounds of formula (I) show an excellent affinity for the CB1 receptor, determined with the experimental conditions described in Devane et.al. Mol. Pharmacol. 34 (1988) 605-613. The compounds of the present invention or their pharmaceutically acceptable salts are antagonists and selective for the CB1 receptor with affinites below $IC_{50}$ =2 µM, preferably 1 nM to 100 nM. They exhibit at least a 10 fold selectivity against the CB2 receptor.

| Compound of Example | $IC_{50}$ [µM] |
| --- | --- |
| 39 | <2 µM |
| 46 | <2 µM |
| 18 | <2 µM |
| 65 | <2 µM |
| 4 | <2 µM |
| 20 | <2 µM |
| 22 | <2 µM |
| 75 | <2 µM |
| 108 | <2 µM |
| 164 | <2 µM |
| 234 | <2 µM |
| 271 | <2 µM |

Effect of CB1 Receptor Antagonist/Inverse Agonist on CP 55,940-Induced Hypothermia in NMRI Mice Animals Male NMRI mice were used in this study and were obtained from Research Consulting Company Ltd (RCC) of Füllinsdorf (Switzerland). Mice, weighing 30-31 g were used in this study. Ambient temperature is approximately 20-21° C. and relative humidity 55-65%. A 12 hour light-dark cycle is maintained in the rooms with all tests being performed during the light phase. Access to tap water and food are ad libitum.

Method

All measurements were made between 12:00 am and 5:00 pm. Mice were brought in this environment and habituated for at least two hours before the start of the experiment. They had always free access to food and water. For each dose, 8 mice were used. Rectal body temperature measurements were recorded by mean of a rectal probe (RET2 of Physitemp) and digital thermometer (Digi-sense n°8528-20 of Cole Parmer, Chicago USA). The probe was inserted about 3.5 cm in each mouse.

The body temperature was taken 15 min before administration of either Vehicle or CB1 receptor antagonist/inverse agonist. 30 or 90 min after i.p. or p.o. administration of this compound, respectively, rectal body temperature was recorded in order to evaluate any influence of the compound itself. The CB receptor agonist CP 55,940 (0.3 mg/kg) was immediately administered intravenously, then 20 min after i.v. administration of CP 55940, body temperature was again measured.

The in vivo activity of compounds of formula (1) was assessed for their ability to regulate feeding behaviour by recording food consumption in food deprived animals.

Rats were trained to have access to food for 2 h per day and were food deprived for 22 h. When they were trained under this schedule, the amount of food taken every day during these 2h food intake session was consistent day after day.

To test the ability of compounds of formula (1) to decrease food intake, 8 animals were used in a cross-over study. Rats were individually housed in Plexiglas boxes with a grid on the floor and a paper was placed below the cage floor to collect any spillage. A food dispenser (becher) filled with a pre-weighed amount of food was presented to them for 2 h. At the end of the food intake session, rats returned to their home cage. Each rat was weighed before the start of the experiment and the amount of food consumed during this 2 h food intake session was recorded. Either various doses of test compound or vehicle was administered orally 60 min before the 2 h food intake session. A positive control Rimonabant (SR141716) was included in the experiment. An Anova analysis with repeated measures was used followed by a posthoc test Student Neumann-Keuls. * P <0.05 compared to Saline-treated rats.

Furthermore the utility of compounds of formula (1) in diseases or disorders may be demonstrated in animal disease models that have been reported in the literature. The following are examples of such animal disease models: a) reduction of sweet food intake in marmosets (Behavioural Pharm, 1998, 9,179-181); b) reduction of sucrose and ethanol intake in mice (Psychopharm. 1997, 132, 104-106); c) increased motor activity and place conditioning in rats (Psychopharm. 1998, 135, 324-332; Psychopharmacol 2000, 151: 25-30); d) spontaneous locomotor activity in mice (J. Pharm. Exp. Ther. 1996, 277, 586-594); e) reduction in opiate self-administration in mice (Sci. 1999, 283, 401-404);

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterary, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

MS=mass spectrometry, ISP=ion spray (positive ion), m.p.=melting point, aq.=aqueous, DMSO=dimethylsulfoxide, NMR=nuclear magnetic resonance spectroscopy, EDCI=N-(3-dimethylaminopropyl)-N'-ethylcarbodiimide hydrochloride, HPLC=high performance liquid chromatography.

Example 1

Preparation of 1-(2,2-diphenyl-benzo[1,3]dioxole-5-sulfonyl)-piperidine

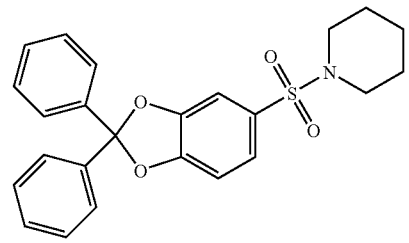

2,2-diphenyl-benzo[1,3]dioxole-5-sulfonyl chloride (3.36 g, 9 mmol) was dissolved in methylene chloride (135 ml). Piperidine (1.33 ml, 13.5 mmol) and ethyldiisopropyl amine (2.3 ml, 13.5 mmol) were added at room temperature. The reaction was stirred at room temperature overnight and washed twice with 1N aqueous HCl solution, twice with 1N aqueous NaOH solution and once with brine. The organic layer was dried over sodium sulfate and filtered. The solvent was evaporated and the residue was purified by column chromatography (4/1 hexane/ethyl acetate eluant). The product was suspended in diethyl ether and filtered to yield a white crystalline solid (1.98 g, 52 %). m.p.: 163-164° C.

Preparation of 2,2-diphenyl-benzo[1,3]dioxole-5-sulfonyl chloride

The sulfonyl chloride derivative was prepared according to literature procedures (WO9218490, EP544166).

Method A

Method A is a general method for the preparation of 2,2-diphenyl-benzo[1,3]dioxole-5-sulfonamides starting from commercially available amines:

2,2-Diphenyl-benzo[1,3]dioxole-5-sulfonyl chloride (93 mg, 0.25 mmol) was dissolved in pyridine (1 ml). The appropriate amine (0.25 mmol) was added and the reaction was heated to 60° C. overnight. Water was added and solids respectively oils separated. The aqueous phase was decanted and the residue was stirred with acetonitrile. A solid precipitated, which was filtered off and washed with a little acetonitrile to yield after drying at high vacuum the product.

The following examples were prepared using the general method A:

Example 2

Preparation of 1-(4-chloro-phenyl)-4-(2,2-diphenyl-benzo[1,3]dioxole-5-sulfonyl)-piperazine

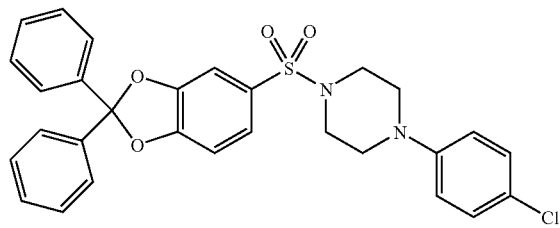

Using 4-(4-chlorophenyl)piperazine (49.2 mg, 0.25 mmol) as an amine, the title compound was obtained as a white solid (27 mg, 20%).

MS (ISP): 533.2 (M+H$^+$, 100). NMR (300 MHz, DMSO-d$_6$) ppm: 7.44-7.56 (m, 10H), 7.41 (s, 1H), 7.37 (d, 1H), 7.32 (d, 1H), 7.26 (d, 2H), 6.90 (d, 2 H), 3.16-3.19 (m, 4H), 2.98-3.02 (m, 4H).

Example 3

Preparation of 1-(2,3-dimethyl-phenyl)-4-(2,2-diphenyl-benzo[1,3]dioxole-5-sulfonyl)-piperazine

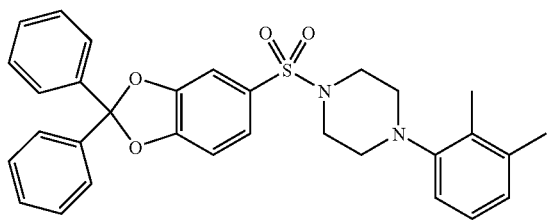

Using 4-(2,3-dimethylphenyl)piperazine hydrochloride (56.7 mg, 0.25 mmol) as an amine, the title compound was obtained as a white solid (8 mg, 6%).

MS (ISP): 527.2 (M+H$^+$, 100). NMR (300 MHz, DMSO-d$_6$) ppm: 7.45-7.60 (m, 5H), 7.47-7.55 (m, 5H), 7.46 (s, 1H), 7.38 (d, 1H), 7.31 (d, 1H), 7.01 (t, 1H), 6.89 (m, 2 H), 3.00-3.12 (m, 4H), 2.82-2.88 (m, 4H), 2.17 (s, 3H), 2.02 (s, 3H).

Example 4

Preparation of 1-(2,4-dichloro-phenyl)-4-(2,2-diphenyl-benzo[1,3]dioxole-5-sulfonyl)-piperazine

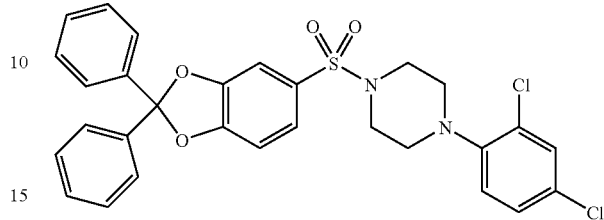

Using 4-(2,4-dichlorophenyl)piperazine hydrochloride (66.9 mg, 0.25 mmol) as an amine, the title compound was obtained as a yellow solid (32 mg, 23%).

MS (ISP): 567.1 (M+H$^+$, 100). NMR (300 MHz, DMSO-d$_6$) ppm: 7.45-7.60 (m, 10H), 7.42 (s, 1H), 7.34-7.39 (m, 4H), 7.31 (d, 1H), 7.16 (d, 1H), 3.00-3.08 (m, 8H).

Example 5

Preparation of 1-(2,2-diphenyl-benzo[1,3]dioxole-5-sulfonyl)-4-(4-fluoro-phenyl)-piperazine

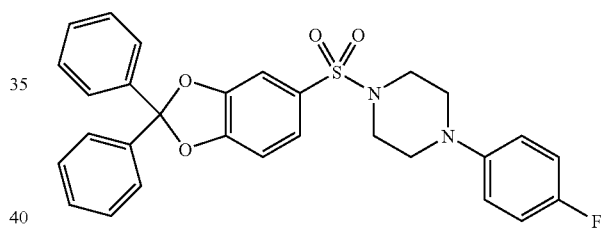

Using 4-(4-fluorophenyl)piperazine (45.1 mg, 0.25 mmol) as an amine, the title compound was obtained as a light yellow solid (66.4 mg 51%).

MS (ISP): 517.2 (M+H$^+$, 100). NMR (300 MHz, DMSO-d$_6$) ppm: 7.51-7.56 (m, 4H), 7.45-7.49 (m, 6H), 7.41 (s, 1H), 7.37 (d, 1H), 7.29 (d, 1H), 7.02 (t, 1H), 6.90-6.94 (m, 1H), 3.11 (m, 4H), 3.01 (m, 4H).

Example 6

Preparation of 1-(2,2-diphenyl-benzo[1,3]dioxole-5-sulfonyl)-4-(3-chloro-phenyl)-piperazine

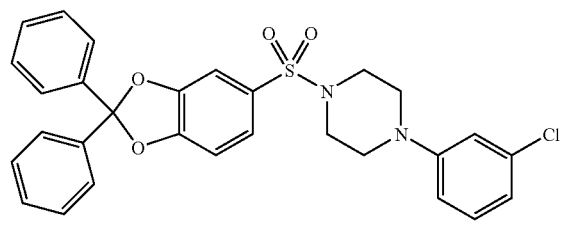

Using 4-(3-chlorophenyl)piperazine (49.2 mg, 0.25 mmol) as an amine, the title compound was obtained as a light yellow solid (91.4 mg, 68%).

MS (ISP): 533.2 (M+H$^+$, 100). NMR (300 MHz, DMSO-d$_6$) ppm: 7.48-7.56 (m, 4H), 7.44-7.48 (m, 6H), 7.41 (s, 1H), 7.36 (d, 1H), 7.29 (d, 1H), 7.19 (t, 1H), 6.82 (d, 1H), 6.79 (d, 1H), 3.23 (m, 4H), 3.00 (m, 4H).

Example 7

Preparation of 4-(2,2-diphenyl-benzo[1,3]dioxole-5-sulfonyl)-morpholine

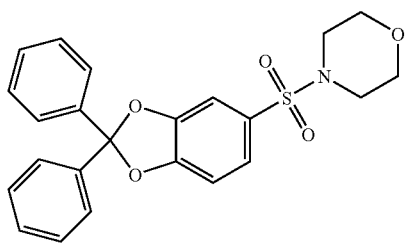

Using morpholine (21.8 mg, 0.25 mmol) as an amine, the title compound was obtained as a white solid (51.1 mg 48%).

MS (ISP): 424.4 (M+H$^+$, 100). NMR (300 MHz, DMSO-d$_6$) ppm: 7.52-7.57 (m, 4H), 7.46-7.49 (m, 6H), 7.37 (s, 1H), 7.33 (d, 1H), 7.29 (d, 1H), 3.61 (m, 4H), 2.86 (m, 4H).

Example 8

Preparation of 1-(2,2-diphenyl-benzo[1,3]dioxole-5-sulfonyl)-4-phenyl-piperazine

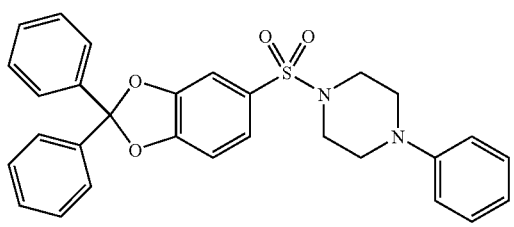

Using 4-phenylpiperazine (40.6 mg, 0.25 mmol) as an amine, the title compound was obtained as a light yellow solid (78.7 mg, 63%).

MS (ISP): 499.3 (M+H$^+$, 100). NMR (300 MHz, DMSO-d$_6$) ppm: 7.52-7.56 (m, 4H), 7.44-7.48 (m, 6H), 7.41 (s, 1H), 7.35 (d, 1H), 7.30 (d, 1H), 7.19 (t, 2H), 6.89 (d, 2H), 6.77 (t, 1H), 3.17 (m, 4H), 3.02 (m, 4H).

Example 9

Preparation of 1-(2,2-diphenyl-benzo[1,3]dioxole-5-sulfonyl)-pyrrolidine

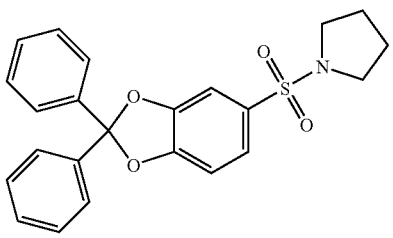

Using pyrrolidine (17.8 mg, 0.25 mmol) as an amine, the title compound was obtained as a white solid (67.8 mg, 67%).

MS (ISP): 408.3 (M+H$^+$, 100). NMR (300 MHz, DMSO-d$_6$) ppm: 7.53-7.57 (m, 4H), 7.43-7.49 (m, 7H), 7.39 (d, 1H), 7.25 (d, 1H), 3.12 (m, 4H), 1.64 (m, 4H).

Example 10

Preparation of 1-(2,2-diphenyl-benzo[1,3]dioxole-5-sulfonyl)-4-(3-methoxy-phenyl)-piperazine

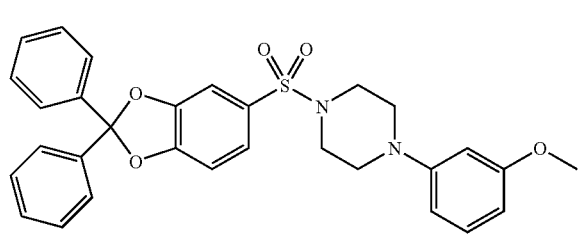

Using 4-(3-methoxyphenyl)piperazine dihydrochloride (66.3 mg, 0.25 mmol) as an amine, the title compound was obtained as a white solid (75.9 mg, 58%).

MS (ISP): 529.3 (M+H$^+$, 100). NMR (300 MHz, DMSO-d$_6$) ppm: 7.52-7.56 (m, 4H), 7.44-7.48 (m, 6H), 7.41 (s, 1H), 7.37 (d, 1H), 7.29 (d, 1H), 7.08 (t, 1H), 6.48 (d, 1H), 6.42 (s, 1H), 6.38 (d, 1H), 3.68 (s, 3H), 3.17 (m, 4H), 3.01 (m, 4H).

Example 11

Preparation of 1-(2,2-diphenyl-benzo[1,3]dioxole-5-sulfonyl)-4-(4-methoxy-phenyl)-piperazine

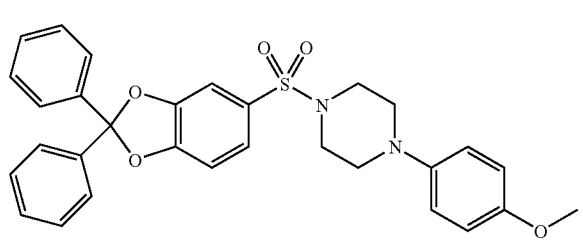

Using 4-(4-methoxyphenyl)piperazine dihydrochloride (66.3 mg, 0.25 mmol) as an amine, the tide compound was obtained as a light brown solid (78.9 mg, 60%).

MS (ISP): 529.2 (M+H+, 100). NMR (300 MHz, DMSO-$d_6$) ppm: 7.52-7.57 (m, 4H), 7.45-7.48 (m, 6H), 7.38 (s, 1H), 7.36 (d, 1H), 7.31 (d, 1H), 6.85 (d, 2H), 6.78 (d, 2H), 3.66 (s, 3H), 3.03 (m, 8H).

Example 12

Preparation of 1-(2,2-diphenyl-benzo[1,3]dioxole-5-sulfonyl)-4-(2-methoxy-phenyl)-piperazine

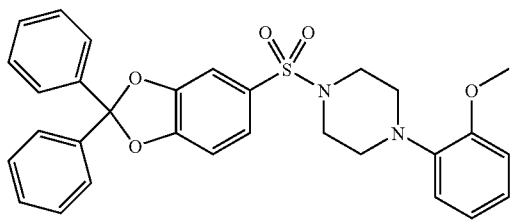

Using 4-(2-methoxyphenyl)piperazine (48.1 mg, 0.25 mmol) as an amine, the title compound was obtained as a light yellow solid (66.3 mg, 50%).

MS (ISP): 529.2 (M+H+, 100). NMR (300 MHz, DMSO-$d_6$) ppm: 7.54-7.58 (m, 4H), 7.45-7.49 (m, 6H), 7.41 (s, 1H), 7.38 (d, 1H), 7.31 (d, 1H), 6.85-6.94 (m, 4H), 3.70 (s, 3H), 3.01 (m, 8H).

Example 13

Preparation of 1-(2,2-diphenyl-benzo[1,3]dioxole-5-sulfonyl)-4-(2-chloro-phenyl)-piperazine

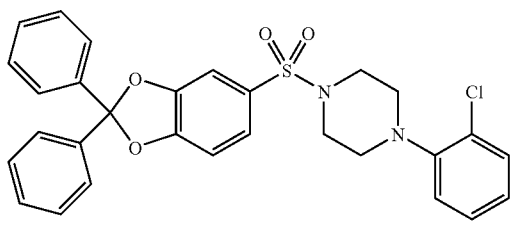

Using 4-(2-chlorophenyl)piperazine hydrochloride (58.3 mg, 0.25 mmol) as an amine, the title compound was obtained as a light yellow solid (80.4 mg, 60%).

MS (ISP): 533.2 (M+H+, 100). NMR (300 MHz, DMSO-$d_6$) ppm: 7.54-7.58 (m, 4H), 7.45-7.49 (m, 7H), 7.43 (s, 1H), 7.38 (d, 1H), 7.32 (d, 1H), 7.30 (t, 1H), 7.15 (d, 1H), 7.06 (t, 1H), 3.04 (m, 8H).

Example 14

Preparation of 1-(2,2-diphenyl-benzo[1,3]dioxole-5-sulfonyl)-4-(2-fluoro-phenyl)-piperazine

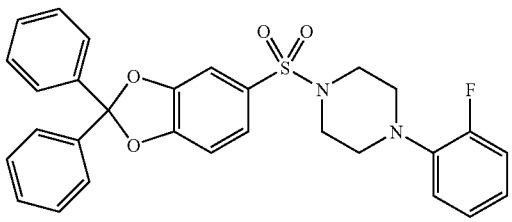

Using 4-(2-fluoroophenyl)piperazine (45.1 mg, 0.25 mmol) as an amine, the title compound was obtained as a light yellow solid (92.8 mg 72%).

MS (ISP): 517.2 (M+H+, 100). NMR (300 MHz, DMSO-$d_6$) ppm: 7.54-7.57 (m, 4H), 7.45-7.49 (m, 6H), 7.42 (s, 1H), 7.37 (d, 1H), 7.31 (d, 1H), 6.96-7.17 (m, 4H), 3.05 (m, 8H).

Example 15

Preparation of 2,2-diphenyl-benzo[1,3]dioxole-5-sulfonic acid phenethyl-amide

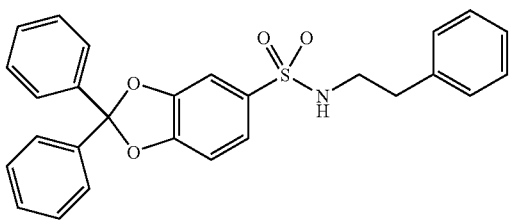

Using phenylethylamine (30.3 mg, 0.25 mmol) as an amine, the title compound was obtained as a white solid (46.0 mg, 40%).

MS (ISP): 458.4 (M+H+, 100), 475.3 (M+NH4+, 45). NMR (300 MHz, DMSO-$d_6$) ppm: 7.44-7.56 (m, 11H), 7.33-7.21 (m, 2H), 7.10-7.21 (m, 6H), 2.95 (q, 2H), 2.64 (t, 2H).

Example 16

Preparation of 1-benzo[1,3]dioxol-5-yl-4-(2,2-diphenyl-benzo[1,3]dioxole-5-sulfonyl)-piperazine

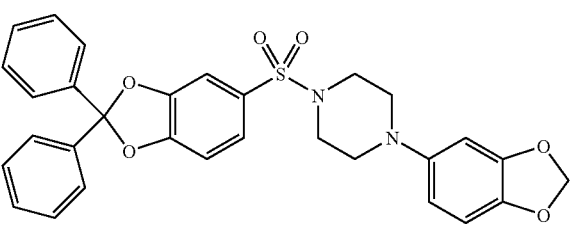

Using 4-(3,4-dioxymethylenephenyl)piperazine hydrochloride (64.7 mg, 0.25 mmol) as an amine, the title compound was obtained as a brown solid (46.6 mg, 42%).

MS (ISP): 543.2 (M+H⁺, 100). NMR (300 MHz, DMSO-d$_6$) ppm: 7.42-7.56 (m, 10H), 7.41 (s, 1H), 7.36 (d, 1H), 7.29 (d, 1H), 6.74 (d, 1H), 6.63 (s, 1H), 6.30 (d, 1H), 5.90 (s, 2H), 3.02 (m, 8H).

Example 17

Preparation of 4-benzyl-1-(2,2-diphenyl-benzo[1,3]dioxole-5-sulfonyl)-piperidine

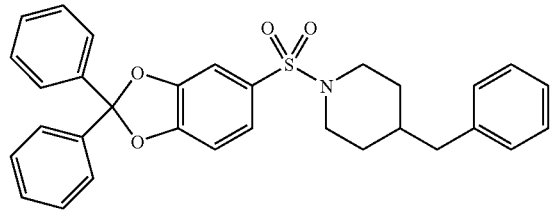

Using 4-benzylpiperidine (43.8 mg, 0.25 mmol) as an amine, the title compound was obtained as a white solid (37.6 mg, 29%).

MS (ISP): 512.3 (M+H⁺, 100). NMR (300 MHz, DMSO-d$_6$) ppm: 7.52-7.56 (m, 4H), 7.45-7.48 (m, 6H), 7.08-7.32 (m, 8H), 3.58 (m, 2H), 2.45 (m, 2H), 2.19 (m, 2H), 1.58 (m, 3H), 1.15 (m, 1H).

Method B

Method B is a general method for the preparation of 2,2-diphenyl-benzo[1,3]dioxole-5-sulfonamides starting from commercially available amines:

2,2-Diphenyl-benzo[1,3]dioxole-5-sulfonyl chloride (93 mg, 0.25 mmol) was dissolved in pyridine (1 ml). The appropriate amine (0.25 mmol) was added and the reaction was heated to 60° C. overnight. Water was added and solids respectively oils separated. The aqueous phase was decanted and the residue was stirred with acetonitrile. A solution was obtained, which was subjected to preparative reversed phase chromatography (gradient of acetonitrile/water containing 0.1% formic acid as the eluant) to yield the product after evaporation of the eluant and drying.

The following examples were prepared using the general method B:

Example 18

Preparation of 2-(2,2-diphenyl-benzo[1,3]dioxole-5-sulfonyl)-1,2,3,4-tetrahydro-isoquinoline

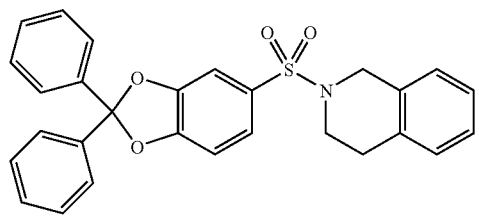

Using 1,2,3,4-tetrahydro-isoquinoline (33.3 mg, 0.25 mmol) as an amine, the title compound was obtained as a yellow solid (35 mg, 30%).

MS (ISP): 470.3 (M+H⁺, 100). NMR (300 MHz, DMSO-d$_6$) ppm: 7.40-7.54 (m, 12H), 7.24 (d, 1H), 7.05-7.13 (m, 4H), 4.19 (s, 2H), 3.30 (t, 2H), 2.82 (m, 2H).

Example 19

Preparation of 2,2-diphenyl-benzo[1,3]dioxole-5-sulfonic acid benzyl-methyl-amide

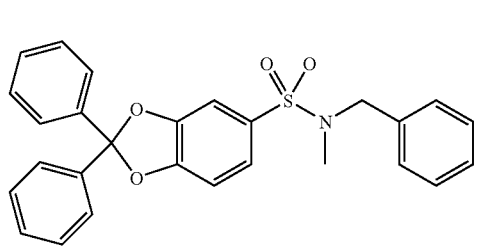

Using N-methylbenzylamine (30.3 mg, 0.25 mmol) as an amine, the title compound was obtained as a yellow solid (48.3 mg, 42%).

MS (ISP): 458.4 (M+H⁺, 100). NMR (300 MHz, DMSO-d$_6$) ppm: 7.43-7.58 (m, 12H), 7.27-7.33 (m, 6H), 4.13 (s, 2H), 2.53 (s, 3H).

Example 20

Preparation of 2,2-diphenyl-benzo[1,3]dioxole-5-sulfonic acid benzylamide

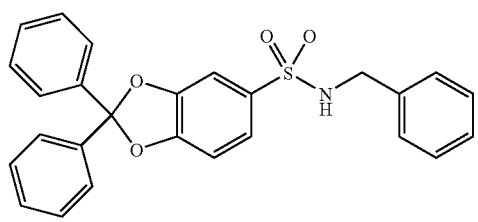

Using benzylamine (26.8 mg, 0.25 mmol) as an amine, the title compound was obtained as a light yellow solid (25.1 mg, 22%).

MS (ISN): 442.2 (M−H⁺, 100), 502.1 (M+OAc⁻, 20). NMR (300 MHz, DMSO-d$_6$) ppm: 8.06 (t, 1H, NH), 7.46-7.56 (m, 11H), 7.36 (d, 1H), 7.32 (s, 1H), 7.14-7.18 (m, 5H), 3.97 (d, 2H).

Example 21

Preparation of 1-(2,2-diphenyl-benzo[1,3]dioxole-5-sulfonyl)-4-methyl-[1,4]diazepane

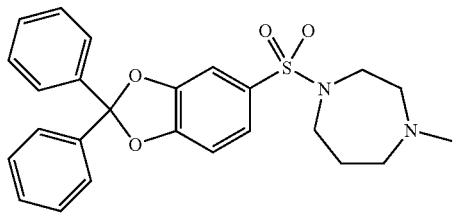

Using N-methylhomopiperazine (28.5 mg, 0.25 mmol) as an amine, the title compound was obtained as a light brown solid (23.6 mg, 21%).

MS (ISP): 451.4 (M+H+, 100). NMR (300 MHz, DMSO-d$_6$) ppm: 7.45-7.56 (m, 10H), 7.41 (s, 1H), 7.36 (d, 1H), 7.23 (s, 1H), 3.22-3.39 (m, 4H), 2.50 (m, 4H, under the DMSO peak), 2.20 (s, 3H), 1.68-1.74 (m, 2H).

Example 22

Preparation of 1-(3-chloro-5-trifluoromethyl-pyridin-2-yl)-4-(2,2-diphenyl-benzo[1,3]dioxole-5-sulfonyl)-[1,4]diazepane

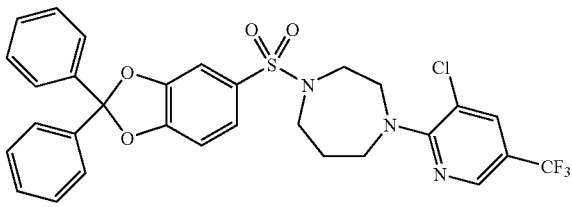

Using 1-(3-chloro-5-trifluoromethyl-pyridin-2-yl)-homopiperazine (69.8 mg, 0.25 mmol) as an amine, the title compound was obtained as a yellow solid (76.9 mg, 52%).

MS (ISP): 616.1 (M+H+, 100). NMR (300 MHz, DMSO-d$_6$) ppm: 8.38 (s, 1H), 7.95 (s, 1H), 7.44-7.55 (m, 10H), 7.41 (s, 1H), 7.33 (d, 1H), 7.15 (s, 1H), 3.84 (t, 2H), 3.76 (t, 2H), 3.44 (t, 2H), 3.28 (t, 2H), 1.89 (m, 2H).

Example 23

Preparation of 2,2-diphenyl-benzo[1,3]dioxole-5-sulfonic acid phenylamide

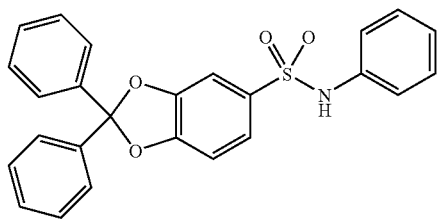

Using aniline (23.3 mg, 0.25 mmol) as an amine, the title compound was obtained as a light yellow solid (18.2 mg, 17%).

MS (ISN): 428.3 (M−H+, 100). NMR (300 MHz, DMSO-d$_6$) ppm: 10.19 (s, 1H, NH), 7.43-7.52 (m, 10H), 7.32-7.35 (m, 2H), 7.14-7.21 (m, 3H), 6.98-7.09 (m, 3H).

Example 24

Preparation of 2,2-diphenyl-benzo[1,3]dioxole-5-sulfonic acid[2-(4-methoxy-phenyl)-ethyl]-amide

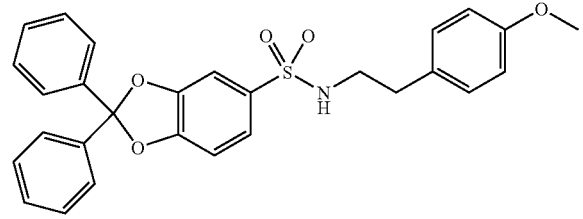

Using 2-(4-methoxyphenyl)ethylamine (37.8 mg, 0.25 mmol) as an amine, the title compound was obtained as a light yellow solid (67.1 mg, 55%).

MS (ISN): 486.2 (M−H+, 100), 546.1 (M+OAc−, 35). NMR (300 MHz, DMSO-d$_6$) ppm: 7.44-7.58 (m, 11H), 7.34-7.37 (m, 2H), 7.19 (d, 1H), 7.03 (d, 2H), 6.79 (d, 2H), 3.69 (s, 3H), 2.89 (q, 2H), 2.58 (t, 2H).

Example 25

Preparation of 1-(2,2-diphenyl-benzo[1,3]dioxole-5-sulfonyl)-4-methyl-piperazine

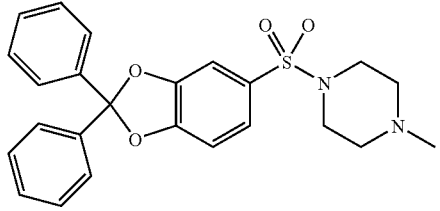

Using N-methylpiperazine (25.0 mg, 0.25 mmol) as an amine, the title compound was obtained as a white solid (11 mg, 10%).

MS (ISP): 437.4 (M+H$^+$, 100). NMR (300 MHz, DMSO-d$_6$) ppm: 7.53-7.57 (m, 4H), 7.45-7.49 (m, 6H), 7.36 (s, 1H), 7.32 (d, 1H), 7.29 (d, 1H), 2.87 (m, 4H), 2.33 (m, 4H), 2.11 (s, 3H).

Example 26

Preparation of 1-(2,2-diphenyl-benzo[1,3]dioxole-5-sulfonyl)-4-(4-fluoro-phenyl)-1,2,3,6-tetrahydropyridine

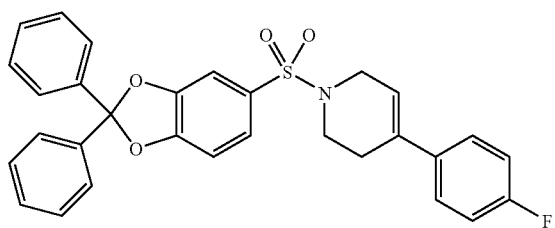

4-(4-Fluorophenyl)-1,2,3,4-tetrahydropyridine hydrochloride (2.56 g, 12 mmol) was suspended in methylene chloride (150 ml). Ethyldiisopropylamine (4.2 ml, 25 mmol) was added and the solution was stirred for 10 minutes at room temperature. 2,2-Diphenyl-benzo[1,3]dioxole-5-sulfonyl chloride (3.72 g, 10 mmol) was added and the reaction was stirred at room temperature for 2 hours. The solvent was evaporated and the residue was purified by column chromatography on silical gel (100 g, dichloromethane eluant). The product was stirred with n-hexane, filtered and dried to yield the sulfonamide as white crystals (3.86 g, 75%).

MS (ISP): 514.3 (M+H$^+$, 100). NMR (300 MHz, DMSO-d$_6$) ppm: 7.50-7.54 (m, 4H), 7.44-7.48 (m, 7H), 7.36-7.40 (m, 3H), 7.26 (d, 1H), 7.09 (t, 2H), 6.03 (m, 1H), 3.68 (m, 2H), 3.23 (t, 2H), 2.50 (s, 2H, under DMSO peak).

Example 27

Preparation of 4-(4-chloro-phenyl)-1-(2,2-diphenyl-benzo[1,3]dioxole-5-sulfonyl)-1,2,3,6-tetrahydropyridine

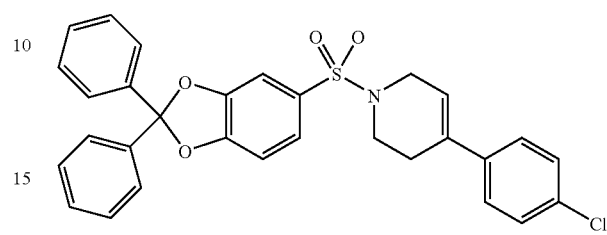

4-(4-Chlorophenyl)-1,2,3,4-tetrahydropyridine hydrochloride (19.37 mg, 0.10 mmol) was suspended in methylene chloride (2 ml). Ethyldiisopropylamine (0.035 ml, 0.20 mmol) was added and the solution was shaken for 10 minutes at room temperature. 2,2-Diphenyl-benzo[1,3]dioxole-5-sulfonyl chloride (37.28 mg, 0.10 mmol) was added and the reaction was shaken at room temperature for 12 hours. Aqueous HCl (0.1 N, 1.0 ml) was added and the mixture shaken for 30 minutes, the aqueous layer removed and the organic phase concentrated and purified by preparative reverse phase HPLC (YMC, ODS-AQ packing; 20%→95% CH$_3$CN/H$_2$O) to yield the sulfonamide (2.6 mg, 5%).

MS (ISP): 530.2 (M+H$^+$, 100). NMR (500 MHz, DMSO-d$_6$) ppm: 7.31-7.56 (m, 16H), 7.26 (d, 1H), 6.10 (m, 1H), 3.70 (m, 2H), 3.24 (m, 2H), 2.50 (m, 2H, under DMSO peak).

Example 28

Preparation of 1-(2,2-diphenyl-benzo[1,3]dioxole-5-sulfonyl)-4-phenyl-1,2,3,6-tetrahydro-pyridine

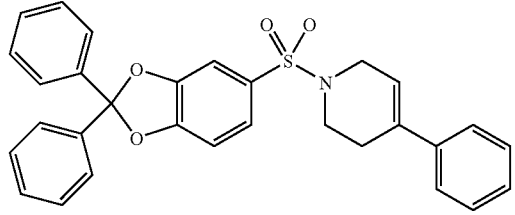

4-Phenyl-1,2,3,4-tetrahydropyridine hydrochloride (15.92 mg, 0.10 mmol) was suspended in methylene chloride (2 ml). Ethyldiisopropylamine (0.035 ml, 0.20 mmol) was added and the solution was shaken for 10 minutes at room temperature. 2,2-Diphenyl-benzo[1,3]dioxole-5-sulfonyl chloride (37.28 mg, 0.10 mmol) was added and the reaction was shaken at room temperature for 12 hours. Aqueous HCl (0.1 N, 1.0 ml) was added and the mixture shaken for 30 minutes, the aqueous layer removed and the organic phase concentrated and purified by preparative reverse phase HPLC (YMC, ODS-AQ packing; 20%→95% CH$_3$CN/H$_2$O) to yield the sulfonamide (23.6 mg, 48%).

MS (ISP): 596.2 (M+H$^+$, 100). NMR (500 MHz, DMSO-d$_6$) ppm: 7.22-7.55 (m, 17H), 6.06 (m, 1H), 3.70 (m, 2H), 3.24 (m, 2H), 2.50 (m, 2H, under DMSO peak).

Example 29

Preparation of racemic 1-[2-(2-chloro-phenyl)-2-(4-methoxy-phenyl)-benzo[1,3]dioxole-5-sulfonyl]-piperidine

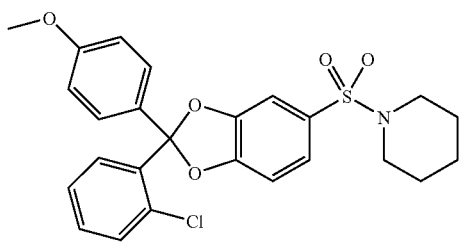

Method C 4-(Piperidine-1-sulfonyl)-benzene-1,2-diol (60 mg, 0.2 mmol) and (4-methoxyphenyl)-(2-chlorophenyl)-dichloromethane (51 mg, 0.2 mmol) was refluxed overnight in toluene (2 ml). After cooling the reaction to room temperature the solvent was evaporated. The residue was dissolved in methylene chloride and purified by column chromatography (methylene chloride eluant) on silica gel to afford the product as a colorless solid (42 mg, 39%).

MS (ISP): 486.3 (M+H$^+$, 100). NMR (300 MHz, CDCl$_3$) ppm: 7.80-7.90 (m, 1H), 7.30-7.43 (m, 8H), 6.97 (d, 1H), 6.89 (d, 1H), 3.82 (s, 3H), 2.98 (m, 4H), 1.60-1.70 (m, 4H), 1.40-1.50 (m, 2H).

The following examples were prepared following method C:

Example 30

Preparation of racemic 1-[2-(2-chloro-phenyl)-2-(4-fluoro-phenyl)-benzo[1,3]dioxole-5-sulfonyl]-piperidine

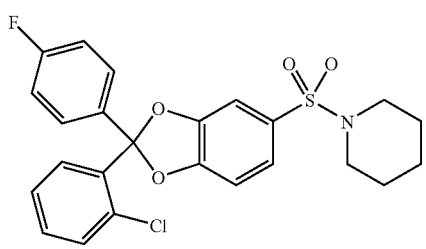

Using 4-fluorophenyl-2-chlorophenyl-dichloromethane (57 mg, 0.2 mmol) as a starting material, the title compound was obtained as a colorless foam (68 mg, 71%). Column chromatography was performed on silica gel (25 g, methylene chloride eluant).

MS (ISP): 474.2 (M+H$^+$, 100). NMR (300 MHz, CDCl$_3$) ppm: 7.84 (m, 1H), 7.32-7.47 (m, 6H), 7.27 (d, 1H), 7.08 (t, 2H), 6.99 (d, 1H), 2.95-3.01 (m, 4H), 1.60-1.68 (m, 4H), 1.42-1.47 (m, 2H).

Example 31

Preparation of racemic 1-[2-(2-chloro-phenyl)-2-p-tolyl-benzo[1,3]dioxole-5-sulfonyl]-piperidine

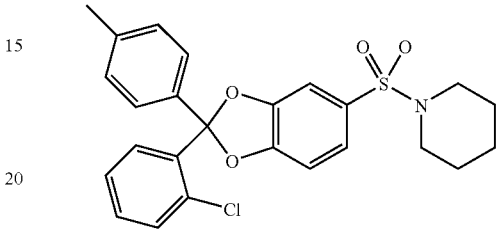

Using 4-methylphenyl-2-chlorophenyl-dichloromethane (57 mg, 0.2 mmol) as a starting material, the title compound was obtained as a light yellow foam (46 mg, 44%). Column chromatography was performed on silica gel (25 g, methylene chloride eluant).

MS (ISP): 470.2 (M+H$^+$, 100). NMR (300 MHz, CDCl$_3$) ppm: 7.83 (m, 1H), 7.31-7.42 (m, 7H), 7.20 (d, 2H), 6.97 (d, 1H), 2.96-3.02 (m, 4H), 1.60-1.68 (m, 4H), 1.42-1.46 (m, 2H).

Example 32

Preparation of racemic 1-[2-(4-chloro-phenyl)-2-(4-methoxy-phenyl)-benzo[1,3]dioxole-5-sulfonyl]-piperidine

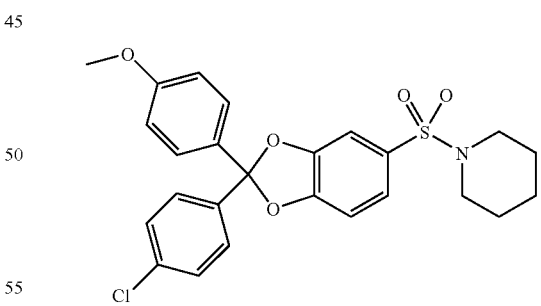

Using 4-methoxphenyl-4-chlorophenyl-dichloromethane (60 mg, 0.2 mmol) as a starting material, the title compound was obtained as a light red solid (35 mg, 36%). Column chromatography was performed on silica gel (25 g, methylene chloride eluant).

MS (EI): 485.2 (M$^+$, 65), 374.2 ([M−PhCl]$^+$, 100). NMR (300 MHz, CDCl$_3$) ppm: 7.49 (d, 2H), 7.42 (d, 2H), 7.32 (d, 2H), 7.22 (s, 1H), 6.94 (d, 1H), 6.90 (d, 2H), 2.95-2.99 (m, 4H), 1.60-1.68 (m, 4H), 1.40-1.44 (m, 2H).

Example 33

Preparation of racemic 1-[2-(4-chloro-phenyl)-2-p-tolyl-benzo[1,3]dioxole-5-sulfonyl]-piperidine

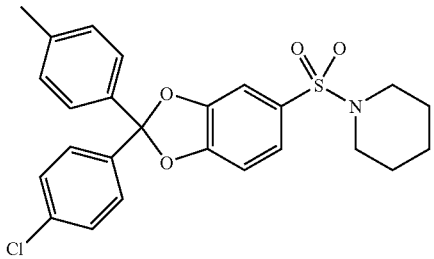

Using 4-methylphenyl-4-chlorophenyl-dichloromethane (85 mg, 0.3 mmol) as a starting material, the title compound was obtained as a colorless foam (138 mg, 97%). Column chromatography was performed on silica gel (25 g, 4/1 hexane/ethyl acetate eluant).

MS (ISP): 470.2 (M$^+$, 100). NMR (300 MHz, CDCl$_3$) ppm: 7.49 (d, 2H), 7.40 (d, 2H), 7.36 (d, 2H), 7.31 (d, 1H), 7.23 (d, 1H), 6.94 (d, 2H), 2.95-2.99 (m, 4H), 1.60-1.68 (m, 4H), 1.39-1.46 (m, 2H).

Example 34

Preparation of 1-[2,2-bis-(4-chloro-phenyl)-benzo[1,3]dioxole-5-sulfonyl]-piperidine

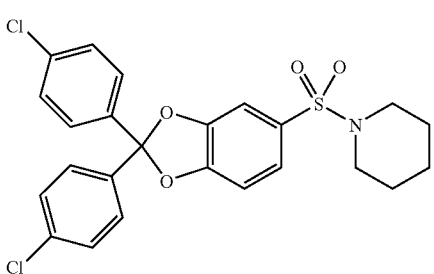

Using bis-(4-chlorophenyl)-dichloromethane (61 mg, 0.2 mmol) as a starting material, the title compound was obtained as a colorless solid (77 mg, 78%). Column chromatography was performed on silica gel (25 g, methylene chloride eluant).

MS (EI): 489.1 (M$^+$, 30), 378.1 ([M−PhCl]$^+$, 30), 231.1 (70), 84.3 (100). NMR (300 MHz, CDCl$_3$) ppm: 7.47 (d, 4H), 7.37 (d, 4H), 7.33 (d, 1H), 7.25 (s, 1H), 6.96 (d, 1H), 2.95-3.00 (m, 4H), 1.60-1.68 (m, 4H), 1.40-1.46 (m, 2H).

Example 35

Preparation of racemic 1-[2-(4-fluoro-phenyl)-2-phenyl-benzo[1,3]dioxole-5-sulfonyl]-piperidine

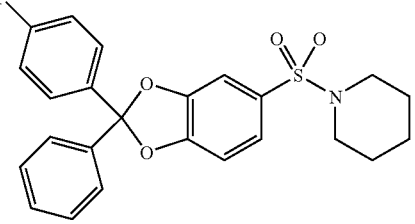

Using 4-fluorophenyl-phenyl-dichloromethane (51 mg, 0.2 mmol) as a starting material, the title compound was obtained as a white crystalline solid (66 mg, 75%) after stirring the crude product in diethyl ether, filtration and drying. m.p.: 125-126° C.

Example 36

Preparation of racemic 1-[2-(4-methoxy-phenyl)-2-phenyl-benzo[1,3]dioxole-5-sulfonyl]-piperidine

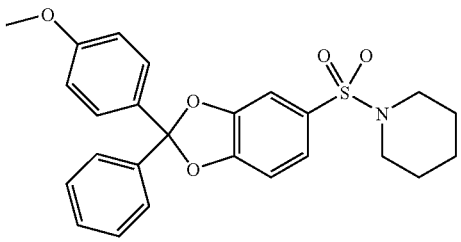

Using 4-methoxyphenyl-phenyl-dichloromethane (53 mg, 0.2 mmol) as a starting material, the title compound was obtained as a white solid (56 mg, 62%). Column chromatography was performed on silica gel (25 g, 4/1 hexane/ethyl acetate).

MS (ISP): 452.4 (M$^+$, 100). NMR (300 MHz, CDCl$_3$) ppm: 7.41-7.54 (m, 7H), 7.33 (s, 1H), 7.31 (d, 4H), 7.23 (d, 1H), 7.00 (d, 2H), 3.76 (s, 3H), 2.87 (m, 4H), 1.53 (m, 4H), 1.35 (m, 2H).

Example 37

Preparation of racemic 1-[2-(4-chloro-phenyl)-2-p-tolyl-benzo[1,3]dioxole-5-sulfonyl]-4-(4-fluoro-phenyl)-1,2,3,6-tetrahydro-pyridine

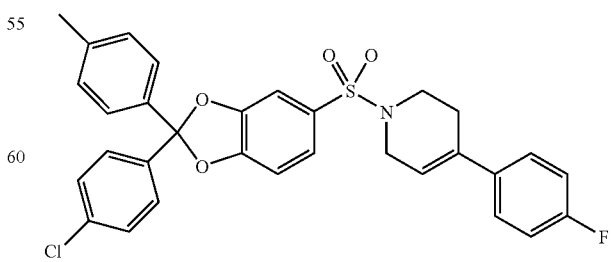

Using 4-chlorophenyl-4-methylphenyl-dichloromethane (57 mg, 0.2 mmol) and 4-[4-(4-fluoro-phenyl)-3,6-dihydro- 2H-pyridine-1-sulfonyl]-benzene-1,2-diol (69 mg, 0.2 mmol) as a starting material, the title compound was obtained as an off-white crystalline solid (90 mg, 80%) after taking the residue up in hexane/ethyl acetate (4/1), stirring for 10 minutes, filtering the solid and drying.

MS (EI): 561.2 (M+, 10), 176.2 (100), 149.2 (50). NMR (300 MHz, CDCl$_3$) ppm: 7.47 (d, 2H), 7.18-7.40 (m, 9H), 6.99 (d, 2H), 6.96 (d, 2H), 5.89 (m, 1H), 3.75 (m, 2H), 3.32 (t, 2H), 2.57 (m, 2H), 2.36 (s, 3H).

Preparation of 4-[4-(4-fluoro-phenyl)-3,6-dihydro-2H-pyridine-1-sulfonyl]-benzene-1,2-diol 1-(2,2-Diphenyl-benzo[1,3]dioxole-5-sulfonyl)-4-(4-fluoro-phenyl)-1,2,3,6-tetrahydro-pyridine (3.2 g, 6.2 mmol) was dissolved in methylene chloride (100 ml). Trifluoroacetic acid (50 ml) was added dropwise and the reaction was stirred for 5 hours at room temperature. The solvent was evaporated and the residue was purified by column chromatography on silica gel (100 g, methylene chloride then ethyl acetate as eluant). The product was crystallized from ether/hexane to give a white solid (2.1 g, 96%).

MS (ISN): 348.2 (M−H+, 100). NMR (300 MHz, DMSO-d$_6$) ppm: 10.0 (br s, 1H, OH), 9.80 (br s, 1H, OH), 7.44 (d, 1H), 7.42 (d, 1H), 7.08-7.19 (m, 4H), 6.92 (d, 1H), 6.07 (brs, 1H), 3.59 (br s, 2H), 3.13 (m, 2H), 2.51 (m, 2H, under DMSO peak).

Example 38

Preparation of racemic 1-[2-(4-chloro-phenyl)-2-(4-fluoro-phenyl)-benzo[1,3]dioxole-5-sulfonyl]-piperidine

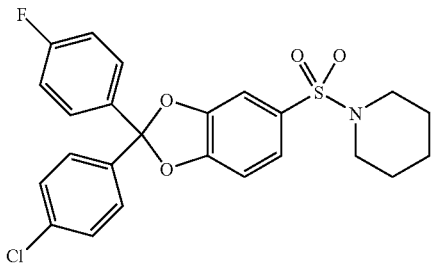

Using 4-chlorophenyl-4-fluorophenyl-dichloromethane (57 mg, 0.2 mmol) as a starting material, the title compound was obtained as a colorless foam (77 mg, 81%). Column chromatography was performed on silica gel (25 g, 4/1 hexane/ethyl acetate eluant).

MS (EI): 473.2 (M+, 30), 215.2 (40), 84.3 (100). NMR (300 MHz, CDCl$_3$) ppm: 7.46-7.53 (m, 4H), 7.32-7.39 (m, 3H), 7.24 (s, 1H), 7.09 (t, 2H), 6.96 (d, 1H), 2.96-3.00 (m, 4H), 1.60-1.68 (m, 4H), 1.40-1.46 (m, 2H).

Example 39

Preparation of racemic 1-[2-(2,4-dichloro-phenyl)-2-(4-fluoro-phenyl)-benzo[1,3]dioxole-5-sulfonyl]-piperidine

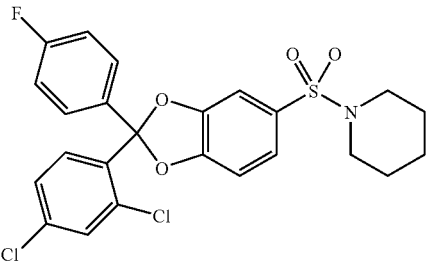

Using 2,4-dichlorophenyl-4-fluorophenyl-dichloromethane (65 mg, 0.2 mmol) as a starting material, the title compound was obtained as a colorless foam (81 mg, 80%). Column chromatography was performed on silica gel (25 g, 4/1 hexane/ethyl acetate eluant).

MS (ISP): 508.2 (M+HF+, 100). NMR (300 MHz, CDCl$_3$) ppm: 7.78 (d, 1H), 7.32-7.47 (m, 3H), 7.32-7.37 (m, 2H), 7.28 (s, 1H), 7.08 (t, 2H), 6.99 (d, 1H), 2.97-3.00 (m, 4H), 1.61-1.68 (m, 4H), 1.40-1.47 (m, 2H).

Example 40

Preparation of 1-[2,2-Bis-(4-fluoro-phenyl)-benzo[1,3]dioxole-5-sulfonyl]-piperidine

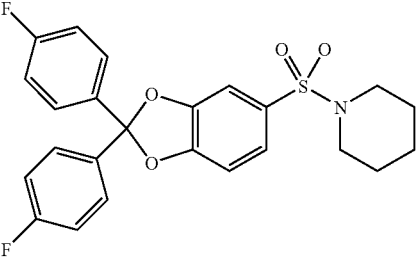

Using bis-(4-fluorophenyl)-dichloromethane (55 mg, 0.2 mmol) as a starting material, the title compound was obtained as a colorless foam (75 mg, 82%). Column chromatography was performed on silica gel (25 g, 4/1 hexane/ethyl acetate eluant). m.p.: 148-149° C.

Example 41

Preparation of racemic 1-[2-(3-chloro-phenyl)-2-(4-fluoro-phenyl)-benzo[1,3]dioxole-5-sulfonyl]-piperidine

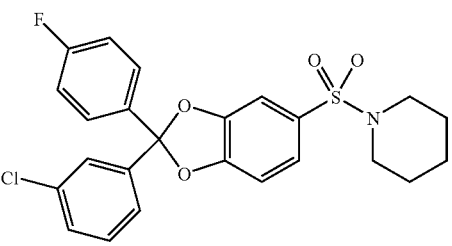

Using 3-chlorophenyl-4-fluorphenyl-dichloromethane (58 mg, 0.2 mmol) as a starting material, the title compound was obtained as a colorless viscous oil (82 mg, 86%). Column chromatography was performed on silica gel (25 g, 4/1 hexane/ethyl acetate eluant).

MS (ISP): 474.2 (M+H+, 100). NMR (300 MHz, CDCl$_3$) ppm: 7.49-7.55 (m, 3H), 7.33-7.44 (m, 4H), 7.26 (s, 1H), 7.09 (t, 2H), 6.97 (d, 1H), 2.96-3.00 (m, 4H), 1.60-1.68 (m, 4H), 1.40-1.46 (m, 2H).

Example 42

Preparation of racemic 1-[2-(4-chloro-phenyl)-2-(2-chloro-phenyl)-benzo[1,3]dioxole-5-sulfonyl]-piperidine

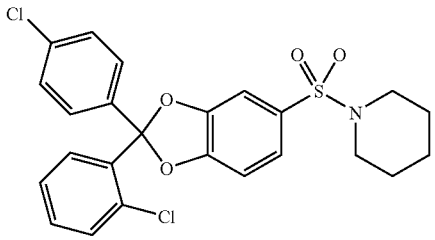

Using 2-chlorophenyl-4-chlorophenyl-dichloromethane (61 mg, 0.2 mmol) as a starting material, the title compound was obtained as a colorless solid (40 mg, 41%). Column chromatography was performed on silica gel (25 g, Dichloromethane eluant).

MS (EI): 489.1 (M+, 30), 378.1 (35), 231.1 (60), 84.2 (100). NMR (300 MHz, CDCl$_3$) ppm: 7.42-7.86 (m, 1H), 7.33-7.44 (m, 8H), 7.27 (d, 1H), 6.99 (d, 1H), 2.96-3.00 (m, 4H), 1.60-1.68 (m, 4H), 1.42-1.47 (m, 2H).

Method D

The bisaryl-dichloromethane derivatives needed for the preparation of the above described examples were prepared according to the following method D following a literature procedure (R. K. Ramchandani, R. D. Wakharkar, A. Sudalai, Tetrahedron Lett. 37 (23) (1996) 4063-4064).

Preparation of (4-methoxyphenyl)(2-chlorophenyl)-dichloromethane

Aluminium trichloride (400 mg, 3 mmol) is suspended in 1,2-dichloroethane (1.4 ml). At 0° C. under argon 2-chlorobenzotrifluoride (180 mg, 1 mmol) is added. A deep red solution is obtained to which anisole (108 mg, 1 mmol) is added. The reaction was stirred at 0° C. for 3 hours. It was poured onto ice, stirred for 5 minutes and extracted twice with methylene chloride. The combined organic layers were washed with brine, dried over sodium sulfate and filtered. The solvent was evaporated to leave the product as dark red viscous oil (416 mg 138%), which was used without purification in the next step.

Known bisaryl-dichloromethanes prepared by this method:
4-Methylphenyl-4-chlorophenyl-dichloromethane
Bis-(4-chlorophenyl)-dichloromethane
Chlorophenyl-4-chlorophenyl-dichloromethane
(4-Methoxyphenyl) (2-chlorophenyl)-dichloromethane The following bisaryl-dichlormethane derivatives are unknown in literature and are prepared according to method D from commercially available starting materials. The compounds were not purified, because some of them are unstable on column chromatography, but were used instead without Purification as crude products in the next step:

Preparation of 4-fluorophenyl-2-chlorophenyl-dichloromethane

From 2-chlorobenzotrifluoride (180 mg, 1 mmol), AlC$_3$ (400 mg, 3 mmol) and fluorobenzene (96 mg, 1 mmol), light yellow oil (380 mg, 131% crude).

Preparation of 4-methylphenyl-2-chlorophenyl-dichloromethane

From 2-chlorobenzotrifluoride (180 mg, 1 mmol), AlCl$_3$ (400 mg, 3 mmol) and toluene (92 mg, 1 mmol), light yellow oil (345 mg, 120% crude).

Preparation of 4-methoxyphenyl-4-chlorophenyl-dichloromethane

From 4-chlorobenzotrifluoride (180 mg, 1 mmol), AlCl$_3$ (400 mg, 3 mmol) and anisole (108 mg, 1 mmol), red solid (345 mg, 120% crude), contains the benzophenone (ca 30%).

Preparation of 4-chlorophenyl-4-fluorophenyl-dichloromethane

From 4-chlorobenzotrifluoride (180 mg, 1 mmol), AlCl$_3$ (400 mg, 3 mmol) and fluorobenzene (96 mg, 1 mmol), light yellow oil (382 mg, 131% crude).

Preparation of 2,4-dichlorophenyl-4-fluorophenyl-dichloromethane

From 2,4-dichlorobenzotrifluoride (215 mg, 1 mmol), AlCl$_3$ (400 mg, 3 mmol) and fluorobenzene (96 mg, 1 mmol), light yellow oil (382 mg, 118% crude).

Preparation of 3-chlorophenyl-4-fluorophenyl-dichloromethane

From 3-chlorobenzotrifluoride (180 mg, 1 mmol), AlCl$_3$ (400 mg, 3 mmol) and fluorobenzene (96 mg, 1 mmol), light yellow oil (384 mg, 132% crude).

Preparation of 4-fluorophenyl-phenyl-dichloromethane

From benzotrifluoride (146 mg, 1 mmol), AlCl$_3$ (400 mg, 3 mmol) and fluorobenzene (96 mg, 1 mmol), light yellow oil (335 mg, 131% crude).

The following bisaryl-dichloromethanes are known in the literature but their synthesis is not described. These compounds were prepared with method D:

Preparation of bis-(4-fluorophenyl)-dichloromethane (EP96008)

From 4-fluorobenzotrifluoride (164 mg, 1 mmol), AlCl$_3$ (400 mg, 3 mmol) and fluorobenzene (96 mg, 1 mmol), light yellow oil (377 mg, 138% crude). Preparation of 4-methoxyphenyl-phenyl-dichloromethane (R. Laatikainen, V. Kral, J. Chem. Soc., Perkin Trans. 2 (8) (1985) 1091-1100; U.S. Pat. No. 3,824,310):

From benzotrifluoride (146 mg, 1 mmol), AlCl₃ (400 mg, 3 mmol) and anisole (108 mg, 1 mmol), dark red viscous oil (352 mg, 132% crude).

Preparation of
4-(piperidine-1-sulfonyl)-benzene-1,2-diol 1-(2,2-Diphenyl-benzo[1,3]dioxole-5-sulfonyl)-piperidine (1.92 g, 4.5 mmol) was dissolved in methylene chloride (69 ml). At room temperature trifluoroacetic acid (20.7 ml) and water (8 drops) were added. The reaction was stirred at room temperature for 24 hours. The solvent was evaporated and the residue was taken up in n-pentane three times and evaporated again in order to remove trifluoroacetic acid. The residue was purified by column chromatography on silica gel (100 g, methylene chloride then 1/19 methanol/methylene chloride eluant). The product was precipitated from diethyl ether/n-pentane. The solvent was evaporated and the residue was stirred with n-pentane. The solid was filtered and dried to yield the product as a white crystalline solid (1.13 g, 97%).

MS (ISN): 256.0 (M−H⁺, 100). NMR (300 MHz, DMSO-D₆) ppm: 9.98(s, 1H, OH), 9.69 (s, 1H, OH), 7.05 (dd, 1H), 7.01 (dd, 1H), 6.90 (d, 1H), 2.78-2.83 (m, 4H), 1.50-1.68 (m, 4H), 1.30-1.40 (m, 2H).

Method E 2,2-Diphenyl-benzo[1,3]dioxole-5-carboxylic acidbenzotriazol-1-yl ester (87 mg, 0.2 mmol), the appropriate amine (22 mg, 0.25 mmol) and ethyldiisopropylamine (32 mg, 0.25 mmol) were dissolved in acetonitrile (2 ml) and stirred at room temperature for 3 hours. Water (20 ml) was added and the reaction was stirred at room temperature for 1 hour. The precipitate was filtered off, washed with water and dried in high vacuum to yield the product as a crystalline white solid.

The preparation of the activated ester, 2,2-diphenyl-benzo[1,3]dioxole-5-carboxylic acid benzotriazol-1-yl ester, is described in the literature (EP544166).

The following examples were prepared following method E:

Example 43

Preparation of racemic (2,2-diphenyl-benzo[1,3]dioxol-5-yl)-(3-hydroxy-pyrrolidin-1-yl)-methanone

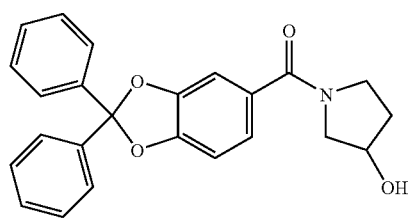

From 2,2-diphenyl-benzo[1,3]dioxole-5-carboxylic acid benzotriazol-1-yl ester (87 mg, 0.2 mmol) and 3-pyrrolidinol (22 mg, 0.25 mmol), the title compound was obtained as a white crystalline solid (73 mg, 94%). m.p.: 106-107° C.

Example 44

Preparation of 4-(2,2-diphenyl-benzo[1,3]dioxole-5-carbonyl)-piperazine-1-carbaldehyde

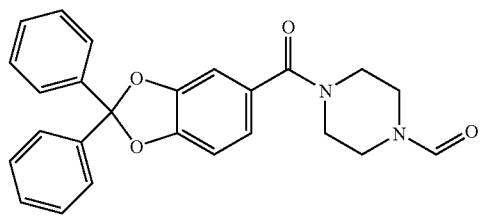

From 2,2-diphenyl-benzo[1,3]dioxole-5-carboxylic acid benzotriazol-1-yl ester (87 mg, 0.2 mmol) and formyl-piperazine (32 mg, 90% pure, 0.25 mmol), the title compound was obtained as a white crystalline solid (73 mg, 88%). m.p. 176-177° C.

Example 45

Preparation of (2,2-diphenyl-benzo[1,3]dioxol-5-yl)-(4-hydroxymethyl-piperidin-1-yl)-methanone

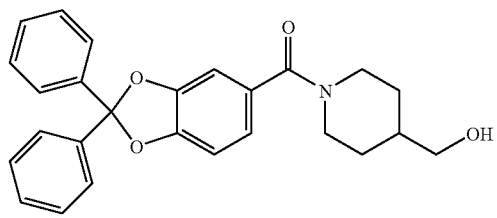

From 2,2-diphenyl-benzo[1,3]dioxole-5-carboxylic acid benzotriazol-1-yl ester (87 mg, 0.2 mmol) and 4-(hydroxymethyl)-piperidine (29 mg, 0.25 mmol), the title compound was obtained as a white crystalline solid (76 mg, 91%). m.p. 197-198° C.

Example 46

Preparation of (1,4-dioxa-8-aza-spiro[4.5]dec-8-yl)-(2,2-diphenyl-benzo[1,3]dioxol-5-yl)-methanone

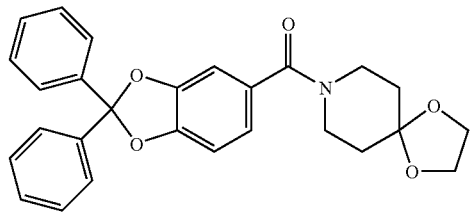

From 2,2-diphenyl-benzo[1,3]dioxole-5-carboxylic acid benzotriazol-1-yl ester (87 mg, 0.2 mmol) and 1,4-dioxa-8-azaspiro(4,5)decan (36 mg, 0.25 mmol), the title compound was obtained as a white crystalline solid (74 mg, 83%). m.p. 150-151° C.

Example 47

Preparation of (2,2-diphenyl-benzo[1,3]dioxol-5-yl)-morpholin-4-yl-methanone

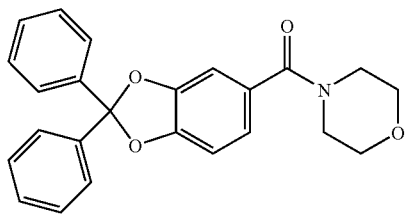

From 2,2-diphenyl-benzo[1,3]dioxole-5-carboxylic acid benzotriazol-1-yl ester (87 mg, 0.2 mmol) and morpholine (22 mg, 0.25 mmol), the title compound was obtained as a white crystalline solid (64 mg, 82%). m.p. 149-150° C.

Example 48

Preparation (2,2-diphenyl-benzo[1,3]dioxol-5-yl)-(4-methyl-piperazin-1-yl)-methanone

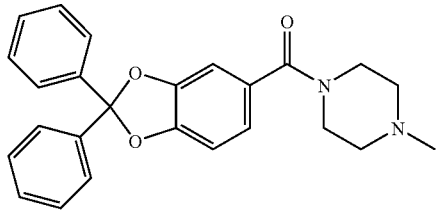

From 2,2-diphenyl-benzo[1,3]dioxole-5-carboxylic acid benzotriazol-1-yl ester (87 mg, 0.2 mmol) and 1-methylpiperazine (25 mg, 0.25 mmol), the title compound was obtained as a white crystalline solid (72 mg, 90%). m.p. 115-116° C.

Example 49

Preparation of (2,2-diphenyl-benzo[1,3]dioxol-5-yl)-(4-isopropyl-piperazin-1-yl)-methanone

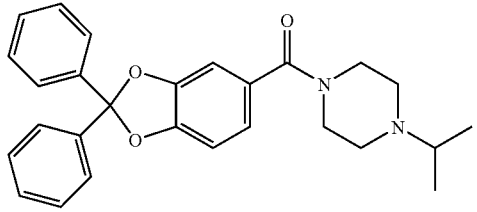

From 2,2-diphenyl-benzo[1,3]dioxole-5-carboxylic acid benzotriazol-1-yl ester (87 mg, 0.2 mmol) and 1-(2-propyl)-piperazine (32 mg, 0.25 mmol), the title compound was obtained as a colorless foam (84 mg, 98%). Work up: after addition of water (20 ml), the reaction was stirred for 1 hour at room temperature. Methylene chloride was added and the mixture was stirred 10 minutes. The organic layer was separated, washed with water and dried over sodium sulfate. The solvent was evaporated to yield the product after drying in high vacuum.

MS (ISP): 429.6 (M+H$^+$, 100). NMR (300 MHz, DMSO-D$_6$) ppm: 7.51-7.56 (m, 4H), 7.43-7.47 (m, 6H), 7.08 (d, 1H), 7.07 (s, 1H), 6.92 (d, 1H), 3.3-3.6 (br m, 4H), 2.65 (sept, 1H), 2.38-2.42 (br m, 4H), 0.95 (d, 6H).

Example 50

Preparation of 1-(2,2-diphenyl-benzo[1,3]dioxole-5-carbonyl)-piperidin-4-one

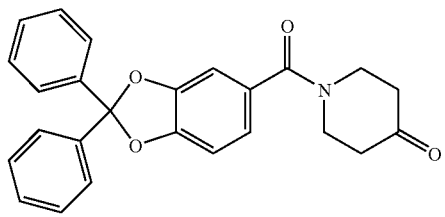

From 2,2-diphenyl-benzo[1,3]dioxole-5-carboxylic acid benzotriazol-1-yl ester (87 mg, 0.2 mmol), 4-piperidone monohydrate hydrochloride (39 mg, 0.25 mmol) and ethyl-diisopropylamine (58 mg, 0.45 mmol), the title compound was obtained as a light yellow foam (75 mg, 94%). Work up: after addition of water (20 ml), the reaction was stirred for 1 hour at room temperature. Methylene chloride was added and the mixture was stirred 10 minutes. The organic layer was separated, washed with water and dried over sodium sulfate. The solvent was evaporated to yield the product after drying in high vacuum.

MS (ISP): 400.5 (M+H$^+$, 100), 417.3 (M+NH$_4^+$, 40), 799.3 (2M+H$^+$, 20). NMR (300 MHz, DMSO-D$_6$) ppm: 7.47-7.57 (m, 4H), 7.44-7.47 (m, 6H), 7.17 (s, 1H), 7.11 (d, 1H), 7.05 (d, 1H), 3.62-3.82 (br m, 4H), 2.39-2.44 (br m, 4H).

Example 51

Preparation of (2,2-diphenyl-benzo[1,3]dioxol-5-yl)-(4-hydroxy-piperidin-1-yl)-methanone

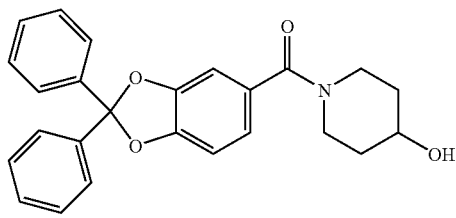

From 2,2-diphenyl-benzo[1,3]dioxole-5-carboxylic acid benzotriazol-1-yl ester (87 mg, 0.2 mmol), 4-hydroxypiperidine hydrochloride (34 mg, 0.25 mmol) and ethyl-diisopropylamine (58 mg, 0.45 mmol), the title compound was obtained as a colorless foam (73 mg, 91%). Work up: after addition of water (20 ml), the reaction was stirred for 1 hour at room temperature. Methylene chloride was added and the mixture was stirred 10 minutes. The organic layer was separated, washed with water and dried over sodium sulfate. The solvent was evaporated to yield the product after drying at high vacuum.

MS (ISP): 402.5 (M+H$^+$, 100). NMR (300 MHz, DMSO-D$_6$) ppm: 7.51-7.56 (m, 4H), 7.43-7.49 (m, 6H), 7.07 (d, 1H), 7.05 (s, 1H), 6.91 (d, 1H), 4,76 (d, 1H, OH), 3.70 (m, 1H), 3.11-3.18 (m, 2H), 2.51 (m, 2H under the DMSO peak), 1.63-1.79 (m, 2H), 1.25-1.39 (m, 2H).

Example 52

Preparation of (2,2-diphenyl-benzo[1,3]dioxol-5-yl)-pyrrolidin-1-yl-methanone

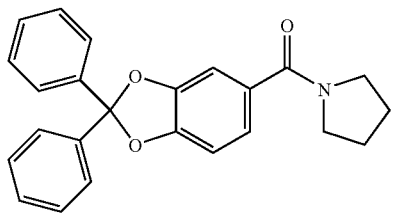

From 2,2-diphenyl-benzo[1,3]dioxole-5-carboxylic acid benzotriazol-1-yl ester (87 mg, 0.2 mmol), pyrrolidin (18 mg, 0.25 mmol) and ethyl-diisopropylamine (32 mg, 0.25 mmol), the title compound was obtained as a light yellow foam (75 mg, 91%). Work up: after addition of water (20 ml), the reaction was stirred for 1 hour at room temperature. Methylene chloride was added and the mixture was stirred 10 minutes. The organic layer was separated, washed with water and dried over sodium sulfate. The solvent was evaporated to yield the product after drying under high vacuum.

MS (ISP): 372.3 (M+H$^+$, 100), 743.3 (2M+H$^+$, 80). NMR (300 MHz, DMSO-D$_6$) ppm: 7.48-7.56 (m, 4H), 7.43-7.48 (m, 6H), 7.18 (s, 1H), 7.09 (d, 1H), 7.05 (d, 1H), 3.35-3.42 (m, 4H), 1.77-1.84 (m, 4H).

Example 53

Preparation of racemic 1-(2,2-diphenyl-benzo[1,3]dioxole-5-carbonyl)-piperidine-3-carboxylic acid ethyl ester

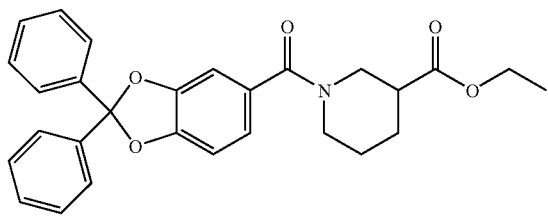

Method F 2,2-Diphenyl-benzo[1,3]dioxole-5-carboxylic acid benzotriazol-1-yl ester (87 mg, 0.2 mmol), (rac)-ethyl nipecotate (36 mg, 0.25 mmol) and ethyl-diisopropylamine (32 mg, 0.25 mmol) were dissolved in acetonitrile (1 ml) and stirred at room temperature over night. The reaction mixture was purified by preparative HPLC (acetonitrile/water 0.1% formic acid as gradient) to yield the product as a white solid (24.8 mg, 27%).

MS (ISP): 458.4 (M+H$^+$, 100). NMR (300 MHz, DMSO-d$_6$) ppm: 7.52-7.56 (m, 4H), 7.43-7.46 (m, 6H), 7.08 (d, 1H), 7.07 (s, 1H), 6.92 (d, 1H), 4.03 (m, 2H), 3.12 (m, 2H), 2.50 (m, 2H, under DMSO peak), 1.92 (m, 1H), 1.63 (m, 2H), 1.43 (m, 2H), 1.12 (m, 3H).

The following examples were prepared according to the above described method F:

Example 54

Preparation of[4-(5-chloro-2-methoxy-phenyl)-piperazin-1-yl]-(2,2-diphenyl-benzo[1,3]dioxol-5-yl)-methanone

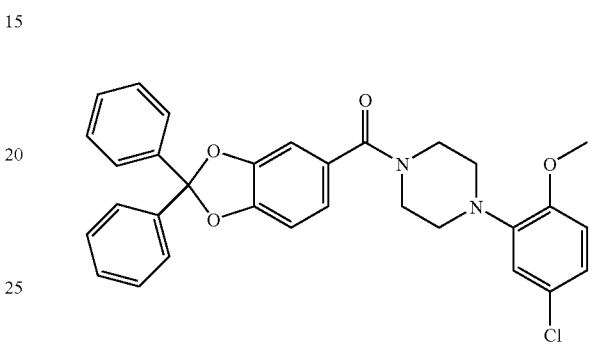

From 2,2-diphenyl-benzo[1,3]dioxole-5-carboxylic acid benzotriazol-1-yl ester (87 mg, 0.2 mmol), 1-(5-chloro-2-methoxy-phenyl)piperazine hydrochloride (66 mg, 0.25 mmol) and ethyl-diisopropylamine (64 mg, 0.50 mmol), the title compound was obtained as a white solid (42.7 mg, 41%).

MS (ISP): 527.1 (M+H$^+$, 100). NMR (300 MHz, DMSO-d$_6$) ppm: 7.44-7.60 (m, 10H), 6.87-7.01 (m, 6H), 3.78 (s, 3H), 3.06 (br m, 4H), 2.97 (br m, 4H).

Example 55

Preparation of (2,2-diphenyl-benzo[1,3]dioxol-5-yl)-(4-m-tolyl-piperazin-1-yl)-methanone

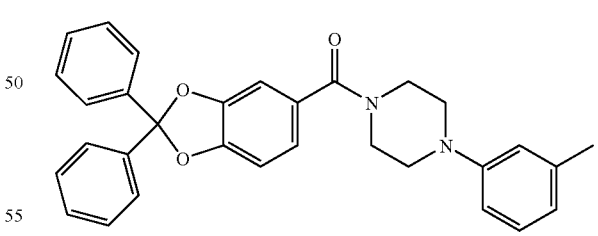

From 2,2-diphenyl-benzo[1,3]dioxole-5-carboxylic acid benzotriazol-1-yl ester (87 mg, 0.2 mmol), 1-(3-tolyl)piperazine dihydrochloride (62 mg, 0.25 mmol) and ethyl-diisopropylamine (96 mg, 0.75 mmol), the title compound was obtained as a light yellow solid (14.0 mg, 15%).

MS (ISP): 477.3 (M+H$^+$, 100). NMR (300 MHz, DMSO-d$_6$) ppm: 7.53-7.57 (m, 4H), 7.44-7.48 (m, 6H), 7.09-7.13 (m, 3H), 6.99 (d, 1H), 6.75 (m, 2H), 6.62 (d, 1H), 3.60 (br m, 4H), 3.12 (br m, 4H), 2.24 (s, 3H).

Example 56

Preparation of (2,2-diphenyl-benzo[1,3]dioxol-5-yl)-piperidin-1-methanone

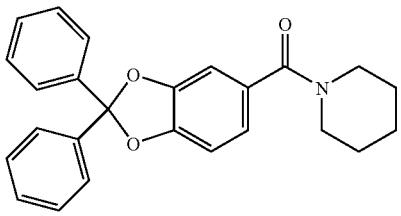

Method G

2,2-Diphenyl-benzo[1,3]dioxole-5-carboxylic acid benzotriazol-1-yl ester (217 mg, 0.5 mmol), piperidine (46 mg, 0.55 mmol) and ethyl-diisopropylamine (0.1 ml, 0.6 mmol) were dissolved in methylene chloride (10 ml). The solution was stirred at room temperature for 4 hours and the solvent was evaporated. The residue was purified by column chromatography on silica gel (20 g, ethyl acetate eluant) to yield the product as a white solid (135 mg, 70%).

MS (ISP): 386.4 (M+H$^+$, 100), 771.3 (2M+H$^+$, 25). NMR (300 MHz, DMSO-d$_6$) ppm: 7.52-7.56 (m, 4H), 7.43-7.48 (m, 6H), 7.07 (d, 1H), 7.04 (s, 1H), 6.90 (d, 1H), 3.40 (br m, 2H), 1.58 (br m, 2H), 1.48 (br m, 6H).

The following examples were prepared according to method G:

Example 57

Preparation of (2,2-diphenyl-benzo[1,3]dioxol-5-yl)-(4-o-tolyl-piperazin-1-yl)-methanone

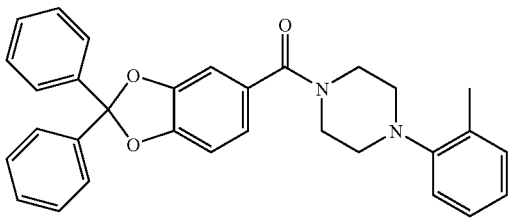

From 2,2-diphenyl-benzo[1,3]dioxole-5-carboxylic acid benzotriazol-1-yl ester (87 mg, 0.2 mmol), 1-(2-tolyl)piperazine dihydrochloride (62 mg, 0.25 mmol) and ethyl-diisopropylamine (96 mg, 0.75 mmol), the title compound was obtained as a light yellow solid (1.1 mg, 1%).

MS (ISP): 477.3 (M+H$^+$, 100). NMR (300 MHz, DMSO-d$_6$) ppm: 7.53-7.57 (m, 4H), 7.44-7.47 (m, 6H), 7.09-7.14 (m, 4H), 6.91-7.03 (m, 3H), 3.61 (br m, 4H), 2.82 (br m, 4H), 2.26 (s, 3H).

Example 58

Preparation of racemic 1-(2,2-diphenyl-benzo[1,3]dioxole-5-carbonyl)-piperidine-2-carboxylic acid ethyl ester

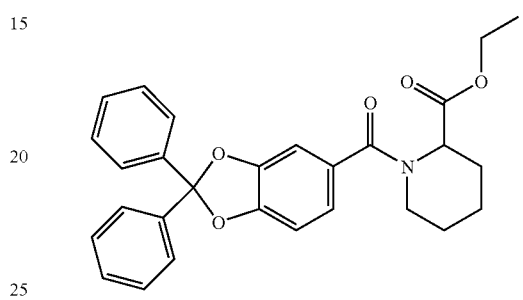

From 2,2-diphenyl-benzo[1,3]dioxole-5-carboxylic acid benzotriazol-1-yl ester (87 mg, 0.2 mmol), racemic ethyl pipecolinate (39 mg, 0.25 mmol) and ethyl-diisopropylamine (32 mg, 0.25 mmol), the title compound was obtained as a white solid (22.6 mg, 24%).

MS (ISP): 458.4 (M+H$^+$, 100). NMR (300 MHz, DMSO-d$_6$) ppm: 7.53-7.56 (m, 4H), 7.43-7.49 (m, 6H), 7.09 (d, 1H), 7.02 (s, 1H), 6.92 (d, 1H), 5.14 (br m, 1H), 4.16 (br q, 2H), 3.58 (br m, 1H), 3.12 (br m, 1H), 2.11 (br m, 1 h), 1.18-1.63 (m, 9 H).

Example 59

Preparation of [4-(2,3-dichloro-phenyl)-piperazin-1-yl]-(2,2-diphenyl-benzo[1,3]dioxol-5-yl)-methanone

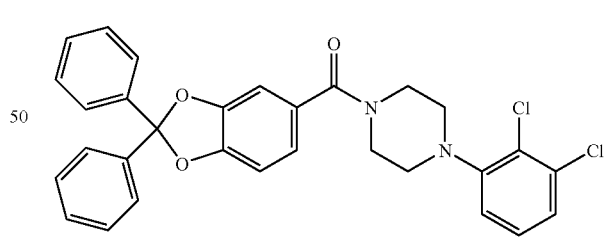

From 2,2-diphenyl-benzo[1,3]dioxole-5-carboxylic acid benzotriazol-1-yl ester (87 mg, 0.2 mmol), 1-(2,3-dichlorophenyl)piperazine hydrochloride (66.9 mg, 0.25 mmol) and ethyl-diisopropylamine (64 mg, 0.50 mmol), the title compound was obtained as a light yellow solid (58.3 mg, 55%).

MS (ISP): 531.1 (M+H$^+$, 100). NMR (300 MHz, DMSO-d$_6$) ppm: 7.53-7.57 (m, 4H), 7.44-7.48 (m, 6H), 7.31-7.33 (m, 2H), 7.11-7.14 (m, 2H), 7.09 (d, 1H), 7.02 (d, 1H), 3.63 (br m, 4H), 2.98 (br m, 4H).

Example 60

Preparation of [4-(4-chloro-3-trifluoromethyl-phenyl)-piperazin-1-yl]-(2,2-diphenyl-benzo[1,3]dioxol-5-yl)-methanone

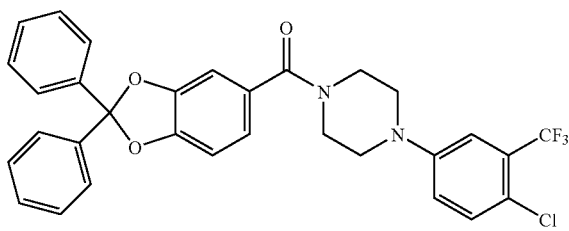

From 2,2-diphenyl-benzo[1,3]dioxole-5-carboxylic acid benzotriazol-1-yl ester (87 mg, 0.2 mmol), 1-(4-chloro-3-trifluoromethyl-phenyl)piperazine (66.2 mg, 0.25 mmol) and ethyl-diisopropylamine (32 mg, 0.25 mmol), the title compound was obtained as a white solid (35.8 mg, 30%).

MS (ISP): 565.2 (M+H$^+$, 100). NMR (300 MHz, DMSO-d$_6$) ppm: 7.52-7.58 (m, 4H), 7.44-7.49 (m, 7H), 7.27 (s, 1H), 7.23 (d, 1H), 7.13 (s, 1H), 7.10 (d, 1H), 7.00 (d, 1H), 3.60 (br m, 4H), 3.28 (br m, 4H).

Example 61

Preparation of racemic (2,2-diphenyl-benzo[1,3]dioxol-5-yl)-(3-hydroxymethyl-piperidin-1-yl)-methanone

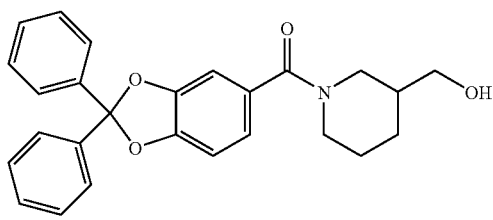

From 2,2-diphenyl-benzo[1,3]dioxole-5-carboxylic acid benzotriazol-1-yl ester (87 mg, 0.2 mmol), racemic 3-hydroxymethylpiperidine (28.8 mg, 0.25 mmol) and ethyl-diisopropylamine (32 mg, 0.25 mmol), the title compound was obtained as a white solid (6.0 mg, 7%).

MS (ISP): 416.4 (M+H$^+$, 100). NMR (300 MHz, DMSO-d$_6$) ppm: 7.52-7.58 (m, 4H), 7.43-7.46 (m, 6H), 7.06 (d, 1H), 7.05 (s, 1H), 6.91 (d, 1H), 4.50 (br s, 1H. OH), 3.32 (m, 2H), 2.45 (m, 2H), 1.10-1.78 (m, 7H).

Example 62

Preparation of (2,2-diphenyl-benzo[1,3]dioxol-5-yl)-(2,3,5,6-tetrahydro-[1,2']bipyrazinyl-4-yl)-methanone

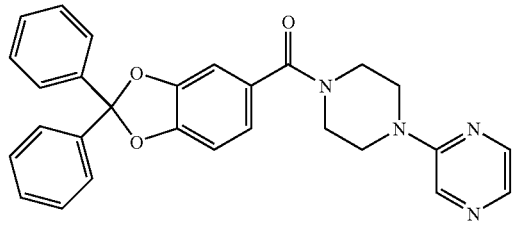

From 2,2-diphenyl-benzo[1,3]dioxole-5-carboxylic acid benzotriazol-1-yl ester (87 mg, 0.2 mmol), 1-(2-pyrazinyl)piperazine (41.1 mg, 0.25 mmol) and ethyl-diisopropylamine (32 mg, 0.25 mmol), the title compound was obtained as a white solid (19.0 mg, 20%).

MS (ISP): 465.3 (M+H$^+$, 100). NMR (300 MHz, DMSO-d$_6$) ppm: 8.31 (s, 1H), 8.13 (s, 1H), 7.86 (s, 1H), 7.53-7.57 (m, 4H), 7.44-7.48 (m, 6H), 7.14 (s, 1H), 7.11 (d, 1H), 7.01 (d, 1H), 3.61 (br m, 8H).

Example 63

Preparation of (2,2-Diphenyl-benzo[1,3]dioxol-5-yl)-(4-pyridin-2-yl-piperazin-1-yl)-methanone

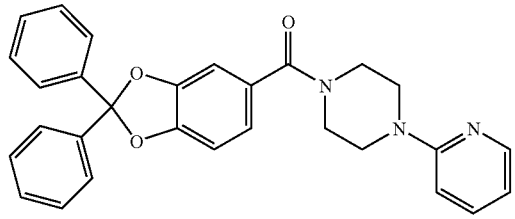

From 2,2-diphenyl-benzo[1,3]dioxole-5-carboxylic acid benzotriazol-1-yl ester (87 mg, 0.2 mmol), 1-(2-pyridyl)piperazine (40.8 mg, 0.25 mmol) and ethyl-diisopropylamine (32 mg, 0.25 mmol), the title compound was obtained as a white solid (53.2 mg, 57%).

MS (ISP): 464.3 (M+H$^+$, 100). NMR (300 MHz, DMSO-d$_6$) ppm: 8.11 (m, 1H), 7.52-7.57 (m, 4H), 7.44-7.48 (m, 7H), 7.13 (s, 1H), 7.10 (d, 1H), 7.00 (d, 1H), 6.82 (d, 1H), 6.64 (dd, 1H), 3.53 (br m, 8H).

Example 64

Preparation of (4-fluoro-2,2-diphenyl-benzo[1,3]dioxol-5-yl)-(4-methyl-piperazin-1-yl)-methanone

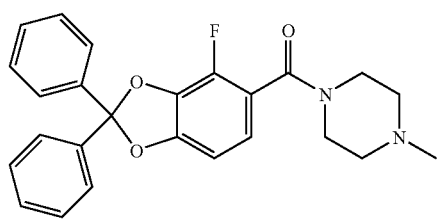

Method H

4-Fluoro-2,2-diphenyl-benzo[1,3]dioxole-5-carboxylic acid (336 mg, 1 mmol) was dissolved in dichloromethane (15 ml). EDCI (210 mg, 1.1 mmol) and 1-methyl-piperazine (220 mg, 2.2 mmol) were added and the solution was stirred for 5 hours at room temperature. The reaction was concentrated and the residue was purified by column chromatography on silica gel (20 g, 5% methanol in dichloromethane eluant) to yield the product as white crystals (150 mg, 37%).

MS (ISP): 419.4 (M+H$^+$, 100), 460.5 (M+MeCN+H$^+$, 70), 837.4 (2M+H$^+$, 50). NMR (300 MHz, DMSO-D$_6$) ppm: 7.52-7.58 (m, 4H), 7.46-7.50 (m, 6H), 7.01 (d, 1H), 6.92 (d, 1H), 3.60 (m, 2H), 3.22 (m, 2H), 2.32 (m, 2H), 2.22 (m, 2H), 2.18 (s, 3H).

Preparation of 4-fluoro-2,2-diphenyl-benzo[1,3]dioxole-5-carboxylic acid

4-Fluoro-2,2-diphenyl-benzo[1,3]dioxole (5.8 g, 20 mmol) were dissolved in THF (40 ml). The reaction was cooled to −78° C. under argon. TMEDA (2.9 ml, 20 mmol) was added followed by n-butyl lithium (12.5 ml, 1.6 N in hexane) dropwise. The reaction was stirred at −78° C. for 2 hours. Carbon dioxide (20 g) was added at that temperature. The reaction was allowed to warm to 0° C. and poured into water (80 ml). The reaction was extracted twice with ethyl acetate. The aqueous layer was neutralized with 1N aqueous HCl solution, extracted twice with ethyl acetate. The organic layer was washed with brine, dried over sodium sulfate and filtered. The solvent was evaporated and the residue suspended in n-hexane, stirred for 10 minutes and the product was filtered off to yield the acid as a white solid (4.0 g, 60%). m.p.: 189-191° C.

Preparation of 4-fluoro-2,2-diphenyl-benzo[1,3]dioxole

3-Fluorocatechol (12.81 g, 100 mmol) and dichlorodiphenylmethane (23.71 g, 100 mol) were dissolved in toluene (250 ml) and heated at reflux overnight. The solvent was evaporated and the residue was chromatographied on silica gel (200 g, 1/1 Dichloromethane/n-hexane eluant) to yield the ketal as a white crystalline solid (26.74 g, 91%). m.p.: 65-67° C.

The following examples were prepared using the method H:

Example 65

Preparation of (4-fluoro-2,2-diphenyl-benzo[1,3]dioxol-5-yl)-morpholin-4-yl-methanone

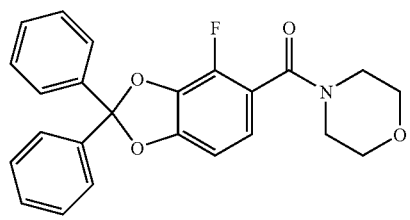

From 4-fluoro-2,2-diphenyl-benzo[1,3]dioxole-5-carboxylic acid (336 mg, 1 mmol), EDCI (210 mg, 1.1. mmol) and morpholine (190 mg, 2.2 mmol), the title compound was obtained as a white solid (183 mg, 46%). Chromatography was performed on silica gel (20 g, 5% methanol in dichloromethane eluant).

MS (ISP): 406.4 (M+H$^+$, 100), 811.2 (2M+H$^+$, 25). NMR (300 MHz, DMSO-D$_6$) ppm: 7.54-7.58 (m, 4H), 7.46-7.50 (m, 6H), 7.01 (d, 1H), 6.96 (d, 1H), 3.63 (m, 4H), 3.52 (m, 2H), 3.27 (m, 2H).

Example 66

Preparation of (4-fluoro-2,2-diphenyl-benzo[1,3]dioxol-5-yl)-piperidin-1-yl-methanone

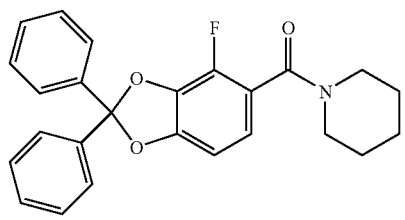

From 4-fluoro-2,2-diphenyl-benzo[1,3]dioxole-5-carboxylic acid (336 mg, 1 mmol), EDCI (210 mg, 1.1. mmol) and piperidine (187 mg, 2.2 mmol), the title compound was obtained as a white solid (103 mg, 26%). Chromatography was performed on silica gel (20 g, 5% methanol in dichloromethane eluant).

MS (ISP): 404.5 (M+H$^+$, 100), 807.4 (2M+H$^+$, 30). NMR (300 MHz, DMSO-D$_6$) ppm: 7.48-7.56 (m, 4H), 7.42-7.48 (m, 6H), 6.98 (d, 1H), 6.89 (d, 1H), 3.58 (m, 2H), 3.20 (m, 2H), 1.46-1.62 (m, 4H), 1.38-1.46 (m, 2H).

Example 67

Preparation of (4,7-dichloro-2,2-diphenyl-benzo[1,3]dioxol-5-yl)-piperidin-1-yl-methanone

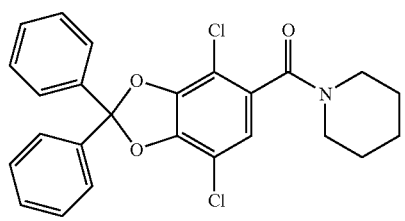

From 4,7-dichloro-2,2-diphenyl-benzo[1,3]dioxole-5-carboxylic acid (154 mg, 0.4 mmol), EDCI (84 mg, 0.44 mmol) and piperidine (75 mg, 0.88 mmol), the title compound was obtained as a white solid (27 mg, 15%). Chromatography was performed on silica gel (20 g, ethyl acetate eluant).

MS (ISP): 454.4 (M+H$^+$, 100). NMR (300 MHz, DMSO-D$_6$) ppm: 7.48-7.55 (m, 1OH), 7.09 (s, 1H), 3.58 (m, 2H), 3.14 (m, 2H), 1.48-1.60 (m, 4H), 1.38-1.48 (m, 2H).

Preparation of 4,7-dichloro-2,2-diphenyl-benzo[1,3]dioxole-5-carboxylic acid 2,5-Dichloro-3,4-dihydroxybenzoic acid (1 g, 4.48 mmol) and dichlorodiphenylmethane (2.12 g, 9.96 mmol) are dissolved in toluene (40 ml) and heated to reflux for 24 hours. After cooling the solvent is evaporated and the residue is purified by column chromatography on silic agel (100 g, dichloromethane then 5% methanol in dichloromethane eluant) to yield the acid as white crystals (490 mg, 28%).

MS (ISN): 385.0 (M–H$^+$, 100). NMR (300 MHz, DMSO-D$_6$) ppm: 13.47 (br s, 1H, OH), 7.59 (s, 1H), 7.54 (br m, 10H).

The preparation of 2,5-dichloro-3,4-dihydroxybenzoic acid is described in the literature (EP416410).

Example 68

Preparation of (4,7-dichloro-2,2-diphenyl-benzo[1,3]dioxol-5-yl)-morpholin-4-yl-methanone

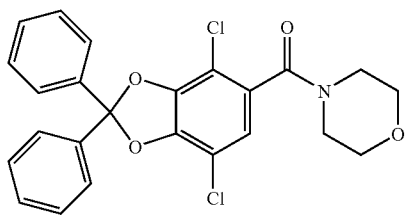

From 4,7-dichloro-2,2-diphenyl-benzo[1,3]dioxole-5-carboxylic acid (154 mg, 0.4 mmol), EDCI (84 mg, 0.44 mmol) and morpholine (77 mg, 0.88 mmol), the title compound was obtained as a white solid (88 mg, 49%). Chromatography was performed on silica gel (20 g, ethyl acetate eluant).

MS (ISP): 456.4 (M+H$^+$, 100). NMR (300 MHz, DMSO-D$_6$) ppm: 7.52 (m, 10H), 7.15 (s, 1H), 3.45-3.72 (m, 6H), 3.20 (m, 2H).

Example 69

Preparation of (4,7-dichloro-2,2-diphenyl-benzo[1,3]dioxol-5-yl)-(4-methyl-piperazin-1-yl)-methanone

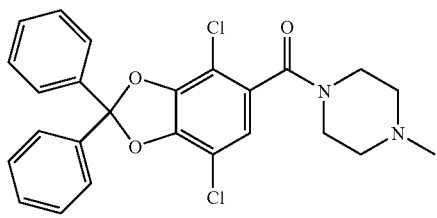

From 4,7-dichloro-2,2-diphenyl-benzo[1,3]dioxole-5-carboxylic acid (115 mg, 0.3 mmol), EDCI (63 mg, 0.33 mmol) and N-methylpiperazine (66 mg, 0.66 mmol), the title compound was obtained as a white solid (28 mg, 20%). Chromatography was performed on silica gel (20 g, 5% methanol in dichloromethane eluant).

MS (ISP): 469.1 (M+H$^+$, 100). NMR (300 MHz, DMSO-D$_6$) ppm: 7.52 (m, 10H), 7.10 (s, 1H), 3.44-3.68 (m, 2H), 3.18 (m, 2H), 2.20-2.40 (m, 4H), 2.18 (s, 3H).

Example 70

Preparation of (7-bromo-4-chloro-2,2-diphenyl-benzo[1,3]dioxol-5-yl)-(4-methyl-piperazin-1-yl)-methanone

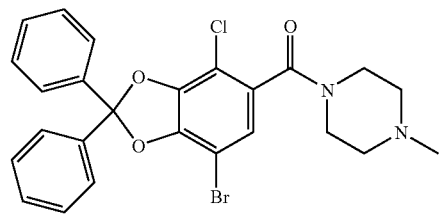

From 7-bromo-4-chloro-2,2-diphenyl-benzo[1,3]dioxole-5-carboxylic acid (100 mg, 0.23 mmol), EDCI (49 mg, 0.25 mmol) and N-methylpiperazine (50 mg, 0.50 mmol), the title compound was obtained as a white solid (9 mg, 8%). Chromatography was performed on silica gel (20 g, 5% methanol in dichloromethane eluant).

MS (ISP): 513.1 (M+H$^+$, 100). NMR (300 MHz, DMSO-D$_6$) ppm: 7.52 (m, 10H), 7.18 (s, 1H), 3.44-3.68 (m, 2H), 3.17 (m, 2H), 2.20-2.40 (m, 4H), 2.09 (s, 3H).

Preparation of 7-bromo-4-chloro-2,2-diphenyl-benzo[1,3]dioxole-5-carboxylic acid 7-Bromo-4-chloro-2,2-diphenyl-benzo[1,3]dioxole-5-carboxylic acid methyl ester (520 mg, 1.16 mmol) is dissolved in THF (6 ml). Lithium hydroxide hydrate (190 mg, 4.64 mmol) in water (6 ml) is added. After addition of methanol (2 ml) the reaction is heated to reflux for 5 hours. After cooling the organic solvents are evaporated and the reaction is diluted with water, acidified with 1N aqueous HCl solution and extracted with ethyl acetate. The combined organic layers are washed with brine, dried over sodium sulfate and filtered. The solvent is evaporated in vacuo. The residue is stirred with n-hexane. The product precipitates as a white solid (350 mg, 70%), which is filtered and dried.

MS (ISP): 429.1 (M+H$^+$, 100). NMR (300 MHz, DMSO-D$_6$) ppm: 13.45 (br s, 1H, QH), 7.68 (s, 1H), 7.52 (m, 10H).

The preparation of 7-bromo-4-chloro-2,2-diphenyl-benzo[1,3]dioxole-5-carboxylic acid methyl ester is described in the literature (EP 0 544 166).

Example 71

Preparation of (7-bromo-4-chloro-2,2-diphenyl-benzo[1,3]dioxol-5-yl)-piperidin-1-yl-methanone

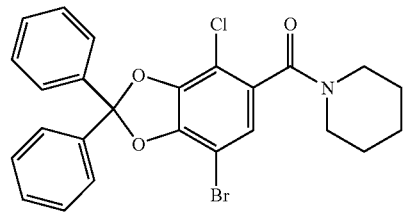

From 7-bromo-4-chloro-2,2-diphenyl-benzo[1,3]dioxole-5-carboxylic acid (100 mg, 0.23 mmol), EDCI (49 mg, 0.25 mmol) and piperidine (50 mg, 0.50 mmol), the title compound was obtained as a white solid (7 mg, 7%). Chromatography was performed on silica gel (20 g, ethyl acetate eluant).

MS (ISP): 498.1 (M+H⁺, 100). NMR (300 MHz, DMSO-D₆) ppm: 7.52 (m, 10H), 7.17 (s, 1H), 3.56 (m, 2H), 3.12 (m, 2H), 1.48-1.60 (m, 4H), 1.40-1.482.09 (m, 2H).

Example 72

Preparation of (7-bromo-4-chloro-2,2-diphenyl-benzo[1,3]dioxol-5-yl)-morpholin-4-yl-methanone

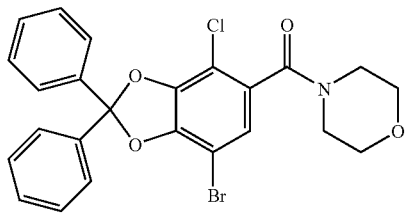

From 7-bromo-4-chloro-2,2-diphenyl-benzo[1,3]dioxole-5-carboxylic acid (1100 mg, 0.23 mmol), EDCI (49 mg, 0.25 mmol) and morpholine (44 mg, 0.50 mmol), the title compound was obtained as a white solid (47 mg, 39%). Chromatography was performed on silica gel (20 g, ethyl acetate eluant).

MS (ISP): 500.1 (M+H⁺, 100). NMR (300 MHz, DMSO-D₆) ppm: 7.52 (m, 10H), 7.23 (s, 1H), 3.42-3.70 (m, 6H), 3.19 (m, 2H).

Example 73

Preparation of (7-hydroxy-2,2-diphenyl-benzo[1,3]dioxol-5-yl)-piperidin-1-yl-methanone

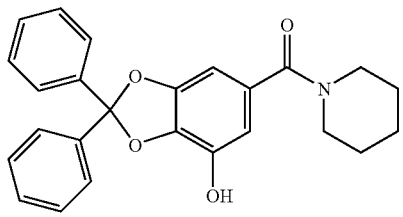

Piperidine (0.3 ml, 2 mmol) and ethyl diisopropylamine (0.5 ml, 3 mmol) were dissolved in methylene chloride (10 ml). 7-Hydroxy-2,2-diphenyl-benzo[1,3]dioxole-5-carbonyl chloride (353 mg, 1 mmol) dissolved in methylene chloride (3 ml) was added dropwise at room temperature. The reaction was stirred at room temperature for 24 hours. The solvent was evaporated and the residue was partitioned between ethyl acetate and water. The organic layer was extracted with 1N aqueous HCl solution, brine, dried over sodium sulfate and filtered. The solvent was evaporated and the residue purified by column chromatography on silica gel (20 g, 5% methanol in dichloromethane eluant) to yield the phenol as a white solid (180 mg, 45%).

MS (ISP): 400.3 (M+H⁺, 100). NMR (300 MHz, DMSO-D₆) ppm: 10.08 (s, 1H, OH), 7.52-7.55 (m, 4H), 7.41-7.48 (m, 6H), 6.52 (s, 1H), 6.46 (s, 1H), 3.38 (br m, 4H), 1.59 (br m, 2H), 1.09 (br m, 4H).

The preparation of 7-hydroxy-2,2-diphenyl-benzo[1,3]dioxole-5-carboxylic acid is described in the literature (K. S. Feldman, S. M. Ensel, J. Am. Chem. Soc. 115 (3) (1993) 1162-3.)

Preparation of 7-hydroxy-2,2-diphenyl-benzo[1,3]dioxole-5-carbonyl chloride

7-Hydroxy-2,2-diphenyl-benzo[1,3]dioxole-5-carboxylic acid (334 mg, 1 mmol) was dissolved in chloroform (5 ml). One drop of triethyl amine was added. At 45 to 50° C. thionylchloride (0.33 ml, 4.5 mmol) was added within 30 minutes. The solution was than stirred for 6 hours at 70° C. The exccess thionyl chloride was removed by evaporation. The crude 7-hydroxy-2,2-diphenyl-benzo[1,3]dioxole-5-carbonyl chloride was used without further purification in the next step.

Example 74

Preparation of 1-(2,2-Diphenyl-benzo[1,3]dioxol-5-yl)-carbonyl-4-(4-fluoro-phenyl)-1,2,3,6-tetrahydro-pyridine

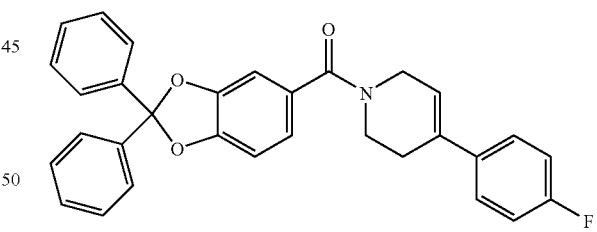

4-(4-Fluorophenyl)-1,2,3,4-tetrahydropyridine hydrochloride (106 mg, 0.5 mmol) was suspended in methylene chloride (10 ml). Ethyldiisopropyl amine (150 mg, 1.2 mmol) was added followed by 2,2-diphenyl-benzo[1,3]dioxole-5-carboxylic acid benzotriazol-1-yl ester (150 mg, 0.5 mmol). The reaction was stirred for 2 hours at room temperature. The solvent was evaporated and the residue was purified by column chromatography on silica gel (20 g, ethyl acetate eluant). The amide was obtained as white crystals (177 mg, 75%).

MS (ISP): 478.4 (M+H⁺, 100). NMR (300 MHz, DMSO-D₆) ppm: 7.53-7.57 (m, 4H), 7.44-7.50 (m, 8H), 7.17 (t, 2H), 7.15 (s, 1H), 7.10 (d, 1H), 7.01 (d, 1H), 6.15 (br s, 1H), 4.15 (br s, CH₂), 3.62 (m, 2H), 2.52 (m, 2H under DMSO peak).

Example 75

Preparation of 1-(2,2-diphenyl-benzo[1,3]dioxol-5-yl-methyl)-4-(4-fluoro-phenyl)-1,2,3,6-tetrahydropyridine

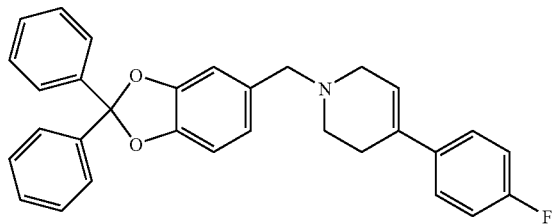

Lithium aluminium hydride (13 mg, 0.36 mmol) was suspended in THF (10 ml). At room temperature (2,2-Diphenyl-benzo[1,3]dioxol-5-yl)-[4-(4-fluoro-phenyl)-3,6-dihydro-2H-pyridin-1-yl]-methanone (104 mg, 0.22 mmol) dissolved in THF (1.5 ml) was added dropwise under argon. The reaction was heated to reflux for 2 hours. Lithium aluminium hydride (50 mg) was added and the reaction was heated to reflux overnight under argon. Lithium aluminium hydride solution (0.3 ml, 1M solution in THF) was added and the reaction heated to reflux for 4 hours. The reaction was cooled (ice bath) and under argon a mixture of water (0.4 ml) and THF (1.5 ml) was added slowly. The reaction was stirred for 10 minutes and solid potassium carbonate (2 g) was added. The reaction was filtered and the filtrate was concentrated in vacuo. The residue was dissolved in ethyl acetate. The organic solution was dried over sodium sulfate, filtered and the solvent was evaporated to yield the product as a white colorless viscous oil (85 mg, 85%).

MS (ISP): 464.4 (M+H$^+$, 100). NMR (300 MHz, DMSO-D$_6$) ppm: 7.52-7.56 (m, 4H), 7.42-7.53 (m, 7H), 7.14 (t, 2H), 6.98 (m, 2H), 6.87 (s, 1H), 6.83 (d, 1H), 6.09 (br s, 1H), 3.48 (s, CH$_2$), 3.01 (m, 2H), 2.59 (m, 2H), 2.52 (m, 2H).

Example 78

Preparation of N-(2,2-diphenyl-benzo[1,3]dioxol-5-yl)-benzenesulfonamide

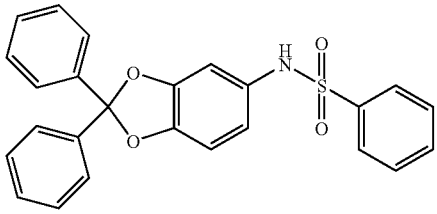

2,2-Diphenyl-1,3-benzodioxol-5-amine was dissolved in dichloromethane (5 ml). N-ethyldiisopropyl amine (0.1 ml. 0.6 mmol) and benzenesulfonyl chloride (88 mg, 0.5 mmol) were added. The reaction was stirred for 5 hours at room temperature. The reaction was washed with cold 1N aqueous HCl, with 1N aqueous NaOH and with saturated aqueous sodium chloride solution. The organic layer was dried over sodium sulfate, filtered and the solvent was evaporated in vacuo. The residue was purified by column chromatography using dichloromethane as the eluant. The product was crystallized from hexane to yield the product as white crystals (12 mg, 6%).

MS: 428.3 ([M–H]$^-$).

NMR (300 MHz, DMSO-d$_6$) ppm: 10.05 (br, 1H, NH), 7.69 (d, 2H), 7.59 (d, 1H), 7.55 (d, 2H), 7.50-7.38 (m, 10H), 6.87 (d, 1H), 6.73 (s, 1H), 6.50 (d, 1H).

The following examples 79-86 (except Example 82) were prepared using the method described for the preparation of Example 78:

Example 79

Preparation of N,N-bis(methylsulfonyl)-2,2-diphenyl-1,3-benzodioxol-5-amine

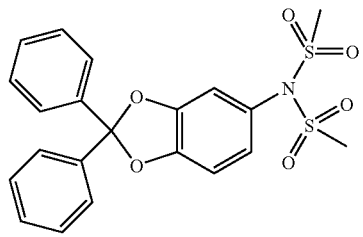

The title compound was produced in accordance with the general method of Example 78 from 2,2-diphenyl-1,3-benzodioxol-5-amine and methanesulfonylchloride. Off white solid.

MS: m/e=446.4 ([M+H]$^+$)

NMR (300 MHz, DMSO-d$_6$) ppm: 7.44-7.58 (m, 10H), 7.28 (s, 1H), 7.13 (d, 1H), 7.06 (d, 1H), 3.49 (s, 6H).

Example 80

Preparation of N,N-bis(butylsulfonyl)-2,2-diphenyl-1,3-benzodioxol-5-amine

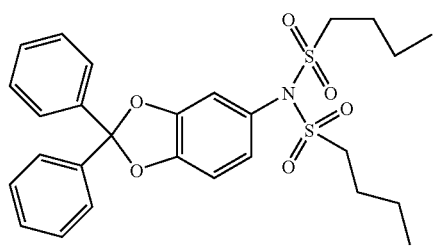

The title compound was produced in accordance with the general method of Example 78 from 2,2-diphenyl-1,3-benzodioxol-5-amine and butansulfonylchloride.

MS: m/e=530.4 ([M+H]$^+$).

NMR (300 MHz, DMSO-d$_6$) ppm: 7.44-7.58 (m, 10H), 7.22 (s, 1H), 7.12 (d, 1H), 7.03 (d, 1H), 3.62 (br, 4H), 1.71 (m, 4H), 1.40 (m, 4H), 0.88 (t, 6H).

Example 81

Preparation of cyclohexanecarboxylic acid (2,2-diphenyl-benzo[1,3]dioxol-5-yl)-amide

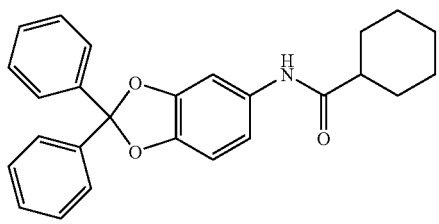

The title compound was produced in accordance with the general method of Example 78 from 2,2-diphenyl-1,3-benzodioxol-5-amine and cyclohexanecarboxylic acid chloride.

MS: m/e=400.5 ([M+H]$^+$).

NMR (300 MHz, DMSO-d$_6$) ppm: 9.71 (br, 1H, NH), 7.41-7.56 (m, 11H), 6.97 (d, 1H), 6.92 (d, 1H), 2.23 (br, 1H), 1.60-1.80 (m, 10H), 1.18-1.42 (m, 10H).

Example 82

Preparation of butane-1-sulfonic acid (2,2-diphenyl-benzo[1,3]dioxol-5-yl)-amide

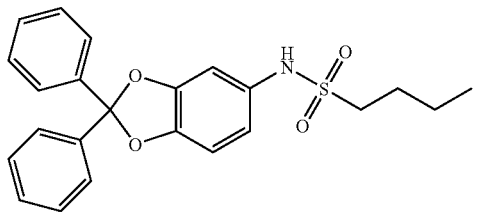

N,N-Bis(butylsulfonyl)-2,2-diphenyl-1,3-benzodioxol-5-amine (Example 80, 79 mg, 0.15 mmol) was dissolved in tetrahydrofuran (4 ml). Tetrabutylammonium fluoride solution in tetrahydrofuran (1M, 0.16 mL, 0.16 mmol) was added dropwise at room temperature and the solution was stirred at room temperature overnight. The reaction was heated to reflux for 30 minutes, poured into water and extracted twice with ethyl acetate. The combined organic layers were washed with saturated aqueous sodium chloride solution, dried over sodium sulfate, filtered and the solvent was evaporated in vacuo. The residue was purified by column chromatography using dichloromethane as the eluant. Crystallization from hexane yielded the product as white crystals (45 mg, 74%).

ISN-MS: m/e=408.2 ([M+H]$^-$, 100).

NMR (300 MHz, DMSO-d$_6$) ppm: 9.53 (br, 1H, NH), 7.55-7.42 (m, 10H), 6.98 (d, 1H), 6.90 (s, 1H), 6.69 (d, 1H), 3.00 (m, 2H), 1.59 (m, 2H), 0.804 (t, 3H).

Example 83

Preparation of N-(2,2-diphenyl-benzo[1,3]dioxol-5-yl)-butyramide

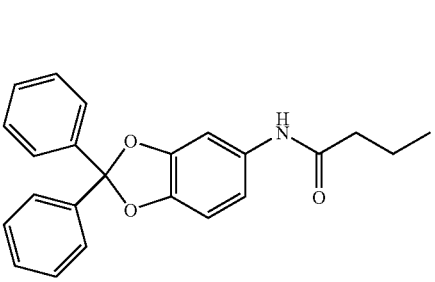

The title compound was produced in accordance with the general method of Example 78 from 2,2-diphenyl-1,3-benzodioxol-5-amine and butanoic acid chloride.

MS: m/e=360.3 ([M+H]$^+$.

NMR (300 MHz, DMSO-d$_6$) ppm: 9.78 (br, 1H, NH), 7.41-7.55 (m, 1H), 6.94 (m, 2H), 2.22 (t, 2H), 1.59 (m, 2H), 0.89 (t, 3H).

Example 84

Preparation of morpholine-4-carboxylic acid (2,2-diphenyl-benzo[1,3]dioxol-5-yl)-amide

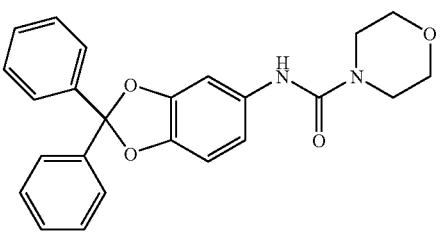

The title compound was produced in accordance with the general method of Example 78 from 2,2-diphenyl-1,3-benzodioxol-5-amine and 4-morpholincarbonylchloride.

MS: m/e=403.4 ([M+H]$^+$).

NMR (300 MHz, DMSO-d$_6$) ppm: 8.41 (br, 1H, NH), 7.40-7.55 (m, 10H), 7.21 (s, 1H), 6.89 (d, 1H), 6.83 (d, 1H), 3.58 (m, 4H), 3.37 (m, 4H).

Example 85

Preparation of piperidine-1-sulfonic acid (2,2-diphenyl-benzo[1,3]dioxol-5-yl)-amide

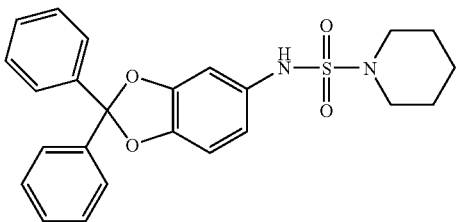

The title compound was produced in accordance with the general method of Example 78 from 2,2-diphenyl-1,3-benzodioxol-5-amine and piperidine-1-sulfonyl chloride.

MS: m/e=435.3 ([M+H]$^+$).

NMR (300 MHz, DMSO-d$_6$) ppm: 9.62 (br, 1H, NH), 7.41-7.55 (m, 10H), 6.97 (d, 1H), 6.87 (s, 1H), 6.68 (d, 1H), 3.04 (m, 4H), 1.37 (m, 6H).

Example 86

Preparation of piperidine-1-carboxylic acid (2,2-diphenyl-benzo[1,3]dioxol-5-yl)-amide

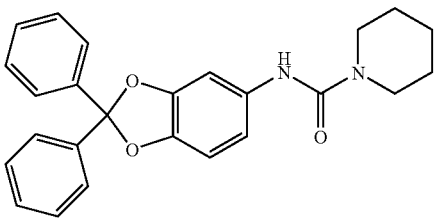

The title compound was produced in accordance with the general method of Example 78 from 2,2-diphenyl-1,3-benzodioxol-5-amine and piperidinecarbonyl chloride.

MS: m/e=401.4 ([M+H]$^+$).

NMR (300 MHz, DMSO-d$_6$) ppm: 8.30 (br, 1H, NH), 7.40-7.55 (m, 10H), 7.22 (d, 1H), 6.84 (m, 2H), 3.36 (m, 2H), 1.45-1.56 (m, 6H).

Example 87

Preparation of [2-(4-chloro-phenyl)-2-(2-fluoro-4-methoxy-phenyl)-benzo[1,3]dioxol-5-yl]-morpholin-4-yl-methanone

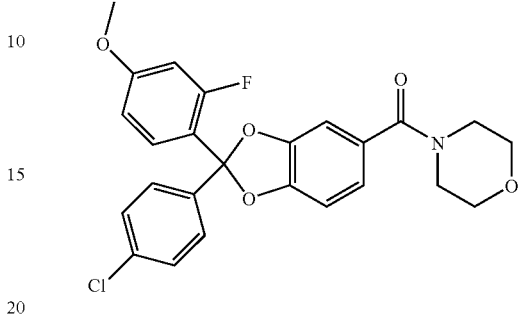

Preparation of (2,2-diphenyl-benzo[1,3]dioxol-5-yl)-morpholin-4-yl-methanone To a mixture of 1H-benzotriazol-1-yl 2,2-diphenyl-1,3-benzodioxole-5-carboxylate (300 mg, 0.689 mmol) in acetonitrile (2.0 mL) was added morpholine (100 mg, 1.15 mmol, 1.67 eq.) at 0° C. After 10 min, the cooling bath was removed and the reaction was stirred 3 h at 20° C. The reaction was partitioned between water and dichloromethane. The aqueous layer was extracted with dichloromethane. The combined organic layer was washed with brine and water and then dried in vacuo, affording the title compound (267 mg, quant.) as a white solid.

MS: m/e=388.4 ([M+H]$^+$).

1H-Benzotriazol-1-yl 2,2-diphenyl-1,3-benzodioxole-5-carboxylate was prepared according to literature procedures (EP 544166).

Preparation of (3,4-dihydroxy-phenyl)-morpholin-4-yl-methanone

To a cooled (0° C.) solution of (2,2-diphenyl-benzo[1,3]dioxol-5-yl)-morpholin-4-yl-methanone (270 mg, 0.7 mmol) in trifluoroacetic acid (4 mL) was added triethylsilane (160 mg, 1.38 mmol, 1.96 eq.). The reaction mixture was stirred 20 min at 0° C. The cooling bath was removed and the reaction mixture was stirred for 4 h at R.T. The reaction mixture was evaporated. Purification by flash chromatography afforded the title compound (147 mg, 95%) as a white solid.

MS: m/e=220.3 ([M–H]$^-$).

Preparation of (4-chloro-phenyl)-(2-fluoro-4-methoxy-phenyl)-methanone

Aluminium trichloride (144 g, 1.08 mol) was added to a cooled (0° C.) solution of nitrobenzene (450 mL). A solution of 4-chlorobenzoyl chloride (128.5 mL, 1 mol) in nitrobenzene (200 mL) was slowly added. 3-Fluoroanisole (108.5 mL, 0.95 mol) was slowly added. The reaction mixture was stirred overnight at 20° C., partitioned between ice water and ethyl acetate. The aqueous layer was extracted with ethyl acetate and the combined organic phase was washed with water, dried over sodium sulfate, filtered and concentrated in vacuo. The warm solution was poured onto cyclohexane. The solid was filtered, washed with cyclohexane and dried in vacuo, affording the title compound (104.5 g, 41%) as an off-white solid.

MS: m/e=264 ([M]$^+$)

Preparation of 4-chloro-2'-fluoro-4'-methoxy-dichlorodiphenylmethane

N,N-Dimethylformamide (0.031 mL, 0.4 mmol, 1 eq.) was added to a solution of (4-chloro-phenyl)-(2-fluoro-4-methoxy-phenyl)-methanone (106 mg, 0.4 mmol, 1 eq.) in thionyl chloride (0.6 mL). The reaction mixture was stirred under reflux for 18 h and the volatiles were removed in vacuo, affording the title compound as an orange oil (135 mg, 87%).

NMR (300 MHz, CDCl$_3$) ppm: 7.82 (dd, 1H), 7.56 (d, 2H), 7.32 (dd, 2H), 6.73 (dd, 1H), 6.63 (dd, 1H), 3.83 (s, 3H).

Preparation of [2-(4-chloro-phenyl)-2-(2-fluoro-4-methoxy-phenyl)-benzo[1,3]dioxol-5-yl]-morpholin-4-yl-methanone A solution of (3,4-dihydroxy-phenyl)-piperidin-1-yl-methanone (37.7 mg, 0.169 mmol) and 2-fluoro-4-methoxy-4'-chlorodiphenyldichloromethane (67.5 mg, 0.175 mmol) in toluene (1.7 mL) was heated at reflux, during 42 h. The reaction mixture was cooled down and adsorbed onto silica. Purification by flash chromatography afforded the title compound (46 mg, 58%) as a yellow semisolid.

MS: m/e=470.2 ([M+H]$^+$).

Example 88

Preparation of the 4-[2-(4-chloro-phenyl)-2-(2-fluoro-4-methoxy-phenyl)-benzo[1,3]dioxole-5-sulfonyl]-morpholine

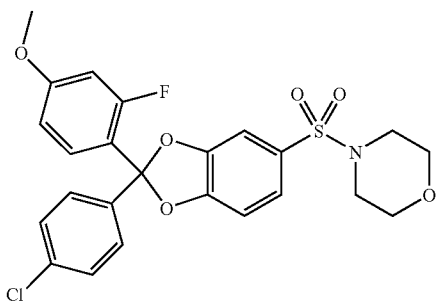

Preparation of 4-(2,2-diphenyl-benzo[1,3]dioxole-5-sulfonyl)-morpholine

To a solution of [3,4-[(diphenylmethylene)dioxy]phenyl] sulfonyl chloride (202 mg, 0.54 mmol) in tetrahydrofuran (2 mL) was added morpholine (52 mg, 0.596 mmol, 1.1 eq.) and potassium tert-butoxide (73 mg, 0.65 mmol, 1.2 eq.). The reaction mixture was stirred 48 h at 20° C. and partitioned between an aqueous solution of hydrochloric acid (1N) and dichloromethane. The aqueous phase was extracted with dichloromethane. The combined organic layer was washed with aqueous solutions of bicarbonate and brine. Purification by flash chromatography afforded the title compound (179 mg, 78%) as an off-white solid MS: m/e=424.5 ([M+H]$^+$).

[3,4-[(Diphenylmethylene)dioxy]phenyl]sulfonyl chloride was prepared according to literature procedures (EP 544166 and WO 9218490).

Preparation of 4-(morpholine-4-sulfonyl)-benzene-1,2-diol

The title compound was produced in accordance with the general method of Example 87b from 4-(2,2-diphenyl-benzo[1,3]dioxole-5-sulfonyl)-morpholine (Example 88a). Off-white solid.

MS: m/e=257.9 ([M–H]).

Preparation of 4-[2-(4-chloro-phenyl)-2-(2-fluoro-4-methoxy-phenyl)-benzo[1,3]dioxole-5-sulfonyl]-morpholine The title compound was produced in accordance with the general method of Example 87e from 4-(morpholine-4-sulfonyl)-benzene-1,2-diol (Example 88b) and 2-fluoro-4-methoxy-4'-chlorodiphenyldichloromethane (Example 87d). White solid.

MS: m/e=506.9 ([M+H]$^+$).

Example 89

Preparation of [2-(4-methoxy-phenyl)-2-(3-nitro-phenyl)-benzo[1,3]dioxol-5-yl]-morpholin-4-yl-methanone

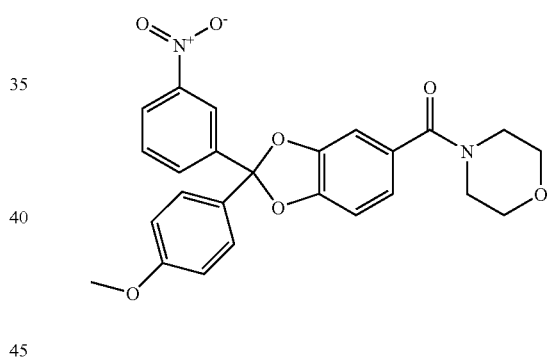

Preparation of (4-methoxyphenyl)-(3-nitrophenyl)-methanone

To a cold (0° C.) mixture of anisole (17.7 mL, 0.162 mol, 1.0 eq.) and aluminium trichloride (26.9 g, 0.202 mol, 1.25 eq.) in 1,2-dichloroethane (140 mL) was slowly added 3-nitrobenzoylchloride (30 g, 0.162 mol). The cooling bath was removed, and the reaction mixture was stirred 2 h at 20° C. The reaction mixture was poured into ice water. Concentrated hydrochloric acid (5 mL) was added. The aqueous layer was extracted with dichloromethane (2 times). The combined organic layers were dried over sodium sulfate, filtered and the volatiles were removed in vacuo. Purification by flash chromatography afforded the title compound (35.1 g, 84%) as an orange solid, m.p.: 88-89° C.

Preparation of 4-methoxy-3'-nitro-dichlorodiphenylmethane

The title compound was produced in accordance with the general method of Example 87d from (4-methoxyphenyl)-(3-nitrophenyl)-methanone (Example 89a). Yellow oil.

NMR (300 MHz, CDCl₃) ppm: 8.53-8.52 (m, 1H), 8.23 (dd, 1H), 7.95 (dd, 1H), 7.59-7.50 (m, 3H), 6.89 (d, 2H), 3.85 (s, 3H).

Preparation of [2-(4-methoxy-phenyl)-2-(3-nitro-phenyl)-benzo[1,3]dioxol-5-yl]-morpholin-4-yl-methanone The title compound was produced in accordance with the general method of Example 87e from (3,4-dihydroxy-phenyl)-morpholine-1-yl-methanone (Example 87b) and 4-methoxy-3'-nitro-dichlorodiphenylmethane (Example 89b). White foam.
MS: m/e=463.3([M+H]⁺).

Example 90

Preparation of [4-[2-(4-methoxy-phenyl)-2-(3-nitro-phenyl)-benzo[1,3]dioxole-5-sulfonyl]-morpholine

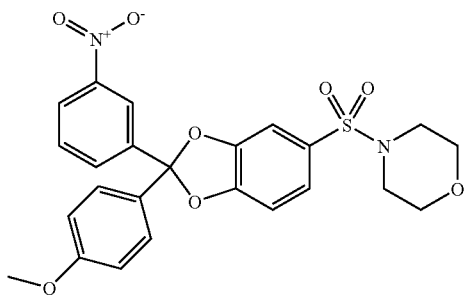

The title compound was produced in accordance with the general method of Example 108c from 4-(Morpholine-4-sulfonyl)-benzene-1,2-diol (Example 88b) and 4-methoxy-3'-nitro-dichlorodiphenylmethane (Example 89b). Light yellow oil.
MS: m/e=499 ([M+H]⁺).

Example 91

Preparation of [4-[2-(4-methoxy-phenyl)-5-(morpholine-4-carbonyl)-benzo[1,3]dioxol-2-yl]-benzonitrile

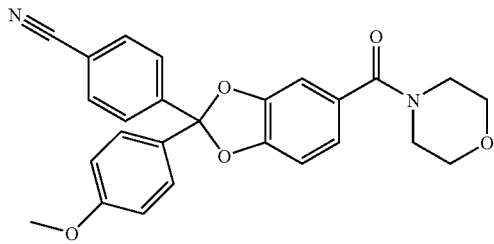

Preparation of 4-(4-methoxy-benzoyl)-benzonitrile

The title compound was produced in accordance with the general method of Example 87d from 4-(4-methoxy-benzoyl)-benzonitrile. Yellow oil. NMR (300 MHz, CDCl₃) ppm: 7.70-7.60 (m, 4H), 7.43 (d, 2H), 6.82 (d, 2H), 3.77 (s, 3H).

Preparation of 4-cyano-4-methoxy-dichlorodiphenylmethane

The title compound was produced in accordance with the general method of Example 87d from 4-(4-methoxy-benzoyl)-benzonitrile (Example 91a). Yellow oil.
MS: m/e=443.4 ([M+H]⁺).

Preparation of 4-[2-(4-methoxy-phenyl)-5-(morpholine-4-carbonyl)-benzo[1,3]dioxol-2-yl]-benzonitrile The title compound was produced in accordance with the general method of Example 87e from (3,4-dihydroxy-phenyl)-morpholine-1-yl-methanone (Example 87b) and 4-cyano-4-methoxy-dichlorodiphenylmethane (Example 91b). Yellow oil
MS: m/e=443.4 ([M+H]⁺).

Example 92

Preparation of 4-[2-(4-methoxy-phenyl)-5-(morpholine-4-sulfonyl)-benzo[1,3]dioxol-2-yl]-benzonitrile

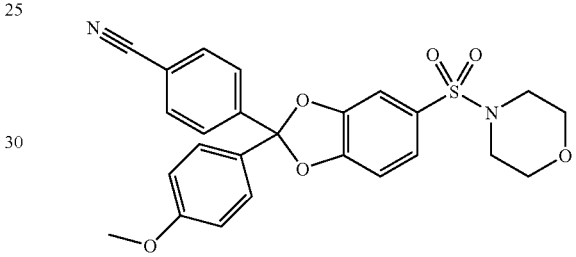

The title compound was produced in accordance with the general method of Example 88c from 4-(morpholine-4-sulfonyl)-benzene-1,2-diol (Example 88b) and 4-cyano-4-methoxy-dichlorodiphenylmethane (Example 91b). Off-white foam.
MS: m/e=479.3 ([M+H]⁺).

Example 93

Preparation of [2-(2-fluoro-4-methoxy-phenyl)-2-(4-fluoro-phenyl)-benzo[1,3]dioxol-5-yl]-morpholin-4-yl-methanone

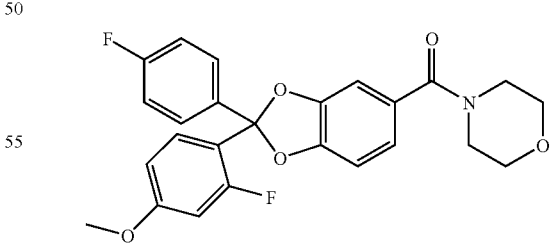

Preparation of (2-fluoro-4-methoxy-phenyl)-(4-fluoro-phenyl)-methanone

To a cold (5° C.) mixture of aluminium trichloride (144 g, 1.08 mol, 1.13 eq.) in nitrobenzene (450 mL) was slowly added a solution of 4-fluorobenzoyl chloride (120 mL, 1 mol, 1.05 eq.) in nitrobenzene (200 mL). 3-fluoroanisole (108.5 mL, 0.95 mol) was slowly added to the reaction mixture. The cooling bath was removed and the reaction mixture was stirred 3 h at 20° C., and poured into ice-water. The aqueous layer was extracted with dichloromethane (2 times). The combined organic layers were dried over sodium sulfate, filtered and the volatiles were removed in vacuo. The crude mixture was crystallized in cyclohexane, filtered and the solid was washed with cyclohexane. The solid was dried in vacuo, affording the title compound (57.78 g, 25%) as a white solid.

m.p.: 89.7-90.1° C.

Preparation of 2-fluoro-4-methoxy-4'-fluoro-dichlorodiphenylmethane

The title compound was produced in accordance with the general method of Example 87d from (2-fluoro-4-methoxy-phenyl)-(4-fluoro-phenyl)-methanone (Example 93a). Yellow semisolid.

MS: m/e=304.2 ([M+H]$^+$).

Preparation of [2-(2-fluoro-4-methoxy-phenyl)-2-(4-fluoro-phenyl)-benzo[1,3]dioxol-5-yl]-morpholin-4-yl-methanone The title compound was produced in accordance with the general method of Example 87e from (3,4-dihydroxy-phenyl)-morpholine-1-yl-methanone (Example 87b) and 2-fluoro-4-methoxy-4'-fluoro-dichlorodiphenylmethane (Example 93b). Brown oil.

MS: m/e=454.5 ([M+H]$^+$).

Example 94

Preparation of 4-[2-(2-fluoro-4-methoxy-phenyl)-2-(4-fluoro-phenyl)-benzo[1,3]dioxole-5-sulfonyl]-morpholine

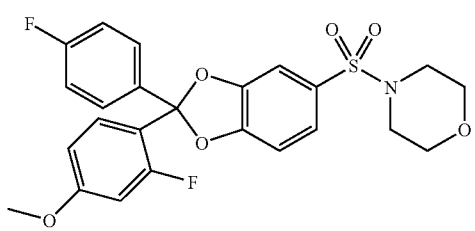

The title compound was produced in accordance with the general method of Example 88c from 4-(morpholine-4-sulfonyl)-benzene-1,2-diol (Example 88b) and 2-fluoro-4-methoxy-4'-fluoro-dichlorodiphenylmethane (Example 93b). White foam.

MS: m/e=490.3 ([M+H]$^+$).

Example 95

Preparation of (6-fluoro-2,2-diphenyl-benzo[1,3]dioxol-5-yl)-piperidin-1-yl-methanone

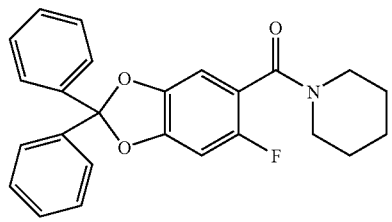

Preparation of 2-fluoro-4,5-dihydroxy-benzaldehyde

To a cooled (−78° C.) solution of 6-fluoroveratraldehyde (2 g, 10.9 mmol) in dichloromethane (40 mL) was added a solution of boron tribromide in dichloromethane (1M, 44 mL, 44 mmol, 4.0 eq.). The reaction was allowed to reach room temperature and was stirred overnight. The reaction mixture was partitioned between ice water and diethyl ether. The aqueous layer was extracted with diethyl ether. The combined organic layer was washed with water dried over sodium sulfate and filtered. Volatiles were removed in vacuo. Purification by flash chromatography afforded the title compound (1.71 mg, quant.) as a dark solid MS: m/e=156.0 ([M]$^+$).

Preparation of 4,5-bis-benzyloxy-2-fluoro-benzaldehyde

To a solution of 2-fluoro-4,5-dihydroxy-benzaldehyde (44.0 g, 282 mmol) in acetone (1 L) was added potassium carbonate (39.0 g, 0.282 mmol, 1.0 eq.) and benzylbromide (33.5 mL, 0.282 mmol, 1.0 eq.). The reaction mixture was stirred overnight at 20° C. The mixture was filtered on a pad of dicalite. After evaporation, purification by flash chromatography afforded the title compound (5.34 g, 6%) as a white solid.

MS: m/e=336.1 ([M]).

Preparation of 4,5-bis-benzyloxy-2-fluoro-benzoic acid

To a cold (0° C.) solution of 4,5-bis-benzyloxy-2-fluoro-benzaldehyde (2.15 g, 6.39 mmol) in acetone (86.0 mL) was slowly added Jones reagent (4.3 mL). The reaction mixture was stirred 19 h at 0° C. Propanol (0.43 mL) was added and the reaction mixture was stirred 40 min at 20° C. The crude mixture was filtered, washed with acetone and poured into water (50 mL). The solid was filtered, washed with water and dried in vacuo, yielding the title compound (1.82 g, 81%) as a white solid.

MS: m/e=351.1 ([M−H]$^-$)

Jones' reagent: to a cold (0° C.) solution of chromium oxide (826 mg, 8.3 mmol) in water (1.3 mL) was slowly added concentrated sulfuric acid (0.86 mL). The solution was diluted with water (2.15 mL).

Preparation of (4,5-bis-benzyloxy-2-fluoro-phenyl)-piperidin-1-yl-methanone

The title compound was produced in accordance with the general method of Example 108e from 4,5-bis-benzyloxy-2-fluoro-benzoic acid (Example 95c) and piperidine. White solid.

MS: m/e=420.5 ([M+H]⁺).

Preparation of (2-fluoro-4,5-dihydroxy-phenyl)-piperidin-1-yl-methanone

The title compound was produced in accordance with the general method of Example 87b from (4,5-bis-benzyloxy-2-fluoro-phenyl)-piperidin-1-yl-methanone (Example 95d). Colorless semisolid.

MS: m/e=240.2 ([M+H]⁺).

Preparation of (6-fluoro-2,2-diphenyl-benzo[1,3]dioxol-5-yl)-piperidin-1-yl-methanone The title compound was produced in accordance with the general method of Example 108c from (2-fluoro-4,5-dihydroxy-phenyl)-piperidin-1-yl-methanone (Example 95e) and dichlorodiphenylmethane. Colorless semisolid.

MS: m/e=404.3 ([M+H]⁺).

Example 96

Preparation of [2-(2,4-dichloro-phenyl)-6-fluoro-2-(4-fluoro-phenyl)-benzo[1,3]dioxol-5-yl]-piperidin-1-yl-methanone

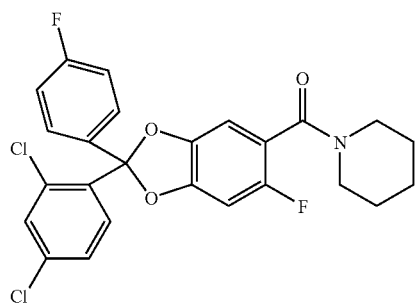

The title compound was produced in accordance with the general method of Example 108c from (2-fluoro-4,5-dihydroxy-phenyl)-piperidin-1-yl-methanone (Example 95e) and 2,4-dichloro-4'-fluoro-chlorodiphenyldichloromethane (Example 108b). White solid.

MS: m/e=404.3([M−C₅H₁₀N*]⁺)

Example 97

Preparation of [6-fluoro-2-(4-fluoro-phenyl)-2-phenyl-benzo[1,3]dioxol-5-yl]-piperidin-1-yl-methanone

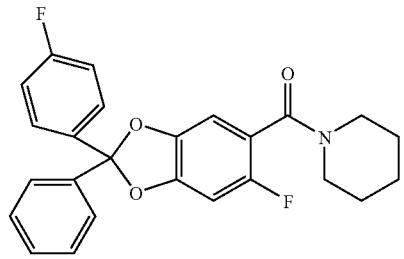

Preparation of 4-fluorodiphenyldichloromethane

The title compound was produced in accordance with the general method of Example 108b from benzotrifluoride and fluorobenzene. Yellow oil.

NMR (300 MHz, CDCl₃) ppm: 7.63-7.57 (m, 4H), 7.38-7.35 (m, 3H), 7.06-7.00 (m, 2H).

Preparation of [6-fluoro-2-(4-fluoro-phenyl)-2-phenyl-benzo[1,3]dioxol-5-yl]-piperidin-1-yl-methanone The title compound was produced in accordance with the general method of Example 108c from (2-fluoro-4,5-dihydroxy-phenyl)-piperidin-1-yl-methanone (Example 95e) and 4-fluorodiphenyldichloromethane (Example 97a). White solid.

MS: m/e=422.2 ([M+H]⁺).

Example 98

Preparation of [2-(2-chloro-phenyl)-6-fluoro-2-(4-methoxy-phenyl)-benzo[1,3]dioxol-5-yl]-piperidin-1-yl-methanone

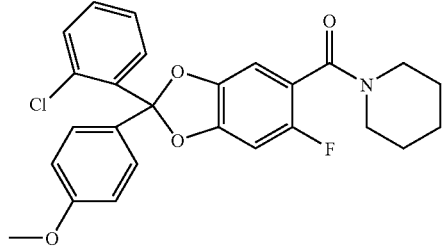

Preparation of 2-chloro-4'-methoxy-diphenyldichloromethane

The title compound was produced in accordance with the general method of Example 108b from 2-chlorobenzotrifluoride and anisole. Brown oil.

NMR (300 MHz, CDCl₃) ppm: 7.46-7.35 (m, 6H), 6.85 (d, 2H), 3.83 (s, 3H).

Preparation of [2-(2-chloro-phenyl)-6-fluoro-2-(4-methoxy-phenyl)-benzo[1,3]dioxol-5-yl]-piperidin-1-yl-methanone The title compound was produced in accordance with the general method of Example 108c from [2-(2-chloro-phenyl)-6-fluoro-2-(4-methoxy-phenyl)-benzo[1,3]dioxol-5-yl]-piperidin-1-yl-methanone (Example 95e) and 2-chloro-4'-methoxy-diphenyldichloromethane (Example 98a). White solid.

MS: m/e=468.1 ([M+H]$^+$).

Example 99

Preparation of (6-fluoro-2,2-diphenyl-benzo[1,3]dioxol-5-yl)-morpholin-4-yl-methanone

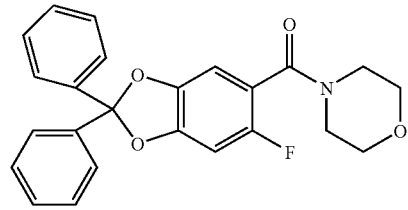

Preparation of (4,5-bis-benzyloxy-2-fluoro-phenyl)-morpholin-4-yl-methanone

The title compound was produced in accordance with the general method of Example 108e from 4,5-bis-benzyloxy-2-fluoro-benzoic acid (Example 95c) and morpholine. White solid.

MS: m/e=421.1 ([M+H]$^+$).

Preparation of (2-fluoro-4,5-dihydroxy-phenyl)-morpholin-4-yl-methanone

The title compound was produced in accordance with the general method of Example 87b from (4,5-bis-benzyloxy-2-fluoro-phenyl)-morpholin-4-yl-methanone (Example 99a). White solid.

MS: m/e=242.2 ([M+H]$^+$).

Preparation of (6-fluoro-2,2-diphenyl-benzo[1,3]dioxol-5-yl)-morpholin-4-yl-methanone The title compound was produced in accordance with the general method of Example 108c from (2-fluoro-4,5-dihydroxy-phenyl)-morpholin-4-yl-methanone (Example 99b) and dichlorodiphenylmethane. White solid.

MS: m/e=406.2 ([M+H]$^+$).

Example 100

Preparation of [6-fluoro-2-(4-fluoro-phenyl)-2-phenyl-benzo[1,3]dioxol-5-yl]-morpholin-4-yl-methanone

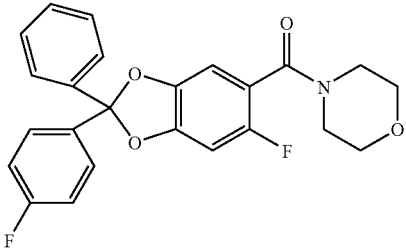

The title compound was produced in accordance with the general method of Example 108c from (2-fluoro-4,5-dihydroxy-phenyl)-morpholin-4-yl-methanone (Example 99b) and 4-fluorodiphenyldichloromethane (Example 97a). White solid.

MS: m/e=424.3 ([M+H]$^+$).

Example 101

Preparation of [2-(2-chloro-phenyl)-6-fluoro-2-(4-methoxy-phenyl)-benzo[1,3]dioxol-5-yl]-morpholin-4-yl-methanone

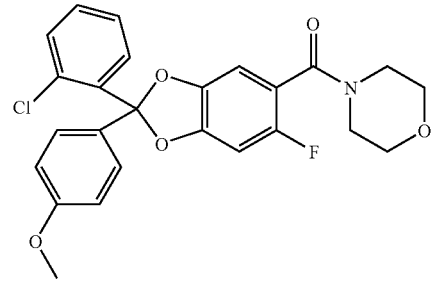

The title compound was produced in accordance with the general method of Example 108c from (2-fluoro-4,5-dihydroxy-phenyl)-morpholin-4-yl-methanone (Example 99b) and 2-chloro-4'-methoxy-diphenyldichloromethane (Example 98a). White solid.

MS: m/e=424.3 ([M+H]$^+$).

Example 102

Preparation of (6-fluoro-2,2-diphenyl-benzo[1,3]dioxol-5-yl)-[4-(4-fluoro-phenyl)-piperazin-1-yl]-methanone

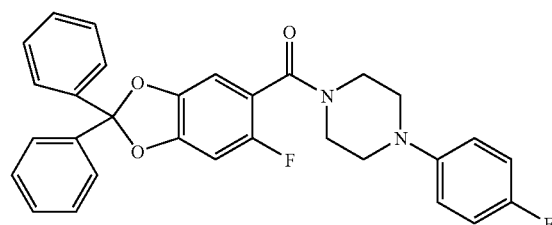

Preparation of (4,5-bis-benzyloxy-2-fluoro-phenyl)-[4-(4-fluoro-phenyl)-piperazin-1-yl]-methanone The title compound was produced in accordance with the general method of Example 108e from 4,5-bis-benzyloxy-2-fluoro-benzoic acid (Example 95c) and 1-(4-fluorophenyl)piperazine. Light yellow solid.

MS: m/e=514.6 ([M+H]$^+$).

Preparation of (2-fluoro-4,5-dihydroxy-phenyl)-[4-(4-fluoro-phenyl)-piperazin-1-yl]-methanone The title compound was produced in accordance with the general method of Example 87b from (4,5-bis-benzyloxy-2-fluoro-phenyl)-[4-(4-fluoro-phenyl)-piperazin-1-yl]-methanone (Example 102a). White solid.

MS: m/e=335.2 ([M+H]$^+$).

Preparation of (6-fluoro-2,2-diphenyl-benzo[1,3]dioxol-5-yl)-[4-(4-fluoro-phenyl)-piperazin-1-yl]-methanone The title compound was produced in accordance with the general method of Example 108c from (2-fluoro-4,5-dihydroxy-phenyl)-[4-(4-fluoro-phenyl)-piperazin-1-yl]-methanone (Example 102b) and dichlorodiphenylmethane. Light brown solid.

MS: m/e=499.2 ([M+H]$^+$).

Example 103

Preparation of [6-fluoro-2-(4-fluoro-phenyl)-2-phenyl-benzo[1,3]dioxol-5-yl]-[4-4-fluoro-phenyl)-piperazin-1-yl]-methanone

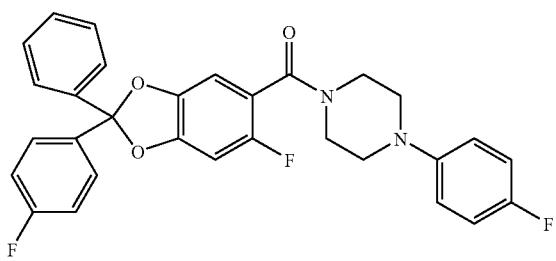

The title compound was produced in accordance with the general method of Example 108c from (2-fluoro-4,5-dihydroxy-phenyl)-[4-(4-fluoro-phenyl)-piperazin-1-yl]-methanone (Example 102b) and 4-fluorodiphenyldichloromethane (Example 97a). Grey solid.

MS: m/e=517.2 ([M+H]$^+$).

Example 104

Preparation of [2-(2-chloro-phenyl)-6-fluoro-2-(4-methoxy-phenyl)-benzo[1,3]dioxol-5-yl]-[4-(4-fluoro-phenyl)-piperazin-1-yl]-methanone

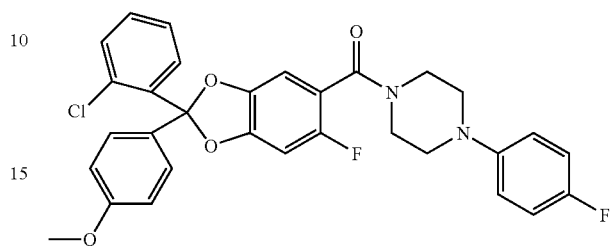

The title compound was produced in accordance with the general method of Example 108c from (2-fluoro-4,5-dihydroxy-phenyl)-[4-(4-fluoro-phenyl)-piperazin-1-yl]-methanone (Example 102b) and 2-chloro-4'-methoxy-diphenyldichloromethane (Example 98a). Orange solid.

MS: m/e=563.2 ([M]$^+$).

Example 105

Preparation of [2-(2,4-dichloro-phenyl)-6-fluoro-2-(4-methoxy-phenyl)-benzo[1,3]dioxol-5-yl]-piperidin-1-yl-methanone

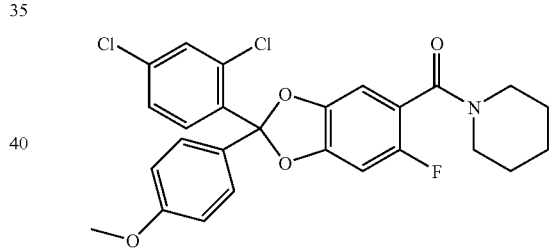

Preparation of 2,4-dichloro-4'-methoxy-diphenyldichloromethane

The title compound was produced in accordance with the general method of Example 108b from 2,4-dichlorobenzotrifluoride and anisole. Red oil.

NMR (300 MHz, CDCl$_3$) ppm: 8.22 (d, 1H), 7.43-7.29 (m, 4H), 6.85 (d, 2H), 3.73 (s, 3H).

Preparation of [2-(2,4-dichloro-phenyl)-6-fluoro-2-(4-methoxy-phenyl)-benzo[1,3]dioxol-5-yl]-piperidin-1-yl-methanone The title compound was produced in accordance with the general method of Example 108c from (2-fluoro-4,5-dihydroxy-phenyl)-piperidin-1-yl-methanone (Example 95e) and 2,4-dichloro-4'-methoxy-diphenyldichloromethane (Example 105a). Orange oil.

MS: m/e=502.3 ([M+H]$^+$).

Example 106

Preparation of [2-(2,4-dichloro-phenyl)-6-fluoro-2-(4-methoxy-phenyl)-benzo[1,3]dioxol-5-yl]-morpholin-4-yl-methanone

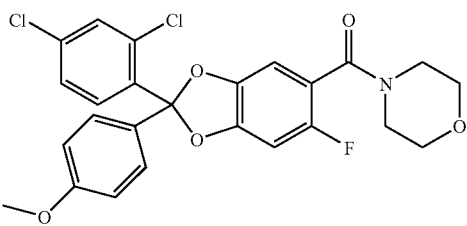

The title compound was produced in accordance with the general method of Example 108c from (2-fluoro-4,5-dihydroxy-phenyl)-morpholin-4-yl-methanone (Example 99b) and 2,4-dichloro-4'-methoxy-diphenyldichloromethane (Example 105a). Yellow oil.

MS: m/e=504.3 ([M+H]$^+$).

Example 107

Preparation of [2-(2,4-dichloro-phenyl)-6-fluoro-2-(4-methoxy-phenyl)-benzo[1,3]dioxol-5-yl]-[4-(4-fluoro-phenyl)-piperazin-1-yl]-methanone

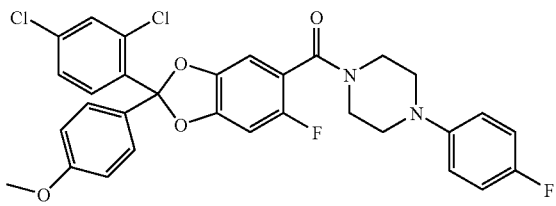

The title compound was produced in accordance with the general method of Example 108c from (2-fluoro-4,5-dihydroxy-phenyl)-[4-(4-fluoro-phenyl)-piperazin-1-yl]-methanone (Example 102b) and 2,4-dichloro-4'-methoxy-diphenyldichloromethane (Example 105a). Brown oil.

MS: m/e=597.2 ([M]$^+$).

Example 108

Preparation of [2-(2,4-dichloro-phenyl)-6-fluoro-2-(4-fluoro-phenyl)-benzo[1,3]dioxol-5-yl]-morpholin-4-yl-methanone

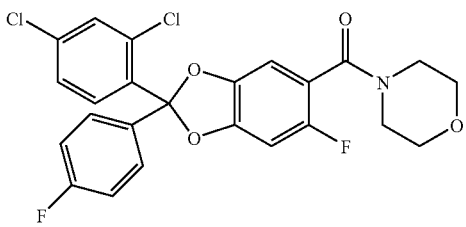

Preparation of 4-bromo-5-fluoro-benzene-1,2-diol

To a cooled (−78° C.) solution of 4-fluoroveratrole (5.0 g, 32 mmol) in dichloromethane (106 mL) was slowly added a solution of tribromoborane in dichloromethane (1M, 96 mL, 96 mmol, 3.0 eq.). The reaction mixture was warmed to 20° C. and stirred overnight. The reaction mixture was poured into ice water, extracted with ethyl acetate (3 times). The combined organic layer was washed with an aqueous solution of sodium bicarbonate, dried over sodium sulfate and filtered. The volatiles were removed in vacuo. The brown solid was diluted with chloroform (50 mL) and dichloromethane (10 mL). A solution of bromine in carbon tetrachloride (5 ml) was slowly added. After 3 hours, the volatiles were removed in vacuo. Purification by flash chromatography afforded the title compound (6.51 g, 98%) as a brown solid MS: m/e=207.9 ([M+H]$^+$).

Preparation of 2,4-dichloro-4'-fluoro-diphenyldichloromethane

To a cooled (0° C.) suspension of aluminium trichloride (2.02 g, 15 mmol, 3.0 eq.) in 1,2-dichloroethane (7 mL) was slowly added 2,4-dichlorobenzotrifluoride (1.1 g, 5 mmol) followed by fluorobenzene (0.483 g, 5 mmol, 1.0 eq.). The reaction mixture was stirred at 0-5° C. for 5 h, then poured onto ice and extracted with dichloromethane. The combined organic layer was washed with brine, dried over sodium sulfate and filtered. The volatiles were removed in vacuo, affording the title compound (1.63 g, quant.) as yellow oil.

MS: m/e=325.0 ([M+H]$^+$).

Preparation of 5-bromo-2-(2,4-dichloro-phenyl)-6-fluoro-2-(4-fluoro-phenyl)-benzo[1,3]dioxole A mixture of 4-bromo-5-fluoro-benzene-1,2-diol (6.43 g, 31.1 mmol) and 2,4-dichloro-4'-fluoro-chlorodiphenyldichloromethane (10.07 g, 31.1 mmol, 1.0 eq.) was heated under stirring at 180° C. for 20 min. The reaction mixture was cooled to 20° C., diluted with dichloromethane and adsorbed onto silica. Purification by flash chromatography afforded the title compound (9.98 g, 70%) as a light yellow solid.

MS: m/e=457.9 ([M+H]$^+$).

Preparation of [2-(2,4-dichloro-phenyl)-6-fluoro-2-(4-fluoro-phenyl)-benzo[1,3]dioxole-5-carboxylic acid To a cooled (-78° C.) solution of 5-bromo-2-(2,4-dichloro-phenyl)-6-fluoro-2-(4-fluoro-phenyl)-benzo[1,3]dioxole (16.5 g, 36.0 mmol) in diethyl ether (250 mL) was slowly added a solution of n-butyl lithium in hexanes (1.6M, 23 mL, 36.0 mmol, 1.0 eq.). After 1 h at −78° C., solid carbon dioxide (50 g approx.) was added to the solution and the reaction was allowed to warm up to 20° C. After 16 h at 20° C. the reaction mixture was partitioned between water (150 mL), ethyl acetate (1.5 L) and hydrochloric acid (1N, 150 mL). The aqueous layer was extracted with ethyl acetate and the combined organic layers were washed with water. The volatiles were removed in vacuo. Purification by flash chromatography afforded the title compound (10.73 g, 69%) as a light yellow solid.

MS: m/e=422.3 ([M−H]$^-$).

Preparation of [2-(2,4-dichloro-phenyl)-6-fluoro-2-(4-fluoro-phenyl)-benzo[1,3]dioxol-5-yl]-morpholin-4-yl-methanone To a solution of [2-(2,4-dichloro-phenyl)-6-fluoro-2-(4-fluoro-phenyl)-benzo[1,3]dioxole-5-carboxylic acid (380 mg, 0.898 mmol) in N,N-dimethylformamide (7 mL) was added carbonyldiimidazole (189 mg, 1.17 mmol, 1.3 eq.). The reaction mixture was stirred 16 h at 20° C.

Morpholine (196 mg, 2.24 mmol, 2.5 eq.) was added and the reaction was stirred 8 h at 90° C. The reaction mixture was partitioned between hydrochloric acid (1N) and ethyl acetate. The organic layer was washed with brine and water the volatiles were removed in vacuo. Purification by flash chromatography afforded the title compound (367 mg, 83%) as a white solid.

MS: m/e=493.43 ([M+H]$^+$).

Example 110

Preparation of (6-methyl-2,2-diphenyl-benzo[1,3]dioxol-5-yl)-piperidin-1-yl-methanone

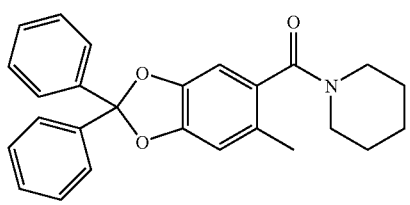

Preparation of 4-bromo-5-methylpyrocatechol

To a solution of homoveratrole (136.4 g, 1.1 mol) in chloroform (1.2 L) and dichloromethane (300 mL) was slowly added a solution of bromine (66 mL, 1.28 mol, 1.2 eq.) in carbon tetrachloride (250 mL). After 5 hours the reaction mixture was neutralized to pH7 with an aqueous solution of sodium hydroxide and the aqueous layer was extracted with chloroform. The combined organic layer was dried over sodium sulfate, filtered, and the volatiles were removed in vacuo, affording the title compound as a light brown solid, m.p.: 92-98° C.

Preparation of 5-bromo-6-methyl-2,2-diphenyl-benzo[1,3]dioxole

The title compound was produced in accordance with the general method of Example 108c from 4-bromo-5-methylpyrocatechol and diphenyldichloromethane. White solid.

MS: m/e=368.0 ([M+H$^+$]).

Preparation of 6-methyl-2,2-diphenyl-1,3-benzodioxole-5-carboxylic acid lithium salt To a cold (−70° C.) solution of 5-bromo-6-methyl-2,2-diphenyl-benzo[1,3]dioxole (Example 110b, 91.8 g, 250 mmol) in tetrahydrofuran (140 mL) was slowly added a solution of n-butyl lithium in hexanes (170 mL, 1.6 M, 1.1 eq.) and tetrahydrofuran (100 mL). After 15 min, an excess of solid carbon dioxide was added. The reaction was allowed to warm to room temperature. The solid was filtered and dried in vacuo, affording the title compound (79.4 g, 77%) as a white solid.

MS: m/e=345.2 ([M +2Li]).

Preparation of (6-methyl-2,2-diphenyl-benzo[1,3]dioxol-5-yl)-piperidin-1-yl-methanone To a solution of 6-methyl-2,2-diphenyl-1,3-benzodioxole-5-carboxylic acid lithium salt (101.5 mg, 0.3 mmol) in N,N-dimethylformamide (3 mL) was added N,N,N',N'-tetramethyl-O-(1H-benzotriazol-1-yl)-uronium-hexafluorophosphate (114 mg, 0.3 mmol, 1.0 eq.). The reaction mixture was stirred 1 h at 20° C. Piperidine (26 mg, 0.3 mmol, 1.0 eq.) was added and the reaction mixture was stirred 20 h at 20° C. The reaction mixture was partitioned between ethyl acetate and water. The aqueous layer was extracted with ethyl acetate. The combined organic layer was washed with water, brine and then dried over sodium sulfate, filtered and evaporated. Purification by flash chromatography afforded the title compound (73 mg, 61%) as a light yellow solid.

MS: m/e=400.2

Example 111

Preparation of [6-fluoro-2,2-bis-(4-fluoro-phenyl)-benzo[1,3]dioxol-5-yl]-morpholin-4-yl-methanone

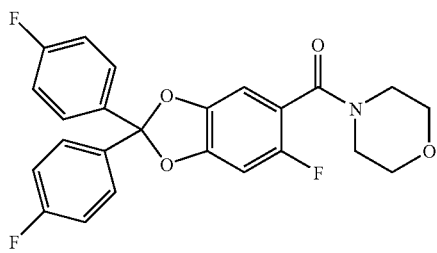

Preparation of 4,4'-difluoro-diphenyldichloromethane

The title compound was produced in accordance with the general method of Example 88d from 4,4'-difluorobenzophenone. Yellow oil.

MS: m/e=272 ([M−H]$^+$).

Preparation of [6-fluoro-2,2-bis-(4-fluoro-phenyl)-benzo[1,3]dioxol-5-yl]-morpholin-4-yl-methanone The title compound was produced in accordance with the general method of Example 108c from (3,4-dihydroxy-phenyl)-morpholin-4-yl-methanone (Example 87b) and 4,4'-difluoro-diphenyldichloromethane (Example 111a). White foam.

MS: m/e=442.3 ([M+H]$^+$).

Example 112

Preparation of (6-bromo-2,2-diphenyl-benzo[1,3]dioxol-5-yl)-piperidin-1-yl-methanone

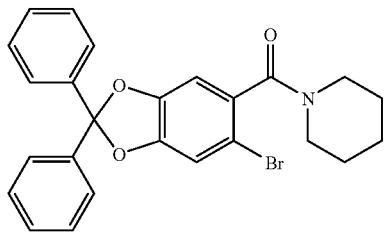

Preparation of 6-bromo-2,2-diphenyl-benzo[1,3]dioxole-5-carboxylic acid

To a solution of 5-bromo-6-methyl-2,2-diphenyl-benzo[1,3]dioxole (5.20 g, 14.1 mmol, Example 110b) in pyridine (52 mL) and water (26 mL) was added potassium permanganate (6.71 g, 42.5 mmol, 3.0 eq.) at room temperature. After 3 hours, the reaction mixture was partitioned between ethyl acetate and hydrochloric acid (1N). The aqueous layer was extracted with ethyl acetate. After evaporation, the residue was adsorbed onto silica. Purification by flash chromatography afforded the title compound (4.656 g, 83%) as an off white solid.

MS: m/e=395.0 ([M–H]−).

Preparation of (6-bromo-2,2-diphenyl-benzo[1,3]dioxol-5-yl)-piperidin-1-yl-methanone The title compound was produced in accordance with the general method of Example 108e from 6-bromo-2,2-diphenyl-benzo[1,3]dioxole-5-carboxylic acid (Example 112a) and piperidine. White solid.

MS: m/e=464.1 ([M+H]+)

Example 113

Preparation of (+)-[2-(2,4-dichloro-phenyl)-6-fluoro-2-(4-fluoro-phenyl)-benzo[1,3]dioxol-5-yl]-morpholin-4-yl-methanone The title compound was produced by preparative chiral HPLC (ChiralPak AD) from racemic [2-(2,4-dichloro-phenyl)-6-fluoro-2-(4-fluoro-phenyl)-benzo[1,3]dioxol-5-yl]-morpholin-4-yl-methanone (Example 108e). White solid.

MS: m/e=493.3 ([M+H]+).

Example 114

Preparation of (−)-[2-(2,4-dichloro-phenyl)-6-fluoro-2-(4-fluoro-phenyl)-benzo[1,3]dioxol-5-yl]-morpholin-4-yl-methanone The title compound was produced by preparative chiral HPLC (ChiralPak AD) from racemic [2-(2,4-dichloro-phenyl)-6-fluoro-2-(4-fluoro-phenyl)-benzo[1,3]dioxol-5-yl]-morpholin-4-yl-methanone (Example 108e). White solid.

MS: m/e=493.3 ([M+H]+).

Example 115

Preparation of [2-(2,4-dichloro-phenyl)-2-(4-fluoro-phenyl)-benzo[1,3]dioxol-5-yl]-morpholin-4-yl-methanone

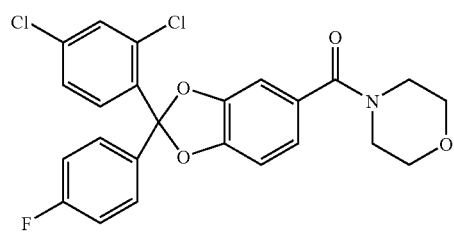

The title compound was produced in accordance with the general method of Example 108c from 2,4-dichloro-4'-fluoro-diphenyldichloromethane (Example 108b) and (3,4-dihydroxy-phenyl)-morpholin-4-yl-methanone (Example 87b). Light yellow gum.

MS: m/e=474.1 ([M+H]+).

Example 116

Preparation of [2-(2,4-dichloro-phenyl)-2-(4-fluoro-phenyl)-benzo[1,3]dioxol-5-yl]-piperidin-1-yl-methanone

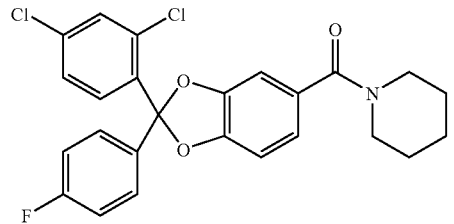

The title compound was produced in accordance with the general method of Example 108c from 2,4-dichloro-4'-fluoro-diphenyldichloromethane (Example 108b) and (3,4-dihydroxy-phenyl)-piperidin-4-yl-methanone. Light yellow gum.

MS: m/e=472.2 ([M+H]+).

Example 117

Preparation of (6-chloro-2,2-diphenyl-benzo[1,3]dioxol-5-yl)-piperidin-1-yl-methanone

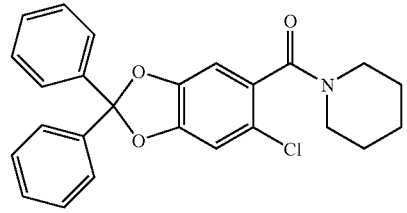

Preparation of (6-chloro-benzo[1,3]dioxol-5-yl)-piperidin-4-yl-methanone

The title compound was produced in accordance with the general method of Example 218c from 6-chloro-1,3-benzodioxole-5-carboxylic acid and piperidine. Colorless solid, m.p.: 138-139° C.
MS: m/e=267.9 ([M+H]$^+$).

Preparation of (2-chloro-4,5-dihydroxy-phenyl)-piperidin-4-yl-methanone

The title compound was produced in accordance with the general method of Example 218b from (6-chloro-benzo[1,3]dioxol-5-yl)-piperidin-4-yl-methanone (Example 117a). Light grey solid.
MS: m/e=256.1 ([M+H]$^+$).

Preparation of (6-chloro-2,2-diphenyl-benzo[1,3]dioxol-5-yl)-piperidin-1-yl-methanone The title compound was produced in accordance with the general method of Example 108c from □□□-diphenyldichloromethane and (2-chloro-4,5-dihydroxy-phenyl)-piperidin-4-yl-methanone (Example 117b). Colorless solid.
MS: m/e=418.1 ([M]$^+$).

Example 118

Preparation of (6-chloro-2,2-diphenyl-benzo[1,3]dioxol-5-yl)-morpholin-4-yl-methanone

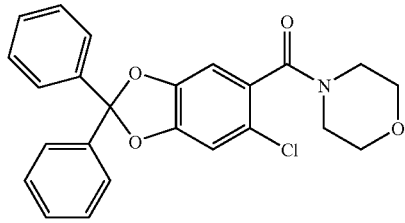

The title compound was produced in accordance with the general method of Example 108c from □□□-diphenyldichloromethane and (2-chloro-4,5-dihydroxy-phenyl)-morpholin-4-yl-methanone (Example 218b). White solid.
MS: m/e=422.0 ([M+H]$^+$).

Example 119

Preparation of 2-(2,4-dichloro-phenyl)-6-fluoro-2-(4-fluoro-phenyl)-benzo[1,3]dioxole-5-carboxylic acid ethyl-methyl-amide

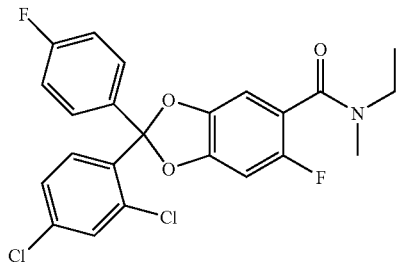

To a solution of [2-(2,4-dichloro-phenyl)-6-fluoro-2-(4-fluoro-phenyl)-benzo[1,3]dioxole-5-carboxylic acid (Example 108d, 220 mg; 0.52 mmol; 1 eq.) in N,N-dimethylformamide (5 mL), was added carbonyl diimidazole (110 mg; 0.68 mmol; 1.3 eq.) and the mixture stirred 2 h at 20° C. A solution of ethyl-methylamine in N,N-dimethylformamide (1M, 1 mL; 1.3 mmol; 2.5 eq.) was added and the reaction mixture stirred 4 days at 20° C. Purification by preparative HPLC (YMC pro C18) afforded the title compound as 10 mM DMSO stock solution.
MS: m/e=464.2 ([M]$^+$).

Example 120

Preparation of 2-(2,4-dichloro-phenyl)-6-fluoro-2-(4-fluoro-phenyl)-benzo[1,3]dioxole-5-carboxylic acid methyl-propyl-amide

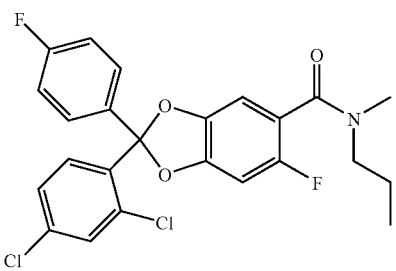

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and methyl-propylamine.
MS: m/e=478.2 ([M]$^+$)

Example 121

Preparation of [2-(2,4-dichloro-phenyl)-6-fluoro-2-(4-fluoro-phenyl)-benzo[1,3]dioxol-5-yl]-(2-methyl-pyrrolidin-1-yl)-methanone

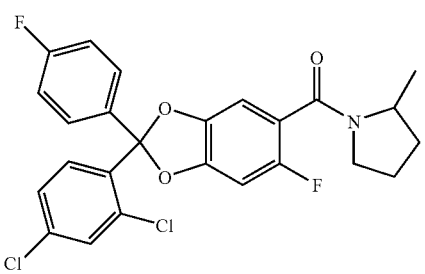

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 2-methyl-pyrrolidine.
MS: m/e=490.2 ([M]$^+$)

Example 122

Preparation of 2-(2,4-dichloro-phenyl)-6-fluoro-2-(4-fluoro-phenyl)-benzo[1,3]dioxole-5-carboxylic acid azepan-1-ylamide

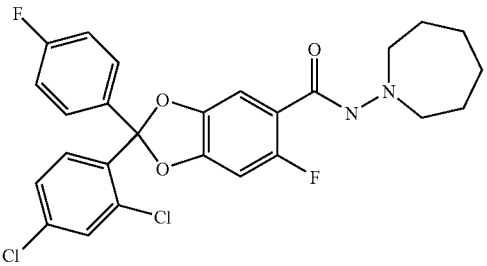

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 1-aminohomopiperidine.
MS: m/e=519.3 ([M]$^+$).

Example 123

Preparation of azetidin-1-yl-[2-(2,4-dichloro-phenyl)-6-fluoro-2-(4-fluoro-phenyl)-benzo[1,3]dioxol-5-yl]-methanone

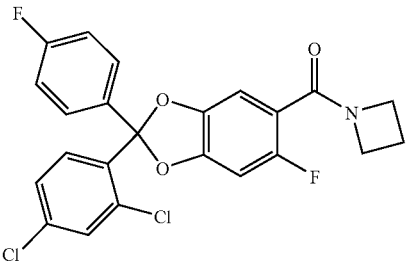

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and azetidine.
MS: m/e=462.2 ([M]$^+$).

Example 124

Preparation of azepan-1-yl-[2-(2,4-dichloro-phenyl)-6-fluoro-2-(4-fluoro-phenyl)-benzo[1,3]dioxol-5-yl]-methanone

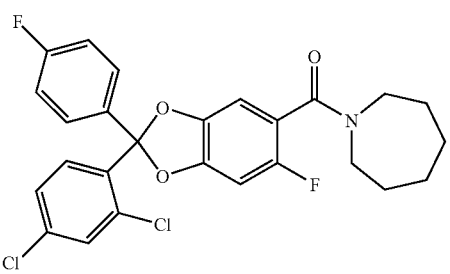

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and azacycloheptane.
MS: m/e=504.2 ([M]$^+$).

Example 125

Preparation of 2-(2,4-dichloro-phenyl)-6-fluoro-2-(4-fluoro-phenyl)-benzo[1,3]dioxole-5-carboxylic acid (2,2-dimethyl-1-methylcarbamoyl-propyl)-amide

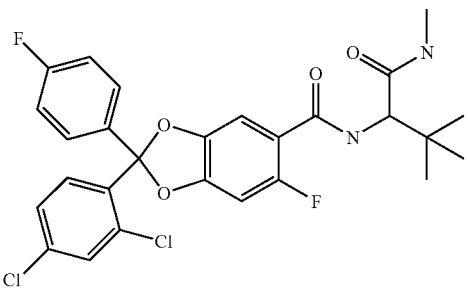

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and L-tert-leucine-N-methylamide.
MS: m/e=549.4 ([M]$^+$).

Example 126

Preparation of [2-(2,4-dichloro-phenyl)-6-fluoro-2-(4-fluoro-phenyl)-benzo[1,3]dioxol-5-yl]-(2S-methoxymethyl-pyrrolidin-1-yl)-methanone

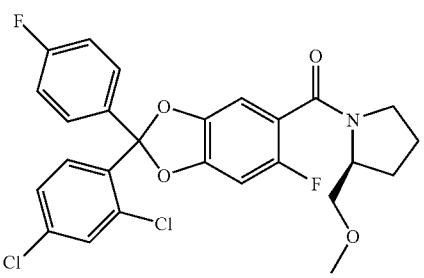

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 2S-methoxymethyl-pyrrolidine.
MS: m/e=520.4 ([M]$^+$)

Example 127

Preparation of [2-(2,4-dichloro-phenyl)-6-fluoro-2-(4-fluoro-phenyl)-benzo[1,3]dioxol-5-yl]-(2R-hydroxymethyl-pyrrolidin-1-yl)-methanone

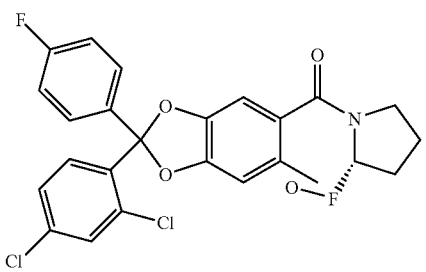

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 2R-hydroxymethyl-pyrrolidine.
MS: m/e=506.2 ([M]$^+$).

Example 128

Preparation of 1-[2-(2,4-dichloro-phenyl)-6-fluoro-2-(4-fluoro-phenyl)-bezno[1,3]dioxole-5-carbonyl]-pyrrolidine-2R-carboxylic acid dimethylamide

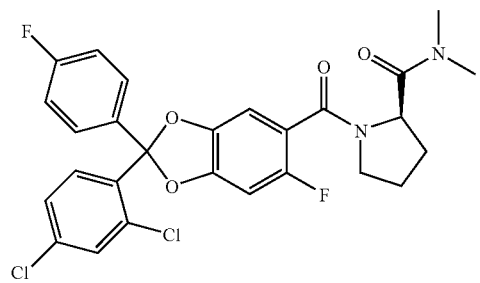

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 2R-carboxylic acid dimethylamine pyrrolidine.
MS: m/e=547.3 ([M]$^+$).

Example 129

Preparation of 2-(2,4-dichloro-phenyl)-6-fluoro-2-(4-fluoro-phenyl)-benzo[1,3]dioxole-5-carboxylic acid cyclobutylamide

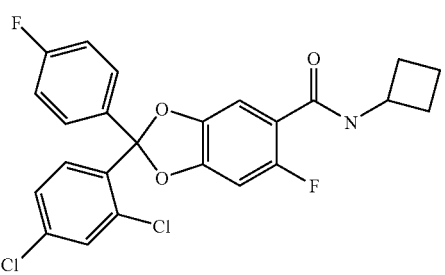

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and cyclobutylamine.
MS: m/e=476.3 ([M]$^+$).

Example 130

Preparation of 2-(2,4-dichloro-phenyl)-6-fluoro-2-(4-fluoro-phenyl)-benzo[1,3]dioxole-5-carboxylic acid morpholin-4-ylamide

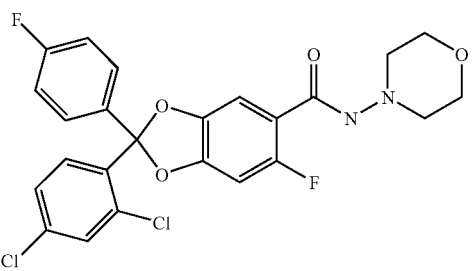

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and N-aminomorpholine.
MS: m/e=507.2 ([M]$^+$).

Example 131

Preparation of [2-(2,4-dichloro-phenyl)-6-fluoro-2-(4-fluoro-phenyl)-benzo[1,3]dioxol-5-yl]-(2,3,5,6-tetrahydro-[1,2']bipyrazinyl-4-yl)-methanone

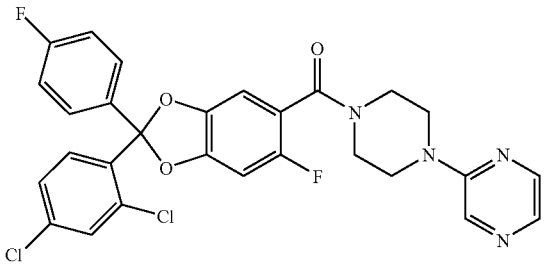

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 1-(2-pyrazinyl)-piperazine.
MS: m/e=569.3 ([M]⁺)

Example 132

Preparation of 1-[2-(2,4-dichloro-phenyl)-6-fluoro-2-(4-fluoro-phenyl)-benzo[1,3]dioxole-5-carbonyl]-pyrrolidine-2S-carboxylic acid amide

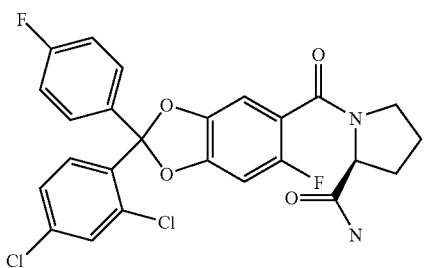

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and pyrrolidine-2S-carboxylic acid amide.
MS: m/e=519.3 ([M]⁺).

Example 133

Preparation of 2-(2,4-dichloro-phenyl)-6-fluoro-2-(4-fluoro-phenyl)-benzo[1,3]dioxole-5-carboxylic acid tert-butoxy-amide

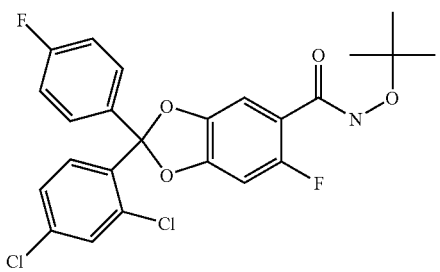

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and tert-butoxy-amine.
MS: m/e=494.2 ([M]⁺).

Example 134

Preparation of 2-(2,4-dichloro-phenyl)-6-fluoro-2-(4-fluoro-phenyl)-benzo[1,3]dioxole-5-carboxylic acid cyclopentylamide

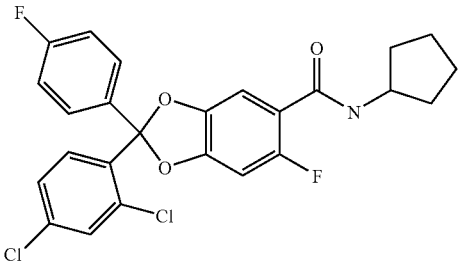

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and cyclopentylamine.
MS: m/e=490.3 ([M]⁺).

Example 135

Preparation of 2-(2,4-dichloro-phenyl)-6-fluoro-2-(4-fluoro-phenyl)-benzo[1,3]dioxole-5-carboxylic acid (tetrahydro-furan-2-ylmethyl)-amide

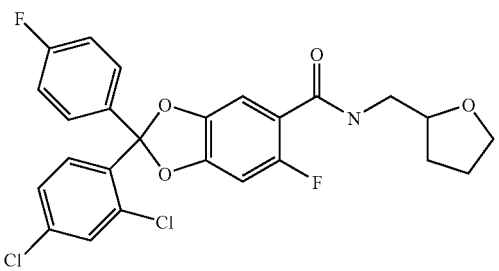

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and (tetrahydro-furan-2-ylmethyl)-amine.
MS: m/e=506.2 ([M]⁺).

Example 136

Preparation of [2-(2,4-dichloro-phenyl)-6-fluoro-2-(4-fluoro-phenyl)-benzo[1,3]dioxol-5-yl]-thiomorpholin-4-yl-methanone

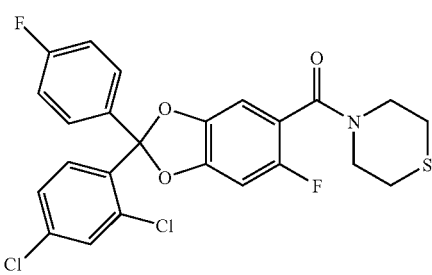

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and thiomorpholine.

MS: m/e=508.2 ([M]+).

Example 137

Preparation of 2-(2,4-dichloro-phenyl)-6-fluoro-2-(4-fluoro-phenyl)-benzo[1,3]dioxole-5-carboxylic acid isopropylamide

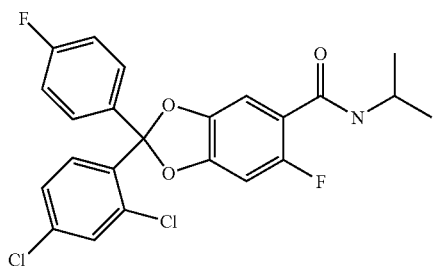

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and isopropylamine.

MS: m/e=464.2 ([M]+).

Example 138

Preparation of 2-(2,4-dichloro-phenyl)-6-fluoro-2-(4-fluoro-phenyl)-benzo[1,3]dioxole-5-carboxylic acid pyrrolidin-1-ylamide

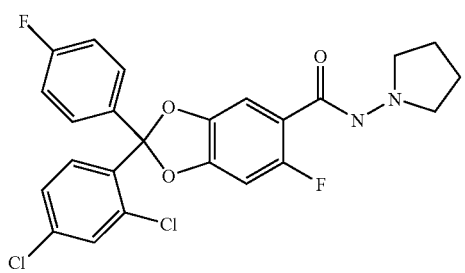

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and pyrrolidinamine.

MS: m/e=491.3 ([M]+).

Example 139

Preparation of 2-(2,4-dichloro-phenyl)-6-fluoro-2-(4-fluoro-phenyl)-benzo[1,3]dioxole-5-carboxylic acid methoxy-methyl-amide

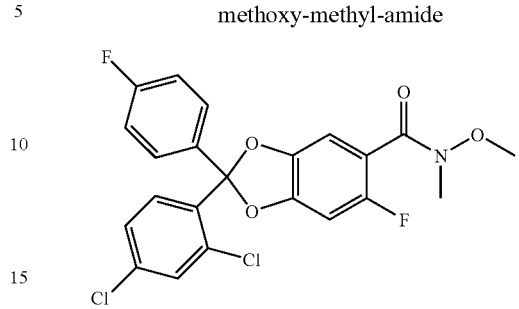

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and methoxy-methyl-amine.

MS: m/e=466.2 ([M]+).

Example 140

Preparation of [2-(2,4-dichloro-phenyl)-6-fluoro-2-(4-fluoro-phenyl)-benzo[1,3]dioxol-5-yl]-(3R-hydroxy-pyrrolidin-1-yl)-methanone

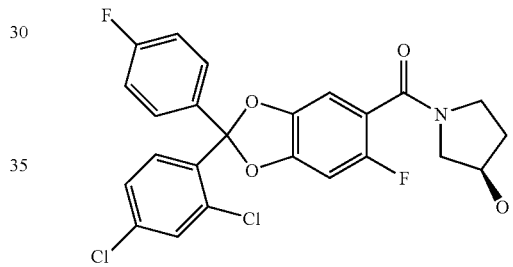

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 3R-hydroxy-pyrrolidine.

MS: m/e=492.2 ([M]+).

Example 141

Preparation of 2-(2,4-dichloro-phenyl)-6-fluoro-2-(4-fluoro-phenyl)-benzo[1,3]dioxole-5-carboxylic acid bis-cyclopropylmethyl-amide

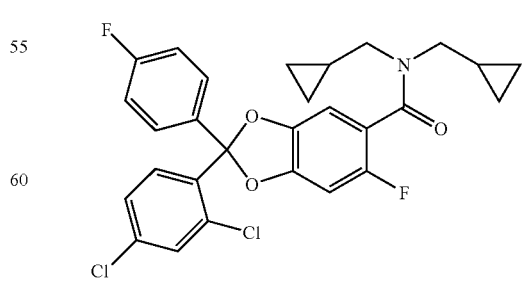

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and bis-cyclopropylmethyl-amine.

MS: m/e=530.2 ([M]$^+$).

Example 142

Preparation of [2-(2,4-dichloro-phenyl)-6-fluoro-2-(4-fluoro-phenyl)-benzo[1,3]dioxol-5-yl]-(4-fluoro-piperidin-1-yl)-methanone

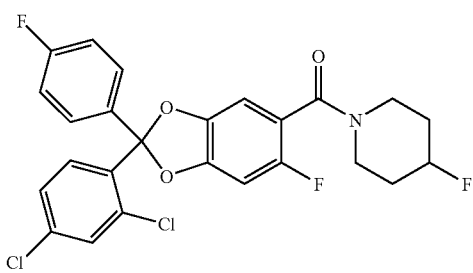

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 4-fluoro-piperidine.

MS: m/e=530.2 ([M]$^+$).

Example 143

Preparation of [2-(2,4-dichloro-phenyl)-6-fluoro-2-(4-fluoro-phenyl)-benzo[1,3]dioxol-5-yl]-(1,4-dioxa-8-aza-spiro[4.5]dec-8-yl)-methanone

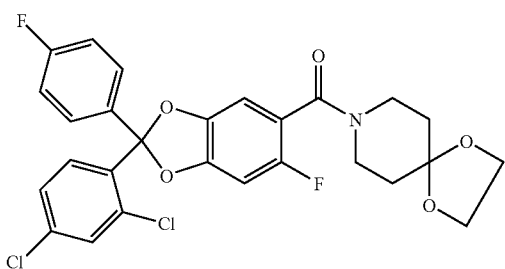

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 1,4-dioxa-8-azaspiro(4.5)decane.

MS: m/e=548.3 ([M]$^+$).

Example 144

Preparation of [2-(2,4-dichloro-phenyl)-6-fluoro-2-(4-fluoro-phenyl)-benzo[1,3]dioxol-5-yl]-(4-hydroxymethyl-piperidin-1-yl)-methanone

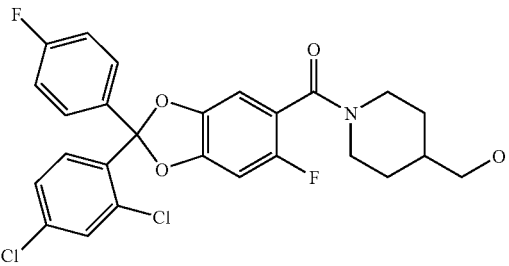

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 4-hydroxymethyl-piperidine.

MS: m/e=520.3 ([M]$^+$).

Example 145

Preparation of [2-(2,4-dichloro-phenyl)-6-fluoro-2-(4-fluoro-phenyl)-benzo[1,3]dioxol-5-yl]-(4-hydroxy-4-methyl-piperidin-1-yl)-methanone

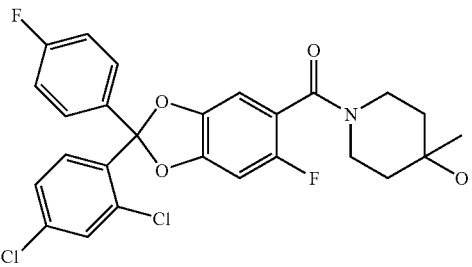

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 4-hydroxy-4-methyl-piperidine.

MS: m/e=520.3 ([M]$^+$).

Example 146

Preparation of [2-(2,4-dichloro-phenyl)-6-fluoro-2-(4-fluoro-phenyl)-benzo[1,3]dioxol-5-yl]-pyrrolidin-1-yl-methanone

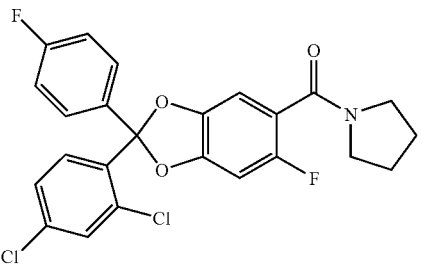

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and pyrrolidine.

MS: m/e=476.1 ([M]$^+$).

Example 147

Preparation of N-{1-[2-(2,4-dichloro-phenyl)-6-fluoro-2-(4-fluoro-phenyl)-benzo[1,3]dioxole-5-carbonyl]-pyrrolidin-3S-yl}-acetamide

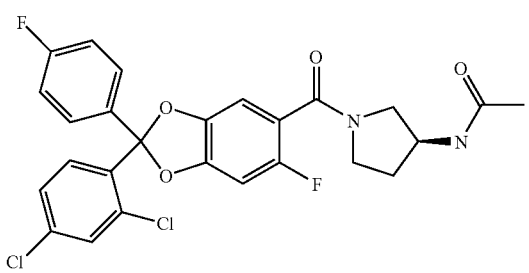

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 3S-acetamidopyrrolidine.

MS: m/e=533.2 ([M]$^+$).

Example 148

Preparation of 2-(2,4-dichloro-phenyl)-6-fluoro-2-(4-fluoro-phenyl)-benzo[1,3]dioxole-5-carboxylic acid cycloheptylamide

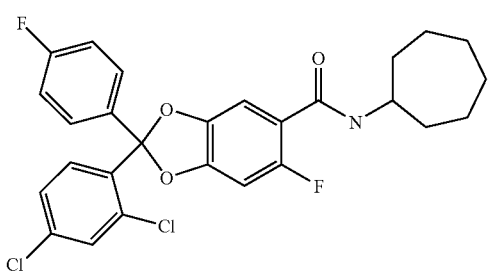

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and cycloheptylamine.

MS: m/e=518.3 ([M]$^+$).

Example 149

Preparation of 2-(2,4-dichloro-phenyl)-6-fluoro-2-(4-fluoro-phenyl)-benzo[1,3]dioxole-5-carboxylic acid N'-pyridin-2-yl-hydrazide

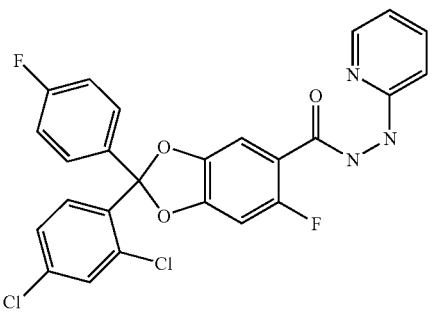

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 2-hydrazinopyridine.

MS: m/e=514.3 ([M]$^+$).

Example 150

Preparation of 2-(2,4-dichloro-phenyl)-6-fluoro-2-(4-fluoro-phenyl)-benzo[1,3]dioxole-5-carboxylic acid (2S-methoxymethyl-pyrrolidin-1-yl)-amide

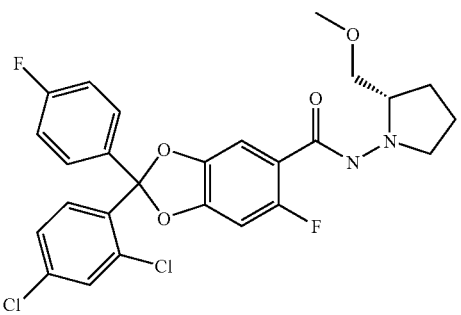

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 2S-methoxymethyl-pyrrolidin-1-amine.

MS: m/e=534.2 ([M]$^+$).

Example 151

Preparation of [2-(2,4-dichloro-phenyl)-6-fluoro-2-(4-fluoro-phenyl)-benzo[1,3]dioxol-5-yl]-(1,1-dioxo-thiomorpholin-4-yl)-methanone

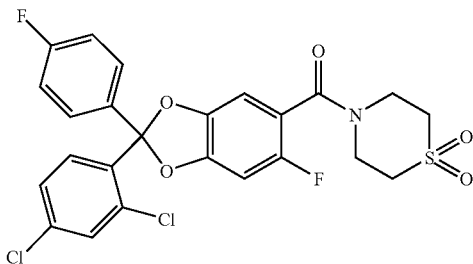

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 1,1-dioxo-1-thiomorpholine.

MS: m/e=540.4 ([M]$^+$).

Example 152

Preparation of [2-(2,4-dichloro-phenyl)-6-fluoro-2-(4-fluoro-phenyl)-benzo[1,3]dioxol-5-yl]-(3-hydroxy-8-aza-bicyclo[3.2.1]oct-8-yl)-methanone

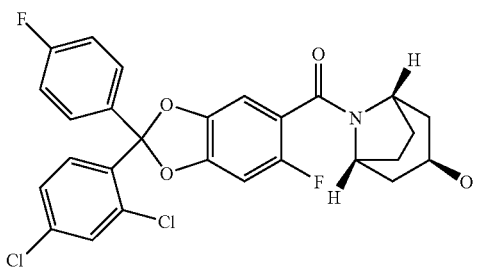

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and nortropine.

MS: m/e=532.2 ([M]$^+$).

Example 153

Preparation of [2-(2,4-dichloro-phenyl)-6-fluoro-2-(4-fluoro-phenyl)-benzo[1,3]dioxol-5-yl]-(2R-methoxymethyl-pyrrolidin-1-yl)-methanone

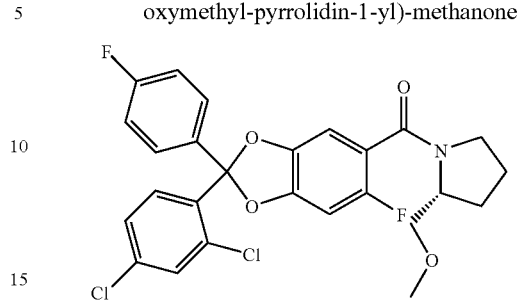

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 2R-methoxymethyl-pyrrolidine.

MS: m/e=520.2 ([M]$^+$).

Example 154

Preparation of [2-(2,4-dichloro-phenyl)-6-fluoro-2-(4-fluoro-phenyl)-benzo[1,3]dioxol-5-yl]-(3S-hydroxy-pyrrolidin-1-yl)-methanone

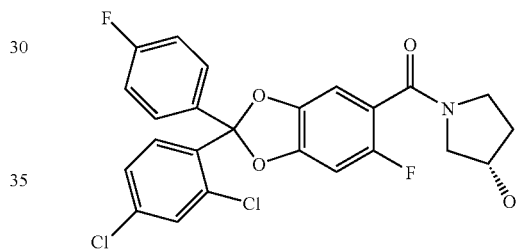

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 3S-hydroxy-pyrrolidine.

MS: m/e=492.2 ([M]$^+$).

Example 155

Preparation of N-{1-[2-(2,4-dichloro-phenyl)-6-fluoro-2-(4-fluoro-phenyl)-benzo[1,3]dioxole-5-carbonyl]-pyrrolidin-3R-yl}-acetamide

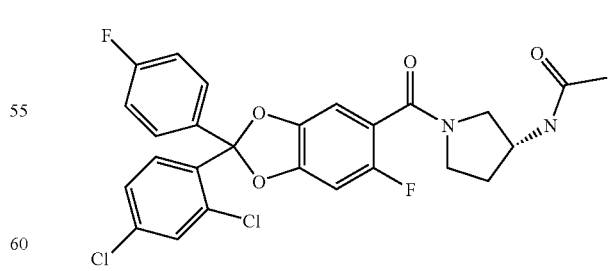

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 3R-acetamido-pyrrolidine.

MS: m/e=533.3 ([M]$^+$).

Example 156

Preparation of [2-(2,4-dichloro-phenyl)-6-fluoro-2-(4-fluoro-phenyl)-benzo[1,3]dioxol-5-yl]-(2S-hydroxymethyl-pyrrolidin-1-yl)-methanone

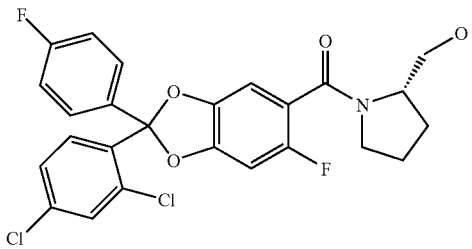

The title compound was produced in accordance with the general method of Example 119 from [2-(2,4-dichloro-phenyl)-6-fluoro-2-(4-fluoro-phenyl)-benzo[1,3]dioxole-5-carboxylic acid (Example 108d) and 2S-hydroxymethyl-pyrrolidine.

MS: m/e=506.2 ([M]$^+$).

Example 157

Preparation of [2-(2,4-dichloro-phenyl)-6-fluoro-2-(4-fluoro-phenyl)-benzo[1,3]dioxol-5-yl]-morpholin-4-yl-methanethione

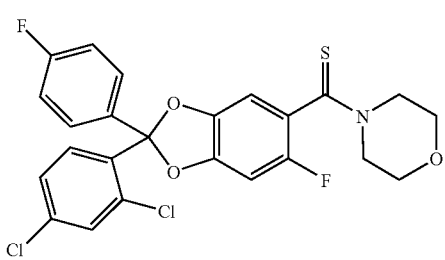

[2-(2,4-Dichloro-phenyl)-6-fluoro-2-(4-fluoro-phenyl)-benzo[1,3]dioxol-5-yl]-morpholin-4-yl-methanone (Example 108e, 79 mg, 0.16 mmol) and Lawesson's reagent (33 mg, 0.08 mmol) were heated in benzene (1 mL) under reflux for 4 h. The reaction mixture was evaporated in vacuo. Purification by flash chromatography afforded the title compound (75 mg, 92%) as a yellow oil.

MS: m/e=508.0 ([M]$^+$).

Example 158

Preparation of [2-(4-chloro-phenyl)-2-(2,4-dichloro-phenyl)-6-fluoro-benzo[1,3]dioxol-5-yl]-morpholin-4-yl-methanone

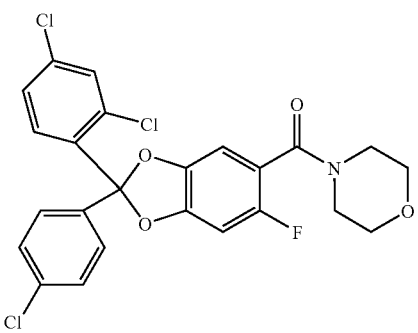

Preparation of 2,4,4'-trichlorodiphenyldichloromethane

The title compound was produced in accordance with the general method of Example 108b from 2,4-dichloro-benzotrifluoride and chlorobenzene. Brown oil.

MS: m/e=339.9 ([M]$^+$).

Preparation of 5-bromo-2-(4-chloro-phenyl)-2-(2,4-dichloro-phenyl)-6-fluoro-benzo[1,3]dioxole The title compound was produced in accordance with the general method of Example 108c from 4-bromo-5-fluoro-benzene-1,2-diol (Example 108a) and 2,4,4'-trichlorodiphenyldichloromethane (Example 158a). White solid.

MS: m/e=473.9 ([M]$^+$).

Preparation of 2-(4-chloro-phenyl)-2-(2,4-dichloro-phenyl)-6-fluoro-benzo[1,3]dioxole-5-carboxylic acid The title compound was produced in accordance with the general method of Example 108d from 5-bromo-2-(4-chloro-phenyl)-2-(2,4-dichloro-phenyl)-6-fluoro-benzo[1,3]dioxole (Example 158b). Orange solid.

MS: m/e=437.0 ([M−H]$^-$).

Preparation of [2-(4-chloro-phenyl)-2-(2,4-dichloro-phenyl)-6-fluoro-benzo[1,3]dioxol-5-yl]-morpholin-4-yl-methanone The title compound was produced in accordance with the general method of Example 108e from 2-(4-chloro-phenyl)-2-(2,4-dichloro-phenyl)-6-fluoro-benzo[1,3]dioxole-5-carboxylic acid (Example 158c) and morpholine. Orange solid.

MS: m/e=508.3 ([M+H]$^+$).

Example 159

Preparation of 6-(morpholine-4-carbonyl)-2,2-diphenyl-benzo[1,3]dioxole5-carbonitrile

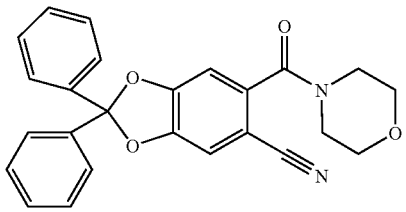

Preparation of (6-bromo-2,2-diphenyl-benzo[1,3]dioxol-5-yl)-morpholin-4-yl-methanone The title compound was produced in accordance with the general method of Example 108e from 6-bromo-2,2-diphenyl-benzo[1,3]dioxole-5-carboxylic acid (Example 110c) and morpholine. White solid.
MS: m/e=466.2 ([M+H]$^+$).

Preparation of 6-(morpholine-4-carbonyl)-2,2-diphenyl-benzo[1,3]dioxole-5-carbonitrile A mixture of (6-bromo-2,2-diphenyl-benzo[1,3]dioxol-5-yl)-morpholin-4-yl-methanone, (204 mg, 0.437 mmol) and copper cyanide (102 mg, 1.139 mmol, 2.6 eq.) in N-methyl pyrrolidinone (3 mL) was heated at 190° C. during 16 h. The reaction mixture partitioned between water and ethyl acetate. The organic layer was washed with brine and evaporated in vacuo. Purification by flash chromatography afforded the title compound (4.656 g, 83 %) as an off white solid.
MS: m/e=413.1 ([M+H]$^+$).

Example 160

Preparation of [2-(4-chloro-phenyl)-2-(2,4-dichloro-phenyl)-6-fluoro-benzo[1,3]dioxol-5-yl]-piperidin-1-yl-methanone

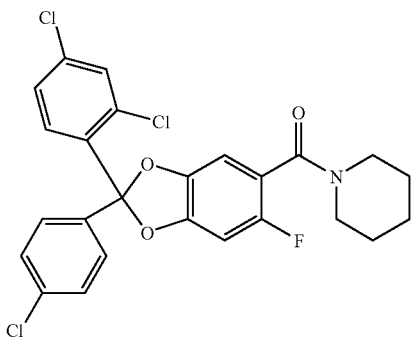

The title compound was produced in accordance with the general method of Example 108e from 2-(4-chloro-phenyl)-2-(2,4-dichloro-phenyl)-6-fluoro-benzo[1,3]dioxole-5-carboxylic acid (Example 158c) and piperidine. White solid.
MS: m/e=506.0 ([M+H]$^+$).

Example 161

Preparation of [2-(4-chloro-phenyl)-2-(2,4-dichloro-phenyl)-6-fluoro-benzo[1,3]dioxol-5-yl]-pyrrolidin-1-yl-methanone

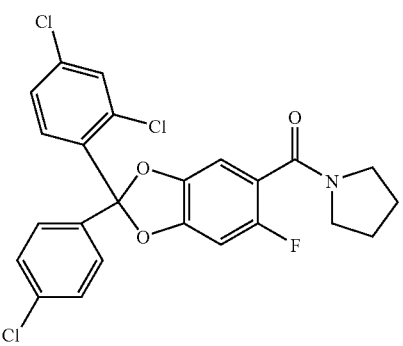

The title compound was produced in accordance with the general method of Example 108e from 2-(4-chloro-phenyl)-2-(2,4-dichloro-phenyl)-6-fluoro-benzo[1,3]dioxole-5-carboxylic acid (Example 158c) and pyrrolidine. Off-white solid.
MS: m/e=491.9 ([M+H]$^+$).

Example 162

Preparation of [2,2-bis-(2,4-difluoro-phenyl)-benzo[1,3]dioxol-5-yl]-morpholin-4-yl-methanone

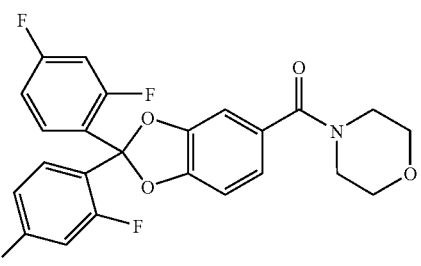

Preparation of 2,2',4,4'-tetrafluorodiphenyldichloromethane

Aluminium trichloride (5.32 g, 39.9 mmol) was added to 1,3-difluorobenzene (8 g, 70.12 mmol) with stirring. The mixture was cooled to ca. 10° C. and carbon tetrachloride (14.5 mL) was added dropwise over a period of 1 h. The mixture was stirred 3.5 h at 30° C., diluted with dichloromethane and poured onto ice. The phases were separated, the organic phase dried over magnesium sulfate and evaporated to afford the title compound as a light brown solid that was used without further purification.
MS: m/e 273.0 ([M–Cl]$^-$).

Preparation of [2,2-bis-(2,4-difluoro-phenyl)-benzo[1,3]dioxol-5-yl]-morpholin-4-yl-methanone The title compound was produced in accordance with the general method of Example 108c from 2,2',4,4'-tetrafluorodiphenyldichloromethane and (3,4-dihydroxy-phenyl)-morpholin-4-yl-methanone (Example 87b). Light brown gum.

MS: m/e=460.1 ([M+H]+).

Example 163

Preparation of [2,2-bis-(2,4-difluoro-phenyl)-benzo[1,3]dioxol-5-yl]-piperidin-1-yl-methanone

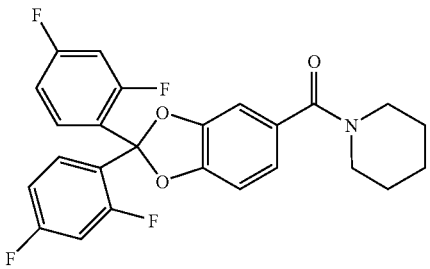

The title compound was produced in accordance with the general method of Example 108c from 2,2',4,4'-tetrafluorodiphenyldichloromethane (Example 162a) and (3,4-dihydroxy-phenyl)-piperidin-4-yl-methanone. Yellow foam.

MS: m/e=458.3 ([M+H]+).

Example 164

Preparation of [6-fluoro-2,2-bis-(4-fluoro-phenyl)-benzo[1,3]dioxol-5-yl]-pyrrolidin-1-yl-methanone

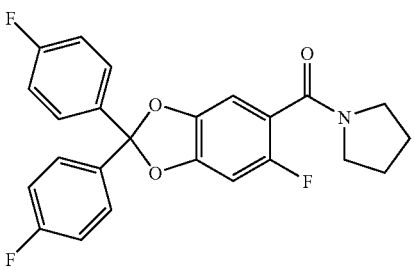

Preparation of 5-bromo-6-fluoro-2,2-bis-(4-fluoro-phenyl)-benzo[1,3]dioxole

The title compound was produced in accordance with the general method of Example 108c from 4-bromo-5-fluoro-benzene-1,2-diol (Example 108a) and 4,4'-difluorodiphenyl-dichloromethane (Example 111a). Colorless oil.

MS: m/e=407.9 ([M]+).

Preparation of [6-fluoro-2,2-bis-(4-fluoro-phenyl)-benzo[1,3]dioxol-5-yl]-pyrrolidin-1-yl-methanone The title compound was produced in accordance with the general method of Example 166b from 5-bromo-6-fluoro-2,2-bis-(4-fluoro-phenyl)-benzo[1,3]dioxole (Example 164a) and 1-pyrrolidine-carbonyl chloride. Light yellow oil.

MS: m/e=426.3 ([M+H]+).

Example 165

Preparation of [6-fluoro-2,2-bis-(4-fluoro-phenyl)-benzo[1,3]dioxol-5-yl]-piperidin-1-yl-methanone

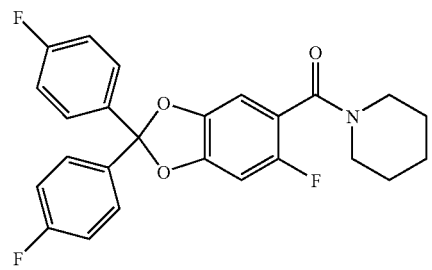

The title compound was produced in accordance with the general method of Example 166b from 5-bromo-6-fluoro-2,2-bis-(4-fluoro-phenyl)-benzo[1,3]dioxole (Example 164a) and 1-piperidine-carbonyl chloride. Yellow oil.

MS: m/e=440.3 ([M+H]+).

Example 166

Preparation of [2,2-bis-(4-bromo-phenyl)-6-fluoro-benzo[1,3]dioxol-5-yl]-morpholin-4-yl-methanone

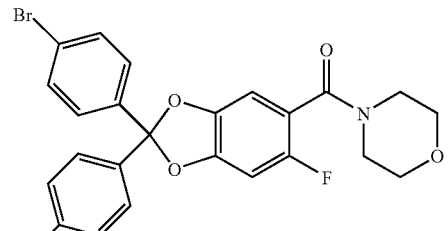

Preparation of 5-bromo-6-fluoro-2,2-diphenyl-benzo[1,3]dioxole

The title compound was produced in accordance with the general method of Example 108c from 4-Bromo-5-fluoro-benzene-1,2-diol (Example 108a) and diphenyldichloromethane. Off white solid.

MS: m/e=370.0 ([M+H+]).

Preparation of (6-fluoro-2,2-diphenyl-benzo[1,3]dioxol-5-yl)-morpholin-4-yl-methanone To a cooled (−78° C.) solution of 5-bromo-6-fluoro-2,2-diphenyl-benzo[1,3]dioxole (17.59 g, 47.4 mmol) in diethyl ether (300 mL) was slowly added a solution of n-butyl lithium in hexanes (1.6M, 30 mL, 48 mmol, 1.0 eq.). The reaction mixture was stirred 1 h at −78° C. before the addition of 4-morpholinecarbonylchloride (8.5 g, 56.9 mmol, 1.2 eq.). The reaction mixture was allowed to warm to 20° C. and poured into an aqueous solution of sodium bicarbonate. The aqueous layer was extracted with ethyl acetate. The combined organic layers were washed with brine. Volatiles were removed in vacuo. Purification by flash chromatography afforded the title compound (13.0 g, 68%) as a light yellow solid.

MS: m/e=406.2 ([M+H]+).

Preparation of (2-fluoro-4,5-dihydroxy-phenyl)-morpholin-4-yl-methanone

The title compound was produced in accordance with the general method of Example 87b from (6-fluoro-2,2-diphenyl-benzo[1,3]dioxol-5-yl)-morpholin-4-yl-methanone. Light brown solid.

MS: m/e=442.2 ([M+H]⁺).

Preparation of 4,4'-dibromodiphenyldichloromethane

The title compound was produced in accordance with the general method of Example 108b from 4-bromobenzotrifluoride and bromobenzene. Light yellow semisolid.

MS: m/e=392.0 ([M+H]⁺).

Preparation of [2,2'-bis-(4-bromo-phenyl)-6-fluoro-benzo[1,3]dioxol-5-yl]-morpholin-4-yl-methanone The title compound was produced in accordance with the general method of Example 108c from (2-fluoro-4,5-dihydroxy-phenyl)-morpholin-4-yl-methanone (Example 166c) and 4,4'-dibromodiphenyldichloromethane (Example 166d). Light yellow solid.

MS: m/e=364.1 ([M+H]⁺).

Example 167

Preparation of 4-[2,2-bis-(4-cyano-phenyl)-6-fluoro-benzo[1,3]dioxole-5-carbonyl]-morpholine

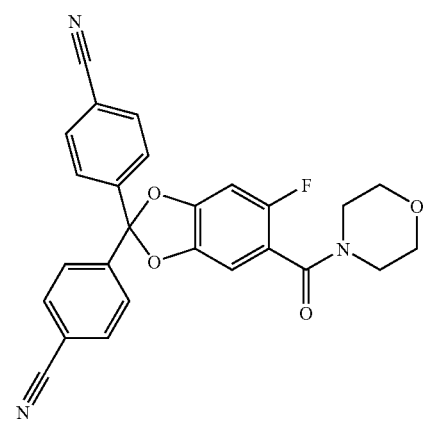

A mixture of [2,2'-bis-(4-bromo-phenyl)-6-fluoro-benzo[1,3]dioxol-5-yl]-morpholin-4-yl-methanone (Example 166e, 400 mg, 0.71 mmol, 1.0 eq.), copper cyanide (381 mg, 4.26 mmol, 6.0 eq.), tris(dibenzylideneacetone)dipalladium (32.5 mg, 0.035 mmol, 0.05 eq.), tetraethylammonium cyanide (111 mg, 0.71 mmol, 1.0 eq.) and 1,1'-bis(diphenylphosphino)ferrocene (78.7 mg, 0.142 mmol, 0.2 eq.) was flushed with nitrogen. Degassed dioxane (10 mL) was added and the reaction mixture was heated to reflux during 4 h. The reaction mixture was diluted with ethyl acetate, filtered and washed with an aqueous solution of sodium bicarbonate, brine and water. Volatiles were removed in vacuo. Purification by flash chromatography afforded the title compound (141 mg, 44%) as a light yellow semisolid.

MS: m/e=456.1 ([M+H]⁺).

Example 168

Preparation of 4-[2-(4-bromo-phenyl)-5-fluoro-6-(morpholine-4-carbonyl)-benzo[1,3]dioxol-2-yl]-benzonitrile

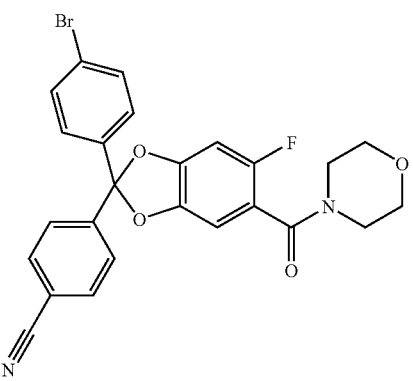

The title compound was produced in accordance with the general method of Example 167, as a side product. Light yellow solid.

MS: m/e=509.0 ([M+H]⁺).

Example 169

Preparation of [2,2-bis-(2,4-difluoro-phenyl)-6-fluoro-benzo[1,3]dioxol-5-yl]-morpholin-4-yl-methanone

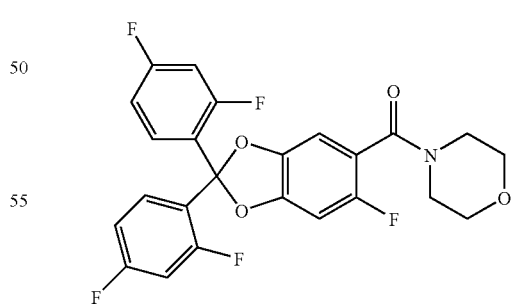

The title compound was produced in accordance with the general method of Example 108c from 2,2',4,4'-tetrafluorodiphenyldichloromethane (Example 162a) and (2-fluoro-4,5-dihydroxy-phenyl)-morpholin-4-yl-methanone (Example 99b). Light brown gum.

MS: m/e=478.1 ([M+H]⁺).

Example 170

Preparation of [2,2-bis-(4-chloro-phenyl)-6-fluoro-benzo[1,3]dioxol-5-yl]-morpholin-4-yl-methanone

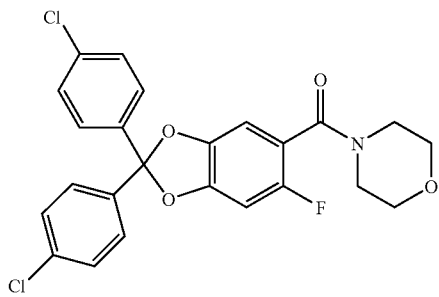

Preparation of dichlorobis(4-chlorophenyl)methane

The title compound was produced in accordance with the general method of Example 87d from 4,4'-dichlorobenzophenone and used without further purification. Yellow solid.
MS: m/e=304.0, 306.0 ([M]+).

Preparation of [2,2-bis-(4-chloro-phenyl)-6-fluoro-benzo[1,3]dioxol-5-yl]-morpholin-4-yl-methanone The title compound was produced in accordance with the general method of Example 108c from dichlorobis(4-chlorophenyl)methane and 2-fluoro-4,5-dihydroxy-phenyl)-morpholin-4-yl-methanone (Example 166c). Beige foam.
MS: m/e=474.0, 476.0 ([M]+).

Example 171

Preparation of [6-chloro-2,2-bis-(2,4-difluoro-phenyl)-benzo[1,3]dioxol-5-yl]-morpholin-4-yl-methanone

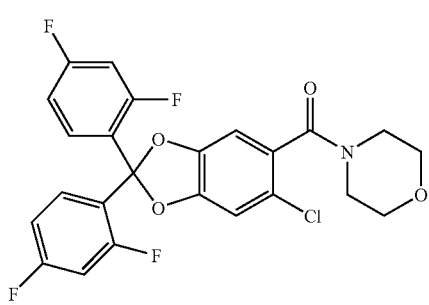

Example 172

Preparation of [2-(2-chloro-4-fluoro-phenyl)-2-(4-fluoro-phenyl)-benzo[1,3]dioxol-5-yl]-piperidin-1-yl-methanone

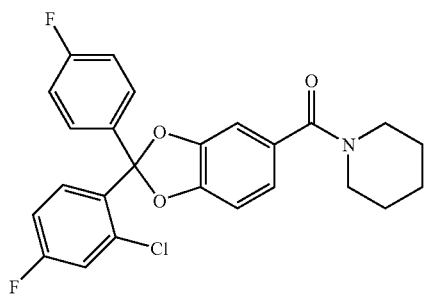

2-Chloro-1-[dichloro-(4-fluoro-phenyl)-methyl]-4-fluoro-benzene (2-Chloro-4-fluoro-phenyl)-(4-fluoro-phenyl)-methanone (0.25 g, 0.99 mmol) and phosphorus pentachloride (0.21 g, 1.01 mmol) were mixed under argon and heated 2 h at 150° C. The mixture was allowed to cool to room temperature, diluted with dichloromethane and poured onto ice. The phases were separated, the organic phase dried over magnesium sulfate and evaporated to afford the title compound as a pale yellow oil (0.2 g) containing ca 50% of the desired product by NMR, along with starting material (35%) and mono-chlorinated compound (15%). This mixture was used without further purification.

Preparation of [2-(2-chloro-4-fluoro-phenyl)-2-(4-fluoro-phenyl)-benzo[1,3]dioxol-5-yl]-piperidin-1-yl-methanone The title compound was produced in accordance with the general method of Example 108c from 2-chloro-1-[dichloro-(4-fluoro-phenyl)-methyl]-4-fluoro-benzene (Example 172a) and (3,4-dihydroxy-phenyl)-piperidin-4-yl-methanone. Light brown gum.
MS: m/e=456.1 ([M+H]+).

Example 173

Preparation of [6-fluoro-2,2-bis-(2-fluoro-phenyl)-benzo[1,3]dioxol-5-yl]-morpholin-4-yl-methanone

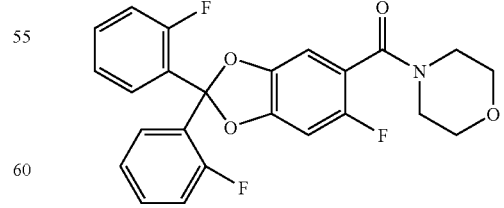

Preparation of bis-(2-fluoro-phenyl)-methanone

To a stirred suspension of 2-fluorobenzeneboronic acid (280 mg, 2 mmol), Cs$_2$CO$_3$ (1.63 g, 5 mmol) and tetrakis (triphenylphosphine)palladium(0) (40 mg, 0.02 mmol) in toluene (35 ml) under nitrogen was added dropwise 2-fluorobenzoyl chloride (634 mg, 4 mmol). The suspension was heated at 100° C. for 16 h, cooled to RT and partitioned between ethyl acetate and water. The organic layer was washed with aqueous potassium hydrogencarbonate solution, brine, dried over sodium sulfate, filtered and evaporated. Purification by flash chromatography afforded the title compound (210 mg, 46%). Colorless liquid.

MS: m/e=218.1 ([M+).

Preparation of bis-(2-fluorophenyl)dichloromethane

The title compound was produced in accordance with the general method of Example 182a from bis-(2-fluoro-phenyl)-methanone (Example 173a) and used without further purification. Brown solid.

Preparation of [6-fluoro-2,2-bis-(2-fluoro-phenyl)-benzo[1,3]dioxol-5-yl]-morpholin-4-yl-methanone The title compound was produced in accordance with the general method of Example 108c from (2-fluoro-4,5-dihydroxy-phenyl)-morpholin-1-yl-methanone (Example 99b) and bis-(2-fluorophenyl)dichloromethane (Example 173b). Light brown amorphous solid.

MS: m/e=442.3 ([M+H]$^+$).

Example 174

Preparation of [2,2-bis-(2,4-dichloro-phenyl)-6-fluoro-benzo[1,3]dioxol-5-yl]-morpholin-4-yl-methanone

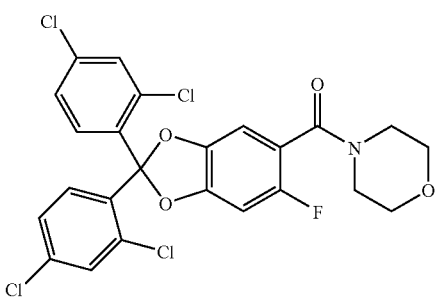

Preparation of 2,2',4,4'-tetrachloro-dichlorodiphenyl-methane

The title compound was produced in accordance with the general method of Example 207a from 2,4-dichlorobenzene and used without further purification. White crystals.

m.p.: 139-142° C.; MS: m/e=373.9, 375.9 ([M]$^+$).

Preparation of [2,2-bis-(2,4-dichloro-phenyl)-6-fluoro-benzo[1,3]dioxol-5-yl]-morpholin-4-yl-methanone The title compound was produced in accordance with the general method of Example 108c from 2,2',4,4'-tetrachloro-dichlorodiphenylmethane and 2-fluoro-4,5-dihydroxy-phenyl)-morpholin-4-yl-methanone (Example 166c). White foam.

MS: m/e=541.9, 543.9 ([M]$^+$).

Example 175

Preparation of 4-[2,2-bis-(2,4-difluoro-phenyl)-6-fluoro-benzo[1,3]dioxole-5-sulfonyl]-morpholine

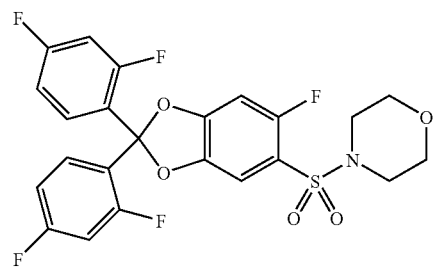

The title compound was produced in accordance with the general method of Example 108c from 2,2',4,4'-tetrafluorodiphenyldichloromethane (Example 162a) and 4-fluoro-5-(morpholine-1-sulfonyl)-benzene-1,2-diol (Example 234b). Off-white foam.

MS: m/e=514.2 ([M+H]$^+$).

Example 176

Preparation of 4-[2-(2,4-dichloro-phenyl)-6-fluoro-2-(4-fluoro-phenyl)-benzo[1,3]dioxole-5-sulfonyl]-morpholine

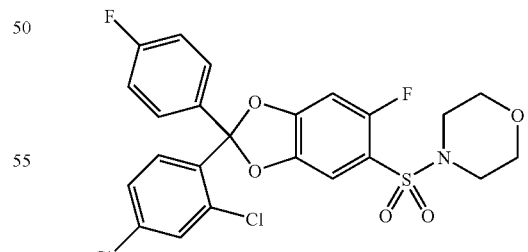

The title compound was produced in accordance with the general method of Example 108c from 2,4-dichloro-4'-fluoro-diphenyldichloromethane and 4-fluoro-5-(morpholine-1-sulfonyl)-benzene-1,2-diol (Example 234b). Off-white foam.

MS: m/e=528.1 ([M+H]$^+$).

Example 177

Preparation of [2-(2,4-dichloro-phenyl)-6-fluoro-2-(4-fluoro-phenyl)-benzo[1,3]dioxol-5-yl]-(4,4-difluoro-piperidin-1-yl)-methaone

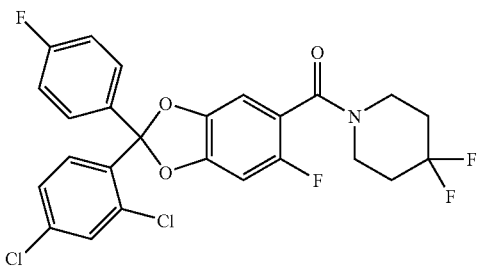

The title compound was produced in accordance with the general method of Example 108e from [2-(2,4-dichloro-phenyl)-6-fluoro-2-(4-fluoro-phenyl)-benzo[1,3]dioxole-5-carboxylic acid (Example 108d) and 4,4'-difluoropiperidine. Yellow gum.

MS: m/e=526.1 ([M]+).

Example 178

Preparation of [2-(2,4-dichloro-phenyl)-6-fluoro-2-(4-fluoro-phenyl)-benzo[1,3]dioxol-5-yl]-(4-trifluoromethyl-piperidin-1-yl)-methanone

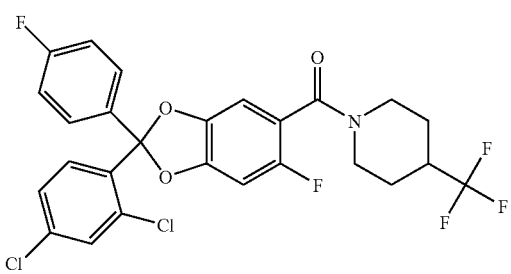

The title compound was produced in accordance with the general method of Example 108e from [2-(2,4-dichloro-phenyl)-6-fluoro-2-(4-fluoro-phenyl)-benzo[1,3]dioxole-5-carboxylic acid (Example 108d) and 4-(trifluoromethyl)piperidine hydrochloride. White foam.

MS: m/e=558.0 ([M]+).

Example 179

Preparation of [2-(2,4-dichloro-phenyl)-6-fluoro-2-(4-fluoro-phenyl)-benzo[1,3]dioxol-5-yl]-(3S-ethoxy-pyrrolidin-1-yl)-methanone

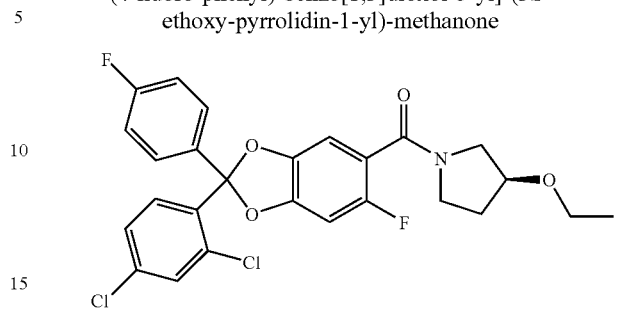

The title compound was produced in accordance with the general method of Example 108e from [2-(2,4-dichloro-phenyl)-6-fluoro-2-(4-fluoro-phenyl)-benzo[1,3]dioxole-5-carboxylic acid (Example 108d) and 3S-ethoxy-pyrrolidine. Colorless oil.

MS: m/e=520.1 ([M]+).

Example 180

Preparation of 2-(2,4-dichloro-phenyl)-6-fluoro-2-(4-fluoro-phenyl)-benzo[1,3]dioxole-5-carboxylic acid (1R-phenyl-ethyl)-amide

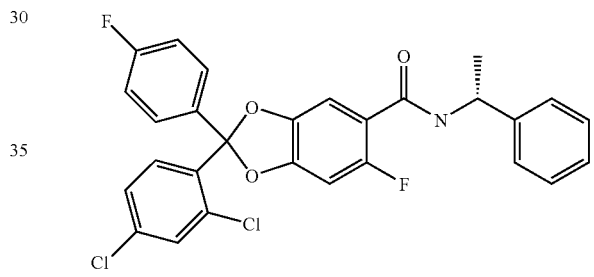

The title compound was produced in accordance with the general method of Example 108e from [2-(2,4-dichloro-phenyl)-6-fluoro-2-(4-fluoro-phenyl)-benzo[1,3]dioxole-5-carboxylic acid (Example 108d) and (1R-phenyl-ethyl)-amine. Colorless oil.

MS: m/e=526.1 ([M]+).

Example 181

Preparation of [2-(2,4-dichloro-phenyl)-6-fluoro-2-(4-fluoro-phenyl)-benzo[1,3]dioxol-5-yl]-(1-oxo-thiomorpholin-4-yl)-methanone

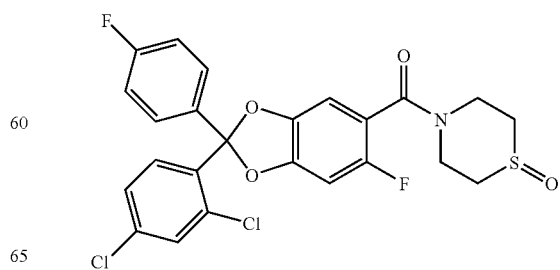

A solution of m-chloroperbenzoic acid (74 mg, 0.3 mmol) in dichloromethane (1.2 mL) was added to a cooled (−20° C.) solution of [2-(2,4-Dichloro-phenyl)-6-fluoro-2-(4-fluoro-phenyl)-benzo[1,3]dioxol-5-yl]-thiomorpholin-4-yl-methanone (Example 136) (153 mg, 0.3 mmol) in dichloromethane (1.7 mL). The reaction mixture was stirred at −20° C. for 3 h, quenched with 5% aqueous sodium thiosulfate solution. The aqueous phase was extracted with dichloromethane and the combined organic phases were washed with 10% sodium bicarbonate solution and brine, dried over sodium sulfate, filtered and the volatiles were removed under vacuo. Purification by flash chromatography afforded the title product as a white foam (141 mg, 89%).

MS: m/e=524.1 ([M]⁺).

Example 182

Preparation of [2,2-bis-(2-chloro-phenyl)-6-fluoro-benzo[1,3]dioxol-5-yl]-morpholin-4-yl-methanone

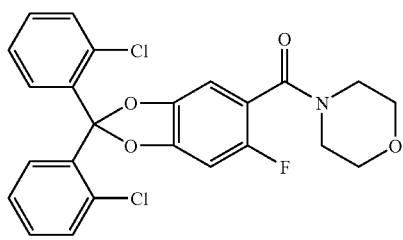

Preparation of bis-(2-chlorophenyl)dichloromethane

A mixture of 2,2'-dichlorobenzophenone (502 mg, 2 mmol) and phosphorus pentachloride (833 mg, 4 mmol, 2.0 eq.) was stirred 28 h at 170° C. The reaction mixture was cooled down to room temperature, diluted with dichloromethane and washed with cold water. The organic layer was dried over sodium sulfate, filtered and the volatiles were removed in vacuo, affording the title compound (629 mg, quant.) as an orange oil.

MS: m/e=306.0 ([M]⁺).

Preparation of [2,2-bis-(2-chloro-phenyl)-6-fluoro-benzo[1,3]dioxol-5-yl]-morpholin-4-yl-methanone A mixture of bis-(2-chlorophenyl)dichloromethane (Example 182, 258 mg, 0.84 mmol, 2.6 eq.) and (2-fluoro-4,5-dihydroxy-phenyl)-morpholin-4-yl-methanone (Example 87b, 72 mg, 0.32 mmol) were heated 5 h at 150° C. in a sealed glass tube. Purification by flash chromatography afforded the title compound (6.8 mg, 4.5%) as an off-white solid, m.p.: 98° C.

MS: m/e=474.0 ([M+H]⁺).

Example 183

Preparation of [6-fluoro-2,2-bis-(4-trifluoromethyl-phenyl)-benzo[1,3]dioxol-5-yl]-morpholin-4-yl-methanone

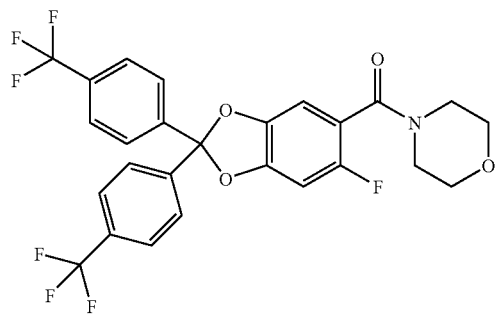

Preparation of bis-(4-trifluoromethyl-phenyl)-methanone

The title compound was produced in accordance with the general method of Example 173a from 4-trifluoromethyl-phenylboronic acid and 4-trifluoromethyl-benzoyl chloride. White crystalline solid.

MS: m/e=318.1 ([M]⁺).

Preparation of bis-(4-trifluoromethyl-phenyl)dichloromethane

The title compound was produced in accordance with the general method of Example 87d from bis-(4-trifluoromethyl-phenyl)-methanone (Example 183a) and used without further purification. Brown solid.

Preparation of [6-fluoro-2,2-bis-(4-trifluoromethyl-phenyl)-benzo[1,3]dioxol-5-yl]-morpholin-4-yl-methanone The title compound was produced in accordance with the general method of Example 108c from (2-fluoro-4,5-dihydroxy-phenyl)-morpholin-1-yl-methanone (Example 99b) and bis-(4-trifluoromethyl-phenyl)dichloromethane (Example 183b). Light-brown amorphous solid.

MS: m/e=542.1 ([M+H]⁺)

Example 184

Preparation of [6-fluoro-2,2-bis-(3-fluoro-phenyl)-benzo[1,3]dioxol-5-yl]-morpholin-4-yl-methanone

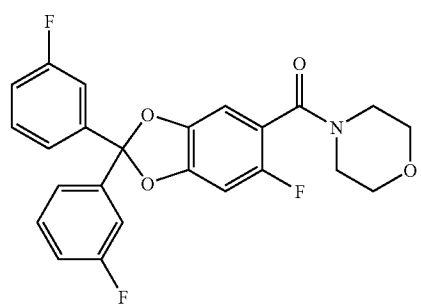

Preparation of bis-(3-fluorophenyl)dichloromethane

The title compound was produced in accordance with the general method of Example 87d from bis-(3-fluoro-phenyl)-methanone and used without further purification. Brown solid.

Preparation of [[6-fluoro-2,2-bis-(3-fluoro-phenyl)-benzo[1,3]dioxol-5-yl]-morpholin-4-yl-methanone The title compound was produced in accordance with the general method of Example 108c from (2-fluoro-4,5-dihydroxy-phenyl)-morpholin-1-yl-methanone (Example 99b) and bis-(3-fluorophenyl)dichloromethane (Example 184a). Off-white amorphous solid.
MS: m/e=442.1 ([M+H]$^+$).

Example 185

Preparation of [2-(2-chloro-4-fluoro-phenyl)-2-(4-fluoro-phenyl)-benzo[1,3]dioxol-5-yl]-morpholin-4-yl-methanone

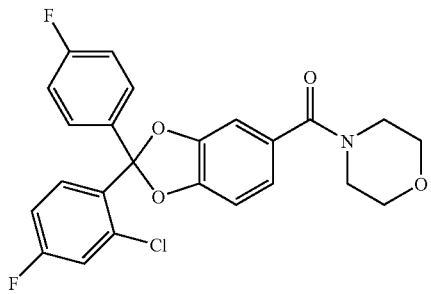

The title compound was produced in accordance with the general method of Example 108c from 2-chloro-1-[dichloro-(4-fluoro-phenyl)-methyl]-4-fluoro-benzene (Example 172a) and (3,4-dihydroxy-phenyl)-morpholin-4-yl-methanone (Example 87b). Light brown gum.
MS: m/e=458.3 ([M+H]$^+$).

Example 186

Preparation of [2,2-bis-(3,4-difluoro-phenyl)-benzo[1,3]dioxol-5-yl]-piperidin-1-yl-methanone

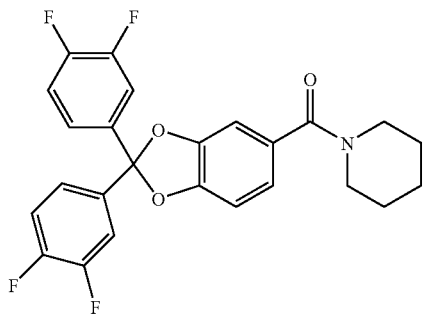

The title compound was produced in accordance with the general method of Example 108c from 1,1'-(dichloromethylene)bis[3,4-difluoro-benzene and (3,4-dihydroxy-phenyl)-piperidin-4-yl-methanone. Light brown gum.
MS: m/e=458.2 ([M+H]$^+$).

Example 187

Preparation of [2,2-bis-(3,4-difluoro-phenyl)-benzo[1,3]dioxol-5-yl]-morpholin-4-yl-methanone

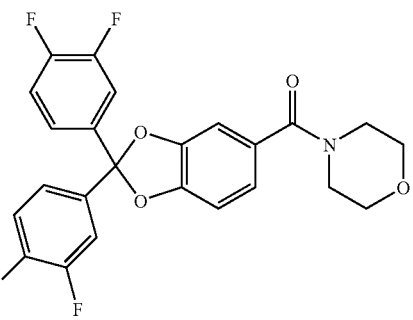

The title compound was produced in accordance with the general method of Example 108c from 1,1'-(dichloromethylene)bis[3,4-difluoro-benzene and (3,4-dihydroxy-phenyl)-morpholin-4-yl-methanone (Example 87b). Colorless gum.
MS: m/e=460.2 ([M+H]$^+$).

Example 188

Preparation of [2,2-bis-(2,4-dichloro-phenyl)-6-fluoro-benzo[1,3]dioxol-5-yl]-(3-hydroxy-pyrrolidin-1-yl)-methanone

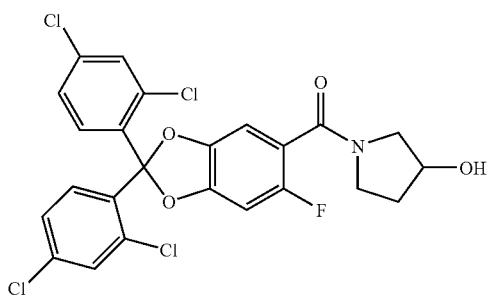

Preparation of 5-bromo-2,2-bis-(2,4-dichloro-phenyl)-6-fluoro-benzo[1,3]dioxole

The title compound was produced in accordance with the general method of Example 108c from 2,2',4,4'-tetrachloro-dichlorodiphenylmethane (Example 174a) and 4-bromo-5-fluoro-benzene-1,2-diol (Example 108a). Colorless solid.
MS: m/e=507.9, 509.9 ([M]$^+$).

Preparation of 2,2-bis-(2,4-dichloro-phenyl)-6-fluoro-benzo[1,3]dioxole-5-carboxylic acid The title compound was produced in accordance with the general method of Example 108d from 5-bromo-2,2-bis-(2,4-dichloro-phenyl)-6-fluoro-benzo[1,3]dioxole. White foam.
MS: m/e=471.0, 473.0 ([M−H]$^−$)

Preparation of [2,2-bis-(2,4-dichloro-phenyl)-6-fluoro-benzo[1,3]dioxol-5-yl]-(3-hydroxy-pyrrolidin-1-yl)-methanone The title compound was produced in accordance with the general method of Example 108e from 2,2-bis-(2,4-dichlorophenyl)-6-fluoro-benzo[1,3]dioxole-5-carboxylic acid and 3-pyrrolidinol. Light yellow foam.
MS: m/e=541.9, 543.9 ([M]$^+$).

Example 189

Preparation of [2,2-bis-(2,4-dichloro-phenyl)-6-fluoro-benzo[1,3]dioxol-5-yl]-(4-hydroxy-piperidin-1-yl)-methanone

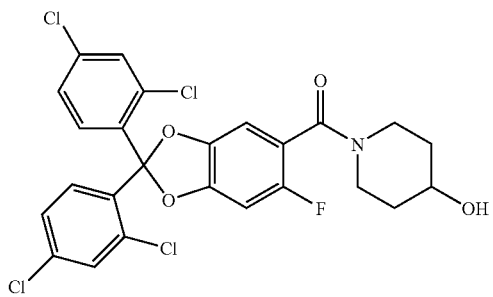

The title compound was produced in accordance with the general method of Example 108e from 2,2-bis-(2,4-dichlorophenyl)-6-fluoro-benzo[1,3]dioxole-5-carboxylic acid and 4-hydroxy-piperidine. Light yellow foam.
MS: m/e=556.0, 558.0 ([M]$^+$).

Example 190

Preparation of 2,2-bis-(2,4-dichloro-phenyl)-6-fluoro-benzo[1,3]dioxole-5-carboxylic acid ethyl-methyl-amide

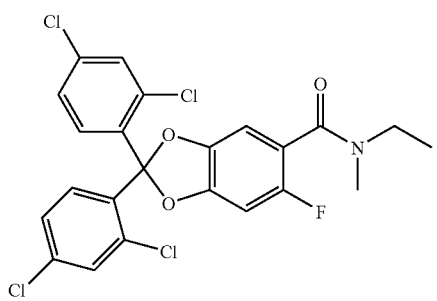

The title compound was produced in accordance with the general method of Example 108e from 2,2-bis-(2,4-dichlorophenyl)-6-fluoro-benzo[1,3]dioxole-5-carboxylic acid and N-ethylmethylamine. White foam.
MS: m/e=514.0, 516.0 ([M]$^+$).

Example 191

Preparation of 2,2-bis-(2,4-dichloro-phenyl)-6-fluoro-benzo[1,3]dioxole-5-carboxylic acid bis-(2-hydroxy-ethyl)-amide

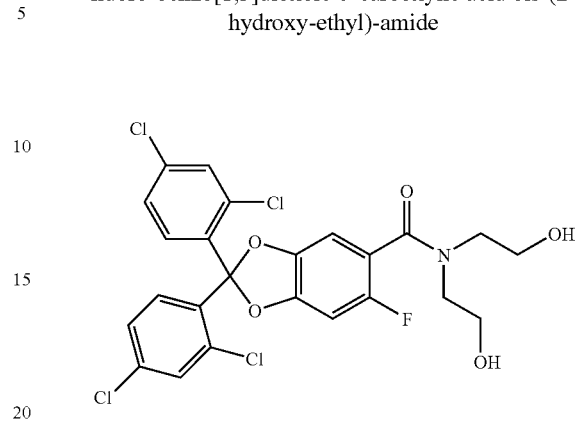

The title compound was produced in accordance with the general method of Example 108e from 2,2-bis-(2,4-dichlorophenyl)-6-fluoro-benzo[1,3]dioxole-5-carboxylic acid and diethanolamine. Light yellow foam.
MS: m/e=560.0, 562.0 ([M]$^+$).

Example 192

Preparation of [2,2-bis-(4-chloro-phenyl)-6-fluoro-benzo[1,3]dioxol-5-yl]-piperidin-1-yl-methanone

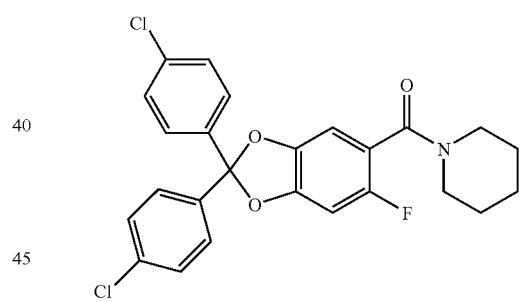

Preparation of 5-bromo-2,2-bis-(4-chloro-phenyl)-6-fluoro-benzo[1,3]dioxole

The title compound was produced in accordance with the general method of Example 108c from dichlorobis(4-chlorophenyl)methane (Example 170a) and 4-bromo-5-fluoro-benzene-1,2-diol (Example 108a). Colorless solid.
MS: m/e=437.9, 439.9, 441.9 ([M]$^+$).

Preparation of 2,2-bis-(4-chloro-phenyl)-6-fluoro-benzo[1,3]dioxole-5-carboxylic acid The title compound was produced in accordance with the general method of Example 108d from 5-bromo-2,2-bis-(4-chloro-phenyl)-6-fluoro-benzo[1,3]dioxole. Yellow solid.
MS: m/e=403.1, 405.1 ([M−H]$^−$).

Preparation of [2,2-bis-(4-chloro-phenyl)-6-fluoro-benzo[1,3]dioxol-5-yl]-piperidin-1-yl-methanone The title compound was produced in accordance with the general method of Example 108e from 2,2-bis-(4-chloro-phenyl)-6-fluoro-benzo[1,3]dioxole-5-carboxylic acid and piperidine. White foam.
MS: m/e=472.1, 474.1 ([M]+).

Example 193

Preparation of [2,2-bis-(4-chloro-phenyl)-6-fluoro-benzo[1,3]dioxol-5-yl]-pyrrolidin-1-yl-methanone

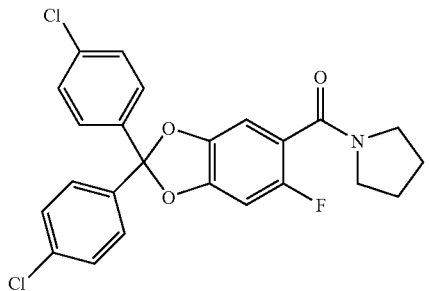

The title compound was produced in accordance with the general method of Example 108e from 2,2-bis-(4-chloro-phenyl)-6-fluoro-benzo[1,3]dioxole-5-carboxylic acid and pyrrolidine. White foam.
MS: m/e=458.1, 460.1 ([M]+).

Example 194

Preparation of [2,2-bis-(2-chloro-4-fluoro-phenyl)-benzo[1,3]dioxol-5-yl]-piperidin-1-yl-methanone

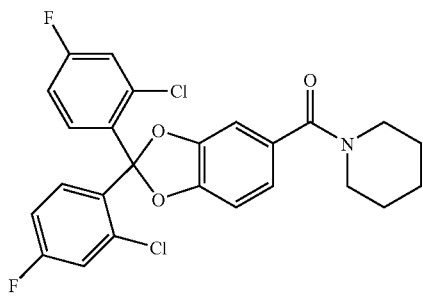

Preparation of 2,2'-dichloro-4,4'difluorodiphenyldichloromethane

Bis(2-chloro-4-fluorophenyl)-methanone (1.6 g, 5.57 mmol) and phosphorus pentachloride (1.4 g, 6.72 mmol) were heated 5 h at 165° C. in a sealed vial. The mixture was allowed to cool to room temperature, diluted with dichloromethane and poured onto ice. The phases were separated, the organic phase dried over magnesium sulfate and evaporated to afford the title compound as a light brown oil (1.46 g) consisting of a ca. 4:1 mixture of desired product and starting ketone (NMR) which was used without further purification.

NMR (300 MHz, CDCl₃) ppm: 8.39 (dd, 2H, J=4.5, 6.6 Hz, product), 7.55 (dd, 0.5H, benzophenone), 7.17 (dd, 0.5H, J=4.5, 6.3 Hz, benzophenone), 7.10 (m, 4.5H, product and benzophenone), 3.14 (m, 4H), 1.70-1.40 (m, 6H).

Preparation of [2,2-bis-(2-chloro-4-fluoro-phenyl)-benzo[1,3]dioxol-5-yl]-piperidin-1-yl-methanone The title compound was produced in accordance with the general method of Example 108c from 2,2'-dichloro-4,4'-difluorodiphenyldichloromethane and (3,4-dihydroxy-phenyl)-piperidin-4-yl-methanone. Light brown gum.
MS: m/e=490.1 ([M+H]+).

Example 195

Preparation of [2,2-bis-(3,4-difluoro-phenyl)-6-fluoro-benzo[1,3]dioxol-5-yl]-morpholin-4-yl-methanone

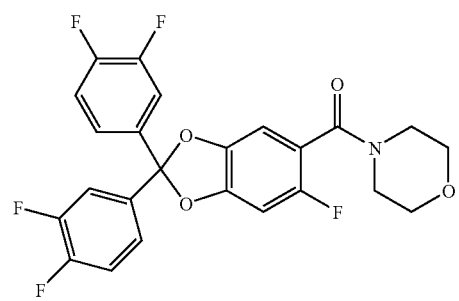

The title compound was produced in accordance with the general method of Example 108c from 1,1'-(dichloromethylene)bis[3,4-difluoro-benzene] and (2-fluoro-4,5-dihydroxyphenyl)-morpholin-4-yl-methanone (Example 99b). Off-white foam.
MS: m/e=478.3 ([M+H]+).

Example 196

Preparation of [2,2-bis-(2,5-difluoro-phenyl)-6-fluoro-benzo[1,3]dioxol-5-yl]-morpholin-4-yl-methanone

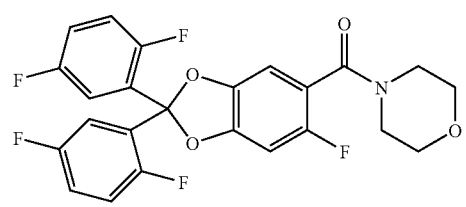

Preparation of bis-(2,5-difluorophenyl)dichloromethane

The title compound was produced in accordance with the general method of Example 207a from 2,5-difluorobenzene. Viscous light-brown oil.
MS: m/e=308.1 ([M]+).

Preparation of [2,2-bis-(2,5-difluoro-phenyl)-6-fluoro-benzo[1,3]dioxol-5-yl]-morpholin-4-yl-methanone The title compound was produced in accordance with the general method of Example 108c from (2-fluoro-4,5-dihydroxy-phenyl)-morpholin-1-yl-methanone (Example 99b) and bis-(2,5-difluorophenyl)dichloromethane (Example 196a). Light brown amorphous solid.

MS: m/e=477.1 ([M]$^+$).

Example 197

Preparation of [2,2-bis-(2-chloro-4-fluoro-phenyl)-benzo[1,3]dioxol-5-yl]-morpholin-4-yl-methanone

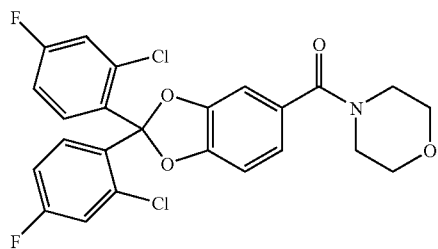

The title compound was produced in accordance with the general method of Example 108c from 2,2'-dichloro-4,4'-difluorodiphenyldichloromethane (Example 194a) and (3,4-dihydroxy-phenyl)-morpholin-4-yl-methanone (Example 87b). Light yellow gum.

MS: m/e=492.2 ([M+H]$^+$).

Example 198

Preparation of [2,2-bis-(2-chloro-4-fluoro-phenyl)-6-fluoro-benzo[1,3]dioxol-5-yl]-morpholin-4-yl-methanone

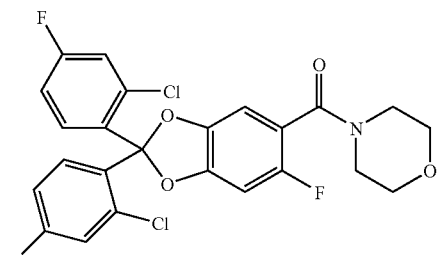

The title compound was produced in accordance with the general method of Example 108c from 2,2'-dichloro-4,4'-difluorodiphenyldichloromethane (Example 194a) and (2-fluoro-4,5-dihydroxy-phenyl)-morpholin-4-yl-methanone (Example 99b). Off-white foam.

MS: m/e=510.1 ([M+H]$^+$).

Example 199

Preparation of [6-chloro-2,2-bis-(2-chloro-4-fluoro-phenyl)-benzo[1,3]dioxol-5-yl]-morpholin-4-yl-methanone

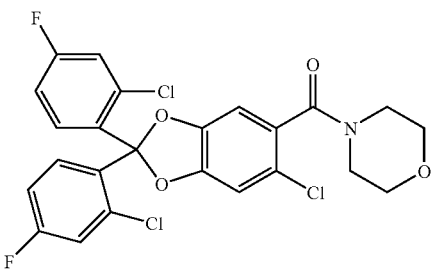

The title compound was produced in accordance with the general method of Example 108c from 2,2'-dichloro-4,4'-difluorodiphenyldichloromethane (Example 194a) and (2-chloro-4,5-dihydroxy-phenyl)-morpholin-4-yl-methanone (Example 218b). Light brown foam.

MS: m/e=526.1 ([M+H]$^+$).

Example 200

Preparation of 2-(2,4-dichloro-phenyl)-6-fluoro-2-(4-fluoro-phenyl)-benzo[1,3]dioxole-5-carboxylic acid amide

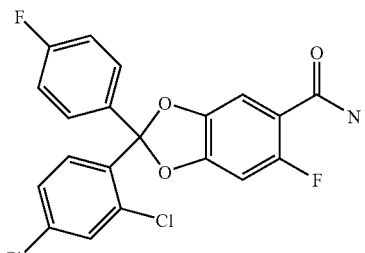

The title compound was produced in accordance with the general method of Example 108e from [2-(2,4-dichloro-phenyl)-6-fluoro-2-(4-fluoro-phenyl)-benzo[1,3]dioxole-5-carboxylic acid (Example 108d) and ammonium hydroxide. White foam.

MS: m/e=422 ([M]$^+$).

Example 201

Preparation of [2,2-bis-(4-bromo-2-fluoro-phenyl)-6-fluoro-benzo[1,3]dioxol-5-yl]-morpholin-4-yl-methanone

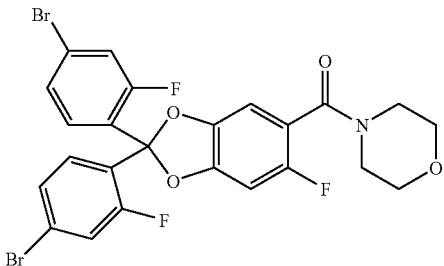

Preparation of 4,4'-dibromo-2,2'-difluoro-benzophenone

Tetrakis(triphenylphosphine)palladium (0.15 g, 0.13 mmol) was dissolved in anisole (15 mL). 1-Bromo-3-fluoro-4-iodobenzene (2.0 g, 6.6 mmol), 4-bromo-2-fluorobenzeneboronic acid (1.45 g, 6.6 mmol) and potassium carbonate (2.7 g, 19.9 mmol) together with another 15 mL anisole were added. The above mixture was stirred for 16 h at 80° C. under 10 bar carbon monoxide pressure. The reaction mixture was allowed to cool, added to a toluene/water mixture (120 mL, 1:1) the phases were separated and the water phase was extracted twice with toluene. Organic phases were pooled, washed with brine and the solvent was evaporated. Crystallization from hexane afforded the title compound as white crystals (1.17 g, 47%).

MS: m/e=375.9, 377.9 ([M+H]$^+$).

Preparation of 4,4'-dibromo-2,2'-difluoro-dichlorodiphenylmethane

A mixture of 4,4'-dibromo-2,2'-difluoro-benzophenone (1.3 g, 3.5 mmol), phosphorus oxychloride (26 mL) and phosphorus pentachloride (4.4 g, 21 mmol) was stirred at boiling temperature for 72 h. The mixture was cooled and poured into ice/water (200 mL). The product was extracted into dichloromethane. Organic phases were pooled, dried with sodium sulfate and the solvent was removed in vacuo yielding the product which was used without further purification. Brownish oil.

MS: m/e=429.8, 431.8 ([M]$^+$).

Preparation of [2,2-bis-(4-bromo-2-fluoro-phenyl)-6-fluoro-benzo[1,3]dioxol-5-yl]-morpholin-4-yl-methanone The title compound was produced in accordance with the general method of Example 108c from 4,4'-dibromo-2,2'-difluoro-dichlorodiphenylmethane and 2-fluoro-4,5-dihydroxy-phenyl)-morpholin-4-yl-methanone (Example 166c). Colorless oil.

MS: m/e=598.0, 600.0, 602.0 ([M]$^+$).

Example 202

Preparation of [2-(2,4-dichloro-phenyl)-6-fluoro-2-(4-fluoro-phenyl)-benzo[1,3]dioxol-5-yl]-(3,4-cis-dihydroxy-pyrrolidin-1-yl)-methanone

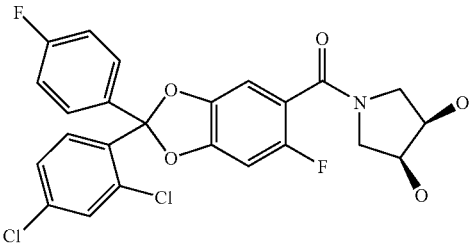

Preparation of [2-(2,4-dichloro-phenyl)-6-fluoro-2-(4-fluoro-phenyl)-benzo[1,3]dioxol-5-yl]-(2,5-dihydro-pyrrol-1-yl)-methanone The title compound was produced in accordance with the general method of Example 108e from [2-(2,4-dichloro-phenyl)-6-fluoro-2-(4-fluoro-phenyl)-benzo[1,3]dioxole-5-carboxylic acid (Example 108d) and 3-pyrroline. Yellow oil.

MS: m/e=474 ([M]$^+$).

Preparation of [2-(2,4-Dichloro-phenyl)-6-fluoro-2-(4-fluoro-phenyl)-benzo[1,3]dioxol-5-yl]-(3,4-cis-dihydroxy-pyrrolidin-1-yl)-methanone To a solution of [2-(2,4-dichloro-phenyl)-6-fluoro-2-(4-fluoro-phenyl)-benzo[1,3]dioxol-5-yl]-(2,5-dihydro-pyrrol-1-yl)-methanone (70 mg, 0.15 mmol) in acetone (3.7 mL) and water (1.5 mL), 4-methylmorpholine-4-oxide monohydrate (23 mg, 0.16 mmol), osmium tetroxide (0.02 mL, 0.0015 mmol) and potassium osmate(VI) dihydrate (2.4 mg, 0.0065 mmol) were added and the reaction stirred 24 h at 20° C. Sodium thiosulfate pentahydrate was added, the reaction mixture was stirred 30 min. and poured onto crushed ice. The aqueous phase was extracted twice with ethyl acetate and the combined organic phases were washed with brine, dried over sodium sulfate, filtered and the volatiles removed in vacuo. Purification by flash chromatography afforded the title product as a black oil (56 mg, 74%).

MS: m/e=508.1 ([M]$^+$).

Example 203

Preparation of [2,2-bis-(2,3-difluoro-phenyl)-6-fluoro-benzo[1,3]dioxol-5-yl]-morpholin-4-yl-methanone

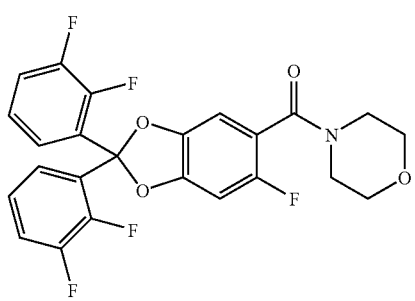

Preparation of bis-(2,3-difluoro-phenyl)-methanone

The title compound was produced in accordance with the general method of Example 173a from 2,3-difluorobenzeneboronic acid and 2,3-difluoro-benzoyl chloride. Off-white crystalline solid.
MS: m/e=254.1 ([M]+).

Preparation of bis-(2,3-difluorophenyl)dichloromethane

The title compound was produced in accordance with the general method of Example 87d from bis-(2,3-difluoro-phenyl)-methanone (Example 203a) and used without further purification. Brown solid.

Preparation of [2,2-bis-(2,3-difluoro-phenyl)-6-fluoro-benzo[1,3]dioxol-5-yl]-morpholin-4-yl-methanone The title compound was produced in accordance with the general method of Example 108c from (2-fluoro-4,5-dihydroxy-phenyl)-morpholin-1-yl-methanone (Example 99b) and bis-(2,3-difluorophenyl)dichloromethane (Example 203b). Off-white amorphous solid.
MS: m/e=478.1 ([M+H]+).

Example 204

Preparation of [6-fluoro-2,2-bis-(4-trifluoromethoxy-phenyl)-benzo[1,3]dioxol-5-yl]-morpholin-4-yl-methanone

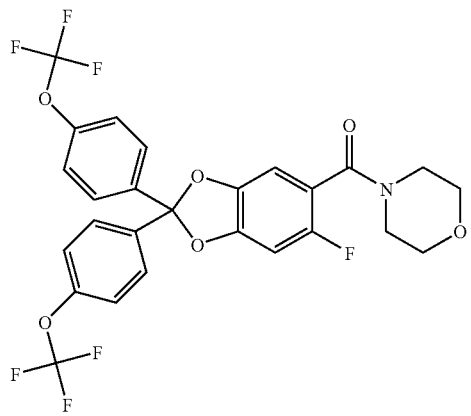

Preparation of bis-(4-trifluoromethoxy-phenyl)-methanone

The title compound was produced in accordance with the general method of Example 173a from 4-trifluoromethoxy-benzeneboronic acid and 4-trifluoromethoxy-benzoyl chloride. Light brown solid.
MS: m/e=350 ([M]+).

Preparation of bis-(4-trifluoromethoxy-phenyl)dichloromethane

The title compound was produced in accordance with the general method of Example 182a from bis-(4-trifluoromethoxy-phenyl)-methanone (Example 203a) in phosphorus oxychloride and used without further purification. Brown solid.

Preparation of [6-fluoro-2,2-bis-(4-trifluoromethoxy-phenyl)-benzo[1,3]dioxol-5-yl]-morpholin-4-yl-methanone The title compound was produced in accordance with the general method of Example 108c from (2-fluoro-4,5-dihydroxy-phenyl)-morpholin-1-yl-methanone (Example 99b) and bis-(4-trifluoromethyl-phenyl)dichloromethane (Example 204b). Off-white amorphous solid.
MS: m/e=574.2 ([M+H]+).

Example 205

Preparation of [2,2-bis-(2-chloro-4,5-difluoro-phenyl)-benzo[1,3]dioxol-5-yl]-piperidin-1-yl-methanone

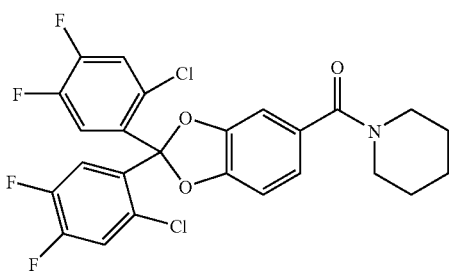

The title compound was produced in accordance with the general method of Example 108c from 1,1'-(dichloromethylene)bis[2-chloro-4,5-difluorobenzene and (3,4-dihydroxy-phenyl)-piperidin-4-yl-methanone. Off-white foam.
MS: m/e=526.1 ([M+H]+).

Example 206

Preparation of 4-[2,2-bis-(2-chloro-4-fluoro-phenyl)-6-fluoro-benzo[1,3]dioxole-5-sulfonyl]-morpholine

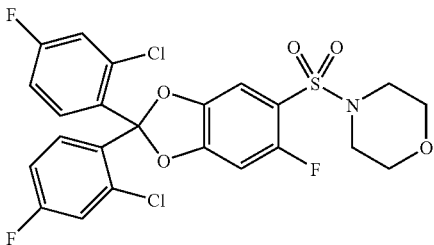

The title compound was produced in accordance with the general method of Example 108c from 2,2'-dichloro-4,4'-difluorodiphenyldichloromethane (Example 194a) and 4-fluoro-5-(morpholine-1-sulfonyl)-benzene-1,2-diol (Example 234b). Light brown solid.
MS: m/e=546.0 ([M+H]+).

Example 207

Preparation of [2,2-bis-(2,4-difluoro-phenyl)-6-fluoro-benzo[1,3]dioxol-5-yl]-piperidin-1-yl-methanone

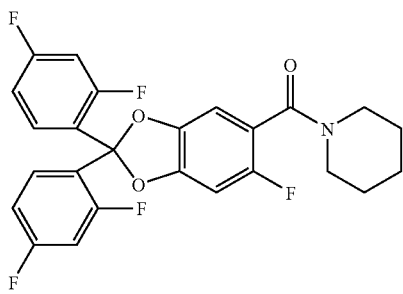

Preparation of 2,2',4,4'-tetrafluorodiphenyldichloromethane

To a cooled (10C) mixture of 1,3-difluorobenzene (50 g, 0.438 mol) and aluminium trichloride (33.3 g, 250 mmol, 0.57 eq.) was slowly added carbon tetrachloride (91 mL). The reaction mixture was warmed to 30° C. during 4 h. Ice water was added. The aqueous layer was extracted with dichloromethane. The combined organic layers were dried over sodium sulfate, filtered and the volatiles were removed in vacuo, affording the title compound 60.3 g, 89%) as a dark brown oil.

MS: m/e=273.2 ([M−Cl*]+).

Preparation of 5-bromo-2,2-bis-(2,4-difluoro-phenyl)-6-fluoro-benzo[1,3]dioxole The title compound was produced in accordance with the general method of Example 108c from 4-bromo-5-fluoro-benzene-1,2-diol (Example 108a) and [2,2-bis-(2,4-difluoro-phenyl)-6-fluoro-benzo[1,3]dioxol-5-yl]-piperidin-1-yl-methanone (Example 207a). Light yellow solid.

MS: m/e=444.0 ([M+H]+).

Preparation of 2,2-bis-(2,4-difluoro-phenyl)-6-fluoro-benzo[1,3]dioxole-5-carboxylic acid The title compound was produced in accordance with the general method of Example 108d from 5-bromo-2,2-bis-(2,4-difluoro-phenyl)-6-fluoro-benzo[1,3]dioxole (Example 207b). Yellow solid.

MS: m/e=407.0 ([M−H]−).

Preparation of [2,2-bis-(2,4-difluoro-phenyl)-6-fluoro-benzo[1,3]dioxol-5-yl]-piperidin-1-yl-methanone The title compound was produced in accordance with the general method of Example 108e from 2,2-bis-(2,4-difluoro-phenyl)-6-fluoro-benzo[1,3]dioxole-5-carboxylic acid (Example 207c) and piperidine. Yellow oil.

MS: m/e=476.1 ([M+H]+).

Example 208

Preparation of [2,2-bis-(2,4-difluoro-phenyl)-6-fluoro-benzo[1,3]dioxol-5-yl]-(4-fluoro-piperidin-1-yl)-methanone

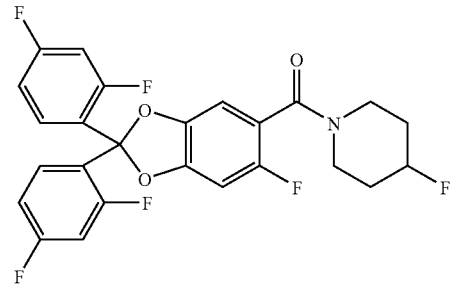

The title compound was produced in accordance with the general method of Example 108e from 2,2-bis-(2,4-difluoro-phenyl)-6-fluoro-benzo[1,3]dioxole-5-carboxylic acid (Example 207c) and 4-fluoropiperidine. White solid.

MS: m/e=494.1 ([M+H]+).

Example 209

Preparation of [2,2-bis-(2,4-difluoro-phenyl)-6-fluoro-benzo[1,3]dioxol-5-yl]-(4,4-difluoro-piperidin-1-yl)-methanone

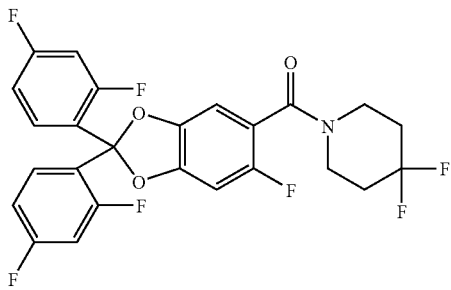

The title compound was produced in accordance with the general method of Example 108e from 2,2-bis-(2,4-difluoro-phenyl)-6-fluoro-benzo[1,3]dioxole-5-carboxylic acid (Example 207c) and 4,4-difluoropiperidine. White solid.

MS: m/e=512.2 ([M+H]+).

Example 210

Preparation of [2,2-bis-(2,4-difluoro-phenyl)-6-fluoro-benzo[1,3]dioxol-5-yl]-(4-trifluoromethyl-piperidin-1-yl)-methanone

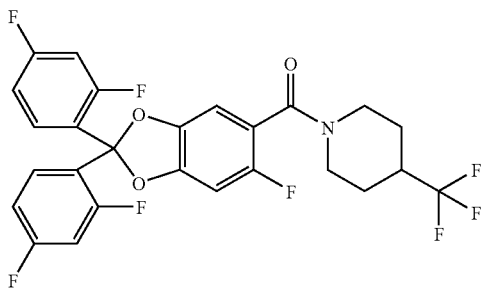

The title compound was produced in accordance with the general method of Example 108e from 2,2-bis-(2,4-difluoro-phenyl)-6-fluoro-benzo[1,3]dioxole-5-carboxylic acid (Example 207c) and 4-(trifluoromethyl)piperidine. Yellow oil.
MS: m/e=544.2 ([M+H]⁺).

Example 211

Preparation of [2,2-bis-(2,4-difluoro-phenyl)-6-fluoro-benzo[1,3]dioxol-5-yl]-(4-hydroxy-piperidin-1-yl)-methanone

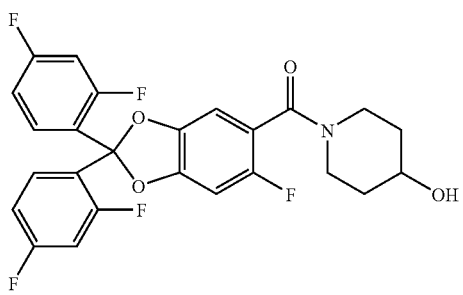

The title compound was produced in accordance with the general method of Example 108e from 2,2-bis-(2,4-difluoro-phenyl)-6-fluoro-benzo[1,3]dioxole-5-carboxylic acid (Example 207c) and 4-hydroxypiperidine. White solid.
MS: m/e=491.1 ([M+H]⁺).

Example 212

Preparation of [2,2-bis-(2,4-difluoro-phenyl)-6-fluoro-benzo[1,3]dioxol-5-yl]-thiomorpholin-4-yl-methanone

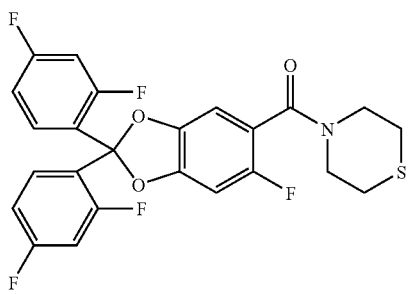

The title compound was produced in accordance with the general method of Example 108e from 2,2-bis-(2,4-difluoro-phenyl)-6-fluoro-benzo[1,3]dioxole-5-carboxylic acid (Example 207c) and 4-hydroxypiperidine. White solid.
MS: m/e=494.1 ([M+H]⁺).

Example 213

Preparation of [2,2-bis-(2,4-difluoro-phenyl)-6-fluoro-benzo[1,3]dioxol-5-yl]-pyrrolidin-1-yl-methanone

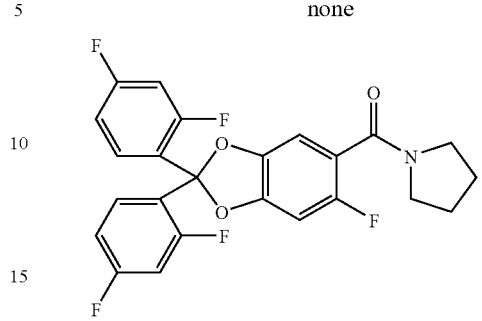

The title compound was produced in accordance with the general method of Example 108e from 2,2-bis-(2,4-difluoro-phenyl)-6-fluoro-benzo[1,3]dioxole-5-carboxylic acid (Example 207c) and pyrrolidine. White solid.
MS: m/e=462.1 ([M+H]⁺).

Example 214

Preparation of [2,2-bis-(2,4-difluoro-phenyl)-6-fluoro-benzo[1,3]dioxol-5-yl]-(3S-hydroxy-pyrrolidin-1-yl)-methanone

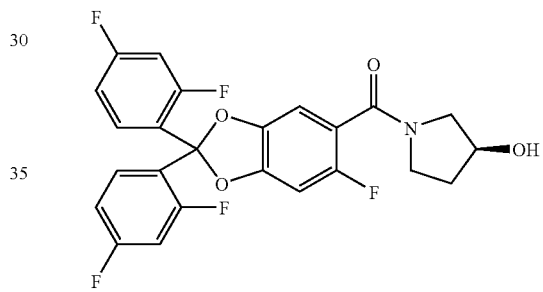

The title compound was produced in accordance with the general method of Example 108e from 2,2-bis-(2,4-difluoro-phenyl)-6-fluoro-benzo[1,3]dioxole-5-carboxylic acid (Example 207c) and 3S-hydroxypyrrolidine. White solid.
MS: m/e=478.1 ([M+H]⁺).

Example 215

Preparation of [2,2-bis-(2,4-difluoro-phenyl)-6-fluoro-benzo[1,3]dioxol-5-yl]-(2S-hydroxymethyl-pyrrolidin-1-yl)-methanone

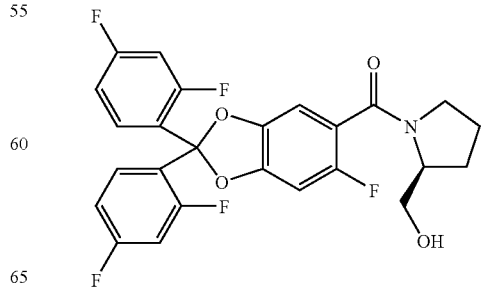

The title compound was produced in accordance with the general method of Example 108e from 2,2-bis-(2,4-difluoro-phenyl)-6-fluoro-benzo[1,3]dioxole5-carboxylic acid (Example 207c) and L-prolinol. White solid.

MS: m/e=492.2 ([M+H]$^+$).

Example 216

Preparation of [2,2-bis-(2,4-difluoro-phenyl)-6-fluoro-benzo[1,3]dioxol-5-yl]-(2S-methoxymethyl-pyrrolidin-1-yl)-methanone

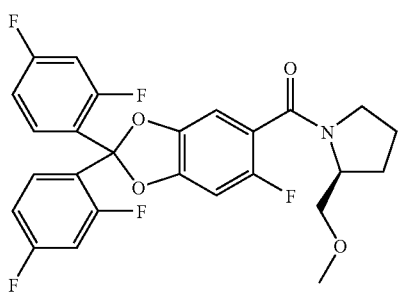

The title compound was produced in accordance with the general method of Example 108e from 2,2-bis-(2,4-difluoro-phenyl)-6-fluoro-benzo[1,3]dioxole-5-carboxylic acid (Example 207c) and 2S-(methoxymethyl)pyrrolidine. Light yellow oil.

MS: m/e=506.1 ([M+H]$^+$).

Example 217

Preparation of (6-chloro-2,2-di-p-tolyl-benzo[1,3]dioxol-5-yl)-morpholin-4-yl-methanone

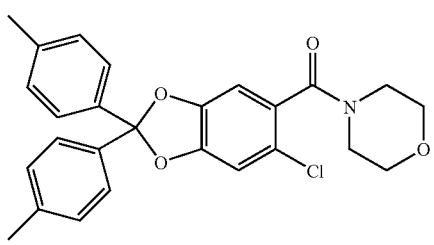

The title compound was produced in accordance with the general method of Example 233d from bis(4-methylphenyl)-methanethione and (2-chloro-4,5-dihydroxy-phenyl)-morpholin-4-yl-methanone (Example 218b). Light brown gum.

MS: m/e450.2 ([M+H]$^+$).

Example 218

Preparation of 4-[{6-chloro-10',11'-dihydro-spiro[1,3-benzodioxole-2,5'-[5H]dibenzo[a,d]cyclohepten]-5-yl}carbonyl]-morpholine

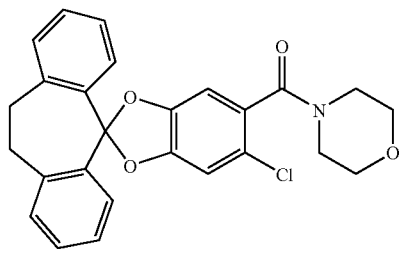

Preparation of (6-Chloro-benzo[1,3]dioxol-5-yl)-morpholin-4-yl-methanone

To a mixture of 6-chloro-1,3-benzodioxole-5-carboxylic acid (0.49 g, 2.44 mmol) and hydroxybenzotriazole (66 mg, 0.49 mmol) in acetonitrile (20 mL) were added morpholine (0.53 mL, 6.1 mmol) and N-(3-dimethylaminopropyl)-N'-ethylcarbodiimide hydrochloride (0.52 g, 2.7 mmol). The orange solution was stirred 72 h at room temperature, diluted with ethyl acetate and poured into water. The phases were separated and the aqueous phase extracted with ethyl acetate. The combined organic phases were washed with brine, dried over magnesium sulfate and evaporated under reduced pressure. The residue was purified by column chromatography on silica gel to afford the title compound as white solid (0.53 g, 80%), mp 155° C.

MS: m/e 270.2 ([M+H]$^+$).

Preparation of 2-chloro-4,5-dihydroxy-phenyl)-morpholin-4-yl-methanone

A 1M solution of boron trichloride in dichloromethane (11 mL) was added dropwise to a cooled (ice bath) solution of (6-chloro-benzo[1,3]dioxol-5-yl)-morpholin-4-yl-methanone (Example 218a) (1.98 g, 7.34 mmol) in dichloromethane (20 mL). The mixture was stirred overnight at room temperature and diluted with 1M aqueous potassium dihydrogenphosphate solution (10 mL). After stirring 1 h, the phases were separated and the aqueous phase extracted with ethyl acetate. The combined organic phases were washed with brine, dried over magnesium sulfate and evaporated to afford the title compound as brown foam (1.82 g, 96%) that was used without further purification.

MS: m/e494.1 ([M+H]$^+$).

Preparation of 4-[{6-chloro-10',11'-dihydro-spiro[1,3-benzodioxole-2,5'-[5H]dibenzo[a,d]cyclohepten]-5-yl}carbonyl]-morpholine The title compound was produced in accordance with the general method of Example 233d from 2,3,6,7-dibenzocyclo-heptane-1-thione and (2-chloro-4,5-dihydroxy-phenyl)-morpholin-4-yl-methanone (Example 218b). Light brown solid.

MS: m/e 448.1 ([M+H]$^+$).

Example 219

Preparation of [6-fluoro-2,2-bis-(4-fluoro-phenyl)-benzo[1,3]dioxol-5-yl]-(4-fluoro-piperidin-1-yl)-methanone

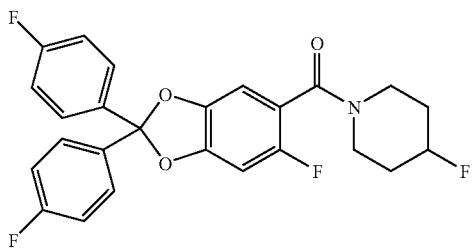

Preparation of 6-fluoro-2,2-bis-(4-fluoro-phenyl)-benzo[1,3]dioxole-5-carboxylic acid The title compound was produced in accordance with the general method of Example 108d from 5-bromo-6-fluoro-2,2-bis-(4-fluoro-phenyl)-benzo[1,3]dioxole (Example 164a). Light yellow foam.

MS: m/e=371.2 ([M−H]$^+$).

Preparation of [6-fluoro-2,2-bis-(4-fluoro-phenyl)-benzo[1,3]dioxol-5-yl]-(4-fluoro-piperidin-1-yl)-methanone The title compound was produced in accordance with the general method of Example 108e from 6-fluoro-2,2-bis-(4-fluoro-phenyl)-benzo[1,3]dioxole-5-carboxylic acid (Example 219a) and 4-fluoropiperidine hydrochloride. Yellow oil.

MS: m/e=458.2 ([M+H]$^+$).

Example 220

Preparation of (4,4-difluoro-piperidin-1-yl)-[6-fluoro-2,2-bis-(4-fluoro-phenyl)-benzo[1,3]dioxol-5-yl]-methanone

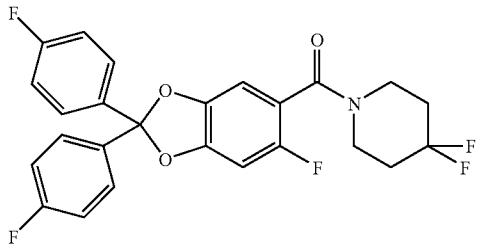

The title compound was produced in accordance with the general method of Example 108e from 6-fluoro-2,2-bis-(4-fluoro-phenyl)-benzo[1,3]dioxole-5-carboxylic acid (Example 219a) and 4,4'-difluoropiperidine. Yellow oil.

MS: m/e=476.1 ([M+H]$^+$).

Example 221

Preparation of [6-fluoro-2,2-bis-(4-fluoro-phenyl)-benzo[1,3]dioxol-5-yl]-(4-trifluoromethyl-piperidin-1-yl)-methanone

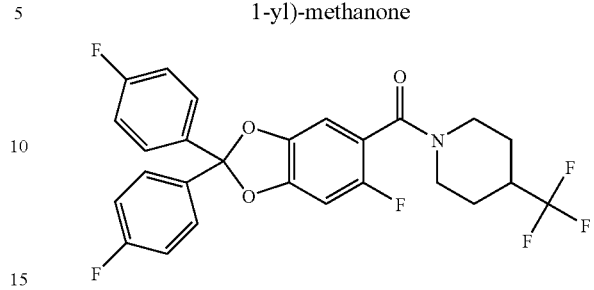

The title compound was produced in accordance with the general method of Example 108e from 6-fluoro-2,2-bis-(4-fluoro-phenyl)-benzo[1,3]dioxole-5-carboxylic acid (Example 219a) and 4-(trifluoromethyl)piperidine hydrochloride. Yellow oil.

MS: m/e=508.2 ([M+H]$^+$).

Example 222

Preparation of [6-fluoro-2,2-bis-(4-fluoro-phenyl)-benzo[1,3]dioxol-5-yl]-thiomorpholin-4-yl-methanone

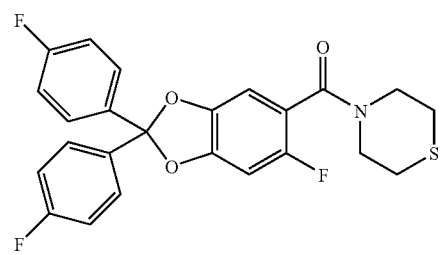

The title compound was produced in accordance with the general method of Example 108e from 6-fluoro-2,2-bis-(4-fluoro-phenyl)-benzo[1,3]dioxole-5-carboxylic acid (Example 219a) and thiomorpholine. Off-white foam.

MS: m/e=458.2 ([M+H]$^+$).

Example 223

Preparation of (3S-ethoxy-pyrrolidin-1-yl)-[6-fluoro-2,2-bis-(4-fluoro-phenyl)-benzo[1,3]dioxol-5-yl]-methanone

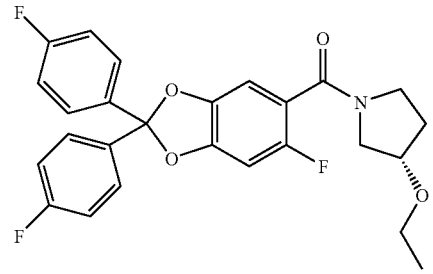

The title compound was produced in accordance with the general method of Example 108e from 6-fluoro-2,2-bis-(4-fluoro-phenyl)-benzo[1,3]dioxole-5-carboxylic acid (Example 219a) and 3S-ethoxypyrrolidine. Yellow oil.

MS: m/e=470.2 ([M+H]$^+$).

Example 224

Preparation of [6-fluoro-2,2-bis-(4-fluoro-phenyl)-benzo[1,3]dioxol-5-yl]-[(S)-(2-methoxymethyl-pyrrolidin-1-yl)]-methanone

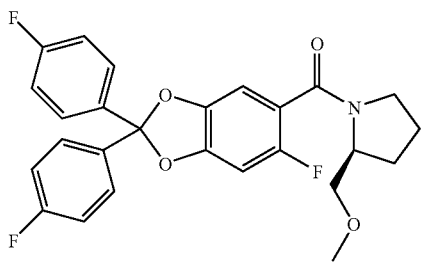

The title compound was produced in accordance with the general method of Example 108e from 6-fluoro-2,2-bis-(4-fluoro-phenyl)-benzo[1,3]dioxole-5-carboxylic acid (Example 219a) and 2S-methoxymethylpyrrolidine. Yellow oil.

MS: m/e=470.2 ([M+H]$^+$).

Example 225

Preparation of [6-fluoro-2,2-bis-(4-fluoro-phenyl)-benzo[1,3]dioxol-5-yl]-[(S)-2-hydroxymethyl-pyrrolidin-1-yl]-methanone

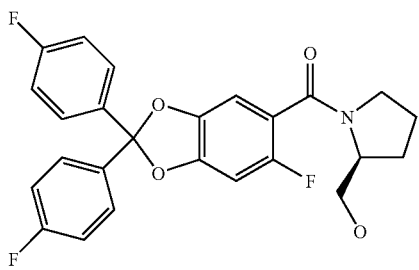

The title compound was produced in accordance with the general method of Example 108e from 6-fluoro-2,2-bis-(4-fluoro-phenyl)-benzo[1,3]dioxole-5-carboxylic acid (Example 219a) and L-prolinol. Yellow oil.

MS: m/e=456.1 ([M+H]$^+$).

Example 226

Preparation of [6-fluoro-2,2-bis-(4-fluoro-phenyl)-benzo[1,3]dioxol-5-yl]-[(S)-3-hydroxy-pyrrolidin-1-yl]-methanone

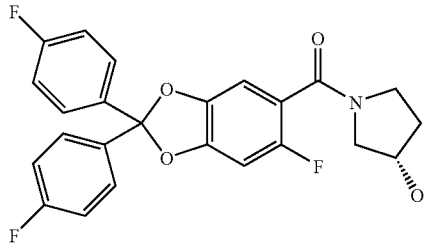

The title compound was produced in accordance with the general method of Example 108e from 6-fluoro-2,2-bis-(4-fluoro-phenyl)-benzo[1,3]dioxole-5-carboxylic acid (Example 219a) and 3S-hydroxypyrrolidine. Yellow foam.

MS: m/e=442.1 ([M+H]$^+$).

Example 227

Preparation of [6-fluoro-2,2-bis-(4-fluoro-phenyl)-benzo[1,3]dioxol-5-yl]-(4-hydroxy-piperidin-1-yl)-methanone

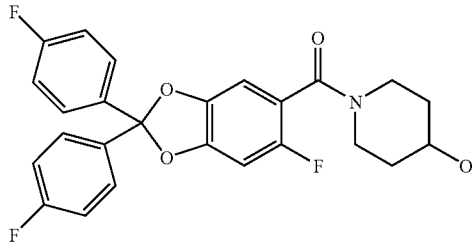

The title compound was produced in accordance with the general method of Example 108e from 6-fluoro-2,2-bis-(4-fluoro-phenyl)-benzo[1,3]dioxole-5-carboxylic acid (Example 219a) 4-hydroxypiperidine. Yellow oil.

MS: m/e=456.1 ([M+H]$^+$).

Example 228

Preparation of 4-[2,2-bis-(2-chloro-4,5-difluoro-phenyl)-6-fluoro-benzo[1,3]dioxole-5-sulfonyl]-morpholine

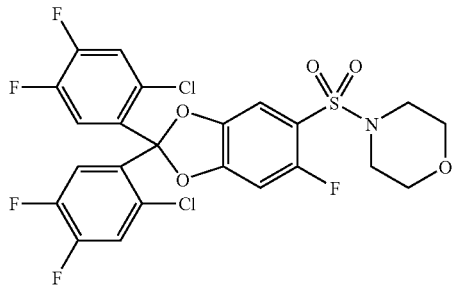

The title compound was produced in accordance with the general method of Example 108c from 1,1'-(dichloromethyl-

Example 229

Preparation of (2,2-di-p-tolyl-benzo[1,3]dioxol-5-yl)-piperidin-1-yl-methanone

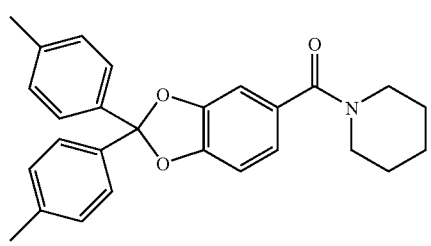

The title compound was produced in accordance with the general method of Example 233d from bis(4-methylphenyl)-methanethione and (3,4-dihydroxy-phenyl)-piperidin-4-yl-methanone. Off-white foam.

MS: m/e 414.2 ([M+H]⁺).

Example 230

Preparation of (2,2-di-p-tolyl-benzo[1,3]dioxol-5-yl)-morpholin-4-yl-methanone

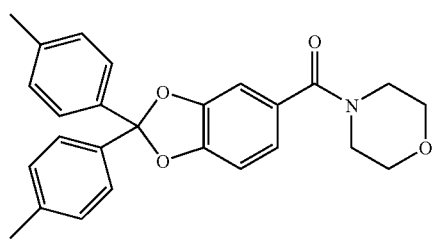

The title compound was produced in accordance with the general method of Example 233d from bis(4-methylphenyl)-methanethione and (3,4-dihydroxy-phenyl)-morpholin-4-yl-methanone (Example 87b). Off-white foam.

MS: m/e 416.2 ([M+H]⁺).

Example 231

Preparation of 4-[6-fluoro-2,2-bis-(4-fluoro-phenyl)-benzo[1,3]dioxole-5-sulfonyl]-morpholine

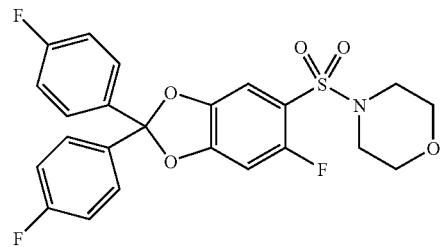

The title compound was produced in accordance with the general method of Example 245d from 2,2-bis-(2,4-difluoro-phenyl)-6-fluoro-benzo[1,3]dioxole-5-sulfonyl chloride (Example 261b) and morpholine. Yellow gum.

MS: m/e=478.1 ([M+H]⁺).

Example 232

Preparation of 4-(6-fluoro-2,2-di-p-tolyl-benzo[1,3]dioxole-5-sulfonyl)-morpholine

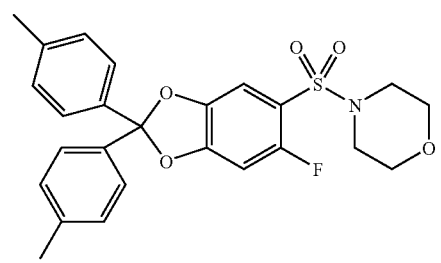

The title compound was produced in accordance with the general method of Example 233d from bis(4-methylphenyl)-methanethione and 4-fluoro-5-(morpholine-1-sulfonyl)-benzene-1,2-diol (Example 234b). Light brown gum.

MS: m/e 470.1 ([M+H]⁺).

Example 233

Preparation of 1-{6-fluoro-10',11'-dihydrospiro[1,3-benzodioxole-2,5'-[5H]dibenzo[a,d]cycloheptene]-5-yl}sulfonyl]-piperidine

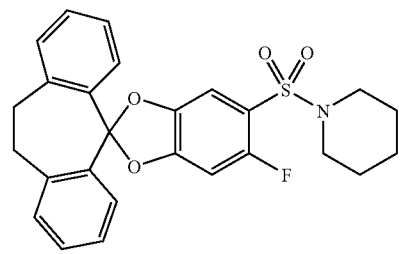

Preparation of 2-fluoro-4,5-dimethoxy-benzenesulfonyl chloride

To a suspension of sulfur trioxide N,N-dimethylformamide complex (4.108 g, 27 mmol) in 1,2-dichloroethane was added 4-fluoroveratrole (3.49 g, 22 mmol) dropwise. The mixture was slowly heated to 85° C. in an oil bath. After 2.5 h, the solids had dissolved to afford a golden yellow solution. A trace of starting material was still present and heating was continued for a further 4.5 h. The oil bath was removed and thionyl chloride (1.95 mL, 27 mmol) added dropwise. The mixture was heated 4 h at 85° C. and allowed to cool to room temperature. The solution was poured into water and extracted with dichloromethane (3×50 mL), the combined organics washed with water, dried over magnesium sulfate and evaporated. Remaining traces of N,N-dimethylformamide were removed azeotropically with toluene to afford the product as an off-white solid that was used without further purification.

MS: m/e 254.0 ([M]$^+$).

Preparation of 1-(2-fluoro-4,5-dimethoxy-benzenesulfonyl)-piperidine

Piperidine (4.15 ml, 42.02 mmol) was slowly added to a cooled (ice-bath) solution of 2-fluoro-4,5-dimethoxy-benzenesulfonyl chloride (5 g, 19.63 mmol) in dichloromethane (110 mL). The mixture was stirred overnight at room temperature, diluted with dichloromethane and poured into water. The aqueous phase was extracted with dichloromethane and the combined organic phases washed with brine, dried over magnesium sulfate and evaporated. The crude product was used without further purification.

NMR (300 MHz, CDCl$_3$) ppm: 7.23 (d, 1H, J=6 Hz), 6.71 (d, 1H, J=11 Hz), 3.93 (s, 3H), 3.90 (s, 3H), 3.14 (m, 4H), 1.70-1.40 (m, 6H).

Preparation of 4-fluoro-5-(piperidine-1-sulfonyl)-benzene-1,2-diol

A 1M solution of boron tribromide in dichloromethane (58 mL) was added dropwise to a cooled solution of 1-(2-fluoro-4,5-dimethoxy-benzenesulfonyl)-piperidine (5.89 g, 19.42 mmol) in dichloromethane (100 mL), maintaining the temperature between 10 and 20° C. The mixture was stirred overnight at room temperature and poured into 1M aqueous potassium dihydrogenphosphate and ice. After stirring 1 h, the phases were separated and the aqueous phase extracted with ethyl acetate. The combined organic phases were washed with brine, dried over magnesium sulfate and evaporated. The residue was purified by column chromatography on silica gel (10:1 dichloromethane/methanol eluant) to afford the title compound as a brown gum (4.17 g, 78%)

MS: m/e 274.1 ([M–H]$^+$).

Preparation of 1-{6-fluoro-10',11'-dihydrospiro[1,3-benzodioxole-2,5'-[5H]dibenzo[a,d]cycloheptene]-5-yl}sulfonyl]-piperidine A mixture of 2,3,6,7-dibenzocycloheptane-1-thione (0.281 g, 1.25 mmol), 4-fluoro-5-(piperidine-1-sulfonyl)-benzene-1,2-diol (0.230 g, 0.84 mmol), copper (I) chloride (0.207 g, 2.09 mmol) and triethylamine (0.46 mL, 3.34 mmol) were heated in acetonitrile (5 mL) 4 h at reflux. The mixture was allowed to cool to room temperature and filtered through a small pad of silica gel, eluting with 1:1 ethyl acetate/heptane. The solvent was evaporated under reduced pressure and the residue purified by column chromatography on silica gel (15:1 heptane/ethyl acetate eluant) to afford the product as a light yellow foam (0.215 g, 55%)

MS: m/e 465.2 ([M]$^+$).

Example 234

Preparation of 4-{6-fluoro-10',11'-dihydrospiro[1,3-benzodioxole-2,5'-[5H]dibenzo[a,d]cycloheptene]-5-yl}sulfonyl]-morpholine

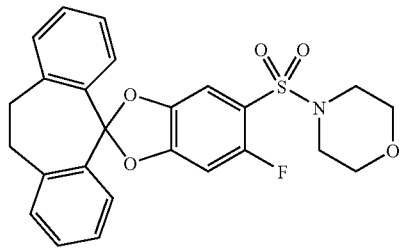

Preparation of 1-(2-fluoro-4,5-dimethoxy-benzenesulfonyl)-piperidine

The title compound was produced in accordance with the general method of Example 233c) from 2-fluoro-4,5-dimethoxy-benzenesulfonyl chloride (Example 233a) and morpholine. Colorless solid, mp 107-108° C.

MS: m/e 305.1 ([M]$^+$).

Preparation of 4-fluoro-5-(morpholine-1-sulfonyl)-benzene-1,2-diol

The title compound was produced in accordance with the general method of Example 233c from 1-(2-fluoro-4,5-dimethoxy-benzenesulfonyl)-piperidine (Example 234a). Light brown solid.

MS: m/e 276.0 ([M–H]$^+$).

Preparation of 4-{6-fluoro-10',11'-dihydrospiro[1,3-benzodioxole-2,5'-[5H]dibenzo[a,d]cycloheptene]-5-yl}sulfonyl]-morpholine The title compound was produced in accordance with the general method of Example 233d from 2,3,6,7-dibenzocycloheptane-1-thione and 4-fluoro-5-(morpholine-1-sulfonyl)-benzene-1,2-diol (Example 234b). Light yellow solid.

MS: m/e 467.2 ([M]$^+$).

Example 235

Preparation of 4-[{10',11'-dihydro-spiro[1,3-benzodioxole-2,5'-[5H]dibenzo[a,d]cycloheptene]-5-yl}carbonyl]-morpholine

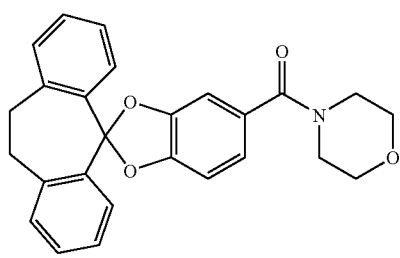

The title compound was produced in accordance with the general method of Example 233d from 2,3,6,7-dibenzocycloheptane-1-thione and (3,4-dihydroxy-phenyl)-morpholin-4-yl-methanone (Example 87b). Light yellow gum.

MS: m/e 414.2 ([M+H]$^+$).

Example 236

Preparation of 1-[{10',11'-dihydro-spiro[1,3-benzodioxole-2,5'-[5H]dibenzo[a,d]cycloheptene]-5-yl}carbonyl]-piperidine

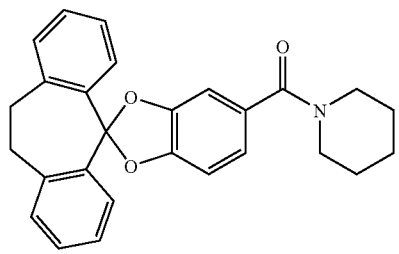

The title compound was produced in accordance with the general method of Example 233d from 2,3,6,7-dibenzocycloheptane-1-thione and (3,4-dihydroxy-phenyl)-piperidin-4-yl-methanone. Light yellow gum.

MS: m/e 412.2 ([M+H]$^+$).

Example 237

Preparation of [6-fluoro-2,2-bis-(4-fluoro-phenyl)-benzo[1,3]dioxol-5-yl]-(3-methoxy-piperidin-1-yl)-methanone

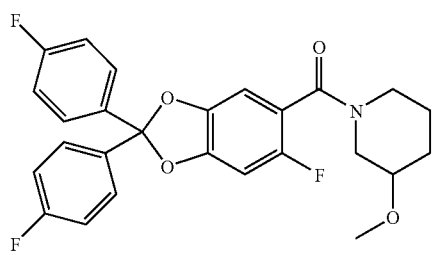

The title compound was produced in accordance with the general method of Example 108e from 6-fluoro-2,2-bis-(4-fluoro-phenyl)-benzo[1,3]dioxole-5-carboxylic acid (Example 219a) and 3-methoxypiperidine. Colorless oil.

MS: m/e=470.1 ([M+H]$^+$).

Example 240

Preparation of 1-[6-fluoro-2,2-bis-(4-fluoro-phenyl)-benzo[1,3]dioxole-5-sulfonyl]-pyrrolidine

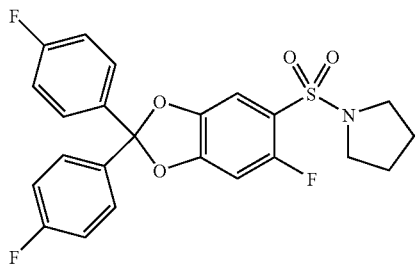

The title compound was produced in accordance with the general method of Example 245d from 2,2-bis-(2,4-difluoro-phenyl)-6-fluoro-benzo[1,3]dioxole-5-sulfonyl chloride (Example 261b) and pyrrolidine. Off white solid.

MS: m/e=462.1 ([M+H$^+$)].

Example 241

Preparation of 1-[6-fluoro-2,2-bis-(4-fluoro-phenyl)-benzo[1,3]dioxole-5-sulfonyl]-piperidine

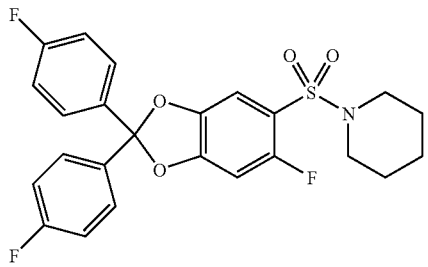

The title compound was produced in accordance with the general method of Example 245d from 2,2-bis-(2,4-difluoro-phenyl)-6-fluoro-benzo[1,3]dioxole-5-sulfonyl chloride (Example 261b) and piperidine. Yellow solid.

MS: m/e=476.1 ([M+H$^+$)].

Example 242

Preparation of 4-[6-fluoro-2,2-bis-(4-fluoro-phenyl)-benzo[1,3]dioxole-5-sulfonyl]-thiomorpholine

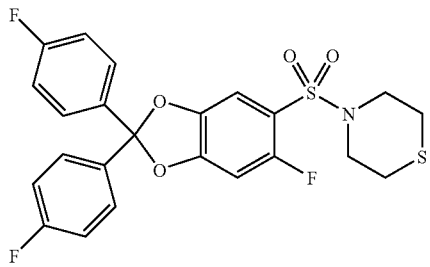

The title compound was produced in accordance with the general method of Example 245d from 2,2-bis-(2,4-difluoro-phenyl)-6-fluoro-benzo[1,3]dioxole-5-sulfonyl chloride (Example 261b) and thiomorpholine. Off white solid.

MS: m/e=494.1 ([M+H$^+$)].

Example 243

Preparation of 1-[2,2-bis-(2,4-difluoro-phenyl)-6-fluoro-benzo[1,3]dioxole-5-sulfonyl]-piperidine

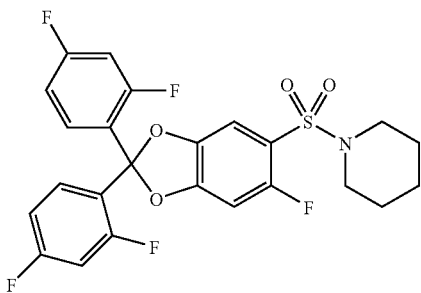

The title compound was produced in accordance with the general method of Example 108c from 2,2',4,4'-tetrafluorodiphenyldichloromethane (Example 162a) and 4-fluoro-5-(piperidine-1-sulfonyl)-benzene-1,2-diol (Example 233c). Light yellow gum.

MS: m/e=512.3 ([M+H]$^+$)

Example 244

Preparation of 1-[2,2-bis-(2-chloro-4-fluoro-phenyl)-6-fluoro-benzo[1,3]dioxole-5-sulfonyl]-piperidine

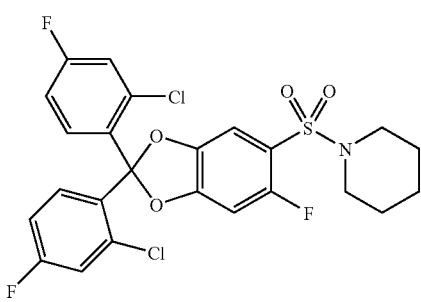

The title compound was produced in accordance with the general method of Example 108c from 2,2'-dichloro-4,4'-difluorodiphenyldichloromethane (Example 194a) and 4-fluoro-5-(piperidine-1-sulfonyl)-benzene-1,2-diol (Example 233c). Colorless gum.

MS: m/e=544.1 ([M+H]$^+$).

Example 245

Preparation of the 1-[2,2-bis-(2,4-difluoro-phenyl)-6-fluoro-benzo[1,3]dioxole-5-sulfonyl]-pyrrolidine

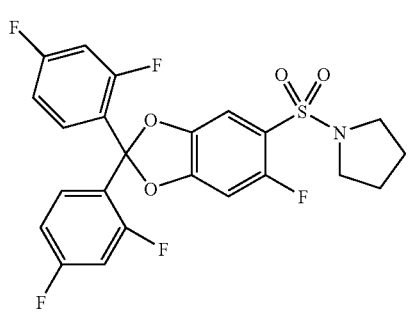

Preparation of 5-bromo-2,2-bis-(2,4-difluoro-phenyl)-6-fluoro-benzo[1,3]dioxole

The title compound was produced in accordance with the general method of Example 108c d from 2,2',4,4'-tetrafluorodiphenyldichloromethane (Example 207 a) and 4-bromo-5-fluoro-benzene-1,2-diol (Example 108a). Light yellow oil.

MS: m/e=444.0 ([M+H]$^+$).

Preparation of 2,2-bis-(2,4-difluoro-phenyl)-6-fluoro-benzo[1,3]dioxole-5 sulfinic acid To a cooled (-78° C.) solution of 5-bromo-2,2-bis-(2,4-difluoro-phenyl)-6-fluoro-benzo[1,3]dioxole (7.3 g, 16 mmol) in diethylether (48 mL) was added a solution of n-butyl lithium in hexanes (1.6 M, 10.3 mL, 16 mmol, 1.0 eq.). After 1 h at −78° C., sulfur dioxide was bubbled into the solution for 45 min. The reaction mixture was flushed with nitrogen and the reaction mixture was allowed to warm to 0° C. The reaction was neutralized with aqueous hydrochloric acid (0.5N), diluted with dichloromethane and the organic layer was washed with water, dried over sodium sulfate and the volatiles were removed in vacuo. Purification by flash chromatography afforded the title compound (4.2 g, 60%) as a white solid.

MS: m/e=427.0 ([M−H]$^-$).

Preparation of 2,2-bis-(2,4-difluoro-phenyl)-6-fluoro-benzo[1,3]dioxole-5-sulfonyl chloride To a solution of 2,2-bis-(2,4-difluoro-phenyl)-6-fluoro-benzo[1,3]dioxole-5 sulfinic acid (3.2 g, 7 mmol) in chloroform (25 mL) was added N-chlorosuccinimide (1.0 g, 7 mmol, 1.0 eq.) at 20° C. After 40 min, the reaction mixture was filtered and the filtrate was evaporated. The residue was suspended in dichloromethane, dried over sodium sulfate and the solvent was removed in vacuo, affording the title product as a light yellow gum.

MS: m/e=462.0 ([M+H]$^+$).

Preparation of 1-[2,2-bis-(2,4-difluoro-phenyl)-6-fluoro-benzo[1,3]dioxole-5-sulfonyl]-pyrrolidine To a solution of 2,2-bis-(2,4-difluoro-phenyl)-6-fluoro-benzo[1,3]dioxole-5-sulfonyl chloride (250 mg, 0.54 mmol) in diethylether (3 mL) was added pyrrolidine (0.11 mL, 1.35 mmol, 2.5 eq.). The reaction mixture was diluted with ethyl acetate (50 mL), washed with an aqueous solution of hydrochloric acid (1N), brine and water. The organic layer was dried over sodium sulfate and the volatiles were removed in vacuo. Purification by flash chromatography afforded the title compound (198 mg, 74%) as a white foam.

MS: m/e=498.2 ([M+H]$^+$).

Example 246

Preparation of 1-[2,2-bis-(2,4-difluoro-phenyl)-6-fluoro-benzo[1,3]dioxole-5-sulfonyl]-4-fluoro-piperidine

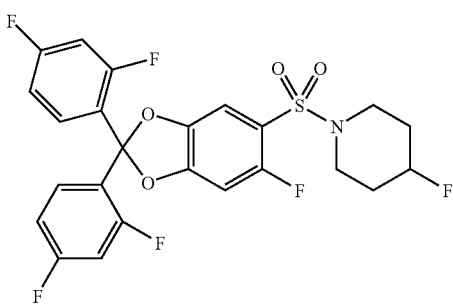

The title compound was produced in accordance with the general method of Example 245d from 2,2-bis-(2,4-difluoro-phenyl)-6-fluoro-benzo[1,3]dioxole-5-sulfonyl chloride (Example 245c) and 4-fluoropiperidine. White foam.

MS: m/e=530.1 ([M+H]$^+$).

Example 247

Preparation of 1-[2,2-bis-(2,4-difluoro-phenyl)-6-fluoro-benzo[1,3]dioxole-5-sulfonyl]-4,4-difluoro-piperidine

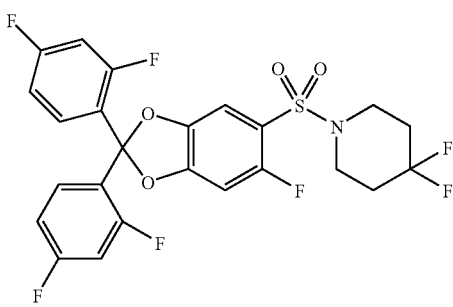

The title compound was produced in accordance with the general method of Example 245d from 2,2-Bis-(2,4-difluoro-phenyl)-6-fluoro-benzo[1,3]dioxole-5-sulfonyl chloride (Example 245c) and 4,4-difluoropiperidine. White foam.

MS: m/e=548.1 ([M+H]$^+$).

Example 248

Preparation of 1-[2,2-bis-(2,4-difluoro-phenyl)-6-fluoro-benzo[1,3]dioxole-5-sulfonyl]-4-trifluoromethyl-piperidine

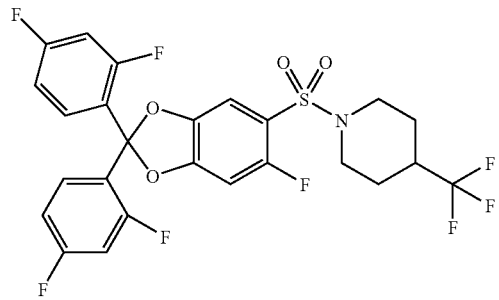

The title compound was produced in accordance with the general method of Example 245d from 2,2-bis-(2,4-difluoro-phenyl)-6-fluoro-benzo[1,3]dioxole-5-sulfonyl chloride (Example 245c) and 4-trifluoromethylpiperidine hydrochloride. White foam.

MS: m/e=580.2 ([M+H]$^+$).

Example 249

Preparation of 4-[2,2-bis-(2,4-difluoro-phenyl)-6-fluoro-benzo[1,3]dioxole-5-sulfonyl]-thiomorpholine

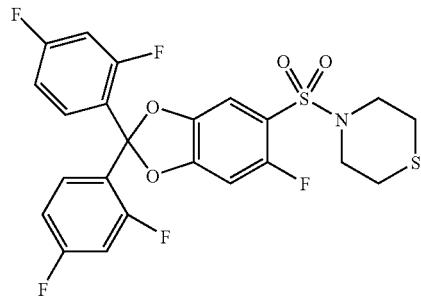

The title compound was produced in accordance with the general method of Example 245d from 2,2-bis-(2,4-difluoro-phenyl)-6-fluoro-benzo[1,3]dioxole-5-sulfonyl chloride (Example 245c) and thiomorpholine. White foam.

MS: m/e=530.0 ([M+H]$^+$).

Example 250

Preparation of 1-[2,2-bis-(2,4-difluoro-phenyl)-6-fluoro-benzo[1,3]dioxole-5-sulfonyl]-2S-methoxymethyl-pyrrolidine

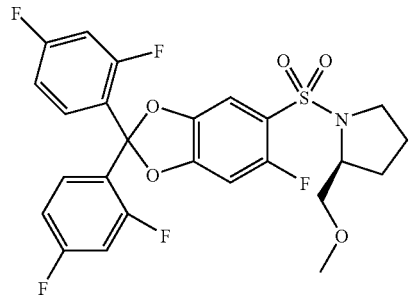

The title compound was produced in accordance with the general method of Example 245d from 2,2-bis-(2,4-difluoro-phenyl)-6-fluoro-benzo[1,3]dioxole-5-sulfonyl chloride (Example 245c) and (2S)-methoxymethylpyrrolidine. White foam.

MS: m/e=542.2 ([M+H]$^+$).

Example 251

Preparation of 2,2-bis-(2,4-difluoro-phenyl)-6-fluoro-benzo[1,3]dioxole-5-sulfonic acid (2S-methoxymethyl-pyrrolidin-1-yl)-amide

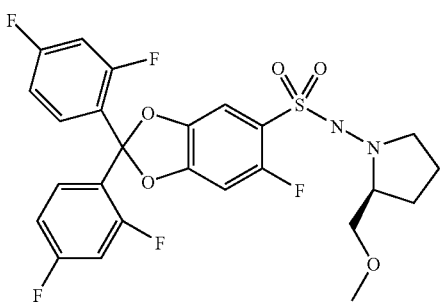

The title compound was produced in accordance with the general method of Example 245d from 2,2-bis-(2,4-difluoro-phenyl)-6-fluoro-benzo[1,3]dioxole-5-sulfonyl chloride (Example 245c) and 1-amino-(2S)-methoxymethylpyrrolidine. Yellow viscous oil.

MS: m/e=556.1 ([M−H]$^-$).

Example 252

Preparation of {1-[2,2-bis-(2,4-difluoro-phenyl)-6-fluoro-benzo[1,3]dioxole-5-sulfonyl]-pyrrolidin-2S-yl}-methanol

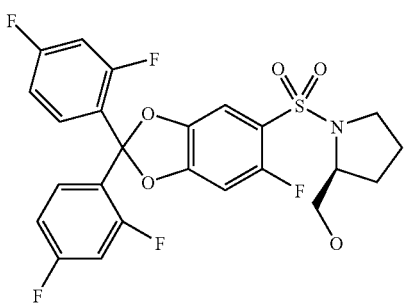

The title compound was produced in accordance with the general method of Example 245d from 2,2-Bis-(2,4-difluoro-phenyl)-6-fluoro-benzo[1,3]dioxole-5-sulfonyl chloride (Example 245c) and L-prolinol. White foam.

MS: m/e=528.2 ([M−H$^-$]).

Example 253

Preparation of 1-[2,2-bis-(2,4-difluoro-phenyl)-6-fluoro-benzo[1,3]dioxole-5-sulfonyl]-pyrrolidin-3S-ol

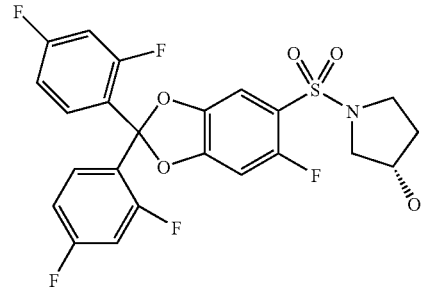

The title compound was produced in accordance with the general method of Example 245d from 2,2-bis-(2,4-difluoro-phenyl)-6-fluoro-benzo[1,3]dioxole-5-sulfonyl chloride (Example 245c) and 3S-hydroxypyrrolidine. White foam.

MS: m/e=514.2 ([M−H$^-$)].

Example 254

Preparation of 1-[2,2-bis-(2,4-difluoro-phenyl)-6-fluoro-benzo[1,3]dioxole-5-sulfonyl]-piperidin-4-ol

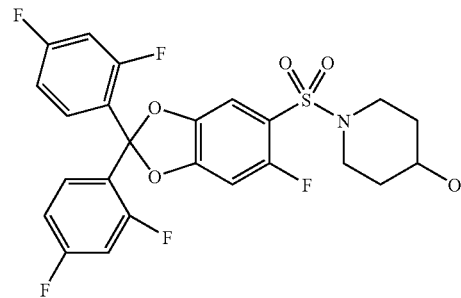

The title compound was produced in accordance with the general method of Example 245d from 2,2-bis-(2,4-difluoro-phenyl)-6-fluoro-benzo[1,3]dioxole-5-sulfonyl chloride (Example 245c) and 4-hydroxypiperidine. White foam.

MS: m/e=528.2 ([M−H]$^-$).

Example 255

Preparation of 1-[2,2-bis-(2-chloro-4,5-difluoro-phenyl)6-fluoro-benzo[1,3]dioxol-5-sulfonyl]-piperidine

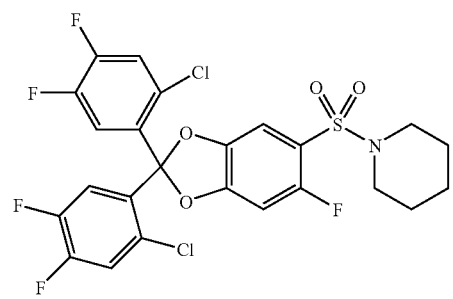

The title compound was produced in accordance with the general method of Example 108c from 1,1'-(dichloromethylene)bis[2-chloro-4,5-difluorobenzene and 4-fluoro-5-(piperidine-1-sulfonyl)-benzene-1,2-diol (Example 233c). Off-white foam.

MS: m/e=580.1 ([M+H]$^+$).

Example 256

Preparation of 4-[{6-fluoro-10',11'-dihydro-spiro[1,3-benzodioxole-2,5'-[5H]dibenzo[a,d]cyclohepten]-5-yl}-carbonyl]-morpholine

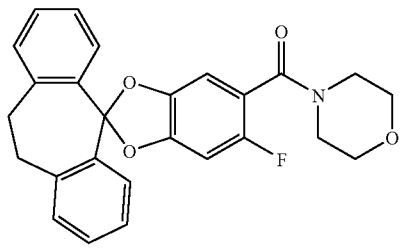

The title compound was produced in accordance with the general method of Example 233d from 2,3,6,7-dibenzocycloheptane-1-thione and (2-fluoro-4,5-dihydroxy-phenyl)-morpholin-4-yl-methanone (Example 99b). Light brown solid.

MS: m/e 432.3 ([M+H]$^+$).

Example 257

Preparation of (6-fluoro-2,2-di-p-tolyl-benzo[1,3]dioxol-5-yl)-morpholin-4-yl-methanone

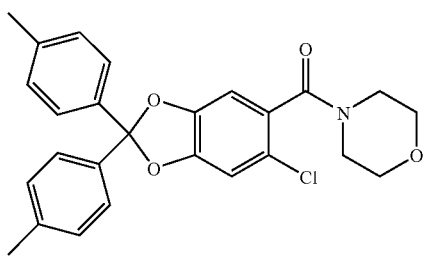

The title compound was produced in accordance with the general method of Example 233d from bis(4-methylphenyl)-methanethione and (2-fluoro-4,5-dihydroxy-phenyl)-morpholin-4-yl-methanone (Example 99b). Light brown gum.

MS: m/e 434.3 ([M+H]$^+$).

Example 258

Preparation of 1-(6-fluoro-2,2-di-p-tolyl-benzo[1,3]dioxole-5-sulfonyl)-piperidine

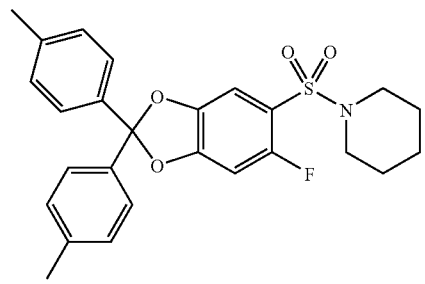

The title compound was produced in accordance with the general method of Example 233d from bis(4-methylphenyl)-methanethione and 4-fluoro-5-(piperidine-1-sulfonyl)-benzene-1,2-diol (Example 233c). Light yellow gum.

MS: m/e 470.2 ([M+H]$^+$).

Example 259

Preparation of [6-fluoro-2,2-bis-(2-fluoro-phenyl)-benzo[1,3]dioxol-5-yl]-piperidin-1-yl methanone

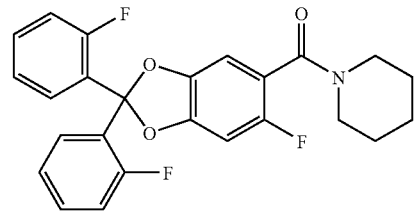

Preparation of 5-bromo-6-fluoro-2,2-bis-(2-fluoro-phenyl)-benzo[1,3]dioxole

The title compound was produced in accordance with the general method of Example 108c from 4-bromo-5-fluorobenzene-1,2-diol (Example 108a) and bis-(2-fluoro-phenyl)methanone (Example 173a). Colorless solid.

MS: m/e=407.9 ([M]$^+$).

Preparation of 6-fluoro-2,2-bis-(2-fluoro-phenyl)-benzo[1,3]dioxole-5-carboxylic acid The title compound was produced in accordance with the general method of Example 108d from 5-bromo-6-fluoro-2,2-bis-(2-fluoro-phenyl)-benzo[1,3]dioxole and carbon dioxide. Light brown solid.

MS: m/e=371.2 ([M−H]$^+$).

Preparation of [6-fluoro-2,2-bis-(2-fluoro-phenyl)-benzo[1,3]dioxol-5-yl]-piperidin-1-yl-methanone The title compound was produced in accordance with the general method of Example 108e from 6-fluoro-2,2-bis-(2-fluoro-phenyl)-benzo[1,3]dioxole-5-carboxylic acid and piperidine, with (benzotriazol-1-yl-oxy-tris-dimethylamino)- phosphonium hexafluorophosphate (BOP) as coupling reagent (instead of carbonyl diimidazole) in acetonitrile as solvent at room temperature (reaction time 20 h). Off-white solid.

MS: m/e=440.3 ([M+H]⁺).

Example 260

Preparation of [6-fluoro-2,2-bis-(2-fluoro-phenyl)-benzo[1,3]dioxol-5-yl]-(4-hydroxy-piperidin-1-yl)-methanone

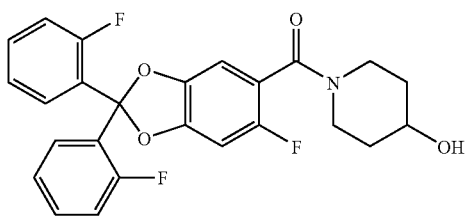

The title compound was produced in accordance with the general method of Example 108e from 6-fluoro-2,2-bis-(2-fluoro-phenyl)-benzo[1,3]dioxole-5-carboxylic acid and 4-hydroxy-piperidine, with (benzotriazol-1-yl-oxy-tris-dimethylamino)-phosphonium hexafluorophosphate (BOP) as coupling reagent (instead of carbonyl diimidazole) in acetonitrile as solvent at room temperature (reaction time 20 h). Off-white solid.

MS: m/e=456.2 ([M+H]⁺).

Example 261

Preparation of 4-fluoro-1-[6-fluoro-2,2-bis-(4-fluoro-phenyl)-benzo[1,3]dioxole-5-sulfonyl]-piperidine

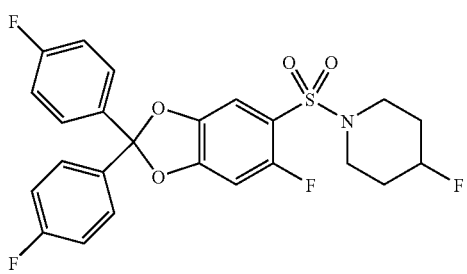

Preparation of 6-fluoro-2,2-bis-(4-fluoro-phenyl)-benzo[1,3]dioxole-5-sulfinic acid The title compound was produced in accordance with the general method of Example 245b from 5-bromo-6-fluoro-2,2-bis-(4-fluoro-phenyl)-benzo[1,3]dioxole (Example 164a). Off-white foam.

MS: m/e=391.1 ([M−H]⁻).

Preparation of 6-fluoro-2,2-bis-(4-fluoro-phenyl)-benzo[1,3]dioxole-5-sulfonyl chloride The title compound was produced in accordance with the general method of Example 245c from 6-fluoro-2,2-bis-(4-fluoro-phenyl)-benzo[1,3]dioxole-5-sulfinic acid (Example 261a). Yellow oil.

MS: m/e=426.0 ([M+H]⁺).

Preparation of 4-fluoro-1-[6-fluoro-2,2-bis-(4-fluoro-phenyl)-benzo[1,3]dioxole-5-sulfonyl]-piperidine The title compound was produced in accordance with the general method of Example 245d from 2,2-bis-(2,4-difluoro-phenyl)-6-fluoro-benzo[1,3]dioxole-5-sulfonyl chloride (Example 261b) and 4-fluoropiperidine. White foam.

MS: m/e=494.4 ([M+H]⁺).

Example 262

Preparation of 4,4-difluoro-1-[6-fluoro-2,2-bis-(4-fluoro-phenyl)-benzo[1,3]dioxole-5-sulfonyl]-piperidine

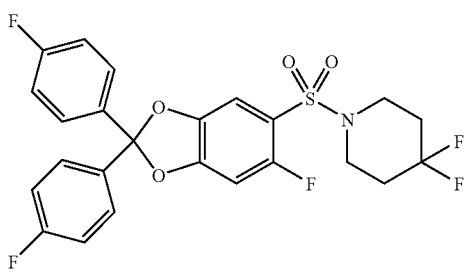

The title compound was produced in accordance with the general method of Example 245d from 2,2-bis-(2,4-difluoro-phenyl)-6-fluoro-benzo[1,3]dioxole-5-sulfonyl chloride (Example 261b) and 4,4-difluoropiperidine. White foam.

MS: m/e=512.4 ([M+H]⁺).

Example 263

Preparation of 1-[6-fluoro-2,2-bis-(4-fluoro-phenyl)-benzo[1,3]dioxole-5-sulfonyl]-4-trifluoromethyl-piperidine

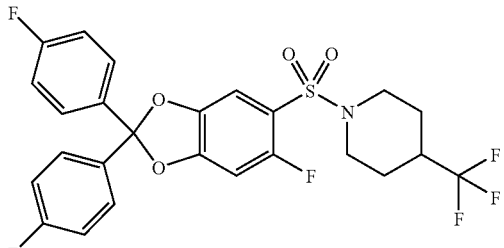

The title compound was produced in accordance with the general method of Example 245d from 2,2-bis-(2,4-difluoro-phenyl)-6-fluoro-benzo[1,3]dioxole-5-sulfonyl chloride (Example 261b) and 4-(trifluoromethyl)-piperidine hydrochloride. White foam.

MS: m/e=544.4 ([M+H]⁺).

Example 264

Preparation of 1-[6-fluoro-2,2-bis-(4-fluoro-phenyl)-benzo[1,3]dioxole-5-sulfonyl]-2S-methoxymethyl-pyrrolidine

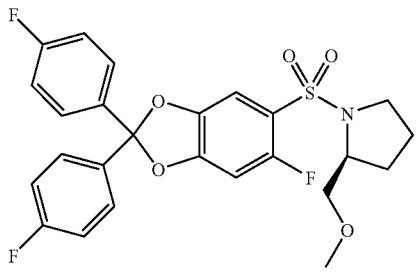

The title compound was produced in accordance with the general method of Example 245d from 2,2-bis-(2,4-difluoro-phenyl)-6-fluoro-benzo[1,3]dioxole-5-sulfonyl chloride (Example 261b) and 2S-methoxymethylpyrrolidine. White foam.

MS: m/e=506.3 ([M+H]$^+$).

Example 265

Preparation of 1-[6-fluoro-2,2-bis-(4-fluoro-phenyl)-benzo[1,3]dioxole-5-sulfonyl]-pyrrolidin-3S-ol

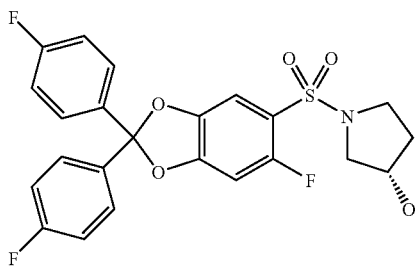

The title compound was produced in accordance with the general method of Example 245d from 2,2-bis-(2,4-difluoro-phenyl)-6-fluoro-benzo[1,3]dioxole-5-sulfonyl chloride (Example 261b) and 3S-hydroxypyrrolidine. White foam.

MS: m/e=478.2 ([M+H]$^+$).

Example 266

Preparation of 1-[6-fluoro-2,2-bis-(4-fluoro-phenyl)-benzo[1,3]dioxole-5-sulfonyl]-piperidin-4-ol

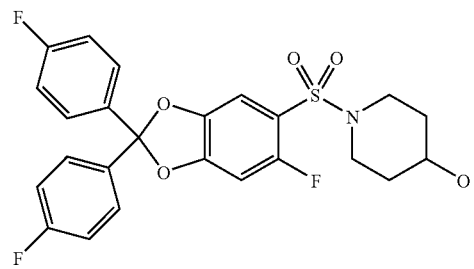

The title compound was produced in accordance with the general method of Example 245d from 2,2-bis-(2,4-difluoro-phenyl)-6-fluoro-benzo[1,3]dioxole-5-sulfonyl chloride (Example 261b) and 4-hydroxypyrrolidine. White solid.

MS: m/e=491.1 ([M+H]$^+$).

Example 267

Preparation of [2,2-bis-(3-chloro-phenyl)-benzo[1,3]dioxol-5-yl]-piperidin-1-yl-methanone

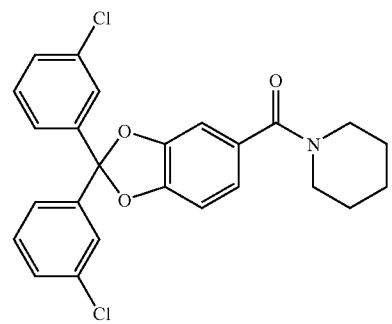

Preparation of bis-(3-chloro-phenyl)-methanol

This compound was prepared from 3-chloro-iodobenzene according to Example 269a; light yellow oil, MS: m/e=252 ([M]$^+$).

Preparation of bis-(3-chloro-phenyl)-methanone

This compound was prepared from bis-(3-chloro-phenyl)-methanol according to Example 269b; white solid, m.p.: 117° C., MS: m/e=250 ([M]$^+$).

Preparation of bis-(3-chloro-phenyl)-dichloromethane

This compound was prepared from bis-(3-chloro-phenyl)-methanone and PCl$_5$ according to Example 269c;

MS: m/e=306 ([M$^+$)].

163

Preparation of 2,2-bis-(3-chloro-phenyl)-benzo[1,3]dioxole-5-carboxylic acid ethyl ester This compound was prepared from bis-(3-chloro-phenyl)-dichloromethane and ethyl 3,4-dihydroxybenzoate according to Example 269d; yellow viscous oil, MS: m/e=415 ([M+H]$^+$).

Preparation of 2,2-bis-(3-chloro-phenyl)-benzo[1,3]dioxole-5-carboxylic acid

This compound was prepared from 2,2-bis-(3-chloro-phenyl)-benzo[1,3]dioxole-5-carboxylic acid ethyl ester according to Example 269e; white solid, m.p.: 166° C., MS: m/e=386 ([M–H]$^-$).

Preparation of [2,2-bis-(3-chloro-phenyl)-benzo[1,3]dioxol-5-yl]-piperidin-1-yl-methanone This compound was prepared from 2,2-bis-(3-chloro-phenyl)-benzo[1,3]dioxole-5-carboxylic acid and piperidine according to Example 269f; light yellow solid, mp.: 54° C., MS: m/e=454 ([M+H]$^+$).

Example 268

Preparation of [2,2-bis-(4-cyano-2-fluoro-phenyl)-6-fluoro-benzo[1,3]dioxol-5-yl]-morpholin-4-yl-methanone

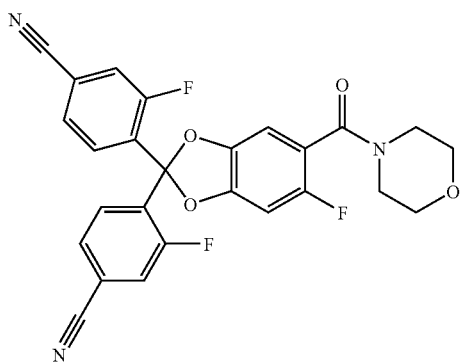

A mixture of [2,2-bis-(4-bromo-2-fluoro-phenyl)-6-fluoro-benzo[1,3]dioxol-5-yl]morpholin-4-yl-methanone (0.3 g, 0.5 mmol), copper (I) cyanide (0.81 g), tris(dibenzylideneacetone)dipalladium(0) chloroform complex (78 mg), tetraethylammonium cyanide (226 mg) and 1,1'-bis-(diphenylphosphino)-ferrocene (165 mg) was boiled for 3 days in dioxane (8 mL). Ethyl acetate (60 mL) and sodium bicarbonate (60 mL) were added to the cooled mixture, the phases were separated and the aqueous phase extracted with ethyl acetate. Organic phases were pooled, washed with brine and dried with sodium sulfate. Volatiles were removed and the residue was purified by chromatography on silica gel (ethyl acetate/heptane) to afford the title product as a light yellow foam (0.17 g; 71%).

MS: m/e=491.1 ([M]$^+$).

164

Example 269

Preparation of [2,2-bis-(3,5-difluoro-phenyl)-benzo[1,3]dioxol-5-yl]-piperidin-1-yl-methanone

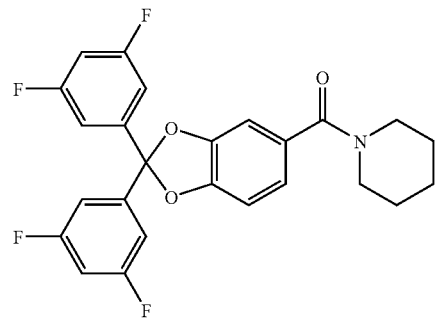

Preparation of bis-(3,5-difluoro-phenyl)-methanol

A mixture of 486 mg magnesium, 8 mL dry ether, a small amount of 3,5-difluoro-bromobenzene and some iodine was warmed to start the Grignard reaction. 2.38 mL 3,5-difluoro-bromobenzene in 40 mL dry ether were added dropwise and the mixture refluxed for one hour. 0.81 mL ethyl formate was added and the mixture stirred for 21 hours at room temperature. The reaction was quenched with 7 mL 1N hydrochloric acid, diluted with ethyl acetate and washed with water and brine. Evaporation of the solvents and chromatography of the residue afforded 1.56 g of a light yellow solid, m.p.: 62° C.; MS: 315 ([M+AcO]$^-$).

Preparation of bis-(3,5-difluoro-phenyl)-methanone 1.56 g bis-(3,5-difluoro-phenyl)-methanol, 1.06 g MnO2 and 36 mL 1,2-dichloroethane were refluxed for 4 hours. The mixture was cooled, filtered and evaporated. Chromatography of the residue afforded 1.47 g of a white solid, m.p.: 79° C.; MS: 254 ([M]$^+$).

Preparation of bis-(3,5-difluoro-phenyl)-dichloromethane 508 mg bis-(3,5-difluoro-phenyl)-methanone and 833 mg PCl$_5$ were placed in a sealed glass tube and heated to 170° C. for 7 hours. The reaction mixture was diluted with dichloromethane and washed twice with water and ice. Evaporation of the solvent afforded 333 mg of light yellow oil, which was not further purified.

Preparation of 2,2-bis-(3,5-difluoro-phenyl)-benzo[1,3]dioxole-5-carboxylic acid ethyl ester 239 mg dichloro-bis(3,5-difluorophenyl)methane and 141 mg ethyl 3,4-dihydroxybenzoate were heated to 180° C. for 2 h 15 min. The brown mixture was diluted with dichloromethane, washed with sat. NaHCO$_3$ solution and water. The dried solution was evaporated and the residue purified on silica gel to provide 284 mg resinous oil. MS: 419 ([M+H]$^+$).

Preparation of 2,2-bis-(3,5-difluoro-phenyl)-benzo[1,3]dioxole-5-carboxylic acid 267 mg 2,2-bis-(3,5-difluoro-phenyl)-benzo[1,3]dioxole-5-carboxylic acid ethyl ester, 3.8 mL ethyl alcohol and 0.96 mL 1N NaOH were stirred at room temperature for 6 h. The solvent was evaporated and the residue worked up with ethyl acetate, diluted hydrochloric acid and water. Purification on silica gel afforded 204 mg white crystals, m.p.: 96° C.; MS: 389 ([M−H]−).

Preparation of [2,2-bis-(3,5-difluoro-phenyl)-benzo[1,3]dioxol-5-yl]-piperidin-1-yl-methanone 96 mg 2,2-bis-(3,5-difluoro-phenyl)-benzo[1,3]dioxole-5-carboxylic acid, 93 mg HBTU, 1 mL DMF and 50 mg N-methylmorpholine were stirred at room temperature. After 5 min 21 mg piperidine were added and the mixture stirred at room temperature for 24 h. The mixture was diluted with ethyl acetate and washed twice with water. Evaporation of the solvents and purification on silica gel afforded 111 mg of a white foam, MS: 457 ([M]+).

Example 270

Preparation of [2,2-bis-(3,5-difluoro-phenyl)-benzo[1,3]dioxol-5-yl]-morpholin-4-yl-methanone

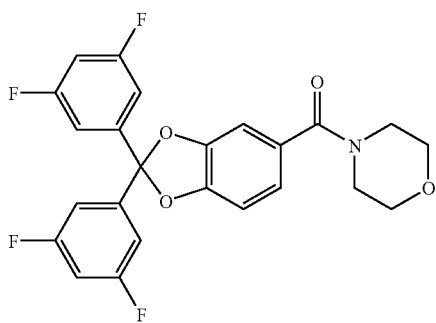

This compound was prepared from 2,2-bis-(3,5-difluoro-phenyl)-benzo[1,3]dioxole-5-carboxylic acid and morpholine according to Example 269f; white foam, MS 459 ([M]+).

Example 271

Preparation of 6-fluoro-[2,2-bis-(2-fluoro-phenyl)-benzo[1,3]dioxol-5-yl]-[(S)-3-hydroxy-pyrrolidin-1-yl)]-methanone

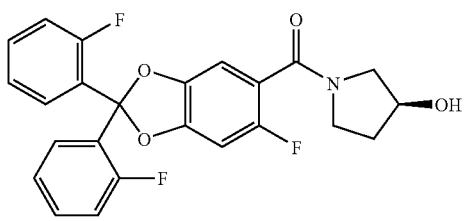

The title compound was produced in accordance with the general method of Example 108e from 6-fluoro-2,2-bis-(2-fluoro-phenyl)-benzo[1,3]dioxole-5-carboxylic acid and (S)-3-hydroxy-pyrrolidine, with (benzotriazol-1-yl-oxy-tris-dimethylamino)-phosphonium hexafluorophosphate (BOP) as coupling reagent (instead of carbonyl diimidazole) in acetonitrile as solvent at room temperature).

MS: m/e=442.3 ([M+H]+).

Example 272

Preparation of 6-fluoro-2,2-bis-(2-fluoro-phenyl)-benzo[1,3]dioxole-5-carboxylic acid ethyl-methyl-amide

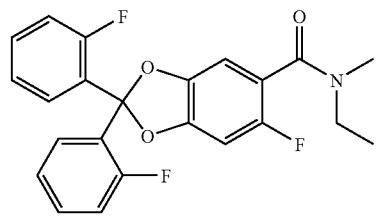

The title compound was produced in accordance with the general method of Example 108e from 6-fluoro-2,2-bis-(2-fluoro-phenyl)-benzo[1,3]dioxole-5-carboxylic acid and ethyl-methyl-amine, with (benzotriazol-1-yl-oxy-tris-dimethylamino)-phosphonium hexafluorophosphate (BOP) as coupling reagent (instead of carbonyl diimidazole) in acetonitrile as solvent at room temperature.

MS: m/e=414.3 ([M+H]+).

Example 273

Preparation of 6-fluoro-2,2-bis-(2-fluoro-phenyl)-benzo[1,3]dioxole-5-carboxylic acid (2-methoxy-ethyl)-methyl-amide

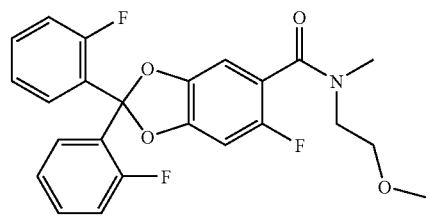

The title compound was produced in accordance with the general method of Example 108e from 6-fluoro-2,2-bis-(2-fluoro-phenyl)-benzo[1,3]dioxole-5-carboxylic acid and (2-methoxy-ethyl)-methyl-amine, with (benzotriazol-1-yl-oxy-tris-dimethylamino)-phosphonium hexafluorophosphate (BOP) as coupling reagent (instead of carbonyl diimidazole) in acetonitrile as solvent at room temperature.

MS: m/e=444.3 ([M+H]+).

Example 274

Preparation of [2,2-bis-(3,5-dichloro-phenyl)-benzo[1,3]dioxol-5-yl]-piperidin-1-yl-methanone

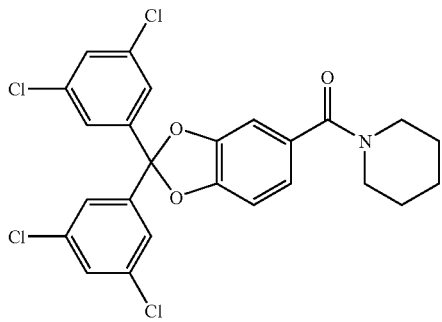

Preparation of bis-(3,5-dichloro-phenyl)-methanol

This compound was prepared from 3,5-dichloro-iodobenzene according to Example 269a; off white solid, m.p.: 126° C.; MS: m/e=322 ([M]$^+$).

Preparation of bis-(3,5-dichloro-phenyl)-methanone

This compound was prepared from bis-(3,5-dichloro-phenyl)-methanol according to Example 269b; off white solid, m.p.: 157° C.; MS: m/e=320 ([M]$^+$).

Preparation of bis-(3,5-dichlorophenyl)dichloromethane

This compound was prepared from bis-(3,5-dichloro-phenyl)-methanone and PC$_5$ according to Example 269c; light red solid.

Preparation of 2,2-bis-(3,5-dichloro-phenyl)-benzo[1,3]dioxole-5-carboxylic acid ethyl ester This compound was prepared from bis-(3,5-dichlorophenyl)dichloromethane and ethyl 3,4-dihydroxybenzoate according to Example 269d; light red solid, m.p.: 89° C.; MS: m/e=484 ([M]$^+$).

Preparation of 2,2-bis-(3,5-dichloro-phenyl)-benzo[1,3]dioxole-5-carboxylic acid This compound was prepared from 2,2-bis-(3,5-dichloro-phenyl)-benzo[1,3]dioxole-5-carboxylic acid ethyl ester according to Example 269e; white foam,
MS: m/e=455 ([M–H]$^-$).

Preparation of [2,2-bis-(3,5-dichloro-phenyl)-benzo[1,3]dioxol-5-yl]-piperidin-1-yl-methanone This compound was prepared from 2,2-bis-(3,5-dichloro-phenyl)-benzo[1,3]dioxole-5-carboxylic acid and piperidine according to Example 269f; waxy solid,
MS: m/e=([M+H]$^+$).

Example 275

Preparation of [2,2-bis-(3,5-dichloro-phenyl)-benzo[1,3]dioxol-5-yl]-morpholin-4-yl-methanone

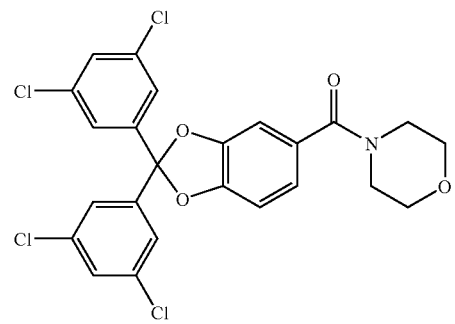

This compound was prepared from 2,2-bis-(3,5-dichloro-phenyl)-benzo[1,3]dioxole-5-carboxylic acid and morpholine according to Example 269f; waxy solid,
MS: m/e=526 ([M+H]$^+$).

Example 276

Preparation of [2,2-bis-(3-bromo-phenyl)-6-fluoro-benzo[1,3]dioxol-5-yl]-morpholin-4-yl-methanone

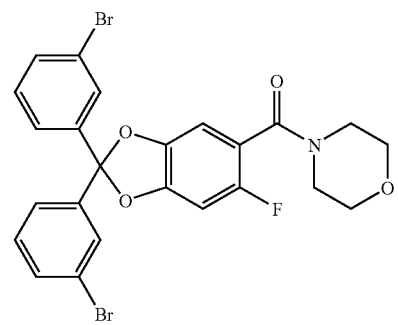

Preparation of bis-(3-bromophenyl)-dichloromethane 340 mg bis-(3-bromo-phenyl)-methanone, 0.08 mL DMF and 5 mL thionylchloride were refluxed for 24 hours. The solvents were evaporated in vacuo to give an off white waxy solid,
MS: m/e=394 ([M]$^+$).

Preparation of [2,2-bis-(3-bromo-phenyl)-6-fluoro-benzo[1,3]dioxol-5-yl]-morpholin-4-yl-methanone 79 mg bis-(3-bromophenyl)-dichloromethane and 48 mg (2-fluoro-4,5-dihydroxy-phenyl)-morpholin-4-yl-methanone were heated to 180° C. for one hour. Chromatography of the dark residue gave 30 mg of an off-white waxy solid, MS: m/e=564 ([M+H])$^+$.

Example 277

Preparation of [6-fluoro-2,2-bis-(3-methoxy-phenyl)-benzo[1,3]dioxol-5-yl]-morpholin-4-yl-methanone

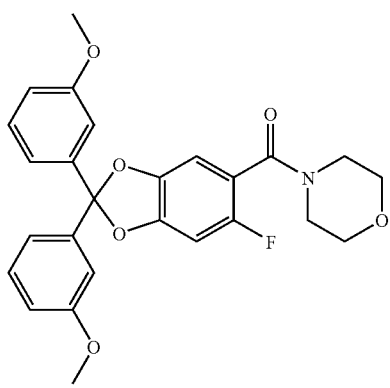

Preparation of dichloro-bis-(3-methoxyphenyl)-methane

This compound was prepared according to Example 276a; brown liquid.

Preparation of [6-fluoro-2,2-bis-(3-methoxy-phenyl)-benzo[1,3]dioxol-5-yl]-morpholin-4-yl-methanone This compound was prepared according to Example 276b; light brown, waxy solid,
MS: m/e=466 ([M+H]$^+$).

Example 278

Preparation of [2,2-bis-(3-methoxy-phenyl)-benzo[1,3]dioxol-5-yl]-piperidin-1-yl-methanone

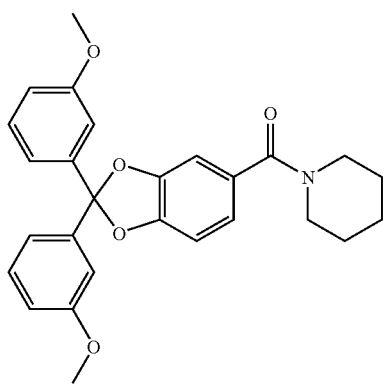

Preparation of 2,2-bis-(3-methoxy-phenyl)-benzo[1,3]dioxole-5-carboxylic acid ethyl ester This compound was prepared from dichloro-bis-(3-methoxyphenyl)-methane and ethyl 3,4-dihydroxybenzoate according to Example 269d; the crude product was used for the next step.

Preparation of 2,2-bis-(3-methoxy-phenyl)-benzo[1,3]dioxole-5-carboxylic acid

This compound was prepared from 2,2-bis-(3-methoxy-phenyl)-benzo[1,3]dioxole-5-carboxylic acid ethyl ester according to Example 269e; waxy solid,
MS: m/e=377 ([M−H]$^-$).

Preparation of [2,2-bis-(3-methoxy-phenyl)-benzo[1,3]dioxol-5-yl]-piperidin-1-yl-methanone This compound was prepared from 2,2-bis-(3-methoxy-phenyl)-benzo[1,3]dioxole-5-carboxylic acid and piperidine according to Example 269f; waxy solid, MS: m/e=446 ([M+H]$^+$).

Example 279

Preparation of [2,2-bis-(3-chloro-phenyl)-6-fluoro-benzo[1,3]dioxol-5-yl]-morpholin-4-yl-methanone

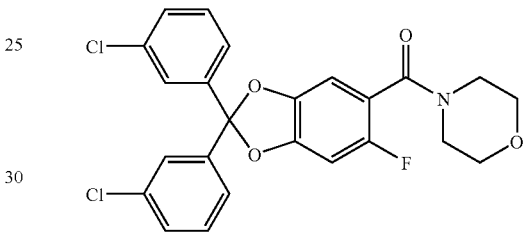

This compound was prepared from bis-(3-chloro-phenyl)-dichloromethane and (2-fluoro-4,5-dihydroxy-phenyl)-morpholin-4-yl-methanone according to Example 276b; viscous brown oil, MS: m/e=474 ([M+H]$^+$).

Galenical Examples

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

The invention claimed is:
1. A compound of the formula:

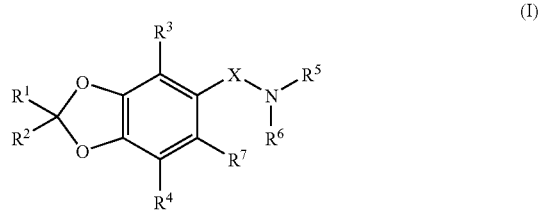

(I)

or a pharmaceticall acceptable salt thereof, wherein:
$R^1$ and $R^2$ are independently unsubstituted phenyl, or phenyl which is mono-, di- or tri-substituted, independently, by hydroxy, lower alkyl, lower alkoxy, perfluoro-lower alkyl, perfluoro-lower alkoxy, alkanoyl, cyano, nitro or halogen; or $R^1$ and $R^2$ together with the carbon atom to which they are attached form a 10',11'-dihydro-2,5'-[5H]dibenzo-[a,d]cycloheptene residue;
$R^3$ and $R^4$ are independently hydrogen, halogen, hydroxy, lower alkyl, lower alkoxy, perfluoro-lower alkyl, alkanoyl or cyano;
$R^5$ and $R^6$ together with the nitrogen atom to which they are attached form a heterocyclic ring which is peperazinyl, azepanyl, diazepanyl, or thiomorpholino, which is optionally mono-, di- or tri-substituted, independently, by lower alkyl, lower alkoxycarbonyl, hydroxy lower alkyl, lower alkoxy-lower alkyl, di-lower alkylcarbamoyl, carbamoyl, lower alkylcarbonyl amino, oxo, dioxo, alkanoyl, amino lower alkyl, hydroxy, lower alkoxy, halogen, perfluoro-lower alkyl, cyano, pyridinyl or pyrazinyl, or by phenyl or phenyl lower alkyl, wherein the phenyl moiety may optionally be mono-, di- or tri-substituted, independently, by lower alkyl, lower alkoxy, halogen, perfluoro-lower alkyl, hydroxy, alkanoyl or cyano;
$R^7$ is hydrogen, halogen, lower alkyl or cyano; and
X is a single bond, —CH$_2$—, —C(O)—, —SO$_2$— or —SO$_2$NH—.

2. The compound of claim 1, wherein $R^1$ and $R^2$ are independently phenyl, optionally mono-, di- or tri-substituted, independently, by hydroxy, lower alkyl, lower alkoxy, perfluoro-lower alkyl, alkanoyl, cyano or halogen; $R^3$ and $R^4$ are independently hydrogen, halogen, hydroxy, lower alkyl, lower alkoxy, perfluoro-lower alkyl, alkanoyl or cyano; $R^5$ and $R^6$ together with the nitrogen atom to which they are attached form a heterocyclic ring which is piperazinyl, azepanyl, diazepanyl, or thiomorpholino, which is optionally mono-, di- or tri-substituted, independently, by lower alkyl, lower alkoxycarbonyl, hydroxy lower alkyl, alkanoyl, amino lower alkyl, hydroxy, lower alkoxy, halogen, perfluoro-lower alkyl, cyano,pyridinyl or pyrazinyl, or by phenyl or phenyl lower alkyl, wherein the phenyl moiety may optionally be mono-, di- or tri-substituted, independently, by lower alkyl, lower alkoxy, halogen, perfluoro-lower alkyl, hydroxy, alkanoyl or cyano; $R^7$ is hydrogen; and X is —CH$_2$—, —C(O)— or —SO$_2$—or a pharmaceutically acceptable salt thereof.

3. The compound of claim 1, wherein $R^1$ and $R^2$ are independently unsubstituted phenyl or phenyl which is mono-, di- or tri-substituted, independently, by lower alkyl, lower alkoxy, perfluoro-lower alkyl, perfluoro-lower alkoxy, cyano, nitro or halogen.

4. The compound of claim 1, wherein $R^1$ and $R^2$ are independently phenyl which is mono- or di-substituted, independently, by halogen or by lower alkoxy.

5. The compound of claim 1, wherein $R^1$ and $R^2$ together with the carbon atom to which they are attached form a 10',11'-dihydro-2,5'-[5H]dibenzo[a,d]cycloheptene residue.

6. The compound of claim 1, wherein $R^3$ and $R^4$ are independently hydrogen, hydroxy or halogen.

7. The compound of claim 1, wherein $R^3$ and $R^4$ are hydrogen.

8. The compound of claim 1, wherein $R^5$ and $R^6$ together with the nitrogen atom to which they are attached form a heterocyclic ring which is piperazinyl, azepanyl, diazepanyl, or thiomorpholino, which is optionally mono-, di- or tri-substituted, independently, by lower alkyl, lower alkoxycarbonyl, hydroxy lower alkyl, lower alkoxy-lower alkyl, di-lower alkylcarbamoyl, carbamoyl, lower alkylcarbonyl amino, oxo, alkanoyl, amino lower alkyl, hydroxy, lower alkoxy, halogen, perfluoro-lower alkyl, cyano, pyridinyl or pyrazinyl,or by phenyl or phenyl lower alkyl, wherein the phenyl moiety may optionally be mono-, di- or tri-substituted, independently, by lower alkyl, lower alkoxy, halogen, perfluoro-lower alkyl, hydroxy, alkanoyl or cyano.

9. The compound of claim 8, wherein $R^5$ and $R^6$ together with the nitrogen atom to which they are attached are piperazinyl, thiomorpholino, azepanyl, or diazepanyl, which is optionally mono-, di- or tri-substituted, independently, by lower alkyl, lower alkoxycarbonyl, hydroxy lower alkyl, lower alkoxy-lower alkyl, di-lower alkylcarbamoyl, carbamoyl, lower alkylcarbonyl amino, oxo, dioxo, alkanoyl, hydroxyl, lower alkoxy, halogen, perfluoro-lower alkyl,pyridinyl or pyrazinyl, or by phenyl or phenyl lower alkyl, wherein the phenyl moiety may optionally be mono-, di- or tri-substituted, independently, by lower alkyl, lower alkoxy, halogen, or perfluoro-lower alkyl.

10. The compound of claim 9, wherein $R^5$ and $R^6$ together with the nitrogen atom to which they are attached is piperazinyl optionally mono- or di-substituted, independently, by hydroxy or by halogen.

11. The compound of claim 1, wherein $R^7$ is hydrogen.

12. The compound of claim 1, wherein $R^7$ is cyano, halogen or lower alkyl.

13. The compound of claim 1, wherein X is —C(O)— or —SO$_2$—.

14. A compound selected from the group consisting of:
1-(4-Chloro-phenyl)-4-(2,2-diphenyl-benzo [1,3]dioxole-5-sulfonyl)-piperazine,
1-(2,3-Dimethyl-phenyl)-4-(2,2-diphenyl-benzo [1,3]dioxole-5-sulfonyl)-piperazine,
1-(2,4-Dichloro-phenyl)-4-(2,2-diphenyl-benzo [1,3]dioxole-5-sulfonyl)-piperazine,
1-(2,2-Diphenyl-benzo[1,3]dioxole-5-sulfonyl)-4-(4-fluoro-phenyl)-piperazine,
1-(2,2-Diphenyl-benzo[1,3]dioxole-5-sulfonyl)-4-(3-chloro-phenyl)-piperazine,
1-(2,2-Diphenyl-benzo[1,3]dioxole-5-sulfonyl)-4-phenyl-piperazine,
1-(2,2-Diphenyl-benzo[1,3]dioxole-5-sulfonyl)-4-(3-methoxy-phenyl)-piperazine,
1-(2,2-Diphenyl-benzo[1,3]dioxole-5-sulfonyl)-4-(4-methoxy-phenyl)-piperazine,
1-(2,2-Diphenyl-benzo[1,3]dioxole-5-sulfonyl)-4-(2-methoxy-phenyl)-piperazine,
1-(2,2-Diphenyl-benzo[1,3]dioxole-5-sulfonyl)-4-(2-chloro-phenyl)-piperazine,
1-(2,2-Diphenyl-benzo[1,3]dioxole-5-sulfonyl)-4-(2-fluoro-phenyl)-piperazine,
1-Benzo[1,3]dioxol-5-yl-4-(2,2-diphenyl-benzo[1,3]dioxole- 5-sulfonyl)-piperazine,
1-(2,2-Diphenyl-benzo[1,3]dioxole-5-sulfonyl)-4-methyl-[1,4]diazepane,
1-(3-Chloro-5-trifluoromethyl-pyridin-2-yl)-4-(2,2-diphenyl-benzo[1,3]dioxole-5-sulfonyl)-[1,4]diazepane,
1-(2,2-Diphenyl-benzo[1,3]dioxole-5-sulfonyl)-4-methyl-piperazine,
4-(2,2-Diphenyl-benzo[1,3]dioxole-5 -carbonyl)-piperazine-1 -carbaldehyde,
(2,2-Diphenyl-benzo [1,3]dioxol-5-yl)-(4-methyl-piperazin-1-yl)-methanone,
(2,2-Diphenyl-benzo [1,3]dioxol-5-yl)-(4-isopropyl-piperazin-1-yl)-methanone,
[4-(5-Chloro-2-methoxy-phenyl)-piperazin-1-yl]-(2,2-diphenyl-benzo [1,3]dioxol-5-yl)-methanone, (
2,2-Diphenyl-benzo [1,3]dioxol-5-yl)-(4-m-toly1-piperazin-1-yl) -methanone,
(2,2-Diphenyl-benzo [1,3]dioxol-5-yl)-(4-o-toly1-piperazin-1-yl)-methanone,
[4-(2,3-Dichloro-phenyl)-piperazin-1-yl]-(2,2-diphenyl-benzo [1,3]dioxol-5-yl)-methanone,
[4-(4-Chloro-3-trifluoromethyl-phenyl)-piperazin-1-yl]-(2,2-diphenyl-benzo [1,3]dioxol-5-yl)-methanone,
(2,2-Diphenyl-benzo [1,3]dioxol-5-yl)-(2,3,5,6-tetrahydro-[1,2']bipyrazinyl-4-yl)-methanone,
(2,2-Diphenyl-benzo [1,3]dioxol-5-yl)-(4-pyridin-2-yl-piperazin-1-yl)-methanone,
(4-Fluoro-2,2-diphenyl-benzo [1,3]dioxol-5-yl)-(4-methyl-piperazin-1-yl)-methanone,
(4,7-Dichloro-2,2-diphenyl-benzo [1,3]dioxol-5-yl)-(4-methyl-piperazin-1-yl)-methanone,
(7-Bromo-4-chloro-2,2-diphenyl-benzo [1,3]dioxol-5-yl)-(4-methyl-piperazin-1-yl)-methanone, and pharmaceutically acceptable salts thereof.

15. A compound selected from the group consisting of:
(6-Fluoro-2,2-diphenyl-benzo [1,3]dioxol-5-yl)-[4-(4-fluoro-phenyl)-piperazin-1-yl]-methanone,
[6-Fluoro-2-(4-fluoro-phenyl)-2-phenyl-benzo [1,3]dioxol-5-yl]-[4-(4-fluoro-phenyl)-piperazin-1-yl]-methanone,
[2-(2-Chloro-phenyl)-6-fluoro-2-(4-methoxy-phenyl)-benzo[1,3]dioxol-5-yl]-[4-(4-fluoro-phenyl)-piperazin-1-yl]-methanone,
[2-(2,4-Dichloro-phenyl)-6-fluoro-2-(4-methoxy-phenyl)-benzo [1,3]dioxol-5-yl]-[4-(4-fluoro-phenyl)-piperazin-1 -yl]-methanone,
2-(2,4-Dichloro-phenyl)-6-fluoro-2-(4-fluoro-phenyl)-benzo [1,3]dioxole-5-carboxylic acid azepan-1-ylamide,
Azepan-1-yl-[2-(2,4-dichloro-phenyl)-6-fluoro-2-(4-fluoro-phenyl)-benzo[1,3]dioxol-5-yl]-methanone,
[2-(2,4-Dichioro-phenyl)-6-fluoro-2-(4-fluoro-phenyl)-benzo[1,3]dioxol-5-yl]-thiomorpholin-4-yl-methanone,
[2-(2,4-Dichioro-phenyl)-6-fluoro-2-(4-fluoro-phenyl)-benzo [1,3]dioxol-5-yl]-(1,1-dioxo-thiomorpholin-4-yl)-methanone,
[2-(2,4-Dichioro-phenyl)-6-fluoro-2-(4-fluoro-phenyl)-benzo [1,3]dioxol-5-yl]-(1-oxo-thiomorpholin-4-yl)-methanone,
[2,2-Bis-(2,4-difluoro-phenyl)-6-fluoro-benzo [1,3]dioxol-5-yl]-thiomorpholin-4-yl-methanone,
[6-Fluoro-2,2-bis-(4-fluoro-phenyl)-benzo [1,3]dioxol-5-yl]-thiomorpholin-4-yl-methanone,
4-[6-Fluoro-2,2-bis-(4-fluoro-phenyl)-benzo[1,3]dioxole-5-sulfonyl]-thiomorpholine,
4-[2,2-Bis-(2,4-difluoro-phenyl)-6-fluoro-benzo[1,3]dioxole-5-sulfonyl]-thiomorpholine, and pharmaceutically acceptable salts thereof.

16. A compound which is [2-(2,4-Dichloro-phenyl)-6-fluoro-2-(4-fluoro-phenyl)-benzo[1,3]dioxol-5-yl]-thiomorpholin-4-yl-methanone, or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 7,576,088 B2 |
| APPLICATION NO. | : 11/062973 |
| DATED | : August 18, 2009 |
| INVENTOR(S) | : Alanine et al. |

It is certified that error appears in the above-identified patent and that said Letters Patent is hereby corrected as shown below:

On the Title page,

[*] Notice:  Subject to any disclaimer, the term of this patent is extended or adjusted under 35 USC 154(b) by 526 days Delete the phrase "by 526 days" and insert -- by 1069 days --

Signed and Sealed this

Twentieth Day of April, 2010

David J. Kappos
*Director of the United States Patent and Trademark Office*